US012723028B2

(12) United States Patent
Tanaka et al.

(10) Patent No.: US 12,723,028 B2
(45) Date of Patent: Sep. 1, 2026

(54) HETEROCYCLIC COMPOUND

(71) Applicant: Takeda Pharmaceutical Company Limited, Osaka (JP)

(72) Inventors: Yuta Tanaka, Kanagawa (JP); Yuta Tanaka, Kanagawa (JP); Keiko Kakegawa, Kanagawa (JP); Takahito Kasahara, Kanagawa (JP); Fumiaki Kikuchi, Kanagawa (JP); Takeshi Yamamoto, Kanagawa (JP); Tomohiro Ohashi, Kanagawa (JP); Zenichi Ikeda, Kanagawa (JP); Florian Puenner, Kanagawa (JP); Minoru Nakamura, Kanagawa (JP); Kazuaki Takami, Kanagawa (JP); Masataka Murakami, Kanagawa (JP); Masaki Daini, Kanagawa (JP); Masaki Seto, Kanagawa (JP); Satoshi Mikami, Kanagawa (JP); Minoru Sasaki, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 1235 days.

(21) Appl. No.: 17/630,442

(22) PCT Filed: Jul. 28, 2020

(86) PCT No.: PCT/JP2020/028784

§ 371 (c)(1),
(2) Date: Jan. 26, 2022

(87) PCT Pub. No.: WO2021/020362

PCT Pub. Date: Feb. 4, 2021

(65) Prior Publication Data

US 2022/0289679 A1 Sep. 15, 2022

(30) Foreign Application Priority Data

Jul. 29, 2019 (JP) ................................ 2019-139174

(51) Int. Cl.

| | |
|---|---|
| *C07D 213/82* | (2006.01) |
| *C07D 237/14* | (2006.01) |
| *C07D 401/12* | (2006.01) |
| *C07D 401/14* | (2006.01) |
| *C07D 405/12* | (2006.01) |
| *C07D 405/14* | (2006.01) |
| *C07D 413/12* | (2006.01) |
| *C07D 471/04* | (2006.01) |

(52) U.S. Cl.

CPC ......... *C07D 213/82* (2013.01); *C07D 237/14* (2013.01); *C07D 401/12* (2013.01); *C07D 401/14* (2013.01); *C07D 405/12* (2013.01); *C07D 405/14* (2013.01); *C07D 413/12* (2013.01); *C07D 471/04* (2013.01)

(58) Field of Classification Search

None

See application file for complete search history.

(56) References Cited

U.S. PATENT DOCUMENTS

| | | | |
|---|---|---|---|
| 7,439,246 | B2 | 10/2008 | Borzilleri et al. |
| 8,445,509 | B2 | 5/2013 | Miyamoto et al. |
| 2005/0288290 | A1 | 12/2005 | Borzilleri et al. |
| 2006/0004006 | A1 | 1/2006 | Borzilleri et al. |
| 2007/0238726 | A1 | 10/2007 | Blake et al. |

(Continued)

FOREIGN PATENT DOCUMENTS

| | | | |
|---|---|---|---|
| EP | 2 562 174 | A1 | 2/2013 |
| JP | 2009-529047 | A | 8/2009 |

(Continued)

OTHER PUBLICATIONS

Shayman et al., "Developing novel chemical entities for the treatment of lysosomal storage disorders: an academic perspective," Am. J. Physiol. Renal Physiol., Oct. 7, 2015, 309(12):F996-F999.

Rocha et al., "Progressive decline of glucocerebrosidase in aging and Parkinson's disease," Annals of Clinical and Translational Neurology, 2015, 2(4):433-438.

Sardi et al., "Glucosylceramide synthase inhibition alleviates aberrations in synucleinopathy models," PNAS, Mar. 7, 2017, 114(10):2699-2704.

(Continued)

*Primary Examiner* — Clinton A Brooks
*Assistant Examiner* — Nicola Maria Bauer
(74) *Attorney, Agent, or Firm* — Foley & Lardner LLP

(57) ABSTRACT

The present invention provides a compound having a glucosylceramide synthase inhibitory action, which is expected to be useful as an agent for the prophylaxis or treatment of lysosomal storage diseases (e.g., Gaucher's disease, Fabry's disease, GM1-gangliosidosis, GM2 activator deficiency, Tay-Sachs disease, Sandhoffs disease), neurodegenerative diseases (e.g., Parkinson's disease, Lewy body dementia, multiple-system atrophy) and the like.

The present invention relates to a compound represented by the formula (I):

(I)

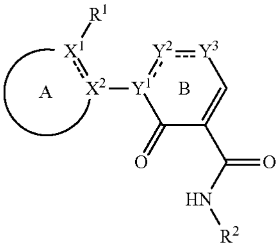

wherein each symbol is as described in the description, or a salt thereof.

12 Claims, No Drawings

(56) References Cited

U.S. PATENT DOCUMENTS

| | | | |
|---|---|---|---|
| 2008/0312232 | A1 | 12/2008 | Kim et al. |
| 2010/0256356 | A1 | 10/2010 | Blake et al. |
| 2011/0009407 | A1 | 1/2011 | Xu et al. |
| 2011/0046169 | A1 | 2/2011 | Miyamoto et al. |
| 2011/0118252 | A1 | 5/2011 | Kim et al. |
| 2012/0070413 | A1 | 3/2012 | Kim et al. |
| 2013/0109682 | A1 * | 5/2013 | Burger .................... A61P 37/02 514/227.8 |
| 2013/0252957 | A1 | 9/2013 | Xu et al. |
| 2015/0072860 | A1 | 3/2015 | Mitchell |
| 2015/0210681 | A1 | 7/2015 | Bourque et al. |
| 2016/0264579 | A1 | 9/2016 | Inukai et al. |
| 2016/0361301 | A1 | 12/2016 | Leonard et al. |
| 2017/0275290 | A1 | 9/2017 | Li et al. |
| 2018/0244667 | A1 * | 8/2018 | Long .................... A61K 31/444 |
| 2018/0327412 | A1 | 11/2018 | Li et al. |
| 2019/0046509 | A1 | 2/2019 | Leonard et al. |
| 2020/0131185 | A1 | 4/2020 | Li et al. |
| 2020/0237757 | A1 | 7/2020 | Schmees et al. |
| 2021/0087186 | A1 | 3/2021 | Tanaka et al. |
| 2021/0147430 | A1 | 5/2021 | Li et al. |
| 2022/0409595 | A1 | 12/2022 | Leonard et al. |

FOREIGN PATENT DOCUMENTS

| | | | | |
|---|---|---|---|---|
| JP | 5463033 | B2 | 1/2014 | |
| JP | 2018-520109 | A | 7/2018 | |
| JP | 2019-510043 | A | 4/2019 | |
| JP | 2019-516744 | A | 6/2019 | |
| WO | WO-2009/096435 | A1 | 8/2009 | |
| WO | WO-2009/136663 | A1 | 11/2009 | |
| WO | WO-2010/126914 | A1 | 11/2010 | |
| WO | WO-2013/139760 | A1 | 9/2013 | |
| WO | WO-2015068767 | A1 * | 5/2015 | ................ A61P 9/00 |
| WO | WO-2015/089067 | A1 | 6/2015 | |
| WO | WO-2019/151269 | A1 | 8/2019 | |
| WO | WO-2021/020363 | A1 | 2/2021 | |

OTHER PUBLICATIONS

Schengrund, Cara-Lynne, “The Role(s) of Gangliosides in Neural Differentiation and Repair: A Perspective,” Brain Research Bulletin, 1990, 24:131-141.

* cited by examiner

HETEROCYCLIC COMPOUND

CROSS-REFERENCE TO RELATED APPLICATIONS

This application is the U.S. National Stage of PCT/JP2020/028784, filed Jul. 28, 2020, which claims priority to JP 2019-139174, filed Jul. 29, 2019.

TECHNICAL FIELD

The present invention relates to a heterocyclic compound having a glucosylceramide synthase inhibitory action, which is useful for the treatment of lysosomal storage diseases (e.g., Gaucher's disease), neurodegenerative diseases (e.g., Parkinson's disease, Lewy body dementia, multiple-system atrophy) and the like, medicament comprising the same, and the like.

BACKGROUND OF THE INVENTION

Glycosphingolipid is a ceramide to which sugars such as glucose, galactose, N-acetylglucosamine, N-acetylgalactosamine, sialic acid and the like are added stepwise by an enzyme. Many glycolipid-accumulating diseases such as lysosomal diseases caused by the accumulation of glycosphingolipid due to mutation of glycosphingolipid-degrading enzyme have been reported. Glycosphingolipid is considered to be essential for the construction and function performance of nervous system tissues (Non-Patent Document 1), and quantitative and qualitative abnormalities of glycosphingolipids are known to contribute to neurodegenerative diseases. From the above, suppression of glycosphingolipid accumulation may lead to treatment of these diseases.

Glucosylceramide is an important glycosphingolipid that is present in all tissues and cells and is a precursor glycolipid common to 400 types or more of glycolipids. Glucosylceramide synthase is an enzyme that synthesizes glucosylceramide from uridine diphosphate glucose and ceramide. Since its inhibitors suppress the abnormal accumulation of glycosphingolipid by suppressing the production of glycosphingolipid, it has been proposed for the treatment of various diseases (Patent Document 1 and Patent Document 2). For example, it has been reported that glycosphingolipids are accumulated in the substantia nigra of the lesion site in patients with Parkinson's disease, which is a neurodegenerative disease (Non-Patent Document 2), and it has been suggested that glucosylceramide synthase inhibitors have the potential to be therapeutic agents for neurodegenerative diseases such as Parkinson's disease, Lewy body dementias and the like (Non-Patent Document 3).

From the above, it is suggested that the glucosylceramide synthase inhibitors have the potential to be prophylactic or therapeutic agent for lysosomal storage diseases (e.g., Gaucher's disease, Fabry's disease, GM1-gangliosidosis, GM2 activator deficiency, Tay-Sachs disease, Sandhoffs disease), neurodegenerative diseases (e.g., Parkinson's disease, Lewy body dementia, multiple-system atrophy) and the like.

As glucosylceramide synthase inhibitors, Patent Document 1 describes a compound represented by the following formula:

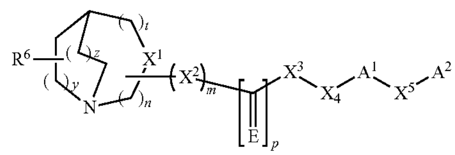

wherein each symbol is as defined in Patent Document 1, and Patent Document 2 describes a compound represented by the following formula:

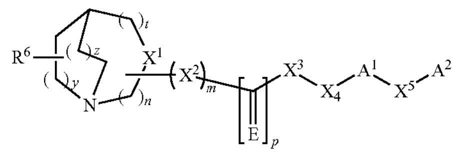

wherein each symbol is as defined in Patent Document 2.

In addition, Non-Patent Document 3 describes the compounds described in Patent Document 1 and Patent Document 2.

As compounds having a glucosylceramide lowering action, Patent Document 3 describes a compound represented by the following formula:

(I)

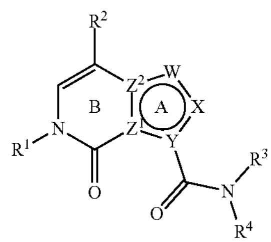

wherein each symbol is as defined in Patent Document 3.

As heterocyclic compounds, the following compounds are known.

Patent Document 4 describes that a compound represented by the following formula:

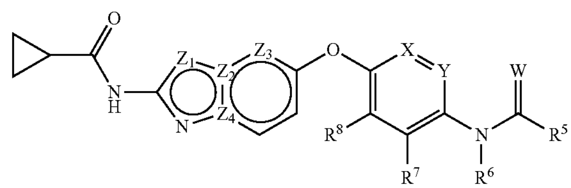

wherein each symbol is as defined in Patent Document 4, is useful for the treatment of cancers.

Patent Document 5 describes that a compound represented by the following formulas:

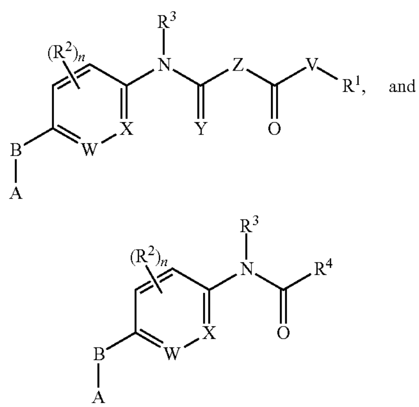

and wherein each symbol is as defined in Patent Document 5, are useful for the treatment of cancers.

Patent Document 6 describes that a compound represented by the following formulas:

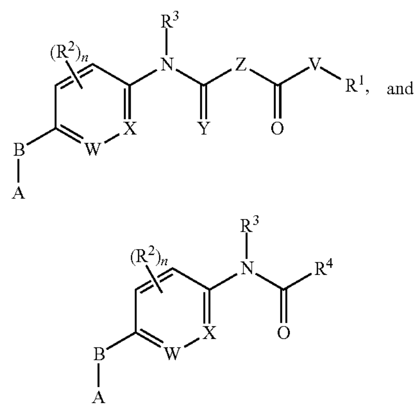

and wherein each symbol is as defined in Patent Document 6, are useful for the treatment of cancers.

Patent Document 7 describes that a compound represented by the following formulas:

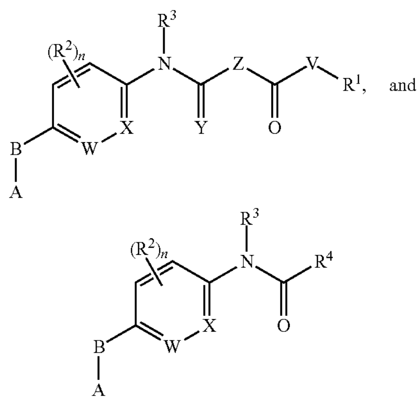

and wherein each symbol is as defined in Patent Document 7, are useful for the treatment of cancers.

DOCUMENT LIST

Patent Document

Patent Document 1: US 2016/0361301
Patent Document 2: US 2015/0210681
Patent Document 3: WO 2019/151269
Patent Document 4: U.S. Pat. No. 8,445,509
Patent Document 5: US 2005/0288290
Patent Document 6: U.S. Pat. No. 7,439,246
Patent Document 7: US 2006/0004006

Non-Patent Document

Non-Patent Document 1: Brain Res Bull 24, 131-141
Non-Patent Document 2: Ann Clin Transl Neurol. 2015 April; 2(4): 433-438
Non-Patent Document 3: Proceedings of the National Academy of Sciences of the United States of America (2017), 114(10), 2699-2704

SUMMARY OF THE INVENTION

Problems to be Solved by the Invention

An object of the present invention is to provide a compound having a glucosylceramide synthase inhibitory action, which is useful as an agent for the prophylaxis or treatment of lysosomal storage diseases (e.g., Gaucher's disease), neurodegenerative diseases (e.g., Parkinson's disease, Lewy body dementia, multiple-system atrophy) and the like.

Means of Solving the Problems

The present inventors have conducted intensive studies in an attempt to solve the above-mentioned problems and found that a compound represented by the following formula (I) has a glucosylceramide synthase inhibitory action, and therefore, the compound is useful as an agent for the prophylaxis or treatment of lysosomal storage diseases (e.g., Gaucher's disease), neurodegenerative diseases (e.g., Parkinson's disease, Lewy body dementia, multiple-system atrophy) and the like, which resulted in the completion of the present invention.

Accordingly, the present invention provides the following.

(1) A compound represented by the formula (I):

(I)

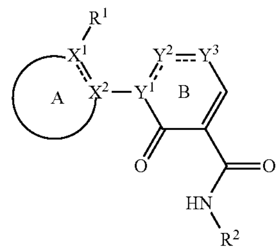

wherein $X^1$ is C or N, $X^2$ is C or N,

------ is a single bond or a double bond,

Ring A is an optionally further substituted 5- or 6-membered aromatic ring, $R^1$ is a chlorine atom, a bromine atom, an iodine atom, a cyano group, a $C_{1-6}$ alkyl group substituted by 1 to 5 fluorine atoms, an optionally substituted hydroxy group, an optionally substituted amino group, or an optionally substituted cyclic group, $Y^1$ is $CR^a$ wherein $R^a$ is absent, a hydrogen atom or a substituent, or N, $Y^2$ is $CR^bR^c$ wherein $R^b$ is a hydrogen atom or a substituent, and $R^c$ is absent, a hydrogen atom or a substituent, or $NR^d$ wherein $R^d$ is absent, a hydrogen atom or a substituent, $Y^3$ is $CR^eR^f$ wherein $R^e$ is a hydrogen atom or a substituent, and $R^f$ is absent, a hydrogen atom or a substituent, or $NR^g$ wherein $R^g$ is absent, a hydrogen atom or a substituent, Ring B is a 6-membered ring, and $R^2$ is

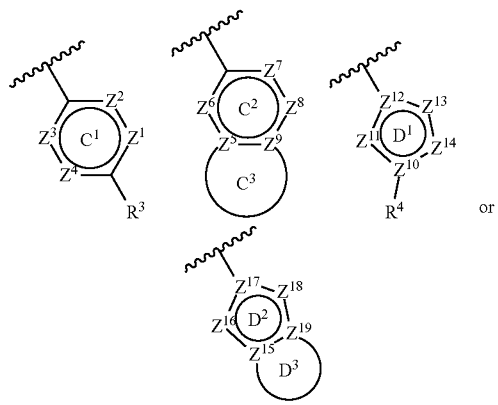

wherein $Z^1$ is $CR^h$ wherein $R^h$ is a hydrogen atom or a substituent, or N, $Z^2$ is $CR^i$ wherein $R^i$ is a hydrogen atom or a substituent, or N, $Z^3$ is $CR^j$ wherein $R^j$ is a hydrogen atom or a substituent, or N, $Z^4$ is $CR^k$ wherein $R^k$ is a hydrogen atom or a substituent, or N, $Z^5$ is C or N, $Z^6$ is $CR^l$ wherein $R^l$ is a hydrogen atom or a substituent, or N, $Z^7$ is $CR^m$ wherein $R^m$ is a hydrogen atom or a substituent, or N, $Z^8$ is $CR^n$ wherein $R^n$ is a hydrogen atom or a substituent, or N, $Z^9$ is C or N, $Z^{10}$ is C or N, $Z^{11}$ is $CR^o$ wherein $R^o$ is a hydrogen atom or a substituent, $NR^p$ wherein $R^p$ is absent, a hydrogen atom or a substituent, O or S, $Z^{12}$ is C or N, $Z^{13}$ is $CR^q$ wherein $R^q$ is a hydrogen atom or a substituent, $NR^r$ wherein $R^r$ is absent, a hydrogen atom or a substituent, O or S, $Z^{14}$ is $CR^s$ wherein $R^s$ is a hydrogen atom or a substituent, $NR^t$ wherein $R^t$ is absent, a hydrogen atom or a substituent, O or S, $Z^{15}$ is C or N, $Z^{16}$ is $CR^u$ wherein $R^u$ is a hydrogen atom or a substituent, $NR^v$ wherein $R^v$ is absent, a hydrogen atom or a substituent, O or S, $Z^{17}$ is C or N, $Z^{18}$ is $CR^w$ wherein $R^w$ is a hydrogen atom or a substituent, $NR^x$ wherein $R^x$ is absent, a hydrogen atom or a substituent, O or S, $Z^{19}$ is C or N, Ring $C^1$ and Ring $C^2$ are each independently a 6-membered aromatic ring, Ring $C^3$ is an optionally substituted ring, $R^3$ is a halogen atom, a cyano group, an optionally substituted $C_{1-6}$ alkyl group, an optionally substituted cyclic group, an optionally substituted amino group, $SO_2R^7$ or $OR^8$, $R^7$ is a substituent, $R^8$ is a hydrogen atom, an optionally substituted $C_{1-6}$ alkyl group, an optionally substituted saturated cyclic group, or an optionally substituted monocyclic unsaturated cyclic group, Ring $D^1$ and Ring $D^2$ are each independently a 5-membered aromatic ring, Ring $D^3$ is an optionally substituted ring, and $R^4$ is a substituent, or a salt thereof.

(2) The compound or salt according to (1), wherein $X^1$ is C or N;

$X^2$ is C;

Ring A is a 5- or 6-membered aromatic ring optionally further substituted by 1 to 3 substituents selected from (1) a halogen atom, and (2) a $C_{1-6}$ alkyl group, in addition to $R^1$ and the group represented by the formula:

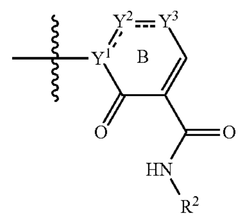

wherein each symbol is defined as in (1);

$R^1$ is (1) a cyano group, (2) a $C_{1-6}$ alkyl group substituted by 1 to 5 fluorine atoms, (3) a $C_{1-6}$ alkoxy group optionally substituted by 1 to 5 substituents selected from (i) a halogen atom, (ii) a hydroxy group, and (iii) a $C_{1-6}$ alkoxy group, or (4) a 3- to 8-membered monocyclic non-aromatic heterocyclic group;

$Y^1$ is C or N;

$Y^2$ is $CR^{b'}$ wherein $R^{b'}$ is (1) a hydrogen atom, or (2) a $C_{1-6}$ alkyl group, or N;

$Y^3$ is $CR^{e'}$ wherein $R^{e'}$ is (1) a hydrogen atom, (2) a $C_{1-6}$ alkyl group optionally substituted by 1 to 5 hydroxy groups, (3) a $C_{1-6}$ alkyl-carbonyl group, or (4) a $C_{1-6}$ alkoxy-carbonyl group, or $NR^{g'}$ wherein $R^{g'}$ is (1) absent, (2) a $C_{1-6}$ alkyl group optionally substituted by 1 to 5 substituents selected from (i) a halogen atom, (ii)

a hydroxy group, and (iii) a 3- to 8-membered monocyclic non-aromatic heterocyclic group, (3) a $C_{3-6}$ cycloalkyl group, or (4) a 3- to 8-membered monocyclic non-aromatic heterocyclic group; and $R^2$ is a group represented by the formula:

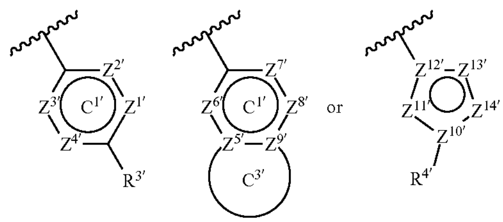

wherein $Z^{1'}$ is $CR^{h'}$ wherein $R^{h'}$ is a hydrogen atom, a halogen atom or a $C_{1-6}$ alkyl group, or N, $Z^{2'}$ is $CR^{i'}$ wherein $R^{i'}$ is a hydrogen atom, a halogen atom, a cyano group, a $C_{1-6}$ alkyl group or a $C_{1-6}$ alkoxy group, or N, $Z^{3'}$ is $CR^{j'}$ wherein $R^{j'}$ is a hydrogen atom or a halogen atom, or N, $Z^{4'}$ is CH or N, $Z^{5'}$ is N, $Z^{6'}$ is CH, $Z^{7'}$ is CH, $Z^{8'}$ is CH, $Z^{9'}$ is C, $Z^{10'}$ is C or N, $Z^{11'}$ is CH, N or S, $Z^{12'}$ is C, $Z^{13'}$ is CH or N, $Z^{14'}$ is $CR^{s'}$ wherein $R^{s'}$ is a hydrogen atom or an optionally halogenated $C_{1-6}$ alkyl group, N or O, Ring $C^{1'}$ is a 6-membered aromatic ring, Ring $C^{2'}$ is a 6-membered aromatic ring, Ring $C^{3'}$ is a 5-membered ring, $R^{3'}$ is (1) a halogen atom, (2) a cyano group, (3) a $C_{1-6}$ alkyl group optionally substituted by 1 to 8 substituents selected from (i) a halogen atom, (ii) a cyano group, (iii) a hydroxy group, (iv) a $C_{3-6}$ cycloalkyl group, (v) an optionally halogenated $C_{1-6}$ alkoxy group, (vi) a 3- to 8-membered monocyclic non-aromatic heterocyclic group, and (vii) an oxo group, (4) a $C_{2-6}$ alkenyl group, (5) a cyclic group optionally substituted by 1 to 3 hydroxy groups, or (6) $OR^{8'}$ wherein $R^{8'}$ is (a) a $C_{1-6}$ alkyl group optionally substituted by 1 to 3 substituents selected from (i) a halogen atom, (ii) a hydroxy group, and (iii) a $C_{3-6}$ cycloalkyl group, or (b) a $C_{6-10}$ aryl group, Ring $D^{1'}$ is a 5-membered aromatic ring, and $R^{4'}$ is (1) a $C_{1-6}$ alkyl group optionally substituted by 1 to 5 substituents selected from (i) a halogen atom, (ii) a $C_{3-6}$ cycloalkyl group optionally substituted by 1 to 3 halogen atoms, and (iii) a 3- to 8-membered monocyclic non-aromatic heterocyclic group optionally substituted by 1 to 3 halogen atoms, (2) a $C_{3-6}$ cycloalkyl group, (3) a $C_{6-10}$ aryl group optionally substituted by 1 to 3 halogen atoms, (4) a $C_{1-6}$ alkoxy-carbonyl group, or (5) a 3- to 8-membered monocyclic non-aromatic heterocyclic group.

(3) The compound or salt according to (1), wherein $X^1$ is C;

$X^2$ is C;

Ring A is a benzene ring optionally further substituted by 1 to 3 halogen atoms, in addition to $R^1$ and the group represented by the formula:

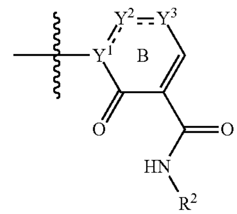

wherein each symbol is defined as in (1);

$R^1$ is a $C_{1-6}$ alkoxy group substituted by 1 to 5 halogen atoms;

$Y^1$ is C or N;

$Y^2$ is N;

$Y^3$ is $CR^{e'}$ wherein $R^{e'}$ is (1) a hydrogen atom, or (2) a $C_{1-6}$ alkyl group, or $NR^{g''}$ wherein $R^{g''}$ is (1) a $C_{1-6}$ alkyl group optionally substituted by 1 to 5 substituents selected from (i) a halogen atom, and (ii) a hydroxy group, or (2) a $C_{3-6}$ cycloalkyl group; and $R^2$ is a group represented by the formula

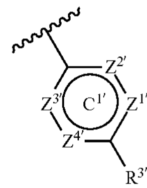

wherein $Z^{1'}$ is CH or N, $Z^{2'}$ is CH or CF, $Z^{3'}$ is CH, $Z^{4'}$ is CH, and $R^{3'}$ is a $C_{1-6}$ alkyl group optionally substituted by 1 to 5 substituents selected from a halogen atom and a hydroxy group.

(4) N-[4-(2-Hydroxypropan-2-yl)phenyl]-3-oxo-2-[2-(2,2,2-trifluoroethoxy)phenyl]-2,3-dihydropyridazine-4-carboxamide or a salt thereof.

(5) 2-[2-(2,2-Difluoroethoxy)phenyl]-N-[4-(2-hydroxypropan-2-yl)phenyl]-3-oxo-2,3-dihydropyridazine-4-carboxamide or a salt thereof.

(6) 2-[2-(2,2-Difluoroethoxy)phenyl]-N-[4-(2-hydroxypropan-2-yl)phenyl]-6-methyl-3-oxo-2,3-dihydropyridazine-4-carboxamide or a salt thereof.

(7) A medicament comprising the compound or salt according to (1).

(8) The medicament according to (7), which is a glucosylceramide synthase inhibitor.

(9) The medicament according to (7), which is an agent for the prophylaxis or treatment of a lysosomal storage disease or a neurodegenerative disease.

(10) The medicament according to (9), wherein the lysosomal storage disease is Gaucher's disease, Fabry's disease, GM1-gangliosidosis, GM2 activator deficiency, Tay-Sachs disease or Sandhoffs disease.

(11) The medicament according to (9), wherein the neurodegenerative disease is Parkinson's disease, Lewy body dementia or multiple-system atrophy.

(12) The compound or salt according to (1) for use in the prophylaxis or treatment of a lysosomal storage disease or a neurodegenerative disease.

(13) The compound or salt according to (12), wherein the lysosomal storage disease is Gaucher's disease, Fabry's disease, GM1-gangliosidosis, GM2 activator deficiency, Tay-Sachs disease or Sandhoffs disease.

(14) The compound or salt according to (12), wherein the neurodegenerative disease is Parkinson's disease, Lewy body dementia or multiple-system atrophy.

(15) A method for inhibiting glucosylceramide synthase in a mammal, which comprises administering an effective amount of the compound or salt according to (1) to the mammal.

(16) A method for preventing or treating a lysosomal storage disease or a neurodegenerative disease in a mammal, which comprises administering an effective amount of the compound or salt according to (1) to the mammal.

(17) The method according to (16), wherein the lysosomal storage disease is Gaucher's disease, Fabry's disease, GM1-gangliosidosis, GM2 activator deficiency, Tay-Sachs disease or Sandhoffs disease.

(18) The method according to (16), wherein the neurodegenerative disease is Parkinson's disease, Lewy body dementia or multiple-system atrophy.

(19) Use of the compound or salt according to (1) for the manufacture of an agent for the prophylaxis or treatment of a lysosomal storage disease or a neurodegenerative disease.

(20) The use according to (19), wherein the lysosomal storage disease is Gaucher's disease, Fabry's disease, GM1-gangliosidosis, GM2 activator deficiency, Tay-Sachs disease or Sandhoffs disease.

(21) The use according to (19), wherein the neurodegenerative disease is Parkinson's disease, Lewy body dementia or multiple-system atrophy.

Effect of the Invention

According to the present invention, a compound having an excellent glucosylceramide synthase inhibitory action, which is useful as an agent for the prophylaxis or treatment of lysosomal storage diseases (e.g., Gaucher's disease), neurodegenerative diseases (e.g., Parkinson's disease, Lewy body dementia, multiple-system atrophy) and the like, can be provided.

DETAILED DESCRIPTION OF THE INVENTION

The present invention is explained in detail in the following.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following Substituent Group A.

[Substituent Group A]

(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,

(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl) amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group, and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 heteroatoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 heteroatoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 heteroatoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the above-mentioned Substituent Group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent Group A".

Preferable examples of the optionally substituted amino group include an amino group, a mono- or di-(optionally halogenated $C_{1-6}$ alkyl) amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl) amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl) amino group (e.g., N-acetyl-N-methylamino) and a ($C_{1-6}$ alkyl) ($C_{6-14}$ aryl-carbonyl) amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxy group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent Group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from Substituent Group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from Substituent Group A".

Preferable examples of the optionally substituted silyl group include a tri-$C_{1-6}$ alkylsilyl group (e.g., trimethylsilyl, tert-butyl(dimethyl)silyl).

In the present specification, examples of the "hydrocarbon ring" include a $C_{6-14}$ aromatic hydrocarbon ring, a —$C_{3-10}$ cycloalkane and a $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azepine, azocane, diazocane, oxepane and the like; and 9- to 14-membered fused polycyclic (preferably hi or tricyclic) non-aromatic heterocycles such as dihydrobenzofuran, dihydrobenzimidazole, dihydrobenzoxazole, dihydrobenzothiazole, dihydrobenzisothiazole, dihydronaphtho [2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

In the present specification, examples of the "5- or 6-membered aromatic ring" include a benzene ring and a "5- or 6-membered monocyclic aromatic heterocycle".

In the present specification, examples of the "5-membered aromatic ring" include a 5-membered aromatic ring, from among the "5- or 6-membered monocyclic aromatic heterocycle".

In the present specification, examples of the "6-membered aromatic ring" include a benzene ring, and a 6-membered aromatic heterocycle, from among the "5- or 6-membered monocyclic aromatic heterocycle".

In the present specification, examples of the "saturated cyclic group" include a saturated cyclic group, from among the "$C_{3-10}$ cycloalkyl group" and "non-aromatic heterocyclic group".

In the present specification, examples of the "monocyclic unsaturated cyclic group" include a phenyl group, a "$C_{3-10}$ cycloalkenyl group", a "5- to 6-membered monocyclic aromatic heterocyclic group", and a unsaturated heterocyclic group, from among the "3- to 8-membered monocyclic non-aromatic heterocyclic group".

In the present specification, examples of the "cyclic group" include a "$C_{3-10}$ cycloalkyl group", a "$C_{3-10}$ cycloalkenyl group", a "$C_{6-14}$ aryl group" and a "heterocyclic group".

In the present specification, examples of the "ring" include a "hydrocarbon ring" and a "heterocycle".

The definition of each symbol in the formula (I) is explained in detail.

$X^1$ is C or N. $X^1$ is preferably C.

$X^2$ is C or N. $X^2$ is preferably C.

$\text{- - - - - -}$ is a single bond or a double bond.

Ring A is an optionally further substituted 5- or 6-membered aromatic ring.

The "5- or 6-membered aromatic ring" of the "optionally further substituted 5- or 6-membered aromatic ring" for Ring A optionally further has substituent(s), in addition to $R^1$ and the group represented by the formula:

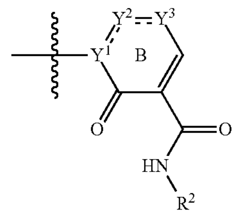

wherein each symbol is as defined above.

Examples of the substituent include those similar to Substituent Group A. The ring optionally has 1 to 4 substituents at substitutable positions.

Ring A is preferably a 5- or 6-membered aromatic ring (e.g., a pyrazole ring, a benzene ring, a pyridine ring, a pyridazine ring, a pyrimidine ring) optionally further substituted by 1 to 3 substituents selected from (1) a halogen atom (e.g., a fluorine atom), and (2) a $C_{1-6}$ alkyl group (e.g., methyl), in addition to $R^1$ and the group represented by the formula:

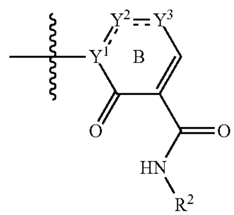

wherein each symbol is as defined above.

Ring A is particularly preferably a benzene ring optionally further substituted by 1 to 3 halogen atoms (e.g., a fluorine atom), in addition to $R^1$ and the group represented by the formula:

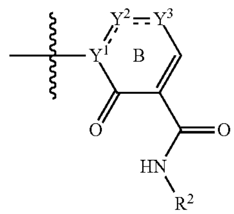

wherein each symbol is as defined above.

$R^1$ is (1) a chlorine atom, (2) a bromine atom, (3) an iodine atom, (4) a cyano group, (5) a $C_{1-6}$ alkyl group substituted by 1 to 5 fluorine atoms, (6) an optionally substituted hydroxy group, (7) an optionally substituted amino group, or (8) an optionally substituted cyclic group.

Examples of the substituent of the "optionally substituted cyclic group" for $R^1$ include those similar to Substituent Group A. The group optionally has 1 to 3 substituents at substitutable positions.

$R^1$ is preferably (1) a cyano group, (2) a $C_{1-6}$ alkyl group substituted by 1 to 5 fluorine atoms (e.g., 3,3,3-trifluoropropyl), (3) a $C_{1-6}$ alkoxy group (e.g., methoxy, ethoxy, propoxy, isobutoxy) optionally substituted by 1 to 5 substituents selected from (i) a halogen atom (e.g., a fluorine atom), (ii) a hydroxy group, and (iii) a $C_{1-6}$ alkoxy group (e.g., methoxy), or (4) a 3- to 8-membered monocyclic non-aromatic heterocyclic group (e.g., morpholinyl, tetrahydropyranyl).

$R^1$ is particularly preferably a $C_{1-6}$ alkoxy group (e.g., ethoxy) substituted by 1 to 5 halogen atoms (e.g., a fluorine atom).

$Y^1$ is $CR^a$ wherein $R^a$ is absent, a hydrogen atom or a substituent, or N.

$Y^1$ is preferably C or N.

$Y^2$ is $CR^bR^c$ wherein $R^b$ is a hydrogen atom or a substituent, and $R^c$ is absent, a hydrogen atom or a substituent, or $NR^d$ wherein $R^d$ is absent, a hydrogen atom or a substituent.

$Y^2$ is preferably $CR^{b'}$ wherein $R^{b'}$ is (1) a hydrogen atom, or (2) a $C_{1-6}$ alkyl group (e.g., methyl), or N.

$Y^2$ is particularly preferably N.

$Y^3$ is $CR^eR^f$ wherein $R^e$ is a hydrogen atom or a substituent, and $R^f$ is absent, a hydrogen atom or a substituent, or $NR^g$ wherein $R^g$ is absent, a hydrogen atom or a substituent.

$Y^3$ is preferably $CR^{e'}$ wherein $R^{e'}$ is (1) a hydrogen atom, (2) a $C_{1-6}$ alkyl group (e.g., methyl, ethyl, isopropyl) optionally substituted by 1 to 5 hydroxy groups, (3) a $C_{1-6}$ alkyl-carbonyl group (e.g., acetyl), or (4) a $C_{1-6}$ alkoxy-carbonyl group (e.g., ethoxycarbonyl), or $NR^{g'}$ wherein $R^{g'}$ is (1) absent, (2) a $C_{1-6}$ alkyl group (e.g., methyl, ethyl, isobutyl) optionally substituted by 1 to 5 substituents selected from (i) a halogen atom (e.g., a fluorine atom), (ii) a hydroxy group, and (iii) a 3- to 8-membered monocyclic non-aromatic heterocyclic group (e.g., oxetanyl), (3) a $C_{3-6}$ cycloalkyl group (e.g., cyclopropyl), or (4) a 3- to 8-membered monocyclic non-aromatic heterocyclic group (e.g., oxetanyl, tetrahydrofuryl).

$Y^3$ is particularly preferably $CR^{e'}$ wherein $R^{e'}$ is (1) a hydrogen atom, or (2) a $C_{1-6}$ alkyl group (e.g., methyl), or $NR^{g''}$ wherein $R^{g''}$ is (1) a $C_{1-6}$ alkyl group (e.g., methyl) optionally substituted by 1 to 5 substituents selected from (i) a halogen atom (e.g., a fluorine atom), and (ii) a hydroxy group, or (2) a $C_{3-6}$ cycloalkyl group (e.g., cyclopropyl).

Ring B is a 6-membered ring. The partial structure represented by the formula:

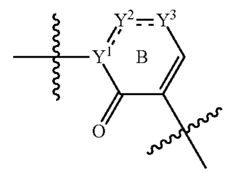

wherein each symbol is as defined above, is preferably a partial structure represented by the formula:

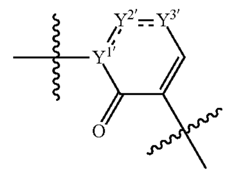

wherein $Y^{1'}$ is C or N, $Y^{2'}$ is $CR^{b'}$ wherein $R^{b'}$ is (1) a hydrogen atom, or (2) a $C_{1-6}$ alkyl group (e.g., methyl), or N, and $Y^{3'}$ is $CR^{e'}$ wherein $R^{e'}$ is (1) a hydrogen atom, or (2) a $C_{1-6}$ alkyl group (e.g., methyl), or $NR^{g'}$ wherein $R^{g'}$ is (1) absent, (2) a $C_{1-6}$ alkyl group (e.g., methyl, isobutyl) optionally substituted by 1 to 5 substituents selected from (i) a halogen atom (e.g., a fluorine atom), and (ii) a hydroxy group, or (3) a $C_{3-6}$ cycloalkyl group (e.g., cyclopropyl).

The partial structure is more preferably the following partial structures.

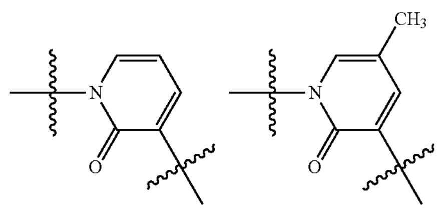

-continued

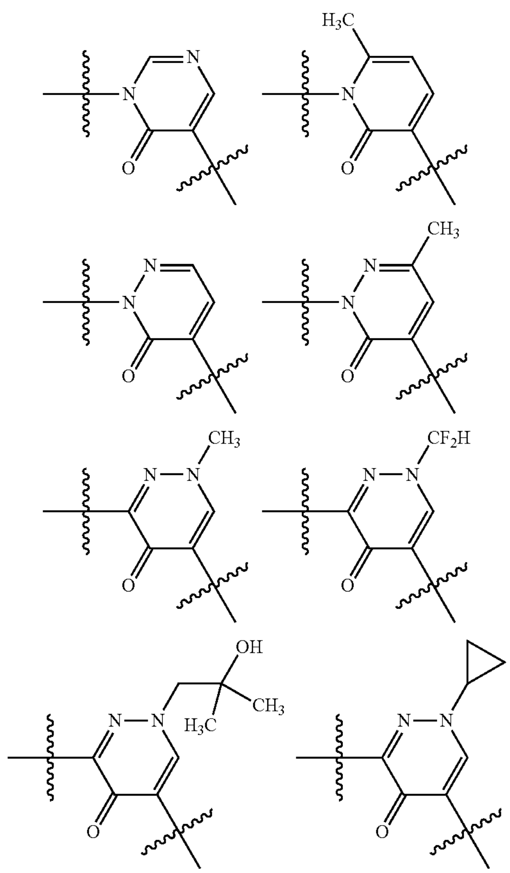

The above-mentioned partial structure is particularly preferably the following partial structures.

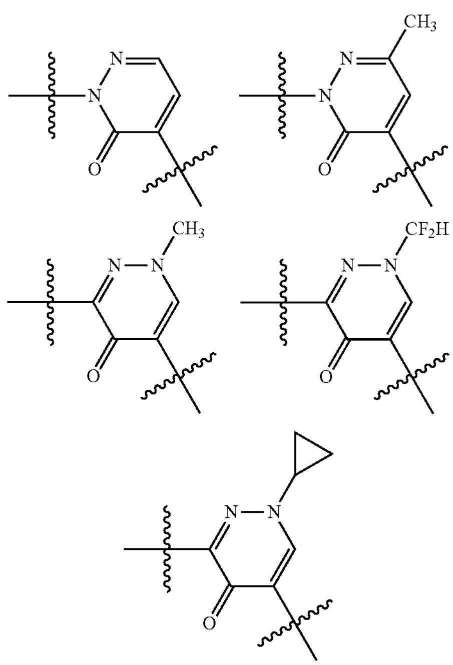

$R^2$ is

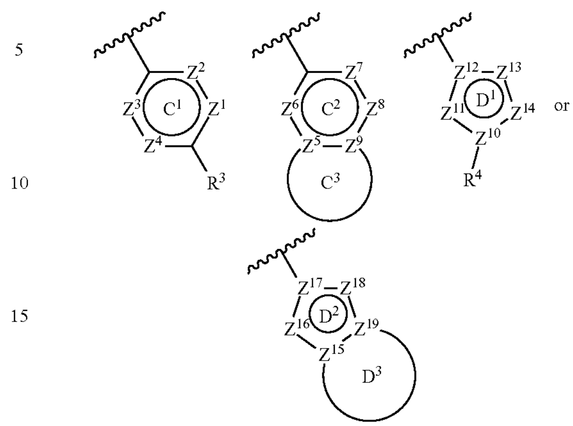

wherein $Z^1$ is $CR^h$ wherein $R^h$ is a hydrogen atom or a substituent, or N, $Z^2$ is $CR^i$ wherein $R^i$ is a hydrogen atom or a substituent, or N, $Z^3$ is $CR^j$ wherein $R^j$ is a hydrogen atom or a substituent, or N, $Z^4$ is $CR^k$ wherein $R^k$ is a hydrogen atom or a substituent, or N, $Z^5$ is C or N, $Z^6$ is $CR^l$ wherein $R^l$ is a hydrogen atom or a substituent, or N, $Z^7$ is $CR^m$ wherein $R^m$ is a hydrogen atom or a substituent, or N, $Z^8$ is $CR^n$ wherein $R^n$ is a hydrogen atom or a substituent, or N, $Z^9$ is C or N, $Z^{10}$ is C or N, $Z^{11}$ is $CR^o$ wherein $R^o$ is a hydrogen atom or a substituent, $NR^p$ wherein $R^p$ is absent, a hydrogen atom or a substituent, O or S, $Z^{12}$ is C or N, $Z^{13}$ is $CR^q$ wherein $R^q$ is a hydrogen atom or a substituent, $NR^r$ wherein $R^r$ is absent, a hydrogen atom or a substituent, O or S, $Z^{14}$ is $CR^s$ wherein $R^s$ is a hydrogen atom or a substituent, $NR^t$ wherein $R^t$ is absent, a hydrogen atom or a substituent, O or S, $Z^{15}$ is C or N, $Z^{16}$ is $CR^u$ wherein $R^u$ is a hydrogen atom or a substituent, $NR^v$ wherein $R^v$ is absent, a hydrogen atom or a substituent, C or S, $Z^{17}$ is C or N, $Z^{18}$ is $CR^w$ wherein $R^w$ is a hydrogen atom or a substituent, $NR^x$ wherein $R^x$ is absent, a hydrogen atom or a substituent, O or S, $Z^{19}$ is C or N, Ring $C^1$ and Ring $C^2$ are each independently a 6-membered aromatic ring, Ring $C^3$ is an optionally substituted ring, $R^3$ is a halogen atom, a cyano group, an optionally substituted $C_{1-6}$ alkyl group, an optionally substituted cyclic group, an optionally substituted amino group, $SO_2R^7$ or $OR^8$, $R^7$ is a substituent, $R^8$ is a hydrogen atom, an optionally substituted $C_{1-6}$ alkyl group, an optionally substituted saturated cyclic group, or an optionally substituted monocyclic unsaturated cyclic group, Ring $D^1$ and Ring $D^2$ are each independently a 5-membered aromatic ring, Ring $D^3$ is an optionally substituted ring, and $R^4$ is a substituent.

Examples of the substituent of the "optionally substituted ring" for Ring $C^3$ include those similar to Substituent Group A. The ring optionally has 1 to 3 substituents at substitutable positions.

Examples of the substituents of the "optionally substituted $C_{1-6}$ alkyl group" and "optionally substituted cyclic group" for $R^3$ include those similar to Substituent Group A. The groups optionally have 1 to 8 substituents at substitutable positions.

Examples of the substituents of the "optionally substituted $C_{1-6}$ alkyl group", "optionally substituted saturated cyclic group" and "optionally substituted monocyclic unsaturated cyclic group" for $R^8$ include those similar to Substituent Group A. The groups optionally have 1 to 5 substituents at substitutable positions.

Examples of the substituent of the "optionally substituted ring" for Ring $D^3$ include those similar to Substituent Group A. The ring optionally has 1 to 3 substituents at substitutable positions.

$R^2$ is preferably

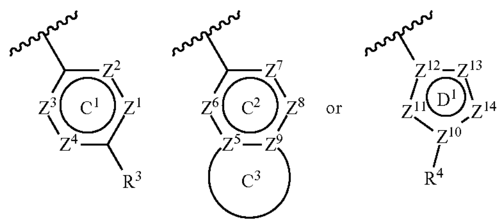

wherein each symbol is as defined above.

$R^2$ is more preferably a group represented by

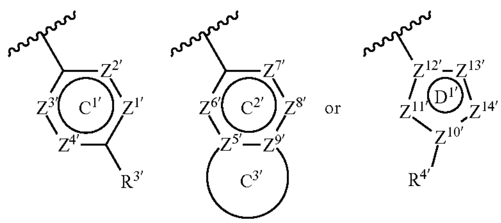

wherein $Z^{1'}$ is $CR^{h'}$ wherein $R^{h'}$ is a hydrogen atom, a halogen atom (e.g., a fluorine atom) or a $C_{1-6}$ alkyl group (e.g., methyl), or N, $Z^{2'}$ is $CR^{i'}$ wherein $R^{i'}$ is a hydrogen atom, a halogen atom (e.g., a fluorine atom, a chlorine atom), a cyano group, a $C_{1-6}$ alkyl group (e.g., methyl) or a $C_{1-6}$ alkoxy group (e.g., methoxy), or N, $Z^{3'}$ is $CR^{j'}$ wherein $R^{j'}$ is a hydrogen atom or a halogen atom (e.g., a fluorine atom), or N, $Z^{4'}$ is CH or N, $Z^{5'}$ is N, $Z^{6'}$ is CH, $Z^{7'}$ is CH, $Z^{8'}$ is CH, $Z^{9'}$ is C, $Z^{10'}$ is C or N, $Z^{11'}$ is CH, N or S, $Z^{12'}$ is C, $Z^{13'}$ is CH or N, $Z^{14'}$ is $CR^{s'}$ wherein $R^{s'}$ is a hydrogen atom or an optionally halogenated $C_{1-6}$ alkyl group (e.g., trifluoromethyl), N or O, Ring $C^{1'}$ is a 6-membered aromatic ring (e.g., a benzene ring, a pyridine ring, a pyrimidine ring, a pyridazine ring, a pyrazine ring), Ring $C^{2'}$ is a 6-membered aromatic ring (e.g., a pyridine ring), Ring $C^{3'}$ is a 5-membered ring (e.g., an imidazole ring), $R^{3'}$ is (1) a halogen atom (e.g., a fluorine atom, a chlorine atom), (2) a cyano group, (3) a $C_{1-6}$ alkyl group (e.g., methyl, ethyl, isopropyl, isobutyl) optionally substituted by 1 to 8 substituents selected from (i) a halogen atom (e.g., a fluorine atom), (ii) a cyano group, (iii) a hydroxy group, (iv) a $C_{3-6}$ cycloalkyl group (e.g., cyclopropyl), (v) an optionally halogenated $C_{1-6}$ alkoxy group (e.g., methoxy, ethoxy, 2,2,2-trifluoroethoxy), (vi) a 3- to 8-membered monocyclic non-aromatic heterocyclic group (e.g., morpholinyl, piperidinyl), and (vii) an oxo group, (4) a $C_{2-6}$ alkenyl group (e.g., propenyl), (5) a cyclic group (a $C_{3-6}$ cycloalkyl group (e.g., cyclopropyl, cyclobutyl), a 3- to 8-membered monocyclic non-aromatic heterocyclic group (e.g., oxetanyl, tetrahydrofuryl, morpholinyl)) optionally substituted by 1 to 3 hydroxy groups, or (6) $OR^{8'}$ wherein $R^{8'}$ is (a) a $C_{1-6}$ alkyl group (e.g., methyl, ethyl, propyl, isobutyl) optionally substituted by 1 to 3 substituents selected from (i) a halogen atom (e.g., a fluorine atom), (ii) a hydroxy group, and (iii) a $C_{3-6}$ cycloalkyl group (e.g., cyclopropyl), or (b) a $C_{6-10}$ aryl group (e.g., phenyl), Ring $D^{1'}$ is a 5-membered aromatic ring (e.g., a pyrazole ring, an isoxazole ring, a thiophene ring), and $R^{4'}$ is (1) a $C_{1-6}$ alkyl group (e.g., methyl, ethyl, propyl, isobutyl, tert-butyl) optionally substituted by 1 to 5 substituents selected from (i) a halogen atom (e.g., a fluorine atom), (ii) a $C_{3-6}$ cycloalkyl group (e.g., cyclopropyl) optionally substituted by 1 to 3 halogen atoms (e.g., a fluorine atom), and (iii) a 3- to 8-membered monocyclic non-aromatic heterocyclic group (e.g., oxetanyl) optionally substituted by 1 to 3 halogen atoms (e.g., a fluorine atom), (2) a $C_{3-6}$ cycloalkyl group (e.g., cyclopropyl), (3) a $C_{6-10}$ aryl group (e.g., phenyl) optionally substituted by 1 to 3 halogen atoms (e.g., a fluorine atom), (4) a $C_{1-6}$ alkoxy-carbonyl group (e.g., ethoxycarbonyl), or (5) a 3- to 8-membered monocyclic non-aromatic heterocyclic group (e.g., tetrahydropyranyl).

$R^2$ is particularly preferably a group represented by

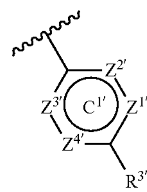

wherein $Z^{1'}$ is CH or N, $Z^{2'}$ is CH or CF, $Z^{3'}$ is CH, $Z^{4'}$ is CH, and $R^{3'}$ is a $C_{1-6}$ alkyl group (e.g., isopropyl) optionally substituted by 1 to 5 substituents selected from a halogen atom (e.g., a fluorine atom) and a hydroxy group.

Compound (I) is preferably the following compounds [Compound (I-1)]

Compound (I) wherein $X^1$ is C or N;

$X^2$ is C;

Ring A is a 5- or 6-membered aromatic ring (e.g., a pyrazole ring, a benzene ring, a pyridine ring, a pyridazine ring, a pyrimidine ring) optionally further having 1 to 3 substituents selected from (1) a halogen atom (e.g., a fluorine atom), and (2) a $C_{1-6}$ alkyl group (e.g., methyl), in addition to $R^1$ and the group represented by the formula:

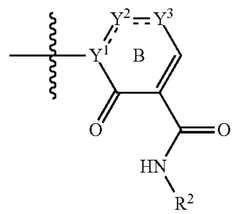

wherein each symbol is as defined above;

$R^1$ is (1) a cyano group, (2) a $C_{1-6}$ alkyl group substituted by 1 to 5 fluorine atoms (e.g., 3,3,3-trifluoropropyl), (3) a $C_{1-6}$ alkoxy group (e.g., methoxy, ethoxy, propoxy, isobutoxy) optionally substituted by 1 to 5 substituents selected from (i) a halogen atom (e.g., a fluorine atom), (ii) a hydroxy group, and (iii) a $C_{1-6}$ alkoxy group (e.g., methoxy), or (4) a 3- to 8-membered monocyclic non-aromatic heterocyclic group (e.g., morpholinyl, tetrahydropyranyl);

$Y^1$ is C or N;

$Y^2$ is $CR^{b'}$ wherein $R^{b'}$ is (1) a hydrogen atom, or (2) a $C_{1-6}$ alkyl group (e.g., methyl), or N;

$Y^3$ is $CR^{e'}$ wherein $R^{e'}$ is (1) a hydrogen atom, (2) a $C_{1-6}$ alkyl group (e.g., methyl, ethyl, isopropyl) optionally substituted by 1 to 5 hydroxy groups, (3) a $C_{1-6}$ alkyl-carbonyl group (e.g., acetyl), or (4) a $C_{1-6}$ alkoxy-carbonyl group (e.g., ethoxycarbonyl), or $NR^{g'}$ wherein $R^{g'}$ is (1) absent, (2) a $C_{1-6}$ alkyl group (e.g., methyl, ethyl, isobutyl) optionally substituted by 1 to 5 substituents selected from (i) a halogen atom (e.g., a fluorine atom), (ii) a hydroxy group, and (iii) a 3- to 8-membered monocyclic non-aromatic heterocyclic group (e.g., oxetanyl), (3) a $C_{3-6}$ cycloalkyl group (e.g., cyclopropyl), or (4) a 3- to 8-membered monocyclic non-aromatic heterocyclic group (e.g., oxetanyl, tetrahydrofuryl); and $R^2$ is a group represented by the formula:

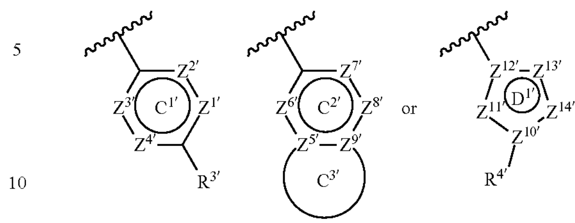

wherein $Z^{1'}$ is $CR^{h'}$ wherein $R^{h'}$ is a hydrogen atom, a halogen atom (e.g., a fluorine atom) or a $C_{1-6}$ alkyl group (e.g., methyl), or N, $Z^{2'}$ is $CR^{i'}$ wherein $R^{i'}$ is a hydrogen atom, a halogen atom (e.g., a fluorine atom, a chlorine atom), a cyano group, a $C_{1-6}$ alkyl group (e.g., methyl) or a $C_{1-6}$ alkoxy group (e.g., methoxy), or N, $Z^{3'}$ is $CR^{j'}$ wherein $R^{j'}$ is a hydrogen atom or a halogen atom (e.g., a fluorine atom), or N, $Z^{4'}$ is CH or N, $Z^{5'}$ is N, $Z^{6'}$ is CH, $Z^{7'}$ is CH, $Z^{8'}$ is CH, $Z^{9'}$ is C, $Z^{10'}$ is C or N, $Z^{11'}$ is CH, N or S, $Z^{12'}$ is C, $Z^{13'}$ is CH or N, $Z^{14'}$ is $CR^{s'}$ wherein $R^{s'}$ is a hydrogen atom or an optionally halogenated $C_{1-6}$ alkyl group (e.g., trifluoromethyl), N or O, Ring $C^{1'}$ is a 6-membered aromatic ring (e.g., a benzene ring, a pyridine ring, a pyrimidine ring, a pyridazine ring, a pyrazine ring), Ring $C^{2'}$ is a 6-membered aromatic ring (e.g., a pyridine ring), Ring $C^{3'}$ is a 5-membered ring (e.g., an imidazole ring), $R^{3'}$ is (1) a halogen atom (e.g., a fluorine atom, a chlorine atom), (2) a cyano group, (3) a $C_{1-6}$ alkyl group (e.g., methyl, ethyl, isopropyl, isobutyl) optionally substituted by 1 to 8 substituents selected from (i) a halogen atom (e.g., a fluorine atom), (ii) a cyano group, (iii) a hydroxy group, (iv) a $C_{3-6}$ cycloalkyl group (e.g., cyclopropyl), (v) an optionally halogenated $C_{1-6}$ alkoxy group (e.g., methoxy, ethoxy, 2,2,2-trifluoroethoxy), (vi) a 3- to 8-membered monocyclic non-aromatic heterocyclic group (e.g., morpholinyl, piperidinyl), and (vii) an oxo group, (4) a $C_{2-6}$ alkenyl group (e.g., propenyl), (5) a cyclic group (a $C_{3-6}$ cycloalkyl group (e.g., cyclopropyl, cyclobutyl), a 3- to 8-membered monocyclic non-aromatic heterocyclic group (e.g., oxetanyl, tetrahydrofuryl, morpholinyl)) optionally substituted by 1 to 3 hydroxy groups, or (6) $OR^{8'}$ wherein $R^{8'}$ is (a) a $C_{1-6}$ alkyl group (e.g., methyl, ethyl, propyl, isobutyl) optionally substituted by 1 to 3 substituents selected from (i) a halogen atom (e.g., a fluorine atom), (ii) a hydroxy group, and (iii) a $C_{3-6}$ cycloalkyl group (e.g., cyclopropyl), or (b) a $C_{6-10}$ aryl group (e.g., phenyl), Ring $D^{1'}$ is a 5-membered aromatic ring (e.g., a pyrazole ring, an isoxazole ring, a thiophene ring), and $R^{4'}$ is (1) a $C_{1-6}$ alkyl group (e.g., methyl, ethyl, propyl, isobutyl, tert-butyl) optionally substituted by 1 to 5 substituents selected from (i) a halogen atom (e.g., a fluorine atom), (ii) a $C_{3-6}$ cycloalkyl group (e.g., cyclopropyl) optionally substituted by 1 to 3 halogen atoms (e.g., a fluorine atom), and (iii) a 3- to 8-membered monocyclic non-aromatic heterocyclic group (e.g., oxetanyl) optionally substituted by 1 to 3 halogen atoms (e.g., a fluorine atom), (2) a $C_{3-6}$ cycloalkyl group (e.g., cyclopropyl), (3) a $C_{6-10}$ aryl group (e.g., phenyl) optionally substituted by 1 to 3 halogen atoms (e.g., a fluorine atom), (4) a $C_{1-6}$ alkoxy-carbonyl group (e.g., ethoxycarbonyl), or (5) a 3- to 8-membered monocyclic non-aromatic heterocyclic group (e.g., tetrahydropyranyl).

[Compound (I-2)]

Compound (I) wherein

Ring A is a 5- or 6-membered aromatic ring (e.g., a pyrazole ring, a benzene ring, a pyridine ring, a pyridazine ring, a pyrimidine ring) optionally further having 1 to 3 substituents selected from (1) a halogen atom (e.g., a fluorine atom), and (2) a $C_{1-6}$ alkyl group (e.g., methyl), in addition to $R^1$ and the group represented by the formula:

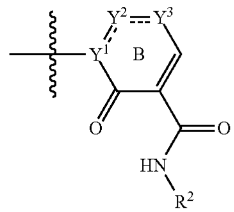

wherein each symbol is as defined above;

$R^1$ is (1) a cyano group, (2) a $C_{1-6}$ alkyl group substituted by 1 to 5 fluorine atoms (e.g., 3,3,3-trifluoropropyl), (3) a $C_{1-6}$ alkoxy group (e.g., methoxy, ethoxy, propoxy, isobutoxy) optionally substituted by 1 to 5 substituents selected from (i) a halogen atom (e.g., a fluorine atom), (ii) a hydroxy group, and (iii) a $C_{1-6}$ alkoxy group (e.g., methoxy), or (4) a 3- to 8-membered monocyclic non-aromatic heterocyclic group (e.g., morpholinyl, tetrahydropyranyl);

the partial structure represented by the formula:

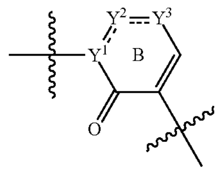

wherein each symbol is as defined above, is a partial structure represented by

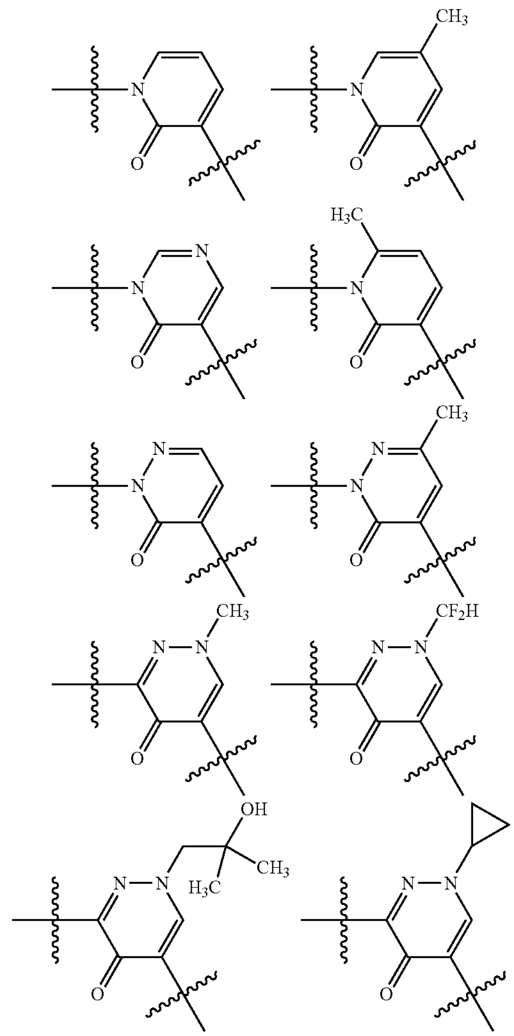

and $R^2$ is a group represented by the formula:

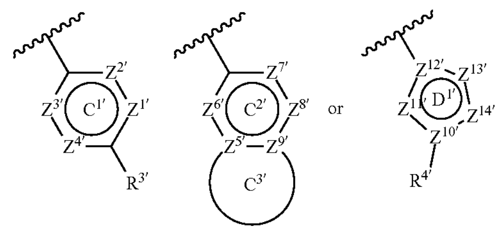

wherein $Z^{1'}$ is $CR^{h'}$ wherein $R^{h'}$ is a hydrogen atom, a halogen atom (e.g., a fluorine atom) or a $C_{1-6}$ alkyl group (e.g., methyl), or N, $Z^{2'}$ is $CR^{i'}$ wherein $R^{i'}$ is a hydrogen atom, a halogen atom (e.g., a fluorine atom, a chlorine atom), a cyano group, a $C_{1-6}$ alkyl group (e.g., methyl) or a $C_{1-6}$ alkoxy group (e.g., methoxy), or N, $Z^{3'}$ is $CR^{j'}$ wherein $R^{j'}$ is a hydrogen atom or a halogen atom (e.g., a fluorine atom), or N, $Z^{4'}$ is CH or N, $Z^{5'}$ is N, $Z^{6'}$ is CH, $Z^{7'}$ is CH, $Z^{8'}$ is CH, $Z^{9'}$ is C, $Z^{10'}$ is C or N, $Z^{11'}$ is CH or N, $Z^{12'}$ is C, $Z^{13'}$ is CH or N, $Z^{14'}$ is $CR^{s'}$ wherein $R^{s'}$ is a hydrogen atom or an optionally halogenated $C_{1-6}$ alkyl group (e.g., trifluoromethyl), N or O, Ring $C^{1'}$ is a 6-membered aromatic ring (e.g., a benzene ring, a pyridine ring, a pyrimidine ring, a pyridazine ring, a pyrazine ring), Ring $C^{2'}$ is a 6-membered aromatic ring (e.g., a pyridine ring), Ring $C^{3'}$ is a 5-membered ring (e.g., an imidazole ring), $R^{3'}$ is (1) a halogen atom (e.g., a fluorine atom, a chlorine atom), (2) a cyano group, (3) a $C_{1-6}$ alkyl group (e.g., methyl, ethyl, isopropyl, isobutyl) optionally substituted by 1 to 8 substituents selected from (i) a halogen atom (e.g., a fluorine atom), (ii) a cyano group, (iii) a hydroxy group, (iv) a $C_{3-6}$ cycloalkyl group (e.g., cyclopropyl), (v) an optionally halogenated $C_{1-6}$ alkoxy group (e.g., methoxy, 2,2,2-trifluoroethoxy), (vi) a 3- to 8-membered monocyclic non-aromatic heterocyclic group (e.g., morpholinyl, piperidinyl), and (vii) an oxo group, (4) a cyclic group (a $C_{3-6}$ cycloalkyl group (e.g., cyclopropyl, cyclobutyl), a 3- to 8-membered monocyclic non-aromatic heterocyclic group (e.g., oxetanyl, tetrahydrofuryl, morpholinyl)) optionally substituted by 1 to 3 hydroxy groups, or (5) $OR^{8'}$ wherein $R^{8'}$ is (a) a $C_{1-6}$ alkyl group (e.g., methyl, ethyl, propyl, isobutyl) optionally substituted by 1 to 3 substituents selected from (i) a halogen atom (e.g., a fluorine atom), (ii) a hydroxy group, and (iii) a $C_{3-6}$ cycloalkyl group (e.g., cyclopropyl), or (b) a $C_{6-10}$ aryl group (e.g., phenyl), Ring $D^{1'}$ is a 5-membered aromatic ring (e.g., a pyrazole ring, an isoxazole ring), and $R^{4'}$ is (1) a $C_{1-6}$ alkyl group (e.g., methyl, ethyl, propyl, isobutyl, tert-butyl) optionally substituted by 1 to 5 substituents selected from (i) a halogen atom (e.g., a fluorine atom), (ii) a $C_{3-6}$ cycloalkyl group (e.g., cyclopropyl) optionally substituted by 1 to 3 halogen atoms (e.g., a fluorine atom), and (iii) a 3- to 8-membered monocyclic non-aromatic heterocyclic group (e.g., oxetanyl) optionally substituted by 1 to 3 halogen atoms (e.g., a fluorine atom), (2) a $C_{3-6}$ cycloalkyl group (e.g., cyclopropyl), (3) a $C_{6-10}$ aryl group (e.g., phenyl) optionally substituted by 1 to 3 halogen atoms (e.g., a fluorine atom), or (4) a 3- to 8-membered monocyclic non-aromatic heterocyclic group (e.g., tetrahydropyranyl).

[Compound (I-3)]

Compound (I) wherein $X^1$ is C;

$X^2$ is C;

Ring A is a benzene ring optionally further having 1 to 3 halogen atoms (e.g., a fluorine atom), in addition to $R^1$ and the group represented by the formula:

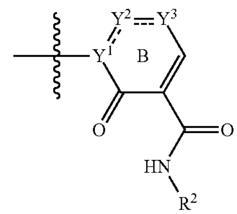

wherein each symbol is as defined above;

$R^1$ is a $C_{1-6}$ alkoxy group (e.g., ethoxy) substituted by 1 to 5 halogen atoms (e.g., a fluorine atom);

$Y^1$ is C or N;

$Y^2$ is N;

$Y^3$ is $CR^{e'}$ wherein $R^{e'}$ is (1) a hydrogen atom, or (2) a $C_{1-6}$ alkyl group (e.g., methyl), or $NR^{g''}$ wherein $R^{g''}$ is (1) a $C_{1-6}$ alkyl group (e.g., methyl) optionally substituted by 1 to 5 substituents selected from (i) a halogen atom (e.g., a fluorine atom), and (ii) a hydroxy group, or (2) a $C_{3-6}$ cycloalkyl group (e.g., cyclopropyl); and $R^2$ is a group represented by the formula:

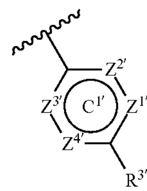

wherein $Z^{1'}$ is CH or N, $Z^{2'}$ is CH or CF, $Z^{3'}$ is CH, $Z^{4'}$ is CH, and $R^{3'}$ is a $C_{1-6}$ alkyl group (e.g., isopropyl) optionally substituted by 1 to 5 substituents selected from a halogen atom (e.g., a fluorine atom) and a hydroxy group.

[Compound (I-4)]

Compound (I) wherein

Ring A is a benzene ring having no additional substituent other than $R^1$ and the group represented by the formula:

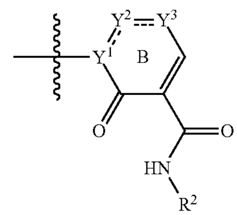

wherein each symbol is as defined above;

$R^1$ is a $C_{1-6}$ alkoxy group (e.g., methoxy, ethoxy, propoxy, isobutoxy) substituted by 1 to 5 halogen atoms (e.g., a fluorine atom);

the partial structure represented by the formula:

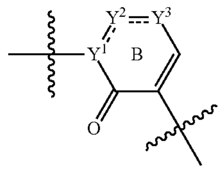

wherein each symbol is as defined above,
is

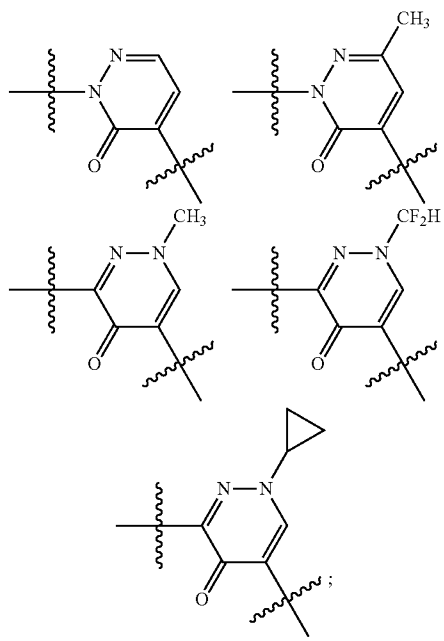

and
$R^2$ is a group represented by the formula:

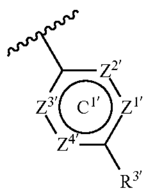

wherein
$Z^{1'}$ is CH or N,
$Z^{2'}$ is CH or CF,
$Z^{3'}$ is CH,
$Z^{4'}$ is CH, and
$R^{3'}$ is a $C_{1-6}$ alkyl group (e.g., isopropyl) optionally substituted by 1 to 5 substituents selected from a halogen atom (e.g., a fluorine atom) and a hydroxy group.

Specific examples of compound (I) include the compounds of Examples 1 to 203.

Among them, compound (I) is preferably

2-[4-fluoro-2-(2,2,2-trifluoroethoxy)phenyl]-N-[4-(2-hydroxypropan-2-yl)phenyl]-3-oxo-2,3-dihydropyridazine-4-carboxamide (Example 95) or a salt thereof, 2-[2-(2,2-difluoroethoxy)phenyl]-6-methyl-3-oxo-N-[6-(1,1,3,3-tetrafluoro-2-hydroxypropan-2-yl)pyridin-3-yl]-2,3-dihydropyridazine-4-carboxamide (Example 109) or a salt thereof, N-[4-(2-hydroxypropan-2-yl)phenyl]-3-oxo-2-[2-(2,2,2-trifluoroethoxy)phenyl]-2,3-dihydropyridazine-4-carboxamide (Example 127) or a salt thereof, 2-[2-(2,2-difluoroethoxy)phenyl]-N-[4-(2-hydroxypropan-2-yl)phenyl]-3-oxo-2,3-dihydropyridazine-4-carboxamide (Example 133) or a salt thereof, 2-[2-(2,2-difluoroethoxy)phenyl]-N-[6-(2-hydroxypropan-2-yl)pyridin-3-yl]-6-methyl-3-oxo-2,3-dihydropyridazine-4-carboxamide (Example 135) or a salt thereof, 2-[2-(2,2-difluoroethoxy)phenyl]-N-[4-(2-hydroxypropan-2-yl)phenyl]-6-methyl-3-oxo-2,3-dihydropyridazine-4-carboxamide (Example 136) or a salt thereof, 2-[2-(2,2-difluoroethoxy)phenyl]-N-[2-fluoro-4-(2-hydroxypropan-2-yl)phenyl]-6-methyl-3-oxo-2,3-dihydropyridazine-4-carboxamide (Example 146) or a salt thereof, N-[2-fluoro-4-(2-hydroxypropan-2-yl)phenyl]-3-oxo-2-[2-(2,2,2-trifluoroethoxy)phenyl]-2,3-dihydropyridazine-4-carboxamide (Example 148) or a salt thereof, 2-[2-(2,2-difluoroethoxy)phenyl]-6-methyl-3-oxo-N-[4-(1,1,3,3-tetrafluoro-2-hydroxypropan-2-yl)phenyl]-2,3-dihydropyridazine-4-carboxamide (Example 152) or a salt thereof, 6-[2-(2,2-difluoroethoxy)phenyl]-N-[4-(2-hydroxypropan-2-yl)phenyl]-2-methyl-5-oxo-2,5-dihydropyridazine-4-carboxamide (Example 158) or a salt thereof, 6-[2-(2,2-difluoroethoxy)phenyl]-2-(difluoromethyl)-N-[4-(2-hydroxypropan-2-yl)phenyl]-5-oxo-2,5-dihydropyridazine-4-carboxamide (Example 161) or a salt thereof, 3-oxo-N-[6-(1,1,3,3-tetrafluoro-2-hydroxypropan-2-yl)pyridin-3-yl]-2-[2-(2,2,2-trifluoroethoxy)phenyl]-2,3-dihydropyridazine-4-carboxamide (Example 162) or a salt thereof, 6-[2-(2,2-difluoroethoxy)phenyl]-2-(difluoromethyl)-5-oxo-N-[4-(1,1,3,3-tetrafluoro-2-hydroxypropan-2-yl)phenyl]-2,5-dihydropyridazine-4-carboxamide (Example 163) or a salt thereof, 2-cyclopropyl-6-[2-(2,2-difluoroethoxy)phenyl]-N-[4-(2-hydroxypropan-2-yl)phenyl]-5-oxo-2,5-dihydropyridazine-4-carboxamide (Example 169) or a salt thereof, or 6-[2-(2,2-difluoroethoxy)phenyl]-2-(difluoromethyl)-5-oxo-N-[6-(1,1,3,3-tetrafluoro-2-hydroxypropan-2-yl)pyridin-3-yl]-2,5-dihydropyridazine-4-carboxamide (Example 177) or a salt thereof.

Compound (I) is particularly preferably

N-[4-(2-hydroxypropan-2-yl)phenyl]-3-oxo-2-[2-(2,2,2-trifluoroethoxy)phenyl]-2,3-dihydropyridazine-4-carboxamide (Example 127) or a salt thereof, 2-[2-(2,2-difluoroethoxy)phenyl]-N-[4-(2-hydroxypropan-2-yl)phenyl]-3-oxo-2,3-dihydropyridazine-4-carboxamide (Example 133) or a salt thereof, or 2-[2-(2,2-difluoroethoxy)phenyl]-N-[4-(2-hydroxypropan-2-yl)phenyl]-6-methyl-3-oxo-2,3-dihydropyridazine-4-carboxamide (Example 136) or a salt thereof.

When compound (I) is a salt, examples of the salt include metal salts, ammonium salts, salts with organic base, salts with inorganic acid, salts with organic acid, and salts with basic or acidic amino acid. Preferable examples of the metal salt include alkali metal salts such as sodium salts, potassium salts and the like; alkali earth metal salts such as calcium salts, magnesium salts, barium salts and the like; and aluminum salts. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salts with basic amino acid include salts with arginine, lysine, ornithine and the like. Preferable examples of the salt with acidic amino acid include salts with aspartic acid, glutamic acid and the like. Among them, a pharmaceutically acceptable salt is preferable. For example, when a compound has an acidic functional group, examples of the salt include inorganic salts such as alkali metal salts (e.g., sodium salt, potassium salt etc.), alkaline earth metal salts (e.g., calcium salt, magnesium salt, barium salt etc.) and the like, ammonium salt etc., and when a compound has a basic functional group, examples of the salt include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, so methanesulfonic acid, p-toluenesulfonic acid and the like.

When compound (I) contains isomers such as tautomers, optical isomers, stereoisomers, position isomers and rotational isomers, any of isomers or mixture are also encompassed in the compound of the present invention. Further, when compound (I) contains an optical isomer, the optical isomer separated from the racemate is encompassed in compound (I).

Compound (I) can be obtained in the crystal form. Either single crystalline form or crystalline mixture can be encompassed in compound (I).

Compound (I) can be a pharmaceutically acceptable co-crystal or a co-crystal salt. The co-crystal or co-crystal salt as used herein means a crystalline material composed of two or more unique solids at room temperature, each of which has distinctive physical characteristics such as structure, melting point, and heats of fusion, hygroscopicity, solubility, and stability. A co-crystal or a co-crystal salt can be produced according to co-crystallization method known per se.

Compound (I) may be a solvate (e.g., a hydrate) or a non-solvate and both are encompassed in compound (I).

Compounds labeled with or substituted by isotopes (e.g., $^{2}H$, $^{3}H$, $^{11}C$, $^{14}C$, $^{18}F$, $^{35}S$, $^{125}I$, etc.) are also encompassed in compound (I). The compound labeled with or substituted by isotopes can be used as, for example, a tracer used for Positron Emission Tomography (PET) (PET tracer), and are expected to be useful in the field of medical diagnosis and the like.

The production method of the compound of the present invention is explained below.

The raw material compound and reagent used and the compound obtained in each step in the following production method may be each in a form of a salt, and examples of such salt include those similar to the salts of the compound of the present invention and the like.

When the compound obtained in each step is a free form, it can be converted to the objective salt according to a method known per se. When the compound obtained in each step is a salt, it can be converted to the objective free form or the other salt according to a method known per se.

The compound obtained in each step can be used directly as the reaction mixture or as a crude product for the next reaction. Alternatively, the compound obtained in each step can be isolated and purified from a reaction mixture according to a method known per se, for example, a separation means such as concentration, crystallization, recrystallization, distillation, solvent extraction, fractional distillation, column chromatography and the like.

When the raw material compound and reagent used in each step are commercially available, the commercially available product can also be used directly.

In the reaction in each step, while the reaction time varies depending on the kind of the reagent and solvent to be used, it is generally 1 min-48 hr, preferably 10 min-8 hr, unless otherwise specified.

In the reaction in each step, while the reaction temperature varies depending on the kind of the reagent and solvent to be used, it is generally −78° C.-300° C., preferably −78° C.-150° C., unless otherwise specified.

In the reaction in each step, while the pressure varies depending on the kind of the reagent and solvent to be used, it is generally 1 atm-20 atm, preferably 1 atm-3 atm, unless otherwise specified.

Microwave synthesizer such as Initiator manufactured by Biotage and the like may be used for the reaction in each step. While the reaction temperature varies depending on the kind of the reagent and solvent to be used, it is generally room temperature −300° C., preferably 50° C.-250° C., unless otherwise specified. While the reaction time varies depending on the kind of the reagent and solvent to be used, it is generally 1 min-48 hr, preferably 1 min-8 hr, unless otherwise specified.

In the reaction in each step, the reagent is used in an amount of 0.5 equivalents-20 equivalents, preferably 0.8 equivalents-5 equivalents, relative to the substrate, unless otherwise specified. When the reagent is used as a catalyst, the reagent is used in an amount of 0.001 equivalent-1 equivalent, preferably 0.01 equivalent-0.2 equivalent, relative to the substrate. When the reagent is used as a reaction solvent, the reagent is used in a solvent amount.

Unless otherwise specified, the reaction in each step is carried out without solvent, or by dissolving or suspending the raw material compound in a suitable solvent. Examples of the solvent include those described in Examples and the following solvents.

alcohols: methanol, ethanol, tert-butyl alcohol, 2-methoxyethanol and the like;

ethers: diethyl ether, diphenyl ether, tetrahydrofuran, 1,2-dimethoxyethane and the like;

aromatic hydrocarbons: chlorobenzene, toluene, xylene and the like;

saturated hydrocarbons: cyclohexane, hexane and the like;

amides: N,N-dimethylformamide, N-methylpyrrolidone and the like;

halogenated hydrocarbons: dichloromethane, carbon tetrachloride and the like;

nitriles: acetonitrile and the like;

sulfoxides: dimethyl sulfoxide and the like;

aromatic organic bases: pyridine and the like;

anhydrides: acetic anhydride and the like;

organic acids: formic acid, acetic acid, trifluoroacetic acid and the like;

inorganic acids: hydrochloric acid, sulfuric acid and the like;

esters: ethyl acetate and the like;

ketones: acetone, methyl ethyl ketone and the like;

water.

The above-mentioned solvent can be used in a mixture of two or more kinds thereof in an appropriate ratio.

When a base is used for the reaction in each step, examples thereof include those described in Examples and the following bases.

inorganic bases: sodium hydroxide, magnesium hydroxide, sodium carbonate, calcium carbonate, sodium hydrogen carbonate and the like;

organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;

metal alkoxides: sodium ethoxide, potassium tert-butoxide and the like;

alkali metal hydrides: sodium hydride and the like;

metal amides: sodium amide, lithium diisopropylamide, lithium hexamethyldisilazide and the like;

organic lithiums: n-butyllithium and the like.

When an acid or an acid catalyst is used for the reaction in each step, examples thereof include those described in Examples and the following acids and acid catalysts.

inorganic acids: hydrochloric acid, sulfuric acid, nitric acid, hydrobromic acid, phosphoric acid and the like;

organic acids: acetic acid, trifluoroacetic acid, citric acid, p-toluenesulfonic acid, 10-camphorsulfonic acid and the like;

Lewis acid: boron trifluoride diethyl ether complex, zinc iodide, anhydrous aluminum chloride, anhydrous zinc chloride, anhydrous iron chloride and the like.

Unless otherwise specified, the reaction in each step is carried out according to a method known per se, for example, the method described in Jikken Kagaku Kouza, 5th Edition, vol. 13-19 (the Chemical Society of Japan ed.); Shin Jikken Kagaku Kouza, vol. 14-15 (the Chemical Society of Japan ed.); Fine Organic Chemistry, Revised 2nd Edition (L. F. Tietze, Th. Eicher, Nankodo); Organic Name Reactions, the Reaction Mechanism and Essence, Revised Edition (Hideo Togo, Kodansha); ORGANIC SYNTHESES Collective Volume I-VII (John Wiley & Sons Inc.); Modern Organic Synthesis in the Laboratory A Collection of Standard Experimental Procedures (Jie Jack Li, OXFORD UNIVERSITY); Comprehensive Heterocyclic Chemistry III, Vol. 1-Vol. 14 (Elsevier Japan); Strategic Applications of Named Reactions in Organic Synthesis (translated by Kiyoshi Tomioka, Kagakudojin); Comprehensive Organic Transformations (VCH Publishers Inc.), 1989, or the like, or the method described in Examples.

In each step, the protection or deprotection reaction of a functional group is carried out according to a method known per se, for example, the method described in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski), or the like, or the method described in Examples.

Examples of the protecting group for a hydroxy group of an alcohol and the like and a phenolic hydroxy group include ether-type protecting groups such as methoxymethyl ether, benzyl ether, tert-butyldimethylsilyl ether, tetrahydropyranyl ether and the like; carboxylate ester-type protecting groups such as acetate ester and the like; sulfonate ester-type protecting groups such as methanesulfonate ester and the like; carbonate ester-type protecting groups such as tert-butylcarbonate and the like, and the like.

Examples of the protecting group for a carbonyl group of an aldehyde include acetal-type protecting groups such as dimethylacetal and the like; cyclic acetal-type protecting groups such as 1,3-dioxane and the like, and the like.

Examples of the protecting group for a carbonyl group of a ketone include ketal-type protecting groups such as dimethylketal and the like; cyclic ketal-type protecting groups such as 1,3-dioxane and the like; oxime-type protecting groups such as O-methyloxime and the like; hydrazone-type protecting groups such as N,N-dimethylhydrazone and the like, and the like.

Examples of the protecting group for a carboxyl group include ester-type protecting groups such as methyl ester and the like; amide-type protecting groups such as N,N-dimethylamide and the like, and the like.

Examples of the protecting group for a thiol include ether-type protecting groups such as benzyl thioether and the like; ester-type protecting groups such as thioacetate ester, thiocarbonate, thiocarbamate and the like, and the like.

Examples of the protecting group for an amino group and an aromatic heterocycle such as imidazole, pyrrole, indole and the like include carbamate-type protecting groups such as benzyl carbamate and the like; amide-type protecting groups such as acetamide and the like; alkyl amine-type protecting groups such as N-triphenylmethylamine and the like; sulfonamide-type protecting groups such as methanesulfonamide and the like, and the like.

The protecting groups can be removed according to a method known per se, for example, by employing a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like.

When reduction reaction is carried out in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When carbon-carbon double bond or triple bond is reduced, a method using a catalyst such as palladium-carbon, Lindlar's catalyst and the like may be employed.

When oxidation reaction is carried out in each step, examples of the oxidizing agent to be used include peroxides such as m-chloroperbenzoic acid (mCPBA), hydrogen peroxide, tert-butylhydroperoxide and the like; perchlorates such as tetrabutylammonium perchlorate and the like; chlorates such as sodium chlorate and the like; chlorites such as sodium chlorite and the like; periodates such as sodium periodate and the like; hypervalent iodine reagents such as iodosylbenzene and the like; reagents containing manganese such as manganese dioxide, potassium permanganate and the like; leads such as lead tetraacetate and the like; reagents containing chromium such as pyridinium chlorochromate (PCC), pyridinium dichromate (PDC), Jones reagent and the like; halogen compounds such as N-bromosuccinimide (NBS) and the like; oxygen; ozone; sulfur trioxide-pyridine complex; osmium tetroxide; selenium dioxide; 2,3-dichloro-5,6-dicyano-1,4-benzoquinone (DDQ) and the like.

When radical cyclization reaction is carried out in each step, examples of the radical initiator to be used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide and the like. Examples of the radical reagent to be used include tributylstannane, tristrimethylsilylsilane, 1,1,2,2-tetraphenyldisilane, diphenylsilane, samarium iodide and the like.

When Wittig reaction is carried out in each step, examples of the Wittig reagent to be used include alkylidene phosphoranes and the like. The alkylidene phosphoranes can be prepared according to a method known per se, for example, by reacting a phosphonium salt with a strong base.

When Horner-Emmons reaction is carried out in each step, examples of the reagent to be used include phosphonoacetates such as methyl dimethylphosphonoacetate, ethyl diethylphosphonoacetate and the like; and bases such as alkali metal hydrides, organic lithiums and the like.

When Friedel-Crafts reaction is carried out in each step, a combination of a Lewis acid and an acid chloride or a combination of a Lewis acid and an alkylating agent (e.g., an alkyl halide, an alcohol, an olefin etc.) is used as a reagent. Alternatively, an organic acid or an inorganic acid can also be used instead of a Lewis acid, and an anhydride such as acetic anhydride and the like can also be used instead of an acid chloride.

When aromatic nucleophilic substitution reaction is carried out in each step, a nucleophile (e.g., an amine, imidazole etc.) and a base (e.g., an organic base etc.) are used as a reagent.

When nucleophilic addition reaction by a carbo anion, nucleophilic 1,4-addition reaction (Michael addition reaction) by a carbo anion or nucleophilic substitution reaction by a carbo anion is carried out in each step, and examples of the base to be used for generation of the carbo anion include organic lithiums, metal alkoxides, inorganic bases, organic bases and the like.

When Grignard reaction is carried out in each step, examples of the Grignard reagent to be used include arylmagnesium halides such as phenylmagnesium bromide and the like; and alkylmagnesium halides such as methylmagnesium bromide and the like. The Grignard reagent can be prepared according to a method known per se, for example, by reacting an alkyl halide or an aryl halide with a metal magnesium in an ether or tetrahydrofuran as a solvent.

When Knoevenagel condensation reaction is carried out in each step, a compound having an activated methylene group with two electron withdrawing groups (e.g., malonic acid, diethyl malonate, malononitrile etc.) and a base (e.g., an organic base, a metal alkoxide, an inorganic base) are used as a reagent.

When Vilsmeier-Haack reaction is carried out in each step, phosphoryl chloride and an amide derivative (e.g., N,N-dimethylformamide etc.) are used as a reagent.

When azidation reaction of an alcohol, an alkyl halide or a sulfonate is carried out in each step, examples of the azidating agent to be used include diphenylphosphorylazide (DPPA), trimethylsilylazide, sodium azide and the like. For example, for the azidation reaction of an alcohol, a method using diphenylphosphorylazide and 1,8-diazabicyclo[5.4.0]undec-7-ene (DBU), a method using trimethylsilylazide and a Lewis acid, and the like are employed.

When reductive amination reaction is carried out in each step, examples of the reducing agent to be used include sodium triacetoxyborohydride, sodium cyanoborohydride, hydrogen, formic acid and the like. When the substrate is an amine compound, examples of the carbonyl compound to be used include paraformaldehyde, aldehydes such as acetaldehyde and the like, and ketones such as cyclohexanone and the like. When the substrate is a carbonyl compound, examples of the amine to be used include ammonia, primary amines such as methylamine and the like; secondary amines such as dimethylamine and the like, and the like.

When Mitsunobu reaction is carried out in each step, an azodicarboxylate (e.g., diethyl azodicarboxylate (DEAD), diisopropyl azodicarboxylate (DIAD) etc.) and triphenylphosphine are used as a reagent.

When esterification reaction, amidation reaction or urea formation reaction is carried out in each step, examples of the reagent to be used include acyl halides such as acid chlorides, acid bromides and the like; activated carboxylic acids such as anhydrides, activated esters, sulfates and the like. Examples of the activating agent of the carboxylic acid include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride n-hydrate (DMT-MM) and the like; carbonate condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphorate (HATU); sulfuric acid; combinations thereof and the like. When carbodiimide condensing agent is used, an additive such as 1-hydroxybenzotriazole (HOBt), N-hydroxysuccinimide (HOSu), dimethylaminopyridine (DMAP) and the like may be added to the reaction system.

When coupling reaction is carried out in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocenepalladium(II) chloride and the like; nickel compounds such as tetrakis(triphenylphosphine)nickel(0) and the like; rhodium compounds such as tris(triphenylphosphine)rhodium(III) chloride and the like; cobalt compounds; copper compounds such as copper oxide, copper(I) iodide and the like; platinum compounds and the like. In addition, a base can be added to the reaction system, and examples thereof include inorganic bases and the like.

When thiocarbonylation reaction is carried out in each step, phosphorus pentasulfide is typically used as the thiocarbonylating agent. Alternatively, a reagent having a 1,3,2,4-dithiadiphosphetane-2,4-disulfide structure (e.g., 2,4-bis(4-methoxyphenyl)-1,3,2,4-dithiadiphosphetane-2,4-disulfide (Lawesson reagent) etc.) can also be used instead of phosphorus pentasulfide.

When halogenation reaction is carried out in each step, examples of the halogenating agent to be used include N-iodosuccinimide, N-bromosuccinimide (NBS), N-chlorosuccinimide (NCS), bromine, sulfuryl chloride and the like. In addition, the reaction can be accelerated by subjecting a radical initiator such as heat, light, benzoyl peroxide, azobisisobutyronitrile and the like to the reaction system reaction.

When halogenation reaction of a hydroxy group is carried out in each step, examples of the halogenating agent to be used include hydrohalic acids and acid halides of inorganic acids, specifically, hydrochloric acid, thionyl chloride, phosphorus oxychloride and the like for chlorination, 48% hydrobromic acid and the like for bromination. In addition, a method of producing an alkyl halide by reacting an alcohol with triphenylphosphine and carbon tetrachloride or carbon tetrabromide or the like can be employed. Alternatively, a method of producing an alkyl halide via two steps comprising converting an alcohol to the corresponding sulfonate, and then reacting the sulfonate with lithium bromide, lithium chloride or sodium iodide can also be employed.

When Arbuzov reaction is carried out in each step, examples of the reagent to be used include alkyl halides such as ethyl bromoacetate and the like; and phosphites such as triethyl phosphite, tri(isopropyl) phosphite and the like.

When sulfonate esterification reaction is carried out in each step, examples of the sulfonating agent to be used include methanesulfonyl chloride, p-toluenesulfonyl chloride, methanesulfonic anhydride, p-toluenesulfonic anhydride and the like.

When hydrolysis reaction is carried out in each step, an acid, a base or a tin reagent such as bis(tributyltin) oxide and the like is used as a reagent. For acid hydrolysis reaction of tert-butyl ester, formic acid, triethylsilane and the like may be added to reductively-trap tert-butyl cation which is by-produced.

When dehydration reaction is carried out in each step, examples of the dehydrating agent to be used include sulfuric acid, diphosphorus pentaoxide, phosphorus oxychloride, N,N'-dicyclohexylcarbodiimide, alumina, polyphosphoric acid and the like.

When alkylation reaction is carried out in each step, a combination of an electrophile (e.g., an alkyl halide etc.) and a base (e.g., an organic base, an inorganic base, a metal alkoxide, a metal amide etc.) is used as a reagent.

Compound (I) can be synthesized according to the following Production Methods A to K or a method analogous thereto. Each symbol in the formulas of the schemes is as defined above, unless otherwise specified. HAL is a halogen atom (e.g., a chlorine atom, a bromine atom, an iodine atom). $R^9$ is an optionally substituted $C_{1-6}$ alkyl group (e.g., methyl, ethyl) or a $C_{7-16}$ aralkyl group (e.g., benzyl). $R^{10}$ is a hydrogen atom or a substituent. $R^{11}$ is an optionally substituted $C_{1-6}$ alkyl group. $R^{g''}$ is a hydrogen atom or a substituent.

Moreover, when desired, compound (I) can be synthesized by performing deprotection reaction, amidation reaction, urea formation, alkylation reaction, Mitsunobu reaction, oxidation reaction, reduction reaction, halogenation reaction, coupling reaction, nucleophilic addition reaction by a carbo anion, Grignard reaction, dehydration reaction and the like singly or two or more thereof in combination.

Production Method A

Among compound (I), the following compound (Ia) can be produced according to the following method.

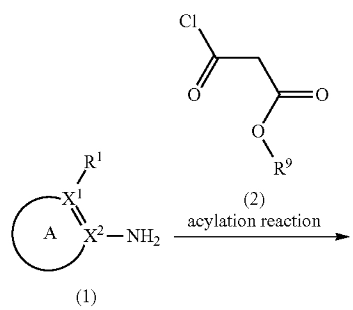

(2)

(1)

-continued

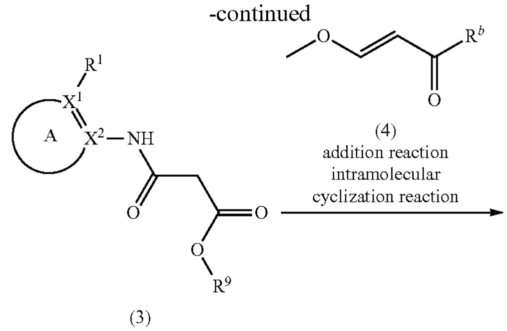

(4)

(3)

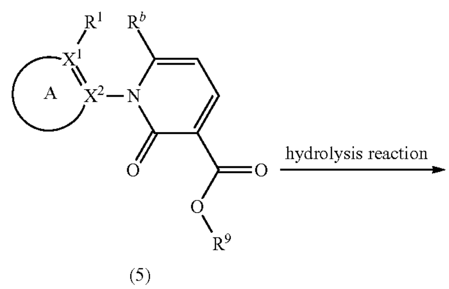

(5)

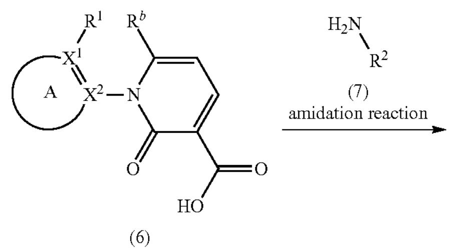

(7)

(6)

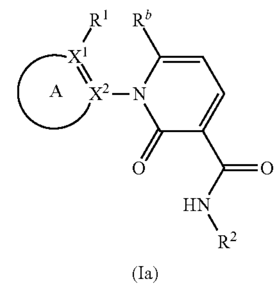

(Ia)

wherein the symbols are as defined above.

Compound (3) can be produced by subjecting compound (1) to an acylation reaction with compound (2).

Compound (5) can be produced by subjecting compound (3) to an addition reaction with compound (4), followed by an intramolecular cyclization reaction.

Compound (6) can be produced by subjecting compound (5) to a hydrolysis reaction.

Compound (Ia) can be produced by subjecting compound (6) to an amidation reaction with compound (7).

Production Method B

Among compound (I), the following compound (Ib) can be produced according to the following method.

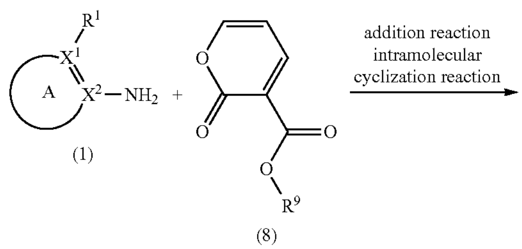

(1) (8)

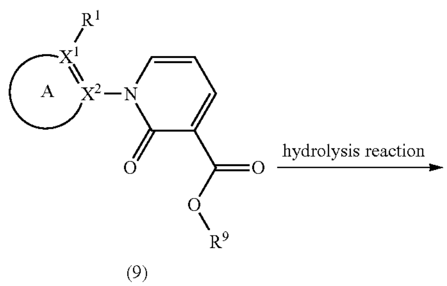

(9)

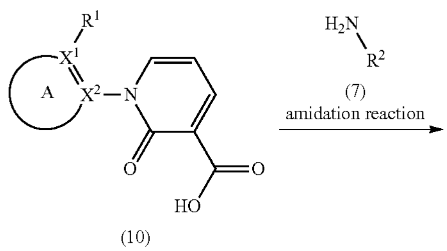

(10)

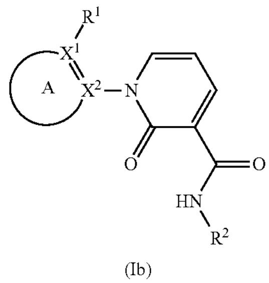

(Ib)

wherein the symbols are as defined above.

Compound (9) can be produced by subjecting compound (1) to an addition reaction with compound (8), followed by an intramolecular cyclization reaction.

Compound (10) can be produced by subjecting compound (9) to a hydrolysis reaction.

Compound (Ib) can be produced by subjecting compound (10) to an amidation reaction with compound (7).

Compound (9) used in Production Method B can also be produced according to the following method.

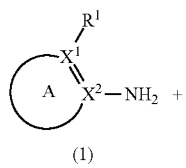

(1)

-continued

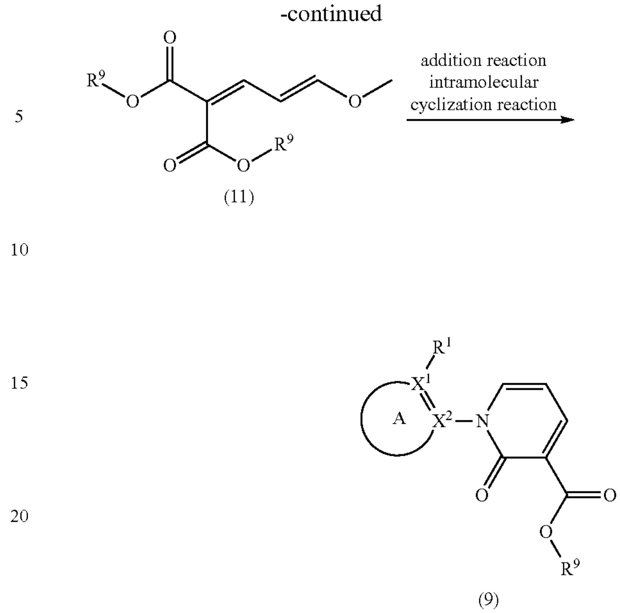

(11)

(9)

wherein the symbols are as defined above.

Compound (9) can be produced by subjecting compound (1) to an addition reaction with compound (11), followed by an intramolecular cyclization reaction.

Compound (9) used in Production Method B can also be produced according to the following method.

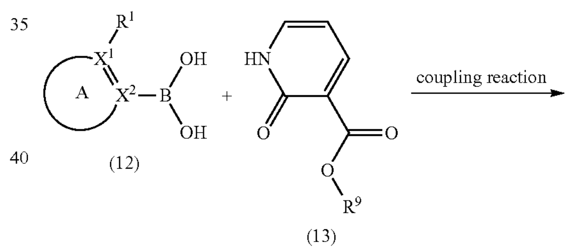

(12) (13)

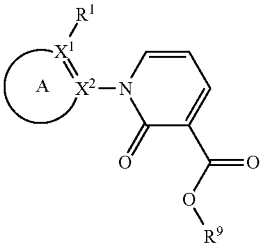

(9)

wherein the symbols are as defined above.

Compound (9) can be produced by subjecting compound (12) to a coupling reaction with compound (13).

Production Method C

Among compound (I), the following compound (Ic) can be produced according to the following method.

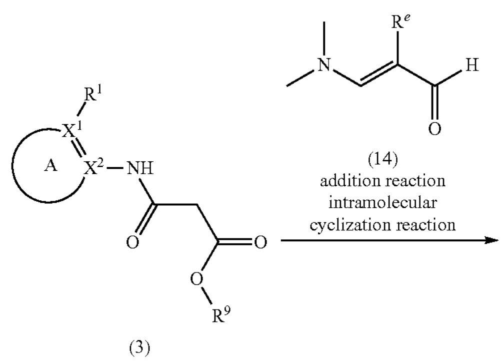

(14)

(3)

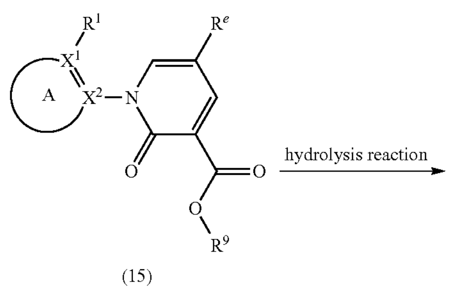

(15)

-continued

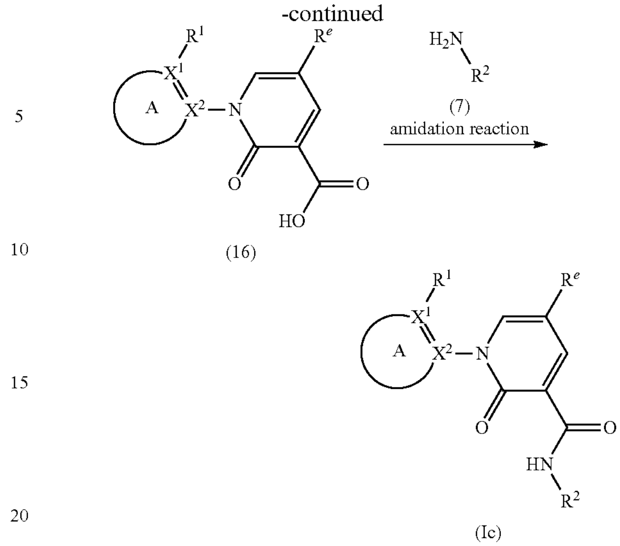

(7)

(16)

(Ic)

wherein the symbols are as defined above.

Compound (15) can be produced by subjecting compound (3) to an addition reaction with compound (14), followed by an intramolecular cyclization reaction.

Compound (16) can be produced by subjecting compound (15) to a hydrolysis reaction.

Compound (Ic) can be produced by subjecting compound (16) to an amidation reaction with compound (7).

Production Method D

Among compound (I), the following compound (Id) can be produced according to the following method.

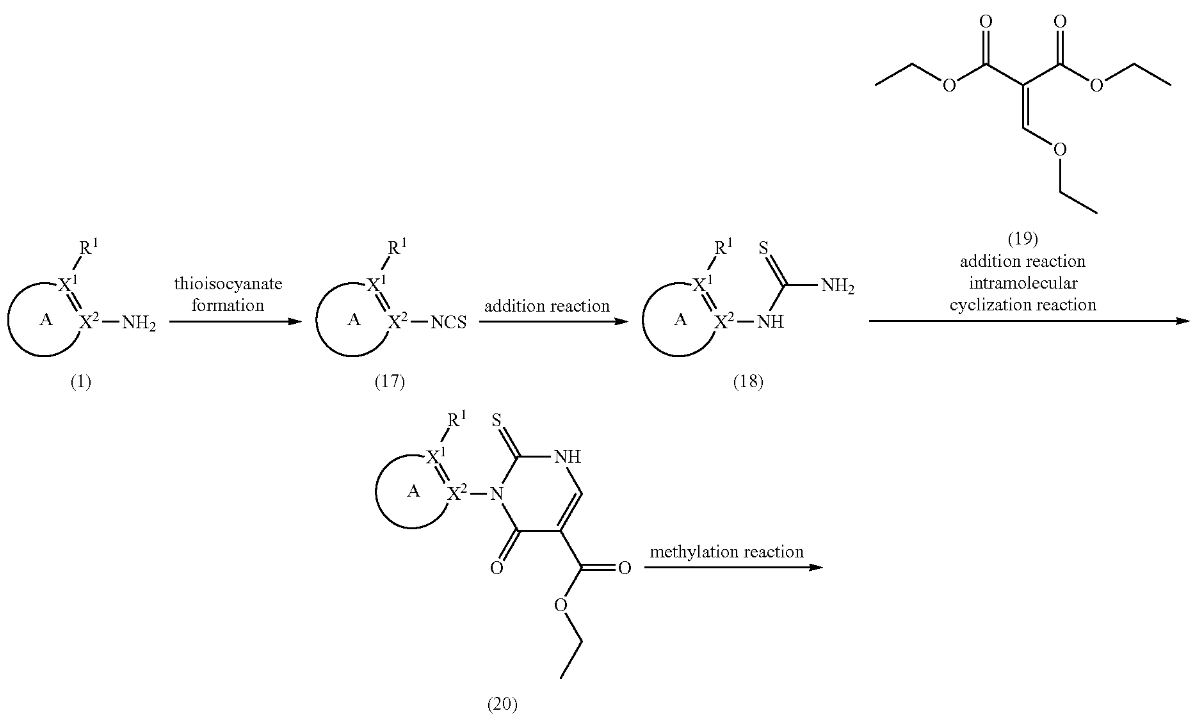

(19)

(1)

(17)

(18)

(20)

-continued

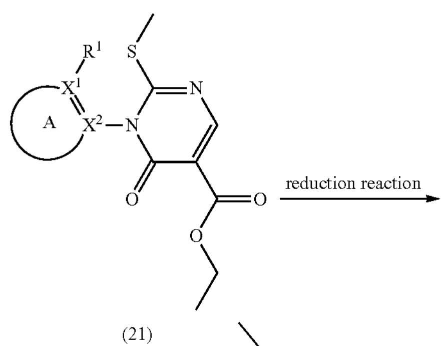

(21)

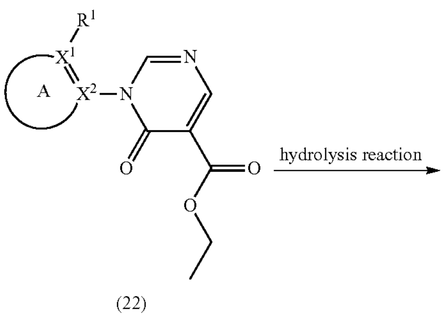

(22)

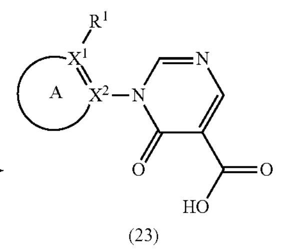

(23)

(7)
amidation reaction (7)
ester-amide
exchange reaction

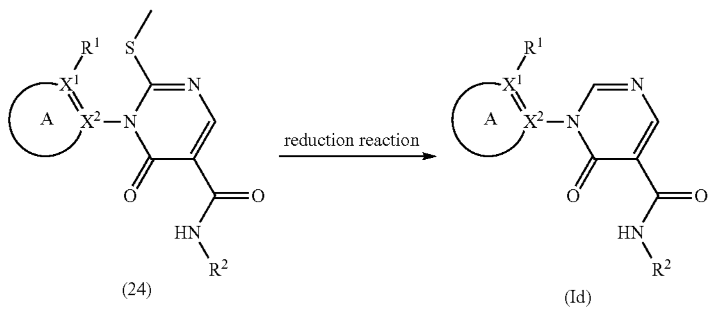

(24)

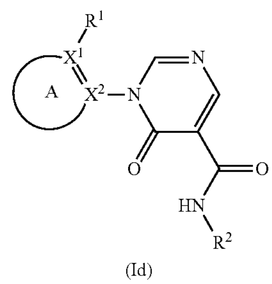

(Id)

wherein the symbols are as defined above.

Compound (17) can be produced by subjecting compound (1) to a thioisocyanate formation. Examples of the reagent to be used include 1,1'-thiocarbonyldiimidazole and the like.

Compound (18) can be produced by subjecting compound (17) to an addition reaction with ammonia.

Compound (20) can be produced by subjecting compound (18) to an addition reaction with compound (19), followed by an intramolecular cyclization reaction.

Compound (21) can be produced by subjecting compound (20) to a methylation reaction.

Compound (22) can be produced by subjecting compound (21) to a reduction reaction. Examples of the reagent to be used include a combination of a metal reagent and a reducing agent and the like. Examples of the metal reagent include a combination of copper thiophene-2-carboxylate and tetrakis(triphenylphosphine)palladium and the like. Examples of the reducing agent include the above-mentioned reducing agent (triethylsilane, etc.).

Compound (23) can be produced by subjecting compound (22) to a hydrolysis reaction.

Compound (24) can be produced by subjecting compound (21) to an ester-amide exchange reaction with compound (7). Examples of the reagent to be used include trimethylaluminium and the like.

Compound (Id) can be produced by subjecting compound (23) to an amidation reaction with compound (7).

Compound (Id) can also be produced by subjecting compound (24) to a reduction reaction. Examples of the reagent to be used include a combination of a metal reagent and a reducing agent and the like. Examples of the metal reagent include a combination of copper thiophene-2-carboxylate and tetrakis(triphenylphosphine)palladium and the like. Examples of the reducing agent include the above-mentioned reducing agent (triethylsilane, etc.).

Production Method E

Among compound (I), the following compound (Ie) can be produced according to the following method.

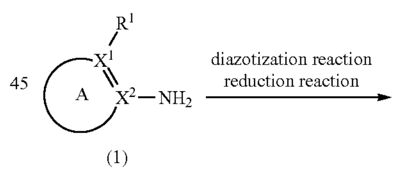

(1)

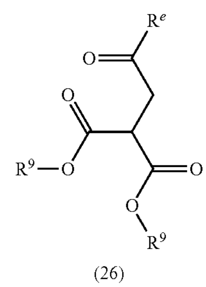

(26)
condensation reaction
intramolecular
cyclization reaction

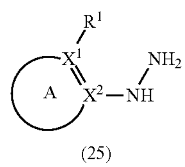

(25)

-continued

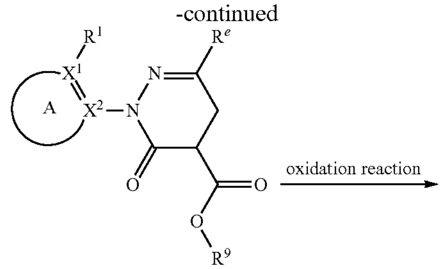

(27)

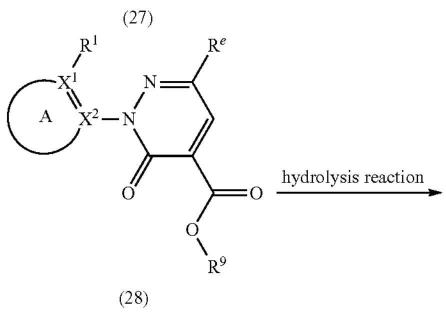

(28)

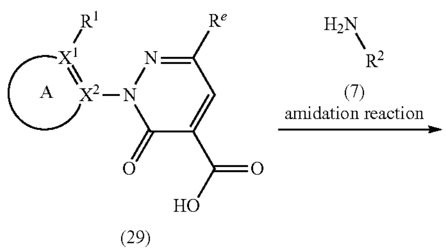

(29)

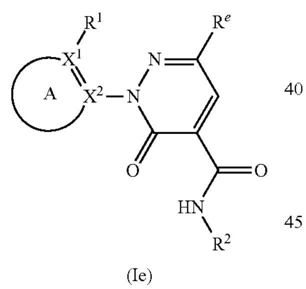

(Ie)

wherein the symbols are as defined above.

Compound (25) can be produced by subjecting compound (1) to a diazotization reaction, followed by a reduction reaction.

Compound (27) can be produced by subjecting compound (25) to a condensation reaction with compound (26), followed by an intramolecular cyclization reaction.

Compound (28) can be produced by subjecting compound (27) to an oxidation reaction.

Compound (29) can be produced by subjecting compound (28) to a hydrolysis reaction.

Compound (Ie) can be produced by subjecting compound (29) to an amidation reaction with compound (7).

Production Method F

Among compound (I), the following compound (If) can be produced according to the following method.

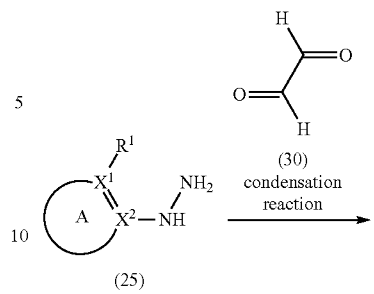

(25)

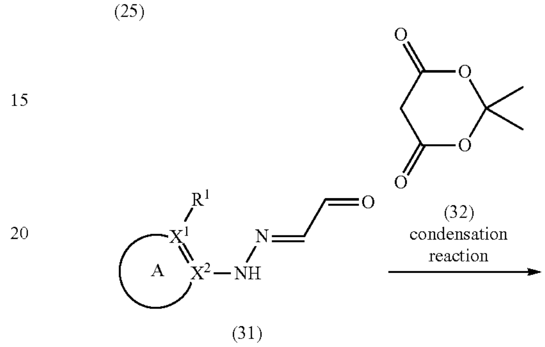

(31)

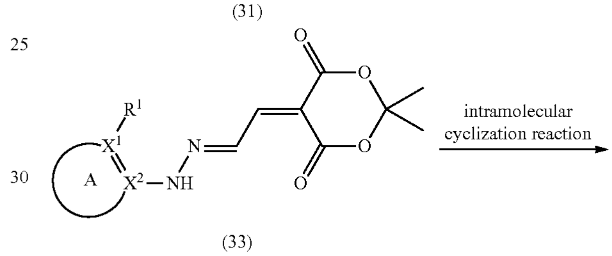

(33)

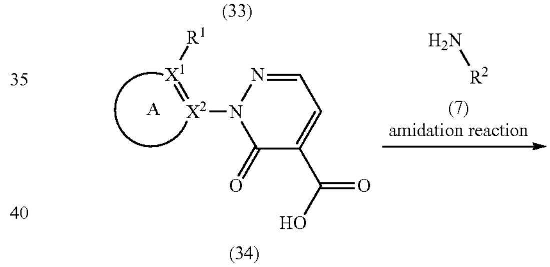

(34)

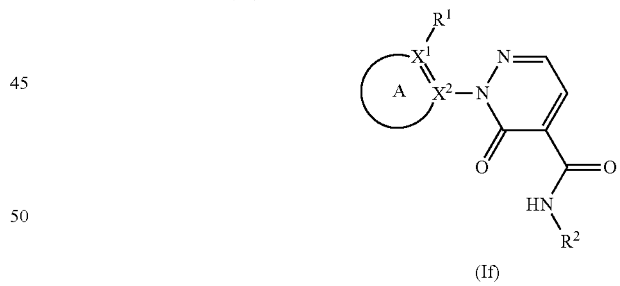

(If)

wherein the symbols are as defined above.

Compound (31) can be produced by subjecting compound (25) to a condensation reaction with compound (30).

Compound (33) can be produced by subjecting compound (31) to a condensation reaction with compound (32).

Compound (34) can be produced by subjecting compound (33) to an intramolecular cyclization reaction.

Compound (If) can be produced by subjecting compound (34) to an amidation reaction with compound (7).

Production Method G

Among compound (I), the following compound (Ig) can be produced according to the following method.

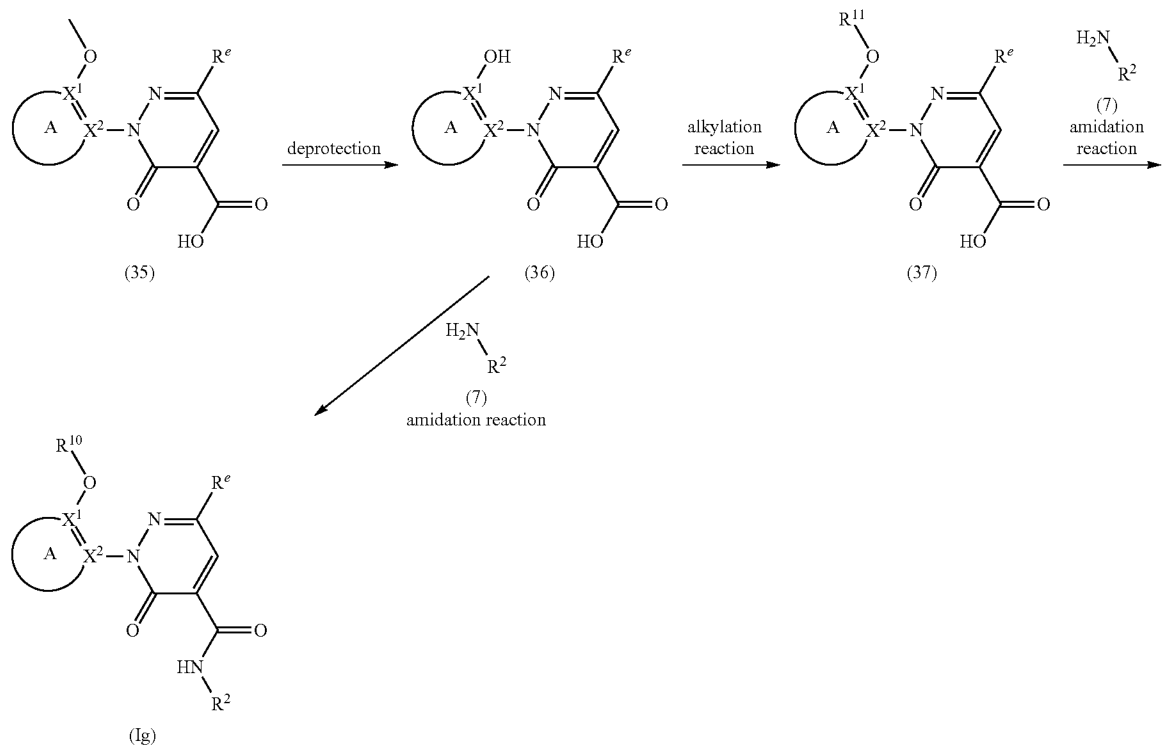

wherein the symbols are as defined above.

Compound (35) can be produced from compound (1) according to the above-mentioned Production Method E and the above-mentioned Production Method F.

Compound (36) can be produced by subjecting compound (35) to a deprotection.

Compound (37) can be produced by subjecting compound (36) to an alkylation reaction.

Compound (Ig) can be produced by subjecting compound (36) to an amidation reaction with compound (7) (in the case that $R^{10}$ is a hydrogen atom), or by subjecting compound (37) to an amidation reaction with compound (7) (in the case that $R^{10}$ is a substituent).

Production Method H

Among compound (I), the following compound (Ih) can be produced according to the following method.

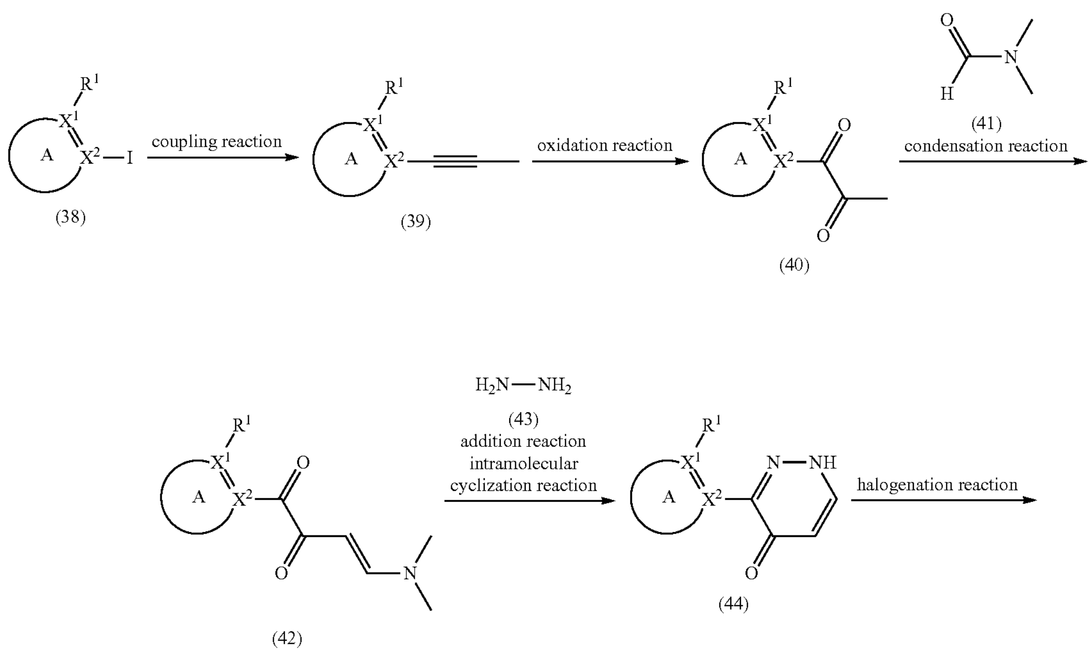

-continued

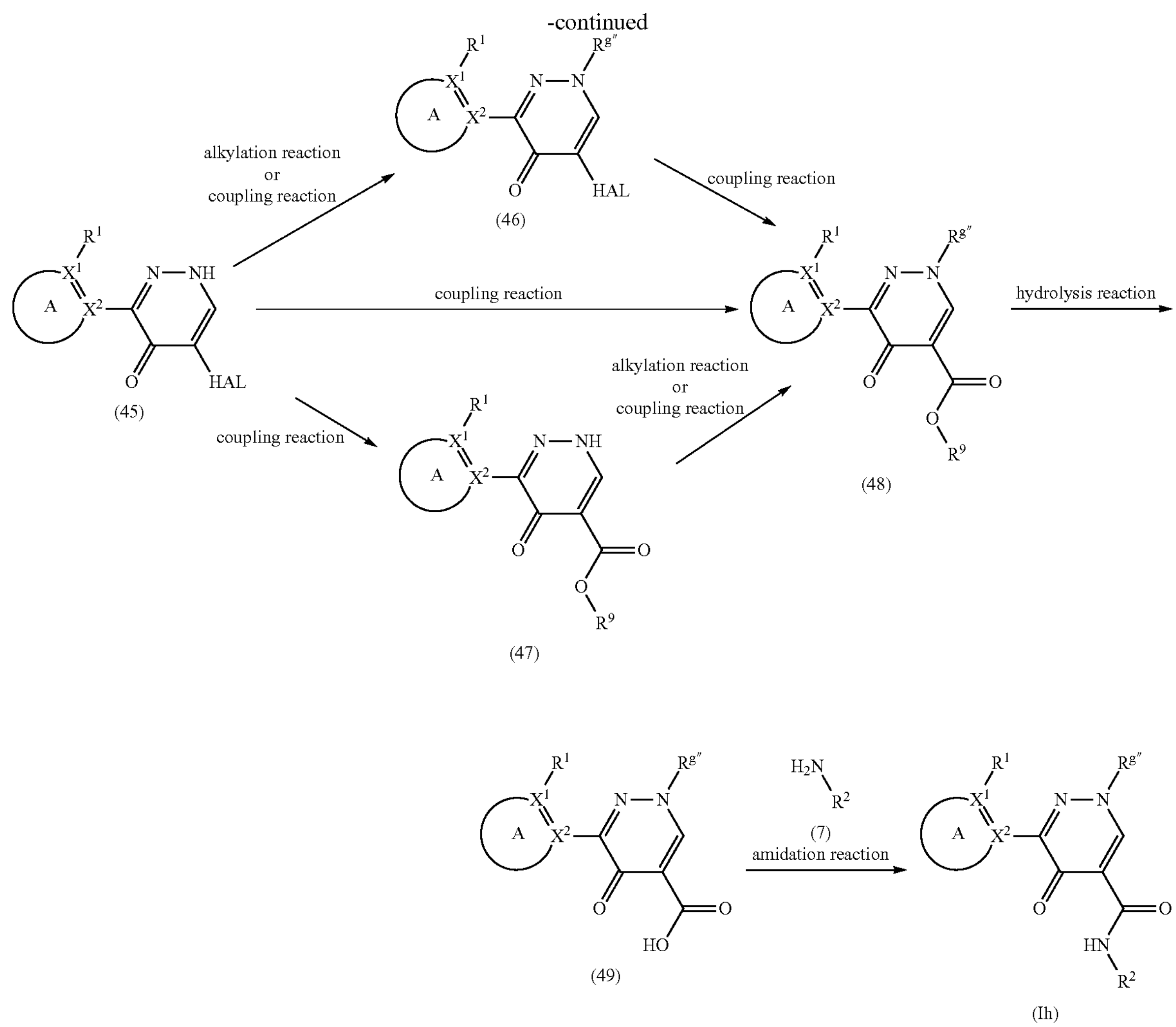

(45) (46) (47) (48) (49) (Ih)

wherein the symbols are as defined above.

Compound (39) can be produced by subjecting compound (38) to a coupling reaction with prop-1-yne. Examples of the reagent to be used include a combination of a palladium catalyst, a copper compound and a base. Examples of the palladium catalyst include bis(triphenylphosphine)palladium(II) dichloride and the like. Examples of the copper compound include copper(I) iodide and the like. Examples of the base include triethylamine and the like.

Compound (40) can be produced by subjecting compound (39) to an oxidation reaction. Examples of the reagent to be used include a combination of a metal reagent, an oxidizing agent, a base and a dehydrating agent. Examples of the metal reagent include ruthenium chloride and the like. Examples of the oxidizing agent include sodium periodate and the like. Examples of the base include sodium hydrogencarbonate and the like. Examples of the dehydrating agent include magnesium sulfate and the like.

Compound (42) can be produced by subjecting compound (40) to a condensation reaction with compound (41).

Compound (44) can be produced by subjecting compound (42) to an addition reaction with compound (43), followed by an intramolecular cyclization reaction.

Compound (45) can be produced by subjecting compound (44) to a halogenation reaction.

Compound (46) can be produced by subjecting compound (45) to an alkylation reaction, or by subjecting compound (45) to a coupling reaction with a trialkyl tin derivative or boronic acid derivative corresponding to $R^{g''}$ (in the case that $R^{g''}$ is a substituent).

Compound (47) can be produced by subjecting compound (45) to a coupling reaction with carbon monoxide in the presence of an alcohol corresponding to $R^9$.

Compound (48) can be produced by subjecting compound (45) to a coupling reaction with carbon monoxide in the presence of an alcohol corresponding to $R^9$ (in the case that $R^{g''}$ is a hydrogen atom). Compound (48) can also be produced by subjecting compound (46) to a coupling reaction with carbon monoxide in the presence of an alcohol corresponding to $R^9$, or by subjecting compound (47) to an alkylation reaction, or by subjecting compound (47) to a coupling reaction with a trialkyl tin derivative or boronic acid derivative corresponding to $R^{g''}$ (in the case that $R^{g''}$ is a substituent).

Compound (49) can be produced by subjecting compound (48) to a hydrolysis reaction.

Compound (Ih) can be produced by subjecting compound (49) to an amidation reaction with compound (7).

Production Method I

Among compound (I), the following compound (Ii) can be produced according to the following method.

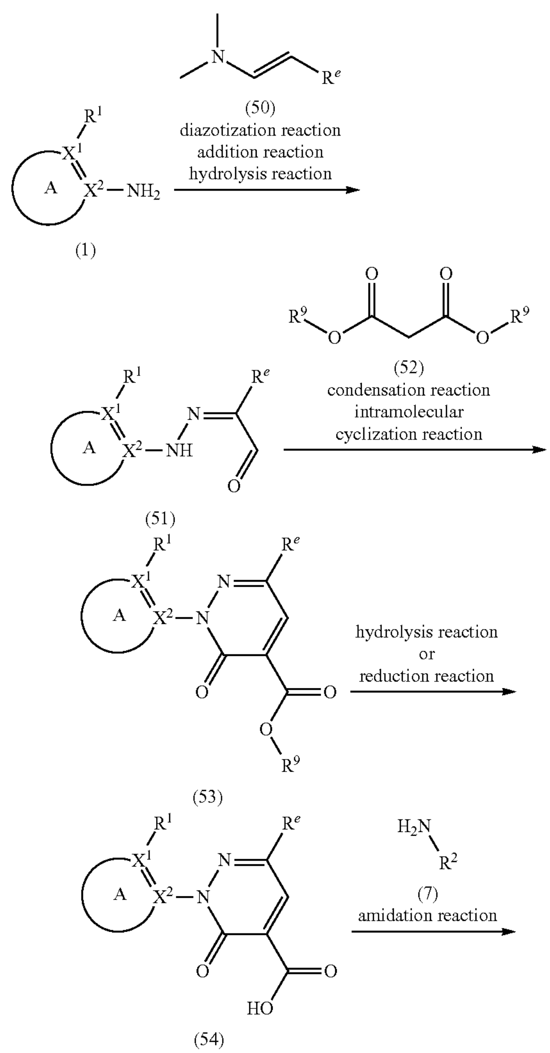

(1)

(51)

(53)

(54)

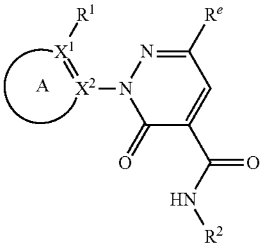

(Ii)

wherein the symbols are as defined above.

Compound (51) can be produced by subjecting compound (1) to a diazotization reaction, followed by an addition reaction with compound (50), and a hydrolysis reaction.

Compound (53) can be produced by subjecting compound (51) to a condensation reaction with compound (52), followed by an intramolecular cyclization reaction.

Compound (54) can be produced by subjecting compound (53) to a hydrolysis reaction or a reduction reaction.

Compound (Ii) can be produced by subjecting compound (54) to an amidation reaction with compound (7).

Production Method J

Among compound (I), the following compound (Ij) can be produced according to the following method.

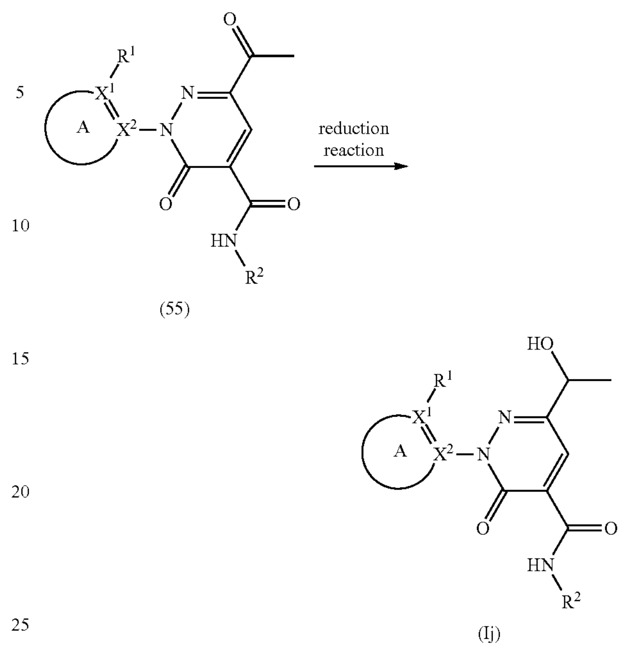

(55)

(Ij)

wherein the symbols are as defined above.

Compound (55) can be produced from compound (1) according to the above-mentioned Production Method I.

Compound (Ij) can be produced by subjecting compound (55) to a reduction reaction.

Production Method K

Among compound (I), the following compound (Ik) can be produced according to the following method.

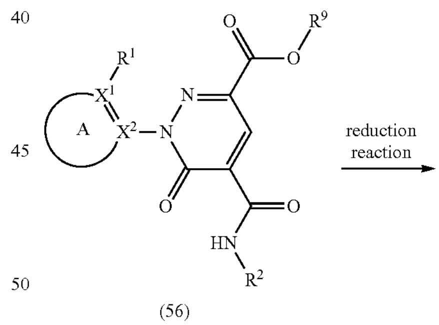

(56)

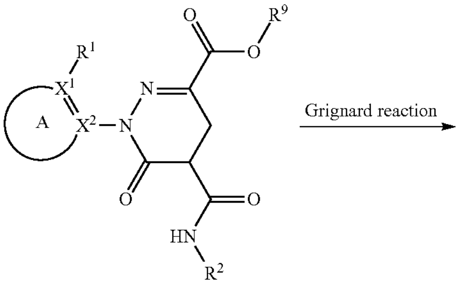

(57)

-continued

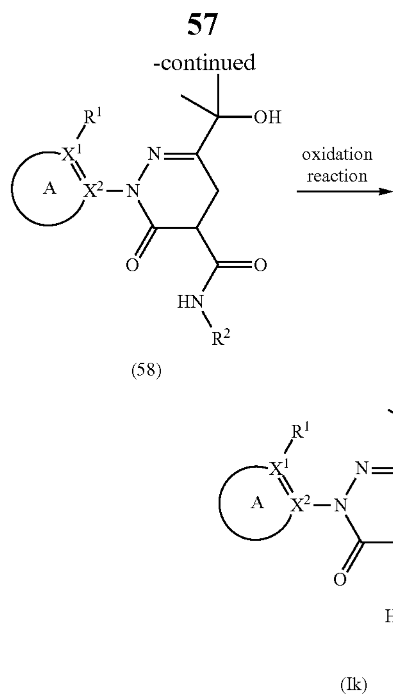

(58)

(Ik)

wherein the symbols are as defined above.

Compound (56) can be produced from compound (1) according to the above-mentioned Production Method I.

Compound (57) can be produced by subjecting compound (56) to a reduction reaction.

Compound (58) can be produced by subjecting compound (57) to Grignard reaction.

Compound (Ik) can be produced by subjecting compound (58) to an oxidation reaction.

Compounds (1), (2), (4), (7), (8), (11), (12), (13), (14), (19), (26), (30), (32), (38), (41), (43), (50) and (52) used as a raw material in each production method may be a commercially available product, or can be produced according to a method known per se.

As for the configurational isomers (E, Z forms) of compound (I), they can be isolated and purified when isomerization occurs, for example, according to a conventional separation means such as extraction, recrystallization, distillation, chromatography and the like to obtain a pure compound. In addition, the corresponding pure isomer can also be obtained by isomerizing a double bond using heating, an acid catalyst, a transition metal complex, a metal catalyst, a radical catalyst, light irradiation, a strong base catalyst and the like, according to the method described in Shin Jikken Kagaku Kouza 14 (The Chemical Society of Japan ed.), pages 251 to 253, 4th Edition Jikken Kagaku Kouza 19 (The Chemical Society of Japan ed.), pages 273 to 274 or a method analogous thereto.

Compound (I) contains a stereoisomer depending on the kind of a substituent, and each stereoisomer and a mixture thereof are encompassed in the present invention.

When the objective product is obtained as a free form by the above-mentioned reaction, it can be converted to a salt according to a conventional method, or when the objective product is obtained as a salt, it can be converted to a free form or other salt according to a conventional method. The thus-obtained compound (I) can also be isolated and purified from a reaction mixture according to a known method such as transfer, concentration, solvent extraction, distillation, crystallization, recrystallization, chromatography and the like.

When compound (I) contains a configurational isomer, a diastereomer, a conformer and the like, each can be isolated according to the above-mentioned separation and purification methods, if desired. In addition, when compound (I) is racemic, d-form and l-form or S-form and R-form can be isolated according to a conventional optical resolution.

The thus-obtained compound (I), other reaction intermediate therefor and starting compounds thereof can be isolated and purified from a reaction mixture according to a method known per se, for example, extraction, concentration, neutralization, filtration, distillation, recrystallization, column chromatography, thin layer chromatography, preparative high performance liquid chromatography (preparative HPLC), moderate-pressure preparative liquid chromatography (moderate-pressure preparative LC) and the like.

A salt of compound (I) can be produced according to a method known per se. For example, when compound (I) is a basic compound, it can be produced by adding an inorganic acid or organic acid, or when compound (I) is an acidic compound, by adding an organic base or inorganic base.

When compound (I) contains an optical isomer, each optical isomer and a mixture thereof are encompassed in the scope of the present invention, and these isomers can be subjected to optical resolution or can be produced respectively, according to a method known per se, if desired.

The compound of the present invention is expected to be useful for mammals (e.g., mouse, rat, hamster, rabbit, cat, dog, bovine, sheep, monkey, human etc.) as an agent for the prophylaxis or treatment of diseases, for example, (1) psychiatric diseases [e.g., depression, major depression, bipolar depression, dysthymic disorder, emotional disorder (seasonal affective disorder and the like), recurrent depression, postpartum depression, stress disorder, depression symptom, mania, anxiety, generalized anxiety disorder, anxiety syndrome, panic disorder, phobia, social phobia, social anxiety disorder, obsessive disorder, post-traumatic stress syndrome, post-traumatic stress disorder, Tourette syndrome, autism, fragile X syndrome, Rett syndrome, adjustment disorder, bipolar disorder, neurosis, schizophrenia (e.g., positive symptom, negative symptom, cognitive impairment), chronic fatigue syndrome, anxiety neurosis, compulsive neurosis, panic disorder, epilepsy, anxiety disorder, anxiety, anxious mental state, emotional abnormality, cyclothymia, nervous erethism, faint, addiction, low sex drive, attention deficit hyperactivity disorder (ADHD), psychotic major depression, refractory major depression, treatment-resistant depression, depressive disorder, catalepsy, hebephrenic schizophrenia, paranoid schizophrenia], (2) neurodegenerative diseases [e.g., Alzheimer's disease, Alzheimer-type senile dementia, Parkinson's disease, Huntington's disease, multi-infarct dementia, frontotemporal dementia, dementia Parkinson's type, progressive supranuclear palsy, Pick's syndrome, corticobasal degeneration, Down's disease, vascular dementia, postencephalitic parkinsonism, Lewy body dementia, multiple-system atrophy, HIV dementia, amyotrophic lateral sclerosis (ALS), motor neurogenesis disease (MND), Creutzfeldt-Jakob disease or prion disease, cerebral palsy, progressive supranuclear palsy, traumatic brain injury, glaucoma, multiple sclerosis, neuromyelitis optica (NMO), postoperative cognitive dysfunction (POCD), postoperative delirium (POD), delirium], (3) age-related cognition memory disorders [e.g., age-related memory disorders, senile dementia], (4) sleep disorders [e.g., intrinsic sleep disorders (e.g., psychophysiological insomnia and the like), extrinsic sleep disorder, circadian rhythm disorders (e.g., time zone change syndrome (jet lag), shift work sleep disorder, irregular sleep-wake pattern, delayed sleep phase syndrome, advanced sleep phase syndrome, non-24-hour sleep-wake and the like), parasomnia, sleep disorders associated with internal medical or psychiatric disorder (e.g., chronic obstructive pulmonary diseases, Alzheimer's disease, Parkinson's disease, cerebrovascular dementia, schizophrenia, depression, anxiety neurosis), stress insomnia, insomnia, insomniac neurosis, sleep apnea syndrome], (5) respiratory depression caused by anesthetics, traumatic disease, or neurodegenerative disease and the like, (6) traumatic brain injury, cerebral apoplexy, cerebral edema, cerebral ischemia, ischemia, neurotic anorexia, eating disorder, anorexia nervosa, hyperorexia, other eating disorder, alcohol dependence, alcohol abuse, alcoholic amnesia, alcohol paranoia, alcohol preference, alcohol withdrawal, alcoholic insanity, alcohol poisoning, alcoholic jealousy, alcoholic mania, alcohol-dependent psychiatric disorder, alcoholic insanity, pharmacophilia, pharmacophobia, pharmacomania, drug withdrawal, migraine, stress headache, catatonic headache, diabetic neuropathy, obesity, diabetes, muscular spasm, Meniere's disease, autonomic ataxia, alopecia, glaucoma, hypertension, cardiac disease, tachycardia, congestive cardiac failure, hyperventilation, bronchial asthma, apnea, sudden infant death syndrome, inflammatory disease, allergic disease, impotence, climacteric disorder, infertility, neoplasms (e.g., cancer, liver neoplasms, colonic neoplasms, breast neoplasms, prostatic neoplasms, neuroblastoma, bone neoplasms, mouth neoplasms, mastocytoma, cholangiocarcinoma, Lewis lung carcinoma etc.), immunodeficiency syndrome caused by HIV infection, immunodeficiency syndrome caused by stress, cerebrospinal meningitis, acromegaly, incontinence, metabolic syndrome, osteoporosis, peptic ulcer, irritable bowel syndrome, inflammatory bowel disease, ulcerative colitis, Crohn's disease, stress gastrointestinal disorder, stress vomiting, diarrhea, constipation, postoperative ileus, rheumatoid arthritis, osteoarthritis, functional dyspepsia, hyperalgesia, insulin resistance, dementia pugilistica, nausea, vomiting, neoplasm metastasis, brain injuries, seizure, body weight changes, weight gain, weight loss, colitis, alcoholism, hypothermia, fatty liver, atherosclerosis, infection, muscle spasticity, hypertension, stroke, malignant migrating partial seizures of infancy, diabetes mellitus, type 2 diabetes mellitus, dyslipidaemia, visceral obesity, ocular hypotension, anorexia, fibrosis, myocardial infarction, cachexia, induced psychotic disorder, ataxia, AIDS wasting syndrome, cirrhotic cardiomyopathy, uremic pruritus, neurobehavioral manifestations, Tubulointerstitial nephritis and uveitis syndrome, interstitial cystitis, retinitis pigmentosa, autoimmune diseases, coronary artery disease, aspirin-induced asthma, platelet storage pool deficiency, diabetic embryopathy, Arthus type urticaria, asthma, toxic oil syndrome, otitis and the like, (7) pain (e.g., inflammatory pain, cancerous pain, neuropathic pain, acute pain, pain associated with peripheral neuropathy, central pain, fibromyalgia, vassooclussive painful crises in sickle cell disease, multiple sclerosis-mediated spasticity or pain, functional chest pain, complex regional pain syndrome etc.), (8) lysosomal storage diseases [e.g., Gaucher's disease, Krabbe's disease, Niemann-Pick syndrome]

and the like.

Since the compound of the present invention has an excellent glucosylceramide synthase inhibitory action, a superior prophylactic or therapeutic effect for the above-mentioned diseases may be expected.

Since the compound of the present invention has an excellent glucosylceramide synthase inhibitory action, a superior prophylactic or therapeutic effect for lysosomal storage diseases (e.g., Gaucher's disease), neurodegenerative diseases (e.g., Parkinson's disease, Lewy body dementia, multiple-system atrophy) and the like may be expected.

Compound (I) can be used as a prodrug.

A prodrug of compound (I) means a compound which is converted to compound (I) with a reaction due to an enzyme, a gastric acid, etc. under the physiological condition in the living body, that is, a compound which is converted to compound (I) with oxidation, reduction, hydrolysis, etc. according to an enzyme; a compound which is converted to compound (I) by hydrolysis etc. due to gastric acid, etc.

A prodrug for compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation, etc.); a compound obtained by subjecting a hydroxy group in compound (I) to an acylation, alkylation, phosphorylation or boration (e.g., a compound obtained by subjecting an hydroxy group in compound (I) to an acetylation, palmitoylation, propanoylation, pivaloylation, succinylation, fumarylation, alanylation or dimethylaminomethylcarbonylation, etc.); a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation, etc.) and the like. Any of these compounds can be produced from compound (I) by a method known per se. The prodrug of compound (I) may be a compound that converts to compound (I) under physiological conditions as described in Development of Pharmaceutical Products, vol. 7, Molecule Design, 163-198, Hirokawa Shoten (1990).

The compound of the present invention is superior in vivo kinetics (e.g., plasma drug half-life, intracerebral transferability, metabolic stability), shows low toxicity (e.g., more superior as a medicament in terms of acute toxicity, chronic toxicity, genetic toxicity, reproductive toxicity, cardiotoxicity, drug interaction, carcinogenicity etc.). The compound of the present invention is directly used as a medicament or a pharmaceutical composition mixed with a pharmaceutically acceptable carrier or the like to be orally or parenterally administered to mammals (e.g., humans, monkeys, cows, horses, pigs, mice, rats, hamsters, rabbits, cats, dogs, sheep and goats) in safety. Examples of the "parenteral" include intravenous, intramuscular, subcutaneous, intra-organ, intranasal, intradermal, instillation, intracerebral, intrarectal, intravaginal, intraperitoneal and intratumor administrations, administration to the vicinity of tumor etc. and direct administration to the lesion.

While the dose of the compound of the present invention varies depending on the administration route, symptom and the like, when, for example, the compound is orally administered to a patient with Parkinson's disease (adult, body weight 40-80 kg, for example, 60 kg), it is, for example, 0.001-1000 mg/kg body weight/day, preferably 0.01-100 mg/kg body weight/day, more preferably 0.1-10 mg/kg body weight/day. This amount can be administered in 1 to 3 portions per day.

A medicament containing the compound of the present invention can be used alone or as a pharmaceutical composition containing the compound of the present invention and a pharmaceutically acceptable carrier according to a method known per se as a production method of a pharmaceutical preparation (e.g., the method described in the Japanese Pharmacopoeia etc.). A medicament containing the compound of the present invention can be safely administered in the form of, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal administrations, and administration to the lesion).

As the aforementioned "pharmaceutically acceptable carrier", various organic or inorganic carriers conventionally used as preparation materials (starting materials) can be used. For example, excipient, lubricant, binder, disintegrant and the like are used for solid preparations, and solvent, solubilizing agent, suspending agent, isotonicity agent, buffer, soothing agent and the like are used for liquid preparations. Where necessary, preparation additives such as preservative, antioxidant, colorant, sweetening agent and the like can also be used.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binder include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonicity agent include glucose, D-sorbitol, sodium chloride, glycerin, D-mannitol and the like.

Examples of the buffer include buffer solutions such as phosphates, acetates, carbonates, citrates and the like.

Examples of the soothing agent include benzyl alcohol and the like.

Examples of the preservative include p-oxybenzoates, chlorobutanol, benzyl alcohol, phenylethyl alcohol, dehydroacetic acid, sorbic acid and the like.

Examples of the antioxidant include sulfite, ascorbic acid, α-tocopherol and the like.

While the pharmaceutical composition varies according to the dosage form, administration method, carrier and the like, it can be produced according to a conventional method by adding the compound of the present invention in a proportion of generally 0.01-100% (w/w), preferably 0.1-95% (w/w), of the total amount of the preparation.

The compound of the present invention can be used in combination with other active ingredients (hereinafter to be abbreviated as concomitant drug).

Examples of the concomitant drug include the following. benzodiazepine (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, desipramine hydrochloride, clomipramine hydrochloride etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenaline reuptake inhibitor (venlafaxine hydrochloride, duloxetine hydrochloride, desvenlafaxine hydrochloride etc.), noradrenaline reuptake inhibitor (reboxetine mesylate etc.), noradrenaline-dopamine reuptake inhibitor (bupropion hydrochloride etc.), mirtazapine, trazodone hydrochloride, nefazodone hydrochloride, bupropion hydrochloride, setiptiline maleate, 5-$HT_{1A}$ agonist (buspirone hydrochloride, tandospirone citrate, osemozotan hydrochloride etc.), 5-$HT_3$ antagonist (Cyamemazine etc.), heart non-selective β inhibitor (propranolol hydrochloride, oxprenolol hydrochloride etc.), histamine $H_1$ antagonist (hydroxyzine hydrochloride etc.), therapeutic drug for schizophrenia (chlorpromazine, haloperidol, sulpiride, clozapine, trifluoperazine hydrochloride, fluphenazine hydrochloride, olanzapine, quetiapine fumarate, risperidone, aripiprazole etc.), CRF antagonist, other antianxiety drug (meprobamate etc.), tachykinin antagonist (MK-869, saredutant etc.), medicament that acts on metabotropic glutamate receptor, CCK antagonist, β3 adrenaline antagonist (amibegron hydrochloride etc.), GAT-1 inhibitor (tiagabine hydrochloride etc.), N-type calcium channel inhibitor, carbonic anhydrase II inhibitor, NMDA glycine moiety agonist, NMDA antagonist (memantine etc.), peripheral benzodiazepine receptor agonist, vasopressin antagonist, vasopressin V1b antagonist, vasopressin V1a antagonist, phosphodiesterase inhibitor, opioid antagonist, opioid agonist, uridine, nicotinic acid receptor agonist, thyroid hormone (T3, T4), TSH, TRH, MAO inhibitor (phenelzine sulfate, tranylcypromine sulfate, moclobemide etc.), 5-$HT_{2A}$ antagonist, 5-$HT_{2A}$ inverse agonist, COMT inhibitor (entacapone etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autism, therapeutic drug for chronic fatigue syndrome, therapeutic drug for spasm, therapeutic drug for fibromyalgia syndrome, therapeutic drug for headache, therapeutic drug for insomnia (etizolam, zopiclone, triazolam, zolpidem, ramelteon, indiplon etc.), therapeutic drug for quitting smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambler, therapeutic drug for restless legs syndrome, therapeutic drug for substance addiction, therapeutic drug for alcohol-related syndrome, therapeutic drug for irritable bowel syndrome, therapeutic drug for Alzheimer's disease (donepezil, galanthamine, memantine, rivastigmine etc.), therapeutic drug for Parkinson's disease (levodopa, carbidopa, benserazide, selegiline, zonisamide, entacapone, amantadine, talipexole, pramipexole, apomorphine, cabergoline, bromocriptine, istradefylline, trihexyphenidyl, promethazine, pergolide, etc.), therapeutic drug for Huntington's disease (chlorpromazine hydrochloride, haloperidol, reserpine etc.), therapeutic drug for Gaucher's disease (imiglucerase, taliglucerase alfa, velaglucerase alfa, eliglustat, miglustat, etc.), therapeutic drug for ALS (riluzole etc., neurotrophic factor etc.), therapeutic drug for multiple sclerosis (molecular target drug such as fingolimod, interferon beta 1b, natalizumab and the like, etc.), antiepilepsy drug (phenytoin, carbamazepine, phenobarbital, primidone, zonisamide, sodium valproate, ethosuximide, diazepam, nitrazepam, clonazepam, clobazam, gabapentin, topiramate, lamotrigine, levetiracetam, stiripentol, rufinamide, etc.), therapeutic drug for lipid abnormality such as cholesterol-lowering drug (statin series (pravastatin sodium, atrovastatin, simvastatin, rosuvastatin etc.), fibrate (clofibrate etc.), squalene synthetase inhibitor), therapeutic drug for abnormal behavior or suppressant of dromomania due to dementia (sedatives, antianxiety drug etc.), apoptosis inhibitor, antiobesity drug, therapeutic drug for diabetes, therapeutic drug for hypertension, therapeutic drug for hypotension, therapeutic drug for rheumatism (DMARD), anti-cancer agent, therapeutic drug for parathyroid (PTH), calcium receptor antagonist, sex hormone or a derivative thereof (progesterone, estradiol, estradiol benzoate etc.), neuronal differentiation promoter, nerve regeneration promoter, non-steroidal anti-inflammatory drug (meloxicam, tenoxicam, indomethacin, ibuprofen, celecoxib, rofecoxib, aspirin etc.), steroid (dexamethasone, cortisone acetate etc.), anti-cytokine drug (TNF inhibitor, MAP kinase inhibitor etc.), antibody medicament, nucleic acid or nucleic acid derivative, aptamer drug and the like.

By combining the compound of the present invention and a concomitant drug, a superior effect such as (1) the dose can be reduced as compared to single administration of the compound of the present invention or a concomitant drug, (2) the drug to be combined with the compound of the present invention can be selected according to the condition of patients (mild case, severe case and the like), (3) the period of treatment can be set longer by selecting a concomitant drug having different action and mechanism from the compound of the present invention, (4) a sustained treatment effect can be designed by selecting a concomitant drug having different action and mechanism from the compound of the present invention, (5) a synergistic effect can be afforded by a combined use of the compound of the present invention and a concomitant drug, and the like, can be achieved.

Hereinafter the compound of the present invention and a concomitant drug used in combination are referred to as the "combination agent of the present invention".

When using the combination agent of the present invention, the administration time of the compound of the present invention and the concomitant drug is not restricted, and the compound of the present invention or a pharmaceutical composition thereof and the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the concomitant drug of the present invention is not particularly restricted, and it is sufficient that the compound of the present invention and the concomitant drug are combined in administration. Examples of such administration mode include the following methods:

(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (for example, administration in the order of the compound of the present invention and the concomitant drug, or in the reverse order) and the like.

The combination agent of the present invention exhibits low toxicity. For example, the compound of the present invention or(and) the aforementioned concomitant drug can be combined with a pharmacologically acceptable carrier according to the known method to prepare a pharmaceutical composition such as tablets (including sugar-coated tablet and film-coated tablet), powders, granules, capsules (including soft capsule), liquids, injections, suppositories, sustained-release agents, etc. These compositions can be administered safely orally or non-orally (e.g., topical, rectal, intravenous administration etc.). Injection can be administered intravenously, intramuscularly, subcutaneously, or by intraorgan administration or directly to the lesion.

Examples of the pharmacologically acceptable carriers usable for the production of the combination agent of the present invention include those similar to the above-mentioned carriers.

The mixing ratio of the compound of the present invention to the concomitant drug in the combination agent of the present invention can be appropriately selected depending on an administration subject, administration route, diseases and the like.

For example, the content of the compound of the present invention in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of the concomitant drug in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

The elution by column chromatography in the Examples was performed under the observation by TLC (Thin Layer Chromatography) unless otherwise specified. In the observation by TLC, 60 $F_{254}$ manufactured by Merck was used as a TLC plate, the solvent used as an elution solvent in column chromatography was used as a developing solvent, and UV detector was used for the detection. In silica gel column chromatography, the indication of NH means use of aminopropylsilane-bonded silica gel and the indication of Diol means use of 3-(2,3-dihydroxypropoxy)propylsilane-bonded silica gel. In preparative HPLC (high performance liquid chromatography), the indication of C18 means use of octadecyl-bonded silica gel. The ratio for elution solvent is, unless otherwise specified, a volume mixing ratio.

For the analysis of $^1H$ NMR, ACD/SpecManager (trade name) software and the like were used. Peaks of a hydroxyl group, an amino group and the like, having very mild proton peak, are not sometimes described.

MS was measured by LC/MS. As the ionization method, ESI method, or APCI method was used. The data indicates actual measured value (found). While molecular ion peak is generally observed, a fragment ion is sometimes observed. In the case of a salt, a molecular ion peak or fragment ion peak of free form is generally observed.

In the following Examples, the following abbreviations are used.

mp: melting point
MS: mass spectrum
M: mol concentration
N: normality
$CDCl_3$: deuterochloroform
DMSO-$d_6$: deuterodimethyl sulfoxide
$^1H$ NMR: proton nuclear magnetic resonance
LC/MS: liquid chromatograph mass spectrometer
ESI: electron spray ionization
APCI: atmospheric pressure chemical ionization
HATU: O-(7-azabenzotriazol-1-yl)-N,N,N',N'-tetramethyluronium hexafluorophosphorate
DPPA: diphenyl phosphorylazide
DIPEA: N,N-diisopropylethylamine
DMF: N,N-dimethylformamide
THF: tetrahydrofuran
MeOH: methanol
EtOH: ethanol
DMSO: dimethyl sulfoxide
TEA: triethylamine

Example 1

1-(2-methoxyphenyl)-6-methyl-2-oxo-N-(4-phenoxyphenyl)-1,2-dihydropyridine-3-carboxamide

A) ethyl 3-[(2-methoxyphenyl)amino]-3-oxopropionate

To a mixture of 2-methoxyaniline (24.74 g), TEA (29.4 mL) and acetone (250 mL) was added dropwise a solution of ethyl 3-chloro-3-oxopropionate (27.0 mL) in acetone (25 mL) under ice-cooling. The mixture was stirred under ice-cooling for 30 min, and then at room temperature for 2 hr. The reaction mixture was concentrated under reduced pressure, water was added thereto, and the mixture was extracted with ethyl acetate. The organic layer was separated, washed with water and saturated brine, dried over anhydrous sodium sulfate, and concentrated under reduced pressure. The residue was washed with ethyl acetate/hexane to give the title compound (20.50 g).

MS: $[M+H]^+$ 238.0.

B) 1-(2-methoxyphenyl)-6-methyl-2-oxo-1,2-dihydropyridine-3-carboxylic acid To a solution of ethyl 3-[(2-methoxyphenyl)amino]-3-oxopropionate (10 g) in EtOH (100 mL) were added 4,4-dimethoxybutan-2-one (6.68 g) and 20% sodium ethoxide-EtOH solution (47.3 g), and the mixture was stirred overnight at 50° C. The reaction mixture was acidified with 1M hydrochloric acid, and the precipitate was collected by filtration, and washed with EtOH and ethyl acetate to give the title compound (6.48 g).

MS: $[M+H]^+$ 260.0.

C) 1-(2-methoxyphenyl)-6-methyl-2-oxo-N-(4-phenoxyphenyl)-1,2-dihydropyridine-3-carboxamide To a mixture of 1-(2-methoxyphenyl)-6-methyl-2-oxo-1,2-dihydropyridine-3-carboxylic acid (50 mg) and DMF (5 mL) was added HATU (110 mg), and the mixture was stirred at room temperature for 30 min. To the reaction mixture was added DIPEA (62 mg), and the mixture was stirred at room temperature for 1 hr. To the reaction mixture was added 4-phenoxyaniline (43 mg), and the mixture was stirred at room temperature for 16 hr. To the reaction mixture was added water, and the mixture was extracted with dichloromethane. The organic layer was separated, washed with saturated brine, dried over anhydrous sodium sulfate, and concentrated under reduced pressure. The residue was purified by preparative liquid chromatography (0.05% aqueous ammonia-containing acetonitrile/0.1% aqueous ammonia) to give the title compound (50 mg).

$^1$H NMR (400 MHz, $CDCl_3$) δ 2.07 (3H, s), 3.84 (3H, s), 6.45 (1H, d, J=7.6 Hz), 6.93-7.01 (4H, m), 7.06 (1H, t, J=7.6 Hz), 7.11-7.21 (3H, m), 7.30 (2H, t, J=8.0 Hz), 7.47-7.55 (1H, m), 7.68 (2H, d, J=8.8 Hz), 8.61 (1H, d, J=7.2 Hz), 11.78 (1H, brs).

Example 54

1-[4-fluoro-2-(2,2,2-trifluoroethoxy)phenyl]-N-[1-(oxan-4-yl)-1H-pyrazol-3-yl]-2-oxo-1,2-dihydropyridine-3-carboxamide A) 3-nitro-1-(oxan-4-yl)-1H-pyrazole To a mixture of 3-nitro-1H-pyrazole (500 mg), triphenylphosphine (1392 mg), tetrahydro-2H-pyran-4-ol (542 mg) and THF (10 mL) was added 20% di-tert-butyl azodicarboxylate-toluene solution (6.10 g), and the mixture was stirred overnight at room temperature. To the reaction mixture was added water, and the mixture was extracted with ethyl acetate. The organic layer was separated, washed with saturated brine, dried over anhydrous sodium sulfate, and concentrated under reduced pressure. The residue was purified by silica gel column chromatography (SI and NH, ethyl acetate/hexane) to give the title compound (597 mg).

MS: $[M+H]^+$ 198.0.

B) 1-(oxan-4-yl)-1H-pyrazol-3-amine

To a solution of 3-nitro-1-(oxan-4-yl)-1H-pyrazole (597 mg) in MeOH (10 mL) was added 10% palladium-carbon (55% wet, 100 mg), and the mixture was stirred overnight under normal pressure of hydrogen atmosphere at room temperature. The catalyst was removed by filtration, and the filtrate was concentrated under reduced pressure to give the title compound (330 mg).

MS: $[M+H]^+$ 168.0.

C) 4-fluoro-1-nitro-2-(2,2,2-trifluoroethoxy)benzene

To a mixture of 5-fluoro-2-nitrophenol (16.73 g), cesium carbonate (52.0 g) and DMF (200 mL) was added 2,2,2-trifluoroethyl trifluoromethanesulfonate (16.11 mL) under ice-cooling, and the mixture was stirred overnight at room temperature. To the reaction mixture was added water, and the mixture was extracted with ethyl acetate. The organic layer was separated, washed with water and saturated brine, dried over anhydrous sodium sulfate, and concentrated under reduced pressure. The residue was purified by silica gel column chromatography (ethyl acetate/hexane) to give the title compound (24.2 g).

$^1$H NMR (300 MHz, DMSO-$d_6$) δ 5.02 (2H, q, J=8.7 Hz), 7.05-7.19 (1H, m), 7.49 (1H, dd, J=10.7, 2.4 Hz), 8.10 (1H, dd, J=9.0, 6.0 Hz).

D) methyl 1-[4-fluoro-2-(2,2,2-trifluoroethoxy)phenyl]-2-oxo-1,2-dihydropyridine-3-carboxylate To a solution of 4-fluoro-1-nitro-2-(2,2,2-trifluoroethoxy)benzene (24.2 g) in MeOH (100 mL) was added 10% palladium-carbon (55% wet, 500 mg), and the mixture was stirred overnight under normal pressure of hydrogen atmosphere at room temperature. The catalyst was removed by filtration, and the filtrate was concentrated under reduced pressure to give 4-fluoro-2-(2,2,2-trifluoroethoxy)aniline (20.21 g) as a crude product. To the obtained crude product were added DMF (150 mL) and 3-carbomethoxy-2-pyrone (13.47 g), and the mixture was stirred at room temperature for 3 days. To the reaction mixture were added 1-ethyl-3-(3-dimethylaminopropyl)carbodiimide hydrochloride (21.79 g) and N,N-dimethyl-4-aminopyridine (2.67 g), and the mixture was stirred at room temperature for 5 hr. To the reaction mixture was added water, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane). The obtained crude product was washed with ethyl acetate/hexane to give the title compound (9.13 g).

MS: $[M+H]^+$ 345.9.

E) 1-[4-fluoro-2-(2,2,2-trifluoroethoxy)phenyl]-2-oxo-1,2-dihydropyridine-3-carboxylic acid To a mixture of methyl 1-[4-fluoro-2-(2,2,2-trifluoroethoxy)phenyl]-2-oxo-1,2-dihydropyridine-3-carboxylate (9.13 g), MeOH (100 mL) and THF (50 mL) was added 4M aqueous lithium hydroxide solution (25 mL), and the mixture was stirred at room temperature for 5 hr. The reaction mixture was adjusted to pH=2 with 1M hydrochloric acid, and extracted with ethyl acetate. The organic layer was separated, washed with saturated brine, dried over anhydrous sodium sulfate, and concentrated under reduced pressure. The residue was recrystallized from ethyl acetate/hexane to give the title compound (6.91 g).

MS: $[M+H]^+$ 331.9.

F) 1-[4-fluoro-2-(2,2,2-trifluoroethoxy)phenyl]-N-[1-(oxan-4-yl)-1H-pyrazol-3-yl]-2-oxo-1,2-dihydropyridine-3-carboxamide To a mixture of 1-[4-fluoro-2-(2,2,2-trifluoroethoxy)phenyl]-2-oxo-1,2-dihydropyridine-3-carboxylic acid (50 mg), 1-(oxan-4-yl)-1H-pyrazol-3-amine (30.3 mg), TEA (0.032 mL) and DMF (0.8 mL) was added HATU (86 mg), and the mixture was stirred at room temperature for 3 hr. The reaction mixture was purified by silica gel column chromatography (ethyl acetate/hexane). The obtained crude product was recrystallized from diethyl ether/hexane to give the title compound (41.0 mg).

$^1$H NMR (300 MHz, DMSO-$d_6$) δ 1.75-1.85 (2H, m), 1.88-2.12 (2H, m), 3.39 (2H, brs), 3.93 (2H, d, J=11.7 Hz), 4.19 (1H, t, J=11.3 Hz), 4.78-5.01 (2H, m), 6.42 (1H, d, J=1.5 Hz), 6.73 (1H, t, J=7.0 Hz), 7.12 (1H, td, J=8.6, 2.4 Hz), 7.36-7.50 (2H, m), 7.62 (1H, dd, J=8.7, 6.0 Hz), 8.06 (1H, dd, J=6.6, 2.1 Hz), 8.58 (1H, dd, J=7.2, 1.9 Hz), 12.08 (1H, s).

Example 60

1-[4-fluoro-2-(2,2,2-trifluoroethoxy)phenyl]-N-[4-(2-hydroxy-2-methylpropoxy)phenyl]-2-oxo-1,2-dihydropyridine-3-carboxamide A) 2-methyl-1-(4-nitrophenoxy)propan-2-ol A mixture of 4-nitrophenol (0.696 g), sodium dihydrogen phosphate (0.600 g), potassium carbonate (0.691 g), acetonitrile (5 mL) and water (2 mL) was stirred at room temperature for 5 min, 2,2-dimethyloxirane (0.668 mL) was added thereto, and the mixture was stirred under microwave irradiation at 150° C. for 3 hr. To the reaction mixture was added ethyl acetate, and the mixture was washed with saturated aqueous ammonium chloride solution and saturated brine, dried over anhydrous sodium sulfate, and concentrated under reduced pressure. The residue was purified by silica gel column chromatography (ethyl acetate/hexane) to give the title compound (1.023 g).

MS: $[M+H]^+$ 212.0.

B) 1-(4-aminophenoxy)-2-methylpropan-2-ol

To a mixture of 2-methyl-1-(4-nitrophenoxy)propan-2-ol (1.023 g) and MeOH (10 mL) was added 10% palladium on carbon (55% wet, 102 mg), and the mixture was stirred under hydrogen atmosphere at room temperature for 2 hr. The catalyst was removed by filtration, and the filtrate was concentrated under reduced pressure to give the title compound (0.845 g).

MS: $[M+H]^+$ 182.0.

C) 1-[4-fluoro-2-(2,2,2-trifluoroethoxy)phenyl]-N-[4-(2-hydroxy-2-methylpropoxy)phenyl]-2-oxo-1,2-dihydropyridine-3-carboxamide To a mixture of 1-[4-fluoro-2-(2,2,2-trifluoroethoxy)phenyl]-2-oxo-1,2-dihydropyridine-3-carboxylic acid (42.2 mg), 1-(4-aminophenoxy)-2-methylpropan-2-ol (30 mg), TEA (0.036 mL) and DMF (0.5 mL) was added HATU (72.6 mg) at room temperature, and the mixture was stirred at the same temperature for 17 hr. To the reaction mixture was added ethyl acetate, and the mixture was washed with saturated aqueous ammonium chloride solution and saturated brine, dried over anhydrous sodium sulfate, and concentrated under reduced pressure. The residue was purified by silica gel column chromatography (ethyl acetate/hexane), and the residue was crystallized from ethyl acetate/hexane to give the title compound (48 mg).

$^1$H NMR (300 MHz, DMSO-$d_6$) δ 1.19 (6H, s), 3.68 (2H, s), 4.60 (1H, s), 4.87 (2H, qd, J=8.7, 1.5 Hz), 6.64-6.73 (1H, m), 6.88-6.97 (2H, m), 7.10 (1H, td, J=8.5, 2.6 Hz), 7.41 (1H, dd, J=10.6, 2.6 Hz), 7.53-7.65 (3H, m), 7.97 (1H, dd, J=6.6, 2.3 Hz), 8.56 (1H, dd, J=7.3, 2.2 Hz), 11.73 (1H, s).

Example 62

1-[4-fluoro-2-(2,2,2-trifluoroethoxy)phenyl]-2-oxo-N-[1-(2,2,3,3,3-pentafluoropropyl)-1H-pyrazol-4-yl]-1,2-dihydropyridine-3-carboxamide A) 4-nitro-1-(2,2,3,3,3-pentafluoropropyl)-1H-pyrazole To a mixture of 4-nitro-1H-pyrazole (1.0 g), cesium carbonate (4.32 g) and DMF (20 mL) was added 2,2,3,3,3-pentafluoropropyl trifluoromethanesulfonate (2.62 g) under ice-cooling, and the mixture was stirred overnight at room temperature. To the reaction mixture was added water, and the mixture was extracted with ethyl acetate. The organic layer was separated, washed with water and saturated brine, dried over anhydrous sodium sulfate, and concentrated under reduced pressure. The residue was purified by silica gel column chromatography (ethyl acetate/hexane) to give the title compound (1.850 g).

$^1$H NMR (300 MHz, DMSO-$d_6$) δ 5.35 (2H, t, J=15.3 Hz), 8.44 (1H, s), 9.05 (1H, s).

B) 1-(2,2,3,3,3-pentafluoropropyl)-1H-pyrazol-4-amine

To a mixture of 4-nitro-1-(2,2,3,3,3-pentafluoropropyl)-1H-pyrazole (1.85 g) and MeOH (20 mL) was added 10% palladium-carbon (55% wet, 200 mg), and the mixture was stirred overnight under normal pressure of hydrogen atmosphere at room temperature. The catalyst was removed by filtration, and the filtrate was concentrated under reduced pressure to give the title compound (1.390 g).

MS: $[M+H]^+$ 215.9.

C) 1-[4-fluoro-2-(2,2,2-trifluoroethoxy)phenyl]-2-oxo-N-[1-(2,2,3,3,3-pentafluoropropyl)-1H-pyrazol-4-yl]-1,2-dihydropyridine-3-carboxamide To a mixture of 1-[4-fluoro-2-(2,2,2-trifluoroethoxy)phenyl]-2-oxo-1,2-dihydropyridine-3-carboxylic acid (50 mg), 1-(2,2,3,3,3-pentafluoropropyl)-1H-pyrazol-4-amine (42.2 mg), TEA (0.032 mL) and DMF (0.8 mL) was added HATU (86 mg), and the mixture was stirred at room temperature for 2 days. The reaction mixture was purified by silica gel column chromatography (ethyl acetate/hexane), and the solid was recrystallized from ethyl acetate/hexane to give the title compound (49.0 mg).

$^1$H NMR (300 MHz, DMSO-$d_6$) δ 4.86 (2H, qd, J=8.6, 4.0 Hz), 5.18 (2H, t, J=15.3 Hz), 6.68 (1H, t, J=7.0 Hz), 7.10 (1H, td, J=8.6, 2.4 Hz), 7.41 (1H, dd, J=10.5, 2.6 Hz), 7.60 (1H, dd, J=8.9, 6.2 Hz), 7.76 (1H, s), 7.97 (1H, dd, J=6.6, 1.7 Hz), 8.29 (1H, s), 8.53 (1H, dd, J=7.3, 1.7 Hz), 11.62 (1H, s).

Example 69

1-[4-fluoro-2-(2,2,2-trifluoroethoxy)phenyl]-N-[4-(1-hydroxycyclopropyl)phenyl]-2-oxo-1,2-dihydropyridine-3-carboxamide A) {[1-(4-bromophenyl)cyclopropyl]oxy}(tert-butyl)dimethylsilane To a mixture of 1-(4-bromophenyl)cyclopropan-1-ol (490 mg), tert-butyldimethylchlorosilane (381 mg) and DMF (5.0 mL) was added imidazole (188 mg), and the mixture was stirred at room temperature for 3 days. To the reaction mixture was added ethyl acetate, and the mixture was poured into water, and extracted with ethyl acetate. The organic layer was separated, washed with water and saturated brine, dried over anhydrous sodium sulfate, and concentrated under reduced pressure. The residue was purified by silica gel column chromatography (ethyl acetate/hexane) to give the title compound (678 mg).

$^1$H NMR (300 MHz, $CDCl_3$) δ −0.01 (6H, s), 0.87 (9H, s), 0.91-0.99 (2H, m), 1.14-1.22 (2H, m), 7.18 (2H, d, J=8.7 Hz), 7.41 (2H, d, J=8.7 Hz).

B) 1-(4-aminophenyl)cyclopropan-1-ol

To a solution of {[1-(4-bromophenyl)cyclopropyl]oxy}(tert-butyl)dimethylsilane (143 mg) in toluene (6 mL) were added benzphenonimine (88 μL), sodium tert-butoxide (63.0 mg), 2,2'-bis(diphenylphosphino)-1,1'-binaphthyl (82 mg) and tris(dibenzylideneacetone)dipalladium(0) (40.0 mg), and the mixture was stirred overnight under nitrogen atmosphere at 100° C. To the reaction mixture was added ethyl acetate, and the insoluble substance was removed by filtration. The filtrate was washed with saturated aqueous ammonium chloride solution and saturated brine, dried over anhydrous sodium sulfate, and concentrated under reduced pressure. To the residue were added THF (3 mL) and 1M hydrochloric acid (6 mL), and the mixture was stirred at room temperature for 1.5 hr. To the reaction mixture was added aqueous sodium hydrogencarbonate solution, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane) to give the title compound (28.0 mg).

MS: $[M+H]^+$ 150.0.

C) 1-[4-fluoro-2-(2,2,2-trifluoroethoxy)phenyl]-N-[4-(1-hydroxycyclopropyl)phenyl]-2-oxo-1,2-dihydropyridine-3-carboxamide To a mixture of 1-[4-fluoro-2-(2,2,2-trifluoroethoxy)phenyl]-2-oxo-1,2-dihydropyridine-3-carboxylic acid (50 mg), 1-(4-aminophenyl)cyclopropan-1-ol (27 mg), TEA (42 μL) and DMF (0.5 mL) was added HATU (86 mg), and the mixture was stirred overnight at room temperature. To the reaction mixture was added ethyl acetate, and the mixture was washed with saturated aqueous ammonium chloride solution and saturated brine, dried over anhydrous sodium sulfate, and concentrated under reduced pressure. The residue was purified by silica gel column chromatography (ethyl acetate/hexane), and crystallized from ethyl acetate/hexane to give the title compound (24 mg).

$^1H$ NMR (300 MHz, DMSO-$d_6$) δ 0.83-0.95 (2H, m), 0.97-1.10 (2H, m), 4.87 (2H, dd, J=8.7, 1.1 Hz), 5.88 (1H, s), 6.69 (1H, t, J=7.0 Hz), 7.06-7.15 (1H, m), 7.21 (2H, d, J=7.8 Hz), 7.41 (1H, dd, J=10.5, 2.6 Hz), 7.53-7.65 (3H, m), 7.98 (1H, dd, J=6.8, 2.3 Hz), 8.57 (1H, dd, J=7.5, 2.3 Hz), 11.83 (1H, s).

Example 72

2-oxo-N-[6-(2,2,2-trifluoroethoxy)pyridin-3-yl]-1-[1-(3,3,3-trifluoropropyl)-1H-pyrazol-5-yl]-1,2-dihydropyridine-3-carboxamide A) 1-(3,3,3-trifluoropropyl)-1H-pyrazol-5-amine To a mixture of 5-nitro-1-(3,3,3-trifluoropropyl)-1H-pyrazole (531 mg) and EtOH (10 mL) was added 10% palladium on carbon (50 mg), and the mixture was stirred under hydrogen atmosphere at room temperature for 16 hr. The catalyst was removed by filtration, and the filtrate was concentrated under reduced pressure to give the title compound (324 mg).

MS: $[M+H]^+$ 179.8.

B) ethyl 3-oxo-3-{[1-(3,3,3-trifluoropropyl)-1H-pyrazol-5-yl]amino}propanoate

To a mixture of 1-(3,3,3-trifluoropropyl)-1H-pyrazol-5-amine (490 mg), TEA (415 mg) and dichloromethane (5 mL) was added ethyl 3-chloro-3-oxopropanoate (453 mg) at 0° C., and the mixture was stirred at room temperature for 12 hr. Ethyl 3-chloro-3-oxopropanoate (205 mg) was added thereto at 0° C., and the mixture was stirred at room temperature for 12 hr. The reaction mixture was poured into water, and extracted with dichloromethane. The organic layer was dried over anhydrous sodium sulfate, and concentrated under reduced pressure. The residue was purified by silica gel column chromatography (ethyl acetate/petroleum ether) to give the title compound (510 mg).

MS: $[M+H]^+$ 293.8.

C) ethyl 2-oxo-1-[1-(3,3,3-trifluoropropyl)-1H-pyrazol-5-yl]-1,2-dihydropyridine-3-carboxylate A mixture of ethyl 3-oxo-3-{[1-(3,3,3-trifluoropropyl)-1H-pyrazol-5-yl]amino}propanoate (510 mg), 3-(dimethylamino)acrolein (345 mg), EtOH (5 mL) and acetic acid (188 mg) was stirred for 48 hr at 80° C. The reaction mixture was poured into water, neutralized with saturated aqueous sodium hydrogencarbonate solution, and extracted with ethyl acetate. The organic layer was dried over anhydrous sodium sulfate, and concentrated under reduced pressure. The residue was purified by silica gel column chromatography (ethyl acetate/petroleum ether) to give the title compound (280 mg).

MS: $[M+H]^+$ 329.7.

D) 2-oxo-1-[1-(3,3,3-trifluoropropyl)-1H-pyrazol-5-yl]-1,2-dihydropyridine-3-carboxylic acid A mixture of ethyl 2-oxo-1-[1-(3,3,3-trifluoropropyl)-1H-pyrazol-5-yl]-1,2-dihydropyridine-3-carboxylate (280 mg), lithium hydroxide monohydrate (71 mg), THF (1 mL), MeOH (1 mL) and water (1 mL) was stirred at room temperature for 12 hr. The reaction mixture was poured into water, acidified with 1N hydrochloric acid, and extracted with ethyl acetate. The organic layer was dried over anhydrous sodium sulfate, and concentrated under reduced pressure to give the title compound (210 mg).

MS: $[M+H]^+$ 302.0.

E) 2-oxo-N-[6-(2,2,2-trifluoroethoxy)pyridin-3-yl]-1-[1-(3,3,3-trifluoropropyl)-1H-pyrazol-5-yl]-1,2-dihydropyridine-3-carboxamide To a mixture of 2-oxo-1-[1-(3,3,3-trifluoropropyl)-1H-pyrazol-5-yl]-1,2-dihydropyridine-3-carboxylic acid (135 mg) and DMF (5 mL) were added HATU (256 mg) and DIPEA (145 mg), and the mixture was stirred at room temperature for 30 min. 6-(2,2,2-Trifluoroethoxy)pyridin-3-amine (86 mg) was added thereto, and the mixture was stirred at room temperature for 16 hr. To the reaction mixture was added water, and the mixture was extracted with ethyl acetate. The organic layer was washed with saturated brine, dried over anhydrous sodium sulfate, and concentrated under reduced pressure. The residue was purified by high-performance liquid chromatography (0.05% aqueous ammonia-containing acetonitrile/water) to give the title compound (27 mg).

$^1H$ NMR (400 MHz, $CDCl_3$) δ 2.66-3.09 (2H, m), 4.10-4.26 (2H, m), 4.77 (2H, q, J=8.4 Hz), 6.38 (1H, d, J=1.6 Hz), 6.69 (1H, t, J=6.8 Hz), 6.90 (1H, d, J=9.2 Hz), 7.53 (1H, dd, J=6.8, 2.4 Hz), 7.73 (1H, d, J=1.6 Hz), 8.14 (1H, dd, J=8.8, 2.8 Hz), 8.42 (1H, d, J=2.4 Hz), 8.81 (1H, dd, J=7.2, 2.0 Hz), 11.45 (1H, brs).

Example 73

1-[4-fluoro-2-(2,2,2-trifluoroethoxy)phenyl]-2-oxo-N-{6-[(2,2,2-trifluoroethoxy)methyl]pyridin-3-yl}-1,2-dihydropyridine-3-carboxamide A) (5-bromopyridin-2-yl)methyl 4-methylbenzene-1-sulfonate To a mixture of (5-bromopyridin-2-yl)methanol (2.0 g), TEA (2.97 mL) and THF (30 mL) was added 4-methylbenzenesulfonyl chloride (2.231 g) under ice-cooling, and the mixture was stirred overnight at room temperature. To the reaction mixture was added water, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane) to give the title compound (1.040 g).

MS: $[M+H]^+$ 341.8.

B) 5-bromo-2-[(2,2,2-trifluoroethoxy)methyl]pyridine

To a solution of 2,2,2-trifluoroethanol (0.278 mL) in DMF (10 mL) was added sodium hydride (60% oil, 93 mg) under ice-cooling, and the mixture was stirred under ice-cooling for 15 min. To the reaction mixture was added (5-bromopyridin-2-yl)methyl 4-methylbenzene-1-sulfonate (660 mg) under ice-cooling, and the mixture was stirred overnight at room temperature. To the reaction mixture was added saturated aqueous ammonium chloride solution, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane) to give the title compound (496 mg).

MS: $[M+H]^+$ 269.8.

C) 6-[(2,2,2-trifluoroethoxy)methyl]pyridin-3-amine

A mixture of 5-bromo-2-[(2,2,2-trifluoroethoxy)methyl]pyridine (496 mg), benzphenonimine (0.339 mL), sodium tert-butoxide (265 mg), 2,2'-bis(diphenylphosphino)-1,1'-binaphthyl (686 mg), tris(dibenzylideneacetone)dipalladium (0) (336 mg) and toluene (10 mL) was stirred under microwave irradiation at 110° C. for 1 hr. To the reaction mixture was added water, and the mixture was extracted with ethyl acetate. The organic layer was separated, washed with saturated brine, dried over anhydrous sodium sulfate, and concentrated under reduced pressure. To the residue were added THF (10.00 mL), EtOH (10.00 mL) and 2M hydrochloric acid (2 mL), and the mixture was stirred at room temperature for 1 hr, and concentrated under reduced pressure. The residue was purified by silica gel column chromatography (NH, ethyl acetate/hexane) to give the title compound (279 mg).

MS: $[M+H]^+$ 207.0.

D) 1-[4-fluoro-2-(2,2,2-trifluoroethoxy)phenyl]-2-oxo-N-{6-[(2,2,2-trifluoroethoxy)methyl]pyridin-3-yl}-1,2-dihydropyridine-3-carboxamide To a mixture of 1-[4-fluoro-2-(2,2,2-trifluoroethoxy)phenyl]-2-oxo-1,2-dihydropyridine-3-carboxylic acid (74.1 mg), 6-[(2,2,2-trifluoroethoxy)methyl]pyridin-3-amine (60 mg), TEA (0.047 mL) and DMF (0.8 mL) was added HATU (128 mg), and the mixture was stirred overnight at room temperature. The reaction mixture was purified by silica gel column chromatography (ethyl acetate/hexane), and the solid was recrystallized from ethyl acetate/hexane to give the title compound (56.0 mg).

$^1$H NMR (300 MHz, DMSO-$d_6$) δ 4.19 (2H, q, J=9.4 Hz), 4.70 (2H, s), 4.80-4.95 (2H, m), 6.72 (1H, t, J=7.0 Hz), 7.11 (1H, td, J=8.6, 2.4 Hz), 7.37-7.49 (2H, m), 7.62 (1H, dd, J=8.7, 6.4 Hz), 8.03 (1H, dd, J=6.4, 1.9 Hz), 8.22 (1H, dd, J=8.5, 2.4 Hz), 8.59 (1H, dd, J=7.5, 1.9 Hz), 8.79 (1H, d, J=2.3 Hz), 12.00 (1H, s).

Example 75 rac-N-{6-[cyclopropyl(hydroxy)methyl]pyridin-3-yl}-1-[4-fluoro-2-(2,2,2-trifluoroethoxy)phenyl]-2-oxo-1,2-dihydropyridine-3-carboxamide A) rac-(5-bromopyridin-2-yl)(cyclopropyl)methanol To a solution of 5-bromopyridine-2-carbaldehyde (1.26 g) in THF (100 mL) was added 0.5M cyclopropylmagnesium bromide-THF solution (14.90 mL) under ice-cooling, and the mixture was stirred under ice-cooling for 20 min, and stirred at room temperature for 3 hr. To the reaction mixture was added saturated aqueous ammonium chloride solution, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane) to give the title compound (1.130 g).

MS: $[M+H]^+$ 227.9.

B) rac-N-{6-[cyclopropyl(hydroxy)methyl]pyridin-3-yl}-1-[4-fluoro-2-(2,2,2-trifluoroethoxy)phenyl]-2-oxo-1,2-dihydropyridine-3-carboxamide A mixture of rac-(5-bromopyridin-2-yl) (cyclopropyl)methanol (580 mg), benzphenonimine (0.469 mL), sodium tert-butoxide (367 mg), rac-2,2'-bis(diphenylphosphino)-1,1'-binaphthyl (950 mg), tris(dibenzylideneacetone)dipalladium(0) (466 mg) and toluene (10 mL) was stirred under microwave irradiation at 110° C. for 1 hr. To the reaction mixture was added water, and the mixture was extracted with ethyl acetate. The organic layer was separated, washed with saturated brine, dried over anhydrous sodium sulfate, and concentrated under reduced pressure. The residue was purified by silica gel column chromatography (NH, ethyl acetate/hexane). To the obtained residue were added THF (10.00 mL), EtOH (10.00 mL) and 2M hydrochloric acid (1.526 mL), and the mixture was stirred at room temperature for 30 min, and concentrated under reduced pressure. The residue was purified by silica gel column chromatography (NH, MeOH/ethyl acetate) to give rac-(5-aminopyridin-2-yl) (cyclopropyl)methanol (367 mg) as a crude product. To a mixture of the obtained crude product (80 mg), 1-[4-fluoro-2-(2,2,2-trifluoroethoxy)phenyl]-2-oxo-1,2-dihydropyridine-3-carboxylic acid (72.0 mg), TEA (0.045 mL) and DMF (0.8 mL) was added HATU (124 mg), and the mixture was stirred overnight at room temperature. The reaction mixture was purified by silica gel column chromatography (ethyl acetate/hexane), and the solid was recrystallized from diethyl ether/hexane to give the title compound (61.0 mg).

$^1$H NMR (300 MHz, DMSO-$d_6$) δ 0.30-0.46 (4H, m), 1.03-1.20 (1H, m), 4.01-4.16 (1H, m), 4.75-4.97 (2H, m), 5.27 (1H, d, J=4.5 Hz), 6.71 (1H, t, J=6.8 Hz), 7.11 (1H, td, J=8.4, 2.4 Hz), 7.35-7.51 (2H, m), 7.62 (1H, dd, J=8.9, 6.2 Hz), 8.02 (1H, dd, J=6.6, 2.1 Hz), 8.14 (1H, dd, J=8.5, 2.4 Hz), 8.59 (1H, dd, J=7.2, 1.9 Hz), 8.71 (1H, d, J=2.3 Hz), 11.93 (1H, s).

Example 80

N-[6-(cyanomethyl)pyridin-3-yl]-1-[4-fluoro-2-(2,2,2-trifluoroethoxy)phenyl]-2-oxo-1,2-dihydropyridine-3-carboxamide A) (5-nitropyridin-2-yl)acetonitrile To a mixture of 2-chloro-5-nitropyridine (2.05 g) and THF (30 mL) were added tert-butyl cyanoacetate (2.215 mL) and potassium carbonate (3.57 g), and the mixture was stirred overnight at 70° C. To the reaction mixture was added water, and the mixture was extracted with ethyl acetate. The organic layer was washed with water, dried over anhydrous magnesium sulfate, and concentrated under reduced pressure to give rac-tert-butyl cyano(5-nitropyridin-2-yl)acetate as a crude product. To a mixture of the obtained crude product and toluene (50 mL) was added 4-methylbenzenesulfonic acid monohydrate (0.246 g), and the mixture was stirred at 110° C. for 1 hr. The reaction mixture was concentrated under reduced pressure. The residue was purified by silica gel column chromatography (ethyl acetate/hexane) to give the title compound (1.24 g).

$^1$H NMR (300 MHz, DMSO-$d_6$) δ 4.46 (2H, s), 7.71 (1H, d, J=8.7 Hz), 8.64 (1H, dd, J=8.7, 2.6 Hz), 9.37 (1H, d, J=2.3 Hz).

B) (5-aminopyridin-2-yl)acetonitrile

A mixture of (5-nitropyridin-2-yl)acetonitrile (930 mg), 3.5-6.5% palladium on carbon-ethylene diamine complex (93 mg) and EtOH (15 mL) was stirred under hydrogen atmosphere at room temperature for 8 hr. The catalyst was removed by filtration, and the filtrate was concentrated under reduced pressure to give the title compound (420 mg).

MS: $[M+H]^+$ 134.0.

C) N-[6-(cyanomethyl)pyridin-3-yl]-1-[4-fluoro-2-(2,2,2-trifluoroethoxy)phenyl]-2-oxo-1,2-dihydropyridine-3-carboxamide A mixture of 1-[4-fluoro-2-(2,2,2-trifluoroethoxy)phenyl]-2-oxo-1,2-dihydropyridine-3-carboxylic acid (60 mg), (5-aminopyridin-2-yl)acetonitrile (31.4 mg), HATU (103 mg), TEA (0.050 mL) and DMF (1 mL) was stirred overnight at room temperature. The reaction mixture was purified by silica gel column chromatography (ethyl acetate/hexane), and the solid was washed with ethyl acetate/diisopropyl ether to give the title compound (26.2 mg).

$^1$H NMR (300 MHz, DMSO-$d_6$) δ 4.16 (2H, s), 4.80-4.95 (2H, m), 6.66-6.77 (1H, m), 7.11 (1H, td, J=8.5, 2.6 Hz), 7.36-7.46 (2H, m), 7.62 (1H, dd, J=8.7, 6.0 Hz), 8.03 (1H, dd, J=6.8, 2.3 Hz), 8.22 (1H, dd, J=8.3, 2.6 Hz), 8.59 (1H, dd, J=7.3, 2.1 Hz), 8.80 (1H, d, J=1.9 Hz), 12.01 (1H, s).

Example 94

1-(4-methoxy-1-methyl-1H-pyrazol-5-yl)-2-oxo-N-[6-(2,2,2-trifluoroethoxy)pyridin-3-yl]-1,2-dihydropyridine-3-carboxamide A) 4-bromo-1-methyl-5-nitro-1H-pyrazole To a mixture of conc. nitric acid (9.87 g) and conc. sulfuric acid (100 mL) was added dropwise 4-bromo-1-methyl-1H-pyrazole (25.0 g) at 0° C., and the mixture was stirred at 100° C. for 1 hr. The reaction mixture was poured into ice water, adjusted to pH=7-8 with 25% ammonia aqueous solution, and extracted with ethyl acetate. The organic layer was separated, washed with saturated brine, dried over anhydrous sodium sulfate, and concentrated under reduced pressure. The residue was purified by silica gel column chromatography (ethyl acetate/petroleum ether) to give the title compound (10.2 g).

$^1$H NMR (400 MHz, $CDCl_3$) δ 4.23 (3H, s), 7.54 (1H, s)

B) 4-methoxy-1-methyl-5-nitro-1H-pyrazole

To a mixture of 4-bromo-1-methyl-5-nitro-1H-pyrazole (10.2 g) and MeOH (100 mL) was added sodium methoxide (13.4 g), and the mixture was stirred at 65° C. for 16 hr. To the reaction mixture was added water, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/petroleum ether) to give the title compound (432 mg).

$^1$H NMR (400 MHz, $CDCl_3$) δ 3.97 (3H, s), 4.19 (3H, s), 7.30 (1H, s).

C) 4-methoxy-1-methyl-1H-pyrazol-5-amine hydrochloride

To a solution of 4-methoxy-1-methyl-5-nitro-1H-pyrazole (712 mg) in MeOH (10 mL) was added 10% palladium-carbon (100 mg), and the mixture was stirred under normal pressure of hydrogen atmosphere at room temperature for 1 hr. The catalyst was removed by filtration, to the filtrate was added 4M hydrogen chloride-dioxane solution (10 mL), and the mixture was concentrated under reduced pressure to give the title compound (623 mg).

$^1$H NMR (400 MHz, DMSO-$d_6$) δ 3.71 (3H, s), 3.73 (3H, s), 7.88 (1H, s).

D) ethyl 3-[(4-methoxy-1-methyl-1H-pyrazol-5-yl)amino]-3-oxopropanoate

To a mixture of 4-methoxy-1-methyl-1H-pyrazol-5-amine hydrochloride (623 mg) and dichloromethane (10 mL) were added TEA (771 mg) and ethyl 3-chloro-3-oxopropanoate (631 mg), and the mixture was stirred at room temperature for 16 hr. To the reaction mixture was added water, and the mixture was extracted with dichloromethane. The organic layer was separated, washed with saturated brine, dried over anhydrous sodium sulfate, and concentrated under reduced pressure. The residue was purified by silica gel column chromatography (ethyl acetate/petroleum ether) to give the title compound (310 mg).

MS: $[M+H]^+$ 241.8.

E) ethyl 1-(4-methoxy-1-methyl-1H-pyrazol-5-yl)-2-oxo-1,2-dihydropyridine-3-carboxylate A mixture of ethyl 3-[(4-methoxy-1-methyl-1H-pyrazol-5-yl)amino]-3-oxopropanoate (310 mg), 3-(dimethylamino)acrolein (382 mg), EtOH (4 mL) and acetic acid (100 μL) was stirred at 80° C. for 16 hr. The reaction mixture was concentrated under reduced pressure, and the residue was purified by silica gel column chromatography (ethyl acetate/petroleum ether) to give the title compound (224 mg).

MS: $[M+H]^+$ 277.8.

F) 1-(4-methoxy-1-methyl-1H-pyrazol-5-yl)-2-oxo-1,2-dihydropyridine-3-carboxylic acid To a mixture of ethyl 1-(4-methoxy-1-methyl-1H-pyrazol-5-yl)-2-oxo-1,2-dihydropyridine-3-carboxylate (224 mg), MeOH (2 mL), THF (2 mL) and water (2 mL) was added lithium hydroxide monohydrate (39 mg), and the mixture was stirred at room temperature for 16 hr. The reaction mixture was concentrated under reduced pressure, to the residue was added water, and the mixture was extracted with ethyl acetate. The aqueous layer was adjusted to pH=6 with 1M hydrochloric acid, and extracted with ethyl acetate. The organic layers were combined, washed with saturated brine, dried over anhydrous sodium sulfate, and concentrated under reduced pressure to give the title compound (86 mg).

MS: $[M+H]^+$ 249.8.

G) 1-(4-methoxy-1-methyl-1H-pyrazol-5-yl)-2-oxo-N-[6-(2,2,2-trifluoroethoxy)pyridin-3-yl]-1,2-dihydropyridine-3-carboxamide To a mixture of 1-(4-methoxy-1-methyl-1H-pyrazol-5-yl)-2-oxo-1,2-dihydropyridine-3-carboxylic acid (40 mg) and DMF (5 mL) were added HATU (92 mg) and DIPEA (52 mg), and the mixture was stirred at room temperature for 30 min. To the reaction mixture was added 6-(2,2,2-trifluoroethoxy)pyridin-3-amine (34 mg), and the mixture was stirred at room temperature for 16 hr. To the reaction mixture was added water, and the mixture was extracted with ethyl acetate. The organic layer was separated, washed with saturated brine, dried over anhydrous sodium sulfate, and concentrated under reduced pressure. The residue was purified by preparative liquid chromatography (0.05% aqueous ammonia-containing acetonitrile/0.1% aqueous ammonia) to give the title compound (21 mg).

$^1H$ NMR (400 MHz, $CDCl_3$) δ 3.72 (3H, s), 3.81 (3H, s), 4.74 (2H, q, J=8.8 Hz), 6.64 (1H, t, J=6.8 Hz), 6.86 (1H, d, J=8.8 Hz), 7.40 (1H, s), 7.48 (1H, dd, J=6.8, 2.0 Hz), 8.12 (1H, dd, J=8.8, 2.4 Hz), 8.40 (1H, d, J=2.4 Hz), 8.76 (1H, dd, J=7.2, 2.0 Hz), 11.55 (1H, brs).

Example 98

1-[4-fluoro-2-(2,2,2-trifluoroethoxy)phenyl]-N-[4-(2-hydroxypropan-2-yl)phenyl]-6-oxo-1,6-dihydropyrimidine-5-carboxamide A) 4-fluoro-1-isothiocyanato-2-(2,2,2-trifluoroethoxy)benzene To a mixture of 4-fluoro-2-(2,2,2-trifluoroethoxy)aniline (8.10 g) and THF (100 mL) was added 1,1'-thiocarbonyldiimidazole (7.59 g), and the mixture was stirred at room temperature for 15 hr. The reaction mixture was concentrated under reduced pressure, and the residue was purified by silica gel column chromatography (ethyl acetate/petroleum ether) to give the title compound (6.90 g).

$^1H$ NMR (400 MHz, DMSO-$d_6$) δ 4.95 (2H, q, J=8.8 Hz), 6.95 (1H, t, J=8.4 Hz), 7.31 (1H, dd, J=10.4, 2.8 Hz), 7.40 (1H, dd, J=8.8, 6.0 Hz).

B) N-[4-fluoro-2-(2,2,2-trifluoroethoxy)phenyl]thiourea

To a mixture of 4-fluoro-1-isothiocyanato-2-(2,2,2-trifluoroethoxy)benzene (6.90 g) and MeOH (10 mL) was added 7N ammonia-MeOH solution (50 mL), and the mixture was stirred at room temperature for 15 hr. The reaction mixture was concentrated under reduced pressure to give the title compound (6.95 g).

MS: $[M+H]^+$ 268.8.

C) ethyl 3-[4-fluoro-2-(2,2,2-trifluoroethoxy)phenyl]-4-oxo-2-thioxo-1,2,3,4-tetrahydropyrimidine-5-carboxylate A mixture of N-[4-fluoro-2-(2,2,2-trifluoroethoxy)phenyl]thiourea (5.90 g), diethyl ethoxymethylenemalonate (14.3 g), conc. hydrochloric acid (6 mL) and EtOH (60 mL) was stirred at 100° C. for 15 hr. The reaction mixture was poured into water, and extracted with ethyl acetate. The organic layer was separated, washed with saturated brine, dried over anhydrous sodium sulfate, and concentrated under reduced pressure. The residue was purified by silica gel column chromatography (ethyl acetate/petroleum ether) to give the title compound (5.90 g).

MS: $[M+H]^+$ 393.1.

D) ethyl 1-[4-fluoro-2-(2,2,2-trifluoroethoxy)phenyl]-2-(methylsulfanyl)-6-oxo-1,6-dihydropyrimidine-5-carboxylate A mixture of ethyl 3-[4-fluoro-2-(2,2,2-trifluoroethoxy)phenyl]-4-oxo-2-thioxo-1,2,3,4-tetrahydropyrimidine-5-carboxylate (6.77 g), sodium carbonate (5.49 g), methyl iodide (2.94 g) and DMF (100 mL) was stirred at room temperature for 15 hr. The reaction mixture was poured into water, and extracted with ethyl acetate. The organic layer was separated, washed with water, dried over anhydrous sodium sulfate, and concentrated under reduced pressure. The residue was purified by silica gel column chromatography (ethyl acetate/petroleum ether) to give the title compound (5.15 g).

MS: $[M+H]^+$ 406.7.

E) ethyl 1-[4-fluoro-2-(2,2,2-trifluoroethoxy)phenyl]-6-oxo-1,6-dihydropyrimidine-5-carboxylate A mixture of ethyl 1-[4-fluoro-2-(2,2,2-trifluoroethoxy)phenyl]-2-(methylsulfanyl)-6-oxo-1,6-dihydropyrimidine-5-carboxylate (5.15 g), triethylsilane (3.09 g), copper(I) 2-thiophenecarboxylate (5.36 g), tetrakis(triphenylphosphine)palladium(0) (1.54 g) and dioxane (60 mL) was stirred under nitrogen atmosphere at 80° C. for 15 hr. The reaction mixture was poured into water, and extracted with ethyl acetate. The organic layer was separated, washed with saturated brine, dried over anhydrous sodium sulfate, and concentrated under reduced pressure. The residue was purified by silica gel column chromatography (ethyl acetate/petroleum ether) to give the title compound (3.15 g).

MS: $[M+H]^+$ 360.8.

F) 1-[4-fluoro-2-(2,2,2-trifluoroethoxy)phenyl]-N-[4-(2-hydroxypropan-2-yl)phenyl]-6-oxo-1,6-dihydropyrimidine-5-carboxamide A mixture of ethyl 1-[4-fluoro-2-(2,2,2-trifluoroethoxy)phenyl]-6-oxo-1,6-dihydropyrimidine-5-carboxylate (370 mg), tributyltin hydride (1.22 g) and toluene (10 mL) was stirred at 110° C. for 15 hr. The reaction mixture was poured into water, adjusted to pH=5-6 with 1N hydrochloric acid, and extracted with ethyl acetate. The organic layer was separated, washed with saturated brine, dried over anhydrous sodium sulfate, and concentrated under reduced pressure to give 1-[4-fluoro-2-(2,2,2-trifluoroethoxy)phenyl]-6-oxo-1,6-dihydropyrimidine-5-carboxylic acid as a crude product. A mixture of the obtained crude product, 2-(4-aminophenyl)propan-2-ol (300 mg), HATU (500 mg), DIPEA (400 mg) and DMF (5 mL) was stirred at room temperature for 15 hr. The reaction mixture was poured into water, and extracted with ethyl acetate. The organic layer was separated, washed with saturated brine, dried over anhydrous sodium sulfate, and concentrated under reduced pressure. The residue was purified by preparative liquid chromatography (0.225% formic acid-containing acetonitrile/0.225% formic acid-containing water) to give a crude product. The obtained crude product was purified by thin layer chromatography (ethyl acetate/petroleum ether) to give the title compound (38 mg).

$^1$H NMR (400 MHz, DMSO-$d_6$) δ 1.40 (6H, s), 4.90 (2H, q, J=8.8 Hz), 5.00 (1H, brs), 7.16 (1H, t, J=8.4 Hz), 7.35-7.50 (3H, m), 7.58 (2H, d, J=8.4 Hz), 7.71 (1H, dd, J=8.8, 6.0 Hz), 8.76 (1H, s), 8.88 (1H, s), 11.04 (1H, brs).

Example 108

1-[4,5-difluoro-2-(2,2,2-trifluoroethoxy)phenyl]-N-[4-(2-hydroxypropan-2-yl)phenyl]-2-oxo-1,2-dihydropyridine-3-carboxamide

A) 4,5-difluoro-2-(2,2,2-trifluoroethoxy)aniline

To a mixture of 2-bromo-4,5-difluorophenol (5.17 g), cesium carbonate (12.09 g) and DMF (100 mL) was added 2,2,2-trifluoroethyl trifluoromethanesulfonate (3.92 mL) under ice-cooling, and the mixture was stirred overnight at room temperature. To the reaction mixture was added water, and the mixture was extracted with ethyl acetate. The organic layer was separated, washed with water and saturated brine, dried over anhydrous sodium sulfate, and concentrated under reduced pressure. The residue was purified by silica gel column chromatography (ethyl acetate/hexane) to give 1-bromo-4,5-difluoro-2-(2,2,2-trifluoroethoxy)benzene (8.43 g) as a crude product. To the obtained crude product were added benzphenonimine (4.49 mL), sodium tert-butoxide (3.50 g), tris(dibenzylideneacetone)dipalladium(0) (1.113 g), 2,2'-bis(diphenylphosphino)-1,1'-binaphthyl (2.270 g) and toluene (100 mL), and the mixture was refluxed for 4 hr. To the reaction mixture were added tris(dibenzylideneacetone)dipalladium(0) (0.556 g) and 2,2'-bis(diphenylphosphino)-1,1'-binaphthyl (1.135 g), and the mixture was refluxed for 3 hr. To the reaction mixture was added water, and the mixture was extracted with ethyl acetate. The organic layer was separated, washed with saturated brine, dried over anhydrous sodium sulfate, and concentrated under reduced pressure. To the residue were added THF (80 mL), EtOH (80 mL) and 2M hydrochloric acid (30 mL), and the mixture was stirred at room temperature for 1 hr, and concentrated under reduced pressure. The residue was purified by silica gel column chromatography (NH, ethyl acetate/hexane) to give the title compound (1.850 g).

MS: $[M+H]^+$ 227.9.

B) ethyl 3-[4,5-difluoro-2-(2,2,2-trifluoroethoxy)anilino]-3-oxopropanoate

To a mixture of 4,5-difluoro-2-(2,2,2-trifluoroethoxy)aniline (1.85 g), TEA (1.703 mL) and THF (30 mL) was added ethyl 3-chloro-3-oxopropanoate (1.251 mL) under ice-cooling, and the mixture was stirred overnight at room temperature. To the reaction mixture was added water, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane) to give the title compound (2.51 g).

MS: $[M+H]^+$ 341.9.

C) ethyl 1-[4,5-difluoro-2-(2,2,2-trifluoroethoxy)phenyl]-2-oxo-1,2-dihydropyridine-3-carboxylate To a mixture of ethyl 3-[4,5-difluoro-2-(2,2,2-trifluoroethoxy)anilino]-3-oxopropanoate (2.184 g), EtOH (30 mL) and acetic acid (1.500 mL) was added 3-(dimethylamino)acrolein (3.20 mL), and the mixture was stirred at 80° C. for 2 hr, and stirred overnight at 70° C. To the reaction mixture was added water, and the mixture was extracted with ethyl acetate. The organic layer was separated, washed with water and saturated brine, dried over anhydrous sodium sulfate, and concentrated under reduced pressure. The residue was purified by silica gel column chromatography (ethyl acetate/hexane) to give the title compound (1.20 g).

MS: $[M+H]^+$ 378.0.

D) 1-[4,5-difluoro-2-(2,2,2-trifluoroethoxy)phenyl]-2-oxo-1,2-dihydropyridine-3-carboxylic acid To a mixture of ethyl 1-[4,5-difluoro-2-(2,2,2-trifluoroethoxy)phenyl]-2-oxo-1,2-dihydropyridine-3-carboxylate (985 mg) and MeOH (10 mL) was added 4M aqueous lithium hydroxide solution (1.958 mL), and the mixture was stirred for 5 days. The reaction mixture was neutralized with 2M hydrochloric acid, and the precipitate was collected by filtration, and washed with water to give the title compound (699 mg).

MS: $[M+H]^+$ 349.9.

E) 1-[4,5-difluoro-2-(2,2,2-trifluoroethoxy)phenyl]-N-[4-(2-hydroxypropan-2-yl)phenyl]-2-oxo-1,2-dihydropyridine-3-carboxamide To a mixture of 1-[4,5-difluoro-2-(2,2,2-trifluoroethoxy)phenyl]-2-oxo-1,2-dihydropyridine-3-carboxylic acid (65.4 mg), 2-(4-aminophenyl)propan-2-ol (34 mg), TEA (0.039 mL) and DMF (0.8 mL) was added HATU (107 mg), and the mixture was stirred overnight at room temperature. The reaction mixture was purified by silica gel column chromatography (ethyl acetate/hexane), and the solid was recrystallized from ethyl acetate/hexane to give the title compound (50.0 mg).

$^1$H NMR (300 MHz, DMSO-$d_6$) δ 1.41 (6H, s), 4.77-4.91 (2H, m), 4.95 (1H, s), 6.71 (1H, t, J=7.0 Hz), 7.34-7.49 (2H, m), 7.58 (2H, d, J=8.7 Hz), 7.70 (1H, dd, J=12.0, 7.2 Hz), 7.92 (1H, dd, J=10.5, 8.3 Hz), 8.00 (1H, dd, J=6.6, 2.1 Hz), 8.57 (1H, dd, J=7.2, 2.3 Hz), 11.75 (1H, s).

Example 109

2-[2-(2,2-difluoroethoxy)phenyl]-6-methyl-3-oxo-N-[6-(1,1,3,3-tetrafluoro-2-hydroxypropan-2-yl)pyridin-3-yl]-2,3-dihydropyridazine-4-carboxamide

A) 1-(2,2-difluoroethoxy)-2-nitrobenzene

To a mixture of 2-nitrophenol (47 g), cesium carbonate (143 g) and DMF (500 mL) was added 2,2-difluoroethyl trifluoromethanesulfonate (76 g) under ice-cooling. The mixture was stirred overnight at room temperature, and to the mixture was added water. The resulting solid was collected by filtration to give the title compound (67.2 g).

$^1$H NMR (300 MHz, DMSO-$d_6$) δ 4.43-4.61 (2H, m), 6.17-6.61 (1H, m), 7.13-7.26 (1H, m), 7.38-7.48 (1H, m), 7.62-7.74 (1H, m), 7.85-7.96 (1H, m).

B) 2-(2,2-difluoroethoxy)aniline

To a solution of 1-(2,2-difluoroethoxy)-2-nitrobenzene (67.2 g) in MeOH (700 mL) was added 10% palladium-carbon (55% wet, 3.0 g). The mixture was stirred under normal pressure of hydrogen atmosphere overnight. The mixture was filtered through Celite with ethyl acetate, and the filtrate was concentrated under reduced pressure to give the title compound (57.0 g).

MS: $[M+H]^+$ 174.1.

C) [2-(2,2-difluoroethoxy)phenyl]hydrazine

A mixture of conc. hydrochloric acid (500 mL) and 2-(2,2-difluoroethoxy)aniline (57 g) was stirred at 0° C. for 30 min, to the mixture was added dropwise a mixture of sodium nitrate (27.3 g) and water (100 mL) at 0° C., and the mixture was stirred at 0° C. for 30 min. Then, to the mixture was added dropwise a mixture of tin chloride (187 g) and conc. hydrochloric acid (300 mL) at 0° C., and the mixture was stirred at 0° C. for 2 hr. The reaction mixture was filtered without washing, and the filter cake was dissolved in 2N aqueous sodium hydroxide solution (500 mL). The mixture was extracted with ethyl acetate. The combined organic layers were washed with saturated brine, dried over anhydrous sodium sulfate, and concentrated under reduced pressure. The resulting solid was collected by filtration with hexane to give the title compound (43.3 g).

MS: $[M+H]^+$ 189.0.

D) rac-ethyl 2-[2-(2,2-difluoroethoxy)phenyl]-6-methyl-3-oxo-2,3,4,5-tetrahydropyridazine-4-carboxylate To a solution of [2-(2,2-difluoroethoxy)phenyl]hydrazine (35.0 g) in THF (400 mL) and acetic acid (40.0 mL) was added diethyl acetonylmalonate (40.2 g) at 0° C. The mixture was stirred at room temperature for 5 hr. The mixture was diluted with toluene, and concentrated under reduced pressure. To a solution of the residue in toluene (400 mL) was added p-toluenesulfonic acid monohydrate (7.08 g) at room temperature. The mixture was stirred overnight at 100° C. p-Toluenesulfonic acid monohydrate (7.08 g) was added again to the mixture. The mixture was stirred at 100° C. for 5 hr. The mixture was poured into saturated aqueous sodium hydrogencarbonate solution, and extracted with ethyl acetate. The organic layer was separated, washed with saturated brine, dried over anhydrous sodium sulfate, and concentrated under reduced pressure. The residue was purified by silica gel column chromatography (SI, followed by NH, ethyl acetate/hexane) to give the title compound (16.8 g)

MS: $[M+H]^+$ 341.1.

E) ethyl 2-[2-(2,2-difluoroethoxy)phenyl]-6-methyl-3-oxo-2,3-dihydropyridazine-4-carboxylate To a solution of rac-ethyl 2-[2-(2,2-difluoroethoxy)phenyl]-6-methyl-3-oxo-2,3,4,5-tetrahydropyridazine-4-carboxylate (16.8 g) in toluene (400 mL) was added 2,3-dichloro-5,6-dicyano-1,4-benzoquinone (11.21 g) at room temperature. The mixture was stirred at 100° C. for 2 hr. The mixture was filtered on NH silica gel with ethyl acetate, and the filtrate was concentrated under reduced pressure. The residue was purified by silica gel column chromatography (NH, ethyl acetate/hexane) to give the title compound (11.2 g).

MS: $[M+H]^+$ 339.1.

F) 2-[2-(2,2-difluoroethoxy)phenyl]-6-methyl-3-oxo-2,3-dihydropyridazine-4-carboxylic acid To a solution of ethyl 2-[2-(2,2-difluoroethoxy)phenyl]-6-methyl-3-oxo-2,3-dihydropyridazine-4-carboxylate (11.2 g) in EtOH (300 mL) was added 2M aqueous sodium hydroxide solution (83 mL) at room temperature. The mixture was stirred at room temperature for 1 hr. The mixture was concentrated under reduced pressure, and the resulting solid was dissolved in water. The solution was acidified with 1N hydrochloric acid at 0° C., and the precipitate was collected by filtration to give the title compound (9.05 g).

MS: $[M+H]^+$ 311.1.

G) 1,1,3,3-tetrafluoro-2-(5-nitropyridin-2-yl)propan-2-ol

To a mixture of 5-nitropyridine-2-carboxylic acid (1.0 g) and THF (20 mL) were added oxalyl chloride (0.604 mL) and DMF (one drop) under ice-cooling. The mixture was stirred at room temperature for 2 hr, and concentrated under reduced pressure to give 5-nitropyridine-2-carbonyl chloride as a crude product. To a mixture of the obtained crude product and acetonitrile (15 mL) were added [bromo(difluoro)methyl] (trimethyl)silane (1.922 mL), triphenylphosphine (2.70 g) and 1,3-dimethyl-3,4,5,6-tetrahydro-2(1H)-pyrimidinone (1.987 mL) at 0° C. The mixture was stirred overnight at room temperature. To the mixture were added water (10 mL) and pyridine (2 mL) at room temperature. The mixture was stirred at 80° C. for 3 hr. To the mixture was added water, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane) to give the title compound (0.606 g).

MS: $[M+H]^+$ 254.9.

H) 2-(5-aminopyridin-2-yl)-1,1,3,3-tetrafluoropropan-2-ol

To a mixture of 1,1,3,3-tetrafluoro-2-(5-nitropyridin-2-yl)propan-2-ol (606 mg), EtOH (6 mL) and water (6 mL) was added ammonium chloride (638 mg) and iron powder (666 mg) at room temperature. The mixture was refluxed for 3 hr. The insoluble substance was removed by filtration. To the filtrate was added saturated aqueous sodium hydrogencarbonate solution, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane) to give the title compound (235 mg).

MS: $[M+H]^+$ 224.9.

I) 2-[2-(2,2-difluoroethoxy)phenyl]-6-methyl-3-oxo-N-[6-(1,1,3,3-tetrafluoro-2-hydroxypropan-2-yl)pyridin-3-yl]-2,3-dihydropyridazine-4-carboxamide To a solution of 2-[2-(2,2-difluoroethoxy)phenyl]-6-methyl-3-oxo-2,3-dihydropyridazine-4-carboxylic acid (60 mg) and 2-(5-aminopyridin-2-yl)-1,1,3,3-tetrafluoropropan-2-ol (52.0 mg) in DMF (1 mL) and TEA (0.040 mL) was added HATU (110 mg) at room temperature. The mixture was stirred at room temperature for 1 hr. To the mixture was added water at room temperature, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane), and crystallized from ethyl acetate/diisopropyl ether/hexane to give the title compound (62.0 mg).

$^1$H NMR (300 MHz, DMSO) δ 2.44 (3H, s), 4.37 (2H, t, J=14.9 Hz), 5.99-6.75 (3H, m), 7.12 (1H, s), 7.19 (1H, td, J=7.7, 1.1 Hz), 7.35 (1H, d, J=7.5 Hz), 7.43-7.58 (2H, m), 7.73 (1H, d, J=8.7 Hz), 8.25-8.34 (2H, m), 8.88 (1H, d, J=1.9 Hz), 11.85 (1H, s).

Example 114

N-[4-(2-hydroxypropan-2-yl)phenyl]-2-oxo-2'-(2,2,2-trifluoroethoxy)-2H-[1,3'-bipyridine]-3-carboxamide A) 3-nitro-2-(2,2,2-trifluoroethoxy)pyridine To a mixture of 2,2,2-trifluoroethanol (3.38 g) and THF (10 mL) was added 1.3M lithium bis(trimethylsilyl)amide-THF solution (23.82 mL) under ice-cooling, and the mixture was stirred under ice-cooling for 15 min. To the reaction mixture was added 2-fluoro-3-nitropyridine (4 g) under ice-cooling, and the mixture was stirred overnight at room temperature. To the reaction mixture was added saturated aqueous ammonium chloride solution, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane) to give the title compound (3.03 g).

MS: $[M+H]^+$ 222.9.

B) 2-(2,2,2-trifluoroethoxy)pyridin-3-amine

To a mixture of 3-nitro-2-(2,2,2-trifluoroethoxy)pyridine (3.03 g) and MeOH (40 mL) was added 10% palladium-carbon (55% wet, 400 mg), and the mixture was stirred overnight under normal pressure of hydrogen atmosphere at room temperature. The catalyst was removed by filtration, and the filtrate was concentrated under reduced pressure to give the title compound (2.490 g).

MS: $[M+H]^+$ 192.9.

C) ethyl 3-oxo-3-{[2-(2,2,2-trifluoroethoxy)pyridin-3-yl]amino}propanoate

To a mixture of 2-(2,2,2-trifluoroethoxy)pyridin-3-amine (2.49 g), TEA (2.71 mL) and THF (40 mL) was added ethyl 3-chloro-3-oxopropanoate (1.991 mL) under ice-cooling, and the mixture was stirred at room temperature for 3 hr. To the reaction mixture was added water, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane) to give the title compound (2.480 g).

MS: $[M+H]^+$ 306.9.

D) 2-oxo-2'-(2,2,2-trifluoroethoxy)-2H-[1,3'-bipyridine]-3-carboxylic acid

To a mixture of ethyl 3-oxo-3-{[2-(2,2,2-trifluoroethoxy)pyridin-3-yl]amino}propanoate (2.48 g), EtOH (40 mL) and acetic acid (2.000 mL) was added 3-(dimethylamino)acrolein (4.05 mL), and the mixture was refluxed for 3 hr, and stirred overnight at 70° C. To the reaction mixture was added water, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane) to give ethyl 2-oxo-2'-(2,2,2-trifluoroethoxy)-2H-[1,3'-bipyridine]-3-carboxylate (1.88 g) as a crude product. To the obtained crude product were added MeOH (20 mL) and 4M aqueous is lithium hydroxide solution (4 mL), and the mixture was stirred for 5 days. The reaction mixture was neutralized with 1M hydrochloric acid, and the precipitate was collected by filtration, and washed with water to give a crude product. The crude product was recrystallized from ethyl acetate/hexane to give the title compound (807 mg).

MS: $[M+H]^+$ 3144.9.

E) N-[4-(2-hydroxypropan-2-yl)phenyl]-2-oxo-2'-(2,2,2-trifluoroethoxy)-2H-[1,3'-bipyridine]-3-carboxamide To a mixture of 2-oxo-2'-(2,2,2-trifluoroethoxy)-2H-[1,3'-bipyridine]-3-carboxylic acid (70 mg), 2-(4-aminophenyl)propan-2-ol (40 mg), TEA (0.047 mL) and DMF (0.8 mL) was added HATU (127 mg), and the mixture was stirred at room temperature for 4 hr. The reaction mixture was purified by silica gel column chromatography (ethyl acetate/hexane), and the solid was recrystallized from diethyl ether/hexane to give the title compound (42.0 mg).

$^1$H NMR (300 MHz, DMSO-$d_6$) δ 1.41 (6H, s), 4.95 (1H, s), 4.99-5.16 (2H, m), 6.66-6.80 (1H, m), 7.30-7.48 (3H, m), 7.53-7.65 (2H, m), 8.08 (2H, ddd, J=7.2, 5.7, 2.1 Hz), 8.38 (1H, dd, J=4.9, 1.5 Hz), 8.59 (1H, dd, J=7.2, 2.3 Hz), 11.73 (1H, s).

Example 119

N-[6-(2-hydroxypropan-2-yl)pyridin-3-yl]-2-oxo-1-[5-(2,2,2-trifluoroethoxy)pyrimidin-4-yl]-1,2-dihydropyridine-3-carboxamide A) 5-(2,2,2-trifluoroethoxy)pyrimidin-4-amine A mixture of 4-aminopyrimidin-5-ol (2.00 g), 2,2,2-trifluoroethyl trifluoromethanesulfonate (4.21 g), cesium carbonate (7.04 g) and DMF (15 mL) was stirred at room temperature for 12 hr. The reaction mixture was poured into water, and extracted with ethyl acetate. The organic layer was separated, dried over anhydrous sodium sulfate, and concentrated under reduced pressure. The residue was purified by silica gel column chromatography (ethyl acetate) to give the title compound (2.40 g).

$^1$H NMR (400 MHz, DMSO-$d_6$) δ 4.79 (2H, q, J=9.2 Hz), 6.81 (2H, brs), 7.96 (1H, s), 8.08 (1H, s).

B) ethyl 3-oxo-3-{[5-(2,2,2-trifluoroethoxy)pyrimidin-4-yl]amino}propanoate

To a mixture of 5-(2,2,2-trifluoroethoxy)pyrimidin-4-amine (1.20 g), TEA (943 mg) and dichloromethane (20 mL) was added ethyl 3-chloro-3-oxopropanoate (1.03 g) at 0° C., and the mixture was stirred at room temperature for 4 hr. To the reaction mixture was added ethyl 3-chloro-3-oxopropanoate (1.03 g) at 0° C., and the mixture was stirred at room temperature for 12 hr. The reaction mixture was poured into water, and extracted with dichloromethane. The organic layer was separated, and concentrated under reduced pressure. The residue was purified by silica gel column chromatography (ethyl acetate/petroleum ether) to give the title compound (1.09 g).

MS: [M+H]$^+$ 307.8.

C) ethyl 2-oxo-1-[5-(2,2,2-trifluoroethoxy)pyrimidin-4-yl]-1,2-dihydropyridine-3-carboxylate A mixture of ethyl 3-oxo-3-{[5-(2,2,2-trifluoroethoxy)pyrimidin-4-yl]amino}propanoate (480 mg), 3-(dimethylamino)acrolein (310 mg), EtOH (5 mL) and acetic acid (169 mg) was stirred at 60° C. for 12 hr. The reaction mixture was poured into water, and extracted with ethyl acetate. The organic layer was separated, dried over anhydrous sodium sulfate, and concentrated under reduced pressure. The residue was purified by silica gel column chromatography (ethyl acetate/petroleum ether) to give the title compound (370 mg).

MS: [M+H]$^+$ 344.1.

D) 2-oxo-1-[5-(2,2,2-trifluoroethoxy)pyrimidin-4-yl]-1,2-dihydropyridine-3-carboxylic acid To a mixture of ethyl 2-oxo-1-[5-(2,2,2-trifluoroethoxy)pyrimidin-4-yl]-1,2-dihydropyridine-3-carboxylate (270 mg), THF (3 mL) and water (3 mL) was added lithium hydroxide monohydrate (33 mg), and the mixture was stirred at room temperature for 16 hr. The reaction mixture was concentrated under reduced pressure, the residue was adjusted to pH=6 with 1M hydrochloric acid, and the precipitate was collected by filtration. To the obtained crude product was added water, and the mixture was extracted with ethyl acetate. The organic layer was separated, washed with saturated brine, dried over anhydrous sodium sulfate, and concentrated under reduced pressure to give the title compound (113 mg).

MS: [M+H]$^+$ 315.9.

E) 2-(5-bromopyridin-2-yl)propan-2-ol

To a mixture of methyl 5-bromopyridine-2-carboxylate (7.29 g) and THF (100 mL) was added dropwise 1M methylmagnesium bromide-2-methyltetrahydrofuran solution (23.62 mL) under ice-cooling, and the mixture was stirred overnight at room temperature. To the reaction mixture was added saturated aqueous ammonium chloride solution, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane) to give the title compound (3.59 g).

MS: [M+H]$^+$ 216.0.

F) 2-(5-aminopyridin-2-yl)propan-2-ol

A mixture of 2-(5-bromopyridin-2-yl)propan-2-ol (1.62 g), benzphenonimine (1.510 mL), cesium carbonate (7.33 g), 4,5-bis(diphenylphosphino)-9,9-dimethylxanthene (0.868 g), tris(dibenzylideneacetone)dipalladium(0) (0.687 g) and 1,2-dimethoxyethane (30 mL) was refluxed under nitrogen atmosphere for 4 hr. To the reaction mixture was added ethyl acetate, and the insoluble substance was removed by filtration. The filtrate was washed with water and saturated brine, dried over anhydrous sodium sulfate, and concentrated under reduced pressure. To the residue were added THF (15 mL), MeOH (15 mL) and 2M hydrochloric acid (10 mL), and the mixture was stirred at room temperature for 30 min, neutralized with 2M aqueous sodium hydroxide solution, and concentrated under reduced pressure. The residue was purified by silica gel column chromatography (NH, ethyl acetate/hexane) to give the title compound (0.713 g).

$^1$H NMR (300 MHz, DMSO-$d_6$) δ 1.35 (6H, s), 4.89 (1H, s), 5.07 (2H, s), 6.89 (1H, dd, J=8.5, 2.8 Hz), 7.26 (1H, d, J=9.0 Hz), 7.82 (1H, dd, J=2.6, 0.8 Hz).

G) N-[6-(2-hydroxypropan-2-yl)pyridin-3-yl]-2-oxo-1-[5-(2,2,2-trifluoroethoxy)pyrimidin-4-yl]-1,2-dihydropyridine-3-carboxamide To a mixture of 2-oxo-1-[5-(2,2,2-trifluoroethoxy)pyrimidin-4-yl]-1,2-dihydropyridine-3-carboxylic acid (50 mg), 2-(5-aminopyridin-2-yl)propan-2-ol (30 mg), TEA (0.033 mL) and DMF (0.8 mL) was added HATU (90 mg), and the mixture was stirred overnight at room temperature. The reaction mixture was purified by silica gel column chromatography (NH, ethyl acetate/hexane), and the solid was recrystallized from diethyl ether/hexane to give the title compound (28.0 mg).

$^1$H NMR (300 MHz, DMSO-$d_6$) δ 1.42 (6H, s), 5.03-5.21 (3H, m), 6.76-6.90 (1H, m), 7.64 (1H, d, J=8.7 Hz), 8.11 (1H, dd, J=8.7, 2.6 Hz), 8.18 (1H, dd, J=6.8, 2.3 Hz), 8.63 (1H, dd, J=7.2, 2.3 Hz), 8.68 (1H, d, J=2.3 Hz), 9.06 (1H, s), 9.09 (1H, s), 11.56 (1H, s).

Example 121 rac-2-oxo-1-[3-(2,2,2-trifluoroethoxy)pyridazin-4-yl]-N-[6-(1,1,1-trifluoro-2-hydroxypropan-2-yl)pyridin-3-yl]-1,2-dihydropyridine-3-carboxamide A) rac-2-(5-bromopyridin-2-yl)-1,1,1-trifluoropropan-2-ol To a solution of 1-(5-bromopyridin-2-yl)-2,2,2-trifluoroethan-1-one (1.0 g) in THF (20 mL) was added 3M methylmagnesium bromide-2-methyltetrahydrofuran solution (1.444 mL) under ice-cooling, and the mixture was stirred overnight at room temperature. To the reaction mixture was added saturated aqueous ammonium chloride solution, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane) to give the title compound (0.190 g).

MS: [M+H]$^+$ 269.8.

B) rac-2-(5-aminopyridin-2-yl)-1,1,1-trifluoropropan-2-ol

To a mixture of rac-2-(5-bromopyridin-2-yl)-1,1,1-trifluoropropan-2-ol (190 mg), benzphenonimine (0.142 mL), cesium carbonate (688 mg), 4,5-bis(diphenylphosphino)-9,9-dimethylxanthene (163 mg) and 1,2-dimethoxyethane (4 mL) was added tris(dibenzylideneacetone)dipalladium(0) (129 mg), and the mixture was refluxed under nitrogen atmosphere for 4 hr. To the reaction mixture was added ethyl acetate, the insoluble substance was removed by filtration, and the filtrate was concentrated under reduced pressure. To the residue were added THF (4 mL), MeOH (4 mL) and 2M hydrochloric acid (2 mL), and the mixture was stirred at room temperature for 30 min, neutralized with 2M aqueous sodium hydroxide solution, and concentrated under reduced pressure. The residue was purified by silica gel column chromatography (ethyl acetate/hexane) to give the title compound (110 mg).

MS: $[M+H]^+$ 207.0.

C) tert-butyl (3,6-dichloropyridazin-4-yl)carbamate

A mixture of 3,6-dichloropyridazine-4-carboxylic acid (3 g), TEA (2.383 mL), DPPA (3.69 mL) and tert-butyl alcohol (30 mL) was stirred overnight at 80° C. The reaction mixture was concentrated under reduced pressure, and the residue was purified by silica gel column chromatography (ethyl acetate/hexane) to give the title compound (2.61 g).

$^1$H NMR (300 MHz, DMSO-$d_6$) δ 1.51 (9H, s), 8.22 (1H, d, J=0.8 Hz), 9.64 (1H, brs).

D) 3,6-dichloropyridazin-4-amine

A mixture of tert-butyl (3,6-dichloropyridazin-4-yl)carbamate (2.61 g), 4M hydrogen chloride/ethyl acetate (37.1 mL) and ethyl acetate (20 mL) was stirred at room temperature for 5 hr. The reaction mixture was concentrated under reduced pressure to give the title compound (1.85 g).

MS: $[M+H]^+$ 163.9.

E) 6-chloro-3-(2,2,2-trifluoroethoxy)pyridazin-4-amine

A mixture of 3,6-dichloropyridazin-4-amine (1.85 g), 2,2,2-trifluoroethanol (1.620 mL), lithium hydroxide monohydrate (1.041 g), DMSO (20 mL) and water (2.000 mL) was stirred overnight at 80° C. To the reaction mixture was added water, and the mixture was stirred at room temperature for 1 hr. The precipitated solid was collected by filtration, and washed with water to give the title compound (2.20 g).

MS: $[M+H]^+$ 227.9.

F) 3-(2,2,2-trifluoroethoxy)pyridazin-4-amine

A mixture of 6-chloro-3-(2,2,2-trifluoroethoxy)pyridazin-4-amine (2.20 g), 10% palladium on carbon (49% wet, 220 mg) and MeOH (40 mL) was stirred under hydrogen atmosphere at room temperature for 5 hr. The catalyst was removed by filtration, and the filtrate was concentrated under reduced pressure to give the title compound (1.84 g).

MS: $[M+H]^+$ 193.9.

G) ethyl 3-oxo-3-{[3-(2,2,2-trifluoroethoxy)pyridazin-4-yl]amino}propanoate

To a mixture of 3-(2,2,2-trifluoroethoxy)pyridazin-4-amine (1.3 g), TEA (1.407 mL) and THF (6 mL) was added ethyl 3-chloro-3-oxopropanoate (1.034 mL) at 0° C., and the mixture was stirred overnight at room temperature. To the reaction mixture were added TEA (0.7 mL) and ethyl 3-chloro-3-oxopropanoate (0.5 mL) at room temperature, and the mixture was stirred at the same temperature for 8 hr. To the reaction mixture was added water, and the mixture was extracted with ethyl acetate. The organic layer was washed with saturated brine, dried over anhydrous magnesium sulfate, and concentrated under reduced pressure. The residue was purified by silica gel column chromatography (ethyl acetate/hexane) to give the title compound (1.534 g).

MS: $[M+H]^+$ 308.0.

H) ethyl 2-oxo-1-[3-(2,2,2-trifluoroethoxy)pyridazin-4-yl]-1,2-dihydropyridine-3-carboxylate To a mixture of ethyl 3-oxo-3-{[3-(2,2,2-trifluoroethoxy)pyridazin-4-yl]amino}propanoate (271 mg), EtOH (4 mL) and acetic acid (0.200 mL) was added 3-(dimethylamino)acrolein (0.422 mL) at room temperature, and the mixture was stirred overnight at 70° C. To the reaction mixture was added water, and the mixture was extracted with ethyl acetate. The organic layer was washed with saturated brine, dried over anhydrous magnesium sulfate, and concentrated under reduced pressure. The residue was purified by silica gel column chromatography (ethyl acetate/hexane) to give the title compound (105 mg).

MS: $[M+H]^+$ 343.9.

I) 2-oxo-1-[3-(2,2,2-trifluoroethoxy)pyridazin-4-yl]-1,2-dihydropyridine-3-carboxylic acid A mixture of ethyl 2-oxo-1-[3-(2,2,2-trifluoroethoxy)pyridazin-4-yl]-1,2-dihydropyridine-3-carboxylate (105 mg), 1M aqueous sodium hydroxide solution (0.918 mL) and MeOH (1.5 mL) was stirred overnight at room temperature. The reaction mixture was acidified with 1M hydrochloric acid, and the solvent was evaporated under reduced pressure. The precipitated solid was collected by filtration, and washed with water and diisopropyl ether to give the title compound (44 mg).

MS: $[M+H]^+$ 315.9.

J) rac-2-oxo-1-[3-(2,2,2-trifluoroethoxy)pyridazin-4-yl]-N-[6-(1,1,1-trifluoro-2-hydroxypropan-2-yl)pyridin-3-yl]-1,2-dihydropyridine-3-carboxamide To a mixture of 2-oxo-1-[3-(2,2,2-trifluoroethoxy)pyridazin-4-yl]-1,2-dihydropyridine-3-carboxylic acid (50 mg), rac-2-(5-aminopyridin-2-yl)-1,1,1-trifluoropropan-2-ol (50 mg), TEA (0.033 mL) and DMF (0.8 mL) was added HATU (90 mg), and the mixture was stirred at room temperature for 4 hr. The reaction mixture was purified by silica gel column chromatography (SI and NH, ethyl acetate/hexane) to give the title compound (3.70 mg).

$^1$H NMR (400 MHz, $CDCl_3$) δ1.72 (3H, s), 5.08 (2H, q, J=8.3 Hz), 6.12 (1H, s), 6.70 (1H, t, J=7.2 Hz), 7.44-7.55 (2H, m), 7.64 (1H, d, J=4.9 Hz), 8.32 (1H, dd, J=8.7, 2.6 Hz), 8.73-8.83 (2H, m), 9.21 (1H, d, J=5.3 Hz), 11.66 (1H, s).

Example 127

N-[4-(2-hydroxypropan-2-yl)phenyl]-3-oxo-2-[2-(2,2,2-trifluoroethoxy)phenyl]-2,3-dihydropyridazine-4-carboxamide To a mixture of 3-oxo-2-[2-(2,2,2-trifluoroethoxy)phenyl]-2,3-dihydropyridazine-4-carboxylic acid (100 mg), 2-(4-aminophenyl)propan-2-ol (69 mg), TEA (48.3 mg) and DMF (0.8 mL) was added HATU (182 mg) at room temperature. The mixture was stirred overnight at room temperature, and purified by silica gel column chromatography (SI, followed by NH, ethyl acetate/hexane), and the solid was recrystallized from diethyl ether/hexane to give the title compound (67 mg).

$^1$H NMR (300 MHz, DMSO-$d_6$) δ 1.41 (6H, s), 4.82 (2H, brs), 4.98 (1H, s), 7.25 (1H, td, J=7.5, 1.1 Hz), 7.39 (1H, d, J=7.5 Hz), 7.43-7.50 (2H, m), 7.51-7.64 (4H, m), 8.30 (1H, d, J=4.1 Hz), 8.34-8.40 (1H, m), 11.53 (1H, s).

Example 133

2-[2-(2,2-difluoroethoxy)phenyl]-N-[4-(2-hydroxypropan-2-yl)phenyl]-3-oxo-2,3-dihydropyridazine-4-carboxamide A) (2E)-{2-[2-(2,2-difluoroethoxy)phenyl]hydrazinylidene}acetaldehyde To a mixture of [2-(2,2-difluoroethoxy)phenyl]hydrazine (2.53 g), acetic acid (15 mL) and water (15.00 mL) was added 40% aqueous glyoxal solution (7.80 g), and the mixture was stirred at room temperature for 1 hr. The precipitate was collected by filtration, and washed with water to give a crude product. To the crude product was added ethyl acetate, and the mixture was washed with saturated brine, dried over anhydrous sodium sulfate, and concentrated under reduced pressure to give the title compound (2.76 g).

MS: $[M+H]^+$ 229.0.

B) 5-[(2E)-2-{2-[2-(2,2-difluoroethoxy)phenyl]hydrazinylidene}ethylidene]-2,2-dimethyl-1,3-dioxane-4,6-dione To a mixture of (2E)-{2-[2-(2,2-difluoroethoxy)phenyl]hydrazinylidene}acetaldehyde (2.76 g) and toluene (50 mL) were added 2,2-dimethyl-1,3-dioxane-4,6-dione (1.743 g), piperidine (0.239 mL) and acetic acid (0.138 mL), and the mixture was stirred at room temperature for 2 hr. The reaction mixture was concentrated under reduced pressure, and the residue was purified by silica gel column chromatography (ethyl acetate/hexane) to give the title compound (3.65 g).

$^1$H NMR (300 MHz, DMSO-$d_6$) δ 1.69 (6H, s), 4.43 (2H, td, J=14.3, 3.8 Hz), 6.19-6.65 (1H, m), 7.00-7.13 (2H, m), 7.15-7.23 (1H, m), 7.48-7.61 (1H, m), 7.96 (1H, d, J=10.5 Hz), 9.06 (1H, d, J=10.5 Hz), 11.95 (1H, s).

C) 2-[2-(2,2-difluoroethoxy)phenyl]-3-oxo-2,3-dihydropyridazine-4-carboxylic acid To a solution of 5-[(2E)-2-{2-[2-(2,2-difluoroethoxy)phenyl]hydrazinylidene}ethylidene]-2,2-dimethyl-1,3-dioxane-4,6-dione (3.65 g) in MeOH (80 mL) was added sodium methoxide (0.668 g), and the mixture was stirred at 70° C. for 5 hr. The reaction mixture was concentrated under reduced pressure, to the residue was added water, and the mixture was washed with ethyl acetate. The organic layer was extracted with 1M aqueous sodium hydroxide solution. The aqueous layers were combined, acidified with 1M hydrochloric acid, and extracted with ethyl acetate. The organic layer was separated, washed with saturated brine, dried over anhydrous sodium sulfate, and concentrated under reduced pressure. The residue was recrystallized from ethyl acetate/hexane to give the title compound (2.62 g).

MS: $[M+H]^+$ 296.9.

D) 2-[2-(2,2-difluoroethoxy)phenyl]-N-[4-(2-hydroxypropan-2-yl)phenyl]-3-oxo-2,3-dihydropyridazine-4-carboxamide To a mixture of 2-[2-(2,2-difluoroethoxy)phenyl]-3-oxo-2,3-dihydropyridazine-4-carboxylic acid (100 mg), 2-(4-aminophenyl)propan-2-ol (77 mg), TEA (0.071 mL) and DMF (1 mL) was added HATU (193 mg), and the mixture was stirred at room temperature for 3 hr. The reaction mixture was purified by silica gel column chromatography (ethyl acetate/hexane), and the solid was recrystallized from ethyl acetate/hexane to give the title compound (83 mg).

$^1$H NMR (300 MHz, DMSO-$d_6$) δ 1.41 (6H, s), 4.27-4.47 (2H, m), 4.98 (1H, s), 5.99-6.43 (1H, m), 7.20 (1H, td, J=7.7, 1.1 Hz), 7.35 (1H, dd, J=8.3, 1.1 Hz), 7.43-7.58 (4H, m), 7.58-7.65 (2H, m), 8.29 (1H, d, J=4.1 Hz), 8.33-8.39 (1H, m), 11.54 (1H, s).

Example 135

2-[2-(2,2-difluoroethoxy)phenyl]-N-[6-(2-hydroxypropan-2-yl)pyridin-3-yl]-6-methyl-3-oxo-2,3-dihydropyridazine-4-carboxamide A mixture of 2-[2-(2,2-difluoroethoxy)phenyl]-6-methyl-3-oxo-2,3-dihydropyridazine-4-carboxylic acid (100 mg), 2-(5-aminopyridin-2-yl)propan-2-ol (63.8 mg), TEA (65.2 mg), HATU (147 mg) and DMF (2 mL) was stirred at room temperature for 5 hr. The reaction mixture was diluted with ethyl acetate, washed with water and saturated brine, dried over anhydrous sodium sulfate, and concentrated under reduced pressure. The residue was purified by silica gel column chromatography (NH, ethyl acetate/hexane) to give the title compound (118 mg).

$^1$H NMR (300 MHz, DMSO-$d_6$) δ 1.43 (6H, s), 2.44 (3H, s), 4.25-4.47 (2H, m), 5.19 (1H, s), 5.99-6.43 (1H, m), 7.16-7.24 (1H, m), 7.31-7.38 (1H, m), 7.44-7.56 (2H, m), 7.63-7.70 (1H, m), 8.14 (1H, dd, J=8.5, 2.4 Hz), 8.26 (1H, s), 8.73 (1H, d, J=2.3 Hz), 11.72 (1H, s).

Example 136

2-[2-(2,2-difluoroethoxy)phenyl]-N-[4-(2-hydroxypropan-2-yl)phenyl]-6-methyl-3-oxo-2,3-dihydropyridazine-4-carboxamide To a solution of 2-[2-(2,2-difluoroethoxy)phenyl]-6-methyl-3-oxo-2,3-dihydropyridazine-4-carboxylic acid (4.00 g) in DMF (40 mL) were added 2-(4-aminophenyl)propan-2-ol (2.144 g), HATU (5.39 g) and TEA (2.61 g) at 0° C. The mixture was stirred at room temperature for 3 hr. The mixture was poured into water, and extracted with ethyl acetate. The organic layer was separated, washed with saturated brine, dried over anhydrous sodium sulfate, and concentrated under reduced pressure. The residue was purified by silica gel column chromatography (NH, ethyl acetate/hexane). The fraction was subjected to dust removal filtration, and concentrated under reduced pressure, and the resulting solid was recrystallized from ethyl acetate to give the title compound (3.80 g).

$^1$H NMR (300 MHz, DMSO-$d_6$) δ 1.41 (6H, s), 2.43 (3H, s), 4.25-4.49 (2H, m), 4.99 (1H, s), 6.00-6.42 (1H, m), 7.15-7.24 (1H, m), 7.31-7.37 (1H, m), 7.42-7.56 (4H, m), 7.57-7.65 (2H, m), 8.25 (1H, s), 11.67 (1H, s).

Example 140 rac-N-[5-(1-hydroxyethyl)pyridin-2-yl]-3-oxo-2-[2-(2,2,2-trifluoroethoxy)phenyl]-2,3-dihydro-pyridazine-4-carboxamide A) [2-(2,2,2-trifluoroethoxy)phenyl]hydrazine A mixture of 2-(2,2,2-trifluoroethoxy)aniline (10.60 g) and conc. hydrochloric acid (60 mL) was stirred at 0° C. for 30 min, to the mixture was added dropwise a mixture of sodium nitrite (4.59 g) and water (10.0 mL) at 0° C., and the mixture was stirred at 0° C. for 30 min. Then, to the mixture was added dropwise a mixture of tin(II) chloride (31.5 g) and conc. hydrochloric acid (80 mL) at 0° C., and the mixture was stirred at 0° C. for 2 hr. The reaction mixture was filtered without washing, and the filter cake was dissolved in 2N aqueous sodium hydroxide solution (100 mL). The mixture was extracted twice with ethyl acetate. The combined organic layers were washed with saturated brine, dried over anhydrous sodium sulfate, and concentrated under reduced pressure. To the residue was added ethyl acetate, and the mixture was washed with 2M aqueous sodium hydroxide solution and saturated brine, dried over anhydrous sodium sulfate, and concentrated under reduced pressure. The residue was collected by filtration with hexane to give the title compound (6.48 g).

MS: $[M+H]^+$ 207.0.

B) (2E)-{2-[2-(2,2,2-trifluoroethoxy)phenyl]hydrazinylidene}acetaldehyde

To 40% aqueous glyoxal solution (15.09 g) was added a mixture of [2-(2,2,2-trifluoroethoxy)phenyl]hydrazine (5.36 g), acetic acid (25 mL) and water (25.00 mL) at room temperature. The mixture was stirred at room temperature for 1 hr. The resulting solid was collected by filtration, and washed with water. The obtained solid was dissolved in ethyl acetate, and the solution was washed with saturated brine, dried over anhydrous sodium sulfate, and concentrated under reduced pressure to give the title compound (6.25 g).

MS: $[M+H]^+$ 246.9.

C) 2,2-dimethyl-5-[(2E)-2-{2-[2-(2,2,2-trifluoroethoxy)phenyl]hydrazinylidene}ethylidene]-1,3-dioxane-4,6-dione To a solution of (2E)-{2-[2-(2,2,2-trifluoroethoxy)phenyl]hydrazinylidene}acetaldehyde (6.25 g) in toluene (75 mL) were added 2,2-dimethyl-1,3-dioxane-4,6-dione (2.159 g), piperidine (0.296 mL) and acetic acid (0.171 mL) at room temperature. The mixture was stirred at room temperature for 2 hr. The mixture was concentrated under reduced pressure. The residue was purified by silica gel column chromatography (ethyl acetate/hexane). To the obtained crude product were added ethyl acetate and hexane, and the resulting solid was collected by filtration to give the title compound (4.55 g).

$^1$H NMR (300 MHz, DMSO-$d_6$) δ 1.69 (6H, s), 4.86 (2H, q, J=8.8 Hz), 7.01-7.15 (2H, m), 7.17-7.29 (1H, m), 7.50-7.63 (1H, m), 7.96 (1H, d, J=10.5 Hz), 9.08 (1H, d, J=10.5 Hz), 11.98 (1H, s).

D) 3-oxo-2-[2-(2,2,2-trifluoroethoxy)phenyl]-2,3-dihydropyridazine-4-carboxylic acid To a mixture of 2,2-dimethyl-5-[(2E)-2-{2-[2-(2,2,2-trifluoroethoxy)phenyl]hydrazinylidene}ethylidene]-1,3-dioxane-4,6-dione (4.55 g) and MeOH (100 mL) was added 5M sodium methoxide-MeOH solution (2.93 mL) at room temperature. The mixture was stirred at 70° C. for 5 hr. The mixture was concentrated under reduced pressure, and the resulting solid was dissolved in water. The solution was acidified with 1N hydrochloric acid, and extracted with ethyl acetate. The organic layer was washed with saturated brine, dried over anhydrous sodium sulfate, and concentrated under reduced pressure. The residue was washed with ethyl acetate/hexane to give the title compound (3.53 g).

MS: $[M+H]^+$ 314.9.

E) 1-(6-aminopyridin-3-yl)ethan-1-one

A mixture of 1-(6-chloropyridin-3-yl)ethanone (1250 mg) and 28% ammonia aqueous solution (25 mL) was stirred under microwave irradiation at 120° C. for 2 hr. The reaction mixture was extracted with ethyl acetate, and the organic layer was dried over anhydrous sodium sulfate, and concentrated under reduced pressure. The residue was purified by silica gel column chromatography (NH, ethyl acetate/hexane) to give the title compound (767 mg).

MS: $[M+H]^+$ 137.0.

F) rac-1-(6-aminopyridin-3-yl)ethan-1-ol

To a mixture of 1-(6-aminopyridin-3-yl)ethan-1-one (667 mg) and MeOH (20 mL) was added sodium borohydride (371 mg) under ice-cooling, and the mixture was stirred at room temperature for 2 hr. To the reaction mixture was added water, and the mixture was concentrated under reduced pressure. The residue was purified by silica gel column chromatography (NH, MeOH/ethyl acetate). The obtained crude product was washed with ethyl acetate/hexane to give the title compound (672 mg).

MS: $[M+H]^+$ 139.0.

G) rac-N-[5-(1-hydroxyethyl)pyridin-2-yl]-3-oxo-2-[2-(2,2,2-trifluoroethoxy)phenyl]-2,3-dihydro-pyridazine-4-carboxamide To a mixture of 3-oxo-2-[2-(2,2,2-trifluoroethoxy)phenyl]-2,3-dihydropyridazine-4-carboxylic acid (100 mg), rac-1-(6-aminopyridin-3-yl)ethan-1-ol (66.0 mg), TEA (0.067 mL) and DMF (0.8 mL) was added HATU (182 mg), and the mixture was stirred at room temperature for 2 hr. The reaction mixture was purified by silica gel column chromatography (ethyl acetate/hexane), and the solid was recrystallized from ethyl acetate/hexane to give the title compound (75 mg).

$^1$H NMR (300 MHz, DMSO-$d_6$) δ 1.35 (3H, d, J=6.4 Hz), 4.67-4.92 (3H, m), 5.28 (1H, d, J=4.1 Hz), 7.25 (1H, td, J=7.5, 1.1 Hz), 7.40 (1H, d, J=7.5 Hz), 7.49-7.62 (2H, m), 7.84 (1H, dd, J=8.5, 2.4 Hz), 8.21 (1H, d, J=8.7 Hz), 8.29-8.41 (3H, m), 11.89 (1H, s).

Example 144 rac-2-[2-(2,2-difluoroethoxy)phenyl]-3-oxo-N-[4-(oxolan-2-yl)phenyl]-2,3-dihydropyridazine-4-carboxamide A) 2-(4-nitrophenyl)furan A mixture of 1-bromo-4-nitrobenzene (1 g), 2-furylboronic acid (0.554 g), [1,1-bis(diphenylphosphino)ferrocene] dichloropalladium(II) (0.362 g), potassium carbonate (1.710 g), 1,2-dimethoxyethane (10 mL) and water (0.250 mL) was stirred at 85° C. for 3 hr. The reaction mixture was concentrated under reduced pressure, and the residue was purified by silica gel column chromatography (ethyl acetate/hexane). The obtained crude product was washed with ethyl acetate/hexane to give the title compound (0.344 g).

$^1$H NMR (300 MHz, DMSO-$d_6$) δ 6.72 (1H, dd, J=3.6, 1.7 Hz), 7.32 (1H, d, J=3.0 Hz), 7.89-8.01 (3H, m), 8.23-8.33 (2H, m).

B) rac-4-(oxolan-2-yl)aniline

To a mixture of 2-(4-nitrophenyl)furan (344 mg) and MeOH (10 mL) was added 10% palladium-carbon (55% wet, 100 mg), and the mixture was stirred overnight under normal pressure of hydrogen atmosphere at room temperature. The catalyst was removed by filtration, and the filtrate was concentrated under reduced pressure. The residue was purified by silica gel column chromatography (ethyl acetate/hexane) to give the title compound (129 mg).

$^1$H NMR (300 MHz, DMSO-$d_6$) δ 1.54-1.69 (1H, m), 1.81-1.97 (2H, m), 2.05-2.19 (1H, m), 3.70 (1H, td, J=7.9, 6.4 Hz), 3.83-3.96 (1H, m), 4.56 (1H, dd, J=8.1, 6.6 Hz), 4.95 (2H, s), 6.45-6.53 (2H, m), 6.88-7.00 (2H, m).

C) rac-2-[2-(2,2-difluoroethoxy)phenyl]-3-oxo-N-[4-(oxolan-2-yl)phenyl]-2,3-dihydropyridazine-4-carboxamide To a mixture of 2-[2-(2,2-difluoroethoxy)phenyl]-3-oxo-2,3-dihydropyridazine-4-carboxylic acid (100 mg), rac-4-(oxolan-2-yl)aniline (66.1 mg), TEA (0.071 mL) and DMF (1 mL) was added HATU (154 mg), and the mixture was stirred overnight at room temperature. The reaction mixture was purified by silica gel column chromatography (ethyl acetate/hexane), and the solid was recrystallized from ethyl acetate/hexane to give the title compound (98 mg).

$^1$H NMR (300 MHz, DMSO-$d_6$) δ 1.55-1.73 (1H, m), 1.86-2.01 (2H, m), 2.18-2.35 (1H, m), 3.72-3.85 (1H, m), 3.92-4.03 (1H, m), 4.37 (2H, br t, J=14.1 Hz), 4.77 (1H, t, J=7.2 Hz), 5.99-6.44 (1H, m), 7.20 (1H, td, J=7.5, 1.1 Hz), 7.27-7.40 (3H, m), 7.46-7.58 (2H, m), 7.60-7.73 (2H, m), 8.24-8.31 (1H, m), 8.36 (1H, d, J=4.5 Hz), 11.57 (1H, s).

Example 146

2-[2-(2,2-difluoroethoxy)phenyl]-N-[2-fluoro-4-(2-hydroxypropan-2-yl)phenyl]-6-methyl-3-oxo-2,3-dihydropyridazine-4-carboxamide A) methyl 3-fluoro-4-nitrobenzoate To a mixture of 3-fluoro-4-nitrobenzoic acid (10.0 g), potassium carbonate (14.93 g) and DMF (100 mL) was added iodomethane (5.04 mL) at room temperature, and the mixture was stirred at room temperature for 3 hr. The reaction mixture was poured into water at 0° C., and extracted with ethyl acetate. The organic layer was washed with water and saturated brine, dried over anhydrous sodium sulfate, and concentrated under reduced pressure. The residue was purified by silica gel column chromatography (ethyl acetate/hexane) to give the title compound (10.62 g).

$^1$H NMR (300 MHz, DMSO-$d_6$) δ 3.92 (3H, s), 7.91-8.00 (1H, m), 8.04 (1H, dd, J=11.4, 1.5 Hz), 8.29 (1H, dd, J=8.5, 7.5 Hz).

B) methyl 4-amino-3-fluorobenzoate

A mixture of methyl 3-fluoro-4-nitrobenzoate (2 g), 10% palladium on carbon (55% wet, 200 mg), ethyl acetate (10 mL) and EtOH (10 mL) was stirred under hydrogen atmosphere at room temperature for 3 hr. The catalyst was removed by filtration, and the filtrate was concentrated under reduced pressure to give the title compound (1.687 g).

MS: $[M+H]^+$ 170.1.

C) 2-(4-amino-3-fluorophenyl)propan-2-ol

To a mixture of methyl 4-amino-3-fluorobenzoate (1.68 g) and THF (20 mL) was added dropwise 3M methylmagnesium bromide-2-methyltetrahydrofuran solution (16.55 mL) at 0° C., and the mixture was stirred overnight at room temperature. To the reaction mixture was added 3M methylmagnesium bromide-2-methyltetrahydrofuran solution (3.31 mL) at 0° C., and the mixture was stirred at 40° C. for 2 hr. To the reaction mixture was added saturated aqueous ammonium chloride solution at 0° C., and the mixture was extracted with ethyl acetate. The organic layer was washed with saturated brine, dried over anhydrous magnesium sulfate, and concentrated under reduced pressure. The residue was purified by silica gel column chromatography (ethyl acetate/hexane) to give the title compound (540 mg).

MS: $[M+H]^+$ 170.1.

D) 2-[2-(2,2-difluoroethoxy)phenyl]-N-[2-fluoro-4-(2-hydroxypropan-2-yl)phenyl]-6-methyl-3-oxo-2,3-dihydropyridazine-4-carboxamide To a mixture of 2-[2-(2,2-difluoroethoxy)phenyl]-6-methyl-3-oxo-2,3-dihydropyridazine-4-carboxylic acid (70 mg), 2-(4-amino-3-fluorophenyl)propan-2-ol (76 mg), TEA (0.047 mL) and DMF (1.5 mL) was added HATU (129 mg) at room temperature, and the mixture was stirred at the same temperature for 1 hr. To the reaction mixture was added ice water, and the mixture was extracted with ethyl acetate. The organic layer was washed with water and saturated brine, dried over anhydrous magnesium sulfate, and concentrated under reduced pressure. The residue was purified by silica gel column chromatography (ethyl acetate/hexane) to give the title compound (90 mg).

$^1$H NMR (300 MHz, DMSO-$d_6$) δ 1.41 (6H, s), 2.44 (3H, s), 4.26-4.48 (2H, m), 5.13 (1H, s), 5.96-6.42 (1H, m), 7.19 (1H, td, J=7.6, 1.3 Hz), 7.27-7.40 (3H, m), 7.42-7.57 (2H, m), 8.24-8.38 (2H, m), 11.96 (1H, d, J=1.9 Hz).

Example 148

N-[2-fluoro-4-(2-hydroxypropan-2-yl)phenyl]-3-oxo-2-[2-(2,2,2-trifluoroethoxy)phenyl]-2,3-dihydropyridazine-4-carboxamide To a mixture of 3-oxo-2-[2-(2,2,2-trifluoroethoxy)phenyl]-2,3-dihydropyridazine-4-carboxylic acid (60 mg), 2-(4- amino-3-fluorophenyl)propan-2-ol (64.6 mg), TEA (0.040 mL) and DMF (1.5 mL) was added HATU (109 mg) at room temperature, and the mixture was stirred at the same temperature for 2 days. To the reaction mixture was added ice water, and the mixture was extracted with ethyl acetate. The organic layer was washed with water and saturated brine, dried over anhydrous magnesium sulfate, and concentrated under reduced pressure. The residue was purified by silica gel column chromatography (ethyl acetate/hexane) to give the title compound (26.5 mg).

$^1$H NMR (300 MHz, DMSO-$d_6$) δ 1.41 (6H, s), 4.72-4.91 (2H, m), 5.13 (1H, s), 7.21-7.43 (4H, m), 7.50-7.61 (2H, m), 8.29-8.41 (3H, m), 11.82 (1H, d, J=1.9 Hz).

Example 152

2-[2-(2,2-difluoroethoxy)phenyl]-6-methyl-3-oxo-N-[4-(1,1,3,3-tetrafluoro-2-hydroxypropan-2-yl)phenyl]-2,3-dihydropyridazine-4-carboxamide A) 1,1,3,3-tetrafluoro-2-(4-nitrophenyl)propan-2-ol To a mixture of 4-nitrobenzoyl chloride (1.002 g) and acetonitrile (10 mL) were added [bromo(difluoro)methyl](trimethyl)silane (2.52 mL), triphenylphosphine (3.54 g) and 1,3-dimethyltetrahydropyrimidin-2(1H)-one (2.60 mL) at 0° C., and the mixture was stirred at room temperature for 72 hr. To the reaction mixture were added water (10 mL) and pyridine (2 mL), and the mixture was stirred at 80° C. for 3 hr. To the reaction mixture was added water, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane) to give the title compound (1.218 g).

MS: $[M-H]^-$ 251.9.

B) 2-(4-aminophenyl)-1,1,3,3-tetrafluoropropan-2-ol

To 1,1,3,3-tetrafluoro-2-(4-nitrophenyl)propan-2-ol (604.5 mg), water (6 mL) and EtOH (6.00 mL) were added ammonium chloride (639 mg) and reduction iron (667 mg), and the mixture was refluxed for 2 hr. The insoluble substance was removed by filtration, to the filtrate was added saturated aqueous sodium hydrogencarbonate solution, and the mixture was extracted with ethyl acetate. The organic layer was separated, washed with saturated brine, dried over anhydrous sodium sulfate, and concentrated under reduced pressure to give the title compound (532 mg).

MS: $[M+H]^+$ 224.0.

C) 2-[2-(2,2-difluoroethoxy)phenyl]-6-methyl-3-oxo-N-[4-(1,1,3,3-tetrafluoro-2-hydroxypropan-2-yl)phenyl]-2,3-dihydropyridazine-4-carboxamide To a mixture of 2-[2-(2,2-difluoroethoxy)phenyl]-6-methyl-3-oxo-2,3-dihydropyridazine-4-carboxylic acid (90 mg), 2-(4-aminophenyl)-1,1,3,3-tetrafluoropropan-2-ol (97 mg), TEA (0.061 mL) and DMF (2 mL) was added HATU (165 mg), and the mixture was stirred at room temperature for 1 hr. The reaction mixture was poured into water, and extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (80 mg).

$^1$H NMR (300 MHz, DMSO) δ 2.44 (3H, s), 4.37 (2H, t, J=14.3 Hz), 6.00-6.65 (3H, m), 6.98 (1H, s), 7.13-7.24 (1H, m), 7.30-7.37 (1H, m), 7.42-7.63 (4H, m), 7.75 (2H, d, J=9.0 Hz), 8.26 (1H, s), 11.78 (1H, s).

Example 154

N-[2-cyano-4-(2-hydroxypropan-2-yl)phenyl]-2-[2-(2,2-difluoroethoxy)phenyl]-6-methyl-3-oxo-2,3-dihydropyridazine-4-carboxamide A) methyl 3-cyano-4-nitrobenzoate A mixture of methyl 3-bromo-4-nitrobenzoate (2.05 g), copper(I) cyanide (1.059 g) and N-methylpyrrolidone (30 mL) was stirred under argon atmosphere at 150° C. for 7 hr. To the reaction mixture were added brine and ethyl acetate, the mixture was filtered through Celite, and the filtrate was extracted with ethyl acetate. The organic layer was washed with saturated brine, dried over anhydrous sodium sulfate, and concentrated under reduced pressure. The residue was purified by silica gel column chromatography (ethyl acetate/hexane) to give the title compound (770 mg).

$^1$H NMR (300 MHz, DMSO-$d_6$) δ 3.94 (3H, s), 8.40-8.46 (1H, m), 8.48-8.53 (1H, m), 8.56 (1H, d, J=1.9 Hz).

B) methyl 4-amino-3-cyanobenzoate

A mixture of methyl 3-cyano-4-nitrobenzoate (760 mg), 10% palladium on carbon (55% wet, 392 mg), MeOH (20 mL) and THF (10 mL) was stirred under hydrogen atmosphere at room temperature for 4 hr. The catalyst was removed by filtration, the filtrate was concentrated under reduced pressure, and the residue was purified by silica gel column chromatography (ethyl acetate/hexane) to give the title compound (480 mg).

MS: $[M+H]^+$ 177.1.

C) 2-amino-5-(2-hydroxypropan-2-yl)benzonitrile

To a mixture of methyl 4-amino-3-cyanobenzoate (480 mg) and THF (5 mL) was added 2M methylmagnesium bromide-THF/2-methyltetrahydrofuran solution (6.81 mL) at 0° C., and the mixture was stirred at 0° C. for 30 min, and then at room temperature for 21 hr. To the reaction mixture were added diethyl ether and water at 0° C., the mixture was stirred at room temperature for 5 min, and water and saturated brine were added thereto. The reaction mixture was extracted with ethyl acetate, and the organic layer was washed with saturated brine, dried over anhydrous sodium sulfate, and concentrated under reduced pressure. The residue was purified by silica gel column chromatography (ethyl acetate/hexane) to give the title compound (336 mg).

$^1$H NMR (300 MHz, DMSO-$d_6$) δ 1.35 (6H, s), 4.90 (1H, s), 5.83 (2H, s), 6.71-6.76 (1H, m), 7.35-7.43 (2H, m).

D) N-[2-cyano-4-(2-hydroxypropan-2-yl)phenyl]-2-[2-(2,2-difluoroethoxy)phenyl]-6-methyl-3-oxo-2,3-dihydropyridazine-4-carboxamide To a mixture of 2-[2-(2,2-difluoroethoxy)phenyl]-6-methyl-3-oxo-2,3-dihydropyridazine-4-carboxylic acid (50 mg), 2-amino-5-(2-hydroxypropan-2-yl)benzonitrile (36.9 mg), TEA (0.034 mL) and DMF (0.5 mL) was added HATU (92 mg) at room temperature, and the mixture was stirred at the same temperature for 2 hr. To the reaction mixture was added brine, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane), and the residue was crystallized from ethyl acetate/diisopropyl ether/hexane to give the title compound (46 mg).

$^1$H NMR (300 MHz, DMSO-$d_6$) δ 1.43 (6H, s), 2.45 (3H, s), 4.23-4.52 (2H, m), 5.24 (1H, s), 5.99-6.43 (1H, m), 7.21 (1H, td, J=7.72, 1.13 Hz), 7.34-7.41 (1H, m), 7.45-7.59 (2H, m), 7.79-7.90 (2H, m), 8.27-8.37 (2H, m), 12.22 (1H, s).

Example 158

6-[2-(2,2-difluoroethoxy)phenyl]-N-[4-(2-hydroxypropan-2-yl)phenyl]-2-methyl-5-oxo-2,5-dihydropyridazine-4-carboxamide

A) 1-(2,2-difluoroethoxy)-2-iodobenzene

To a solution of 2-iodophenol (23 g) in DMF (150 mL) were added 2,2-difluoroethyl trifluoromethanesulfonate (15.20 mL) and cesium carbonate (44.3 g) under ice-cooling, and the mixture was stirred at room temperature for 22 hr. The reaction mixture was cooled to 0° C., water was added thereto, and the mixture was extracted with diethyl ether. The organic layer was separated, washed with saturated brine, dried over anhydrous sodium sulfate, and concentrated under reduced pressure. To the residue was added diethyl ether, and the mixture was washed with water, washed with saturated brine, dried over anhydrous sodium sulfate, and concentrated under reduced pressure to give the title compound (31 g).

$^1$H NMR (300 MHz, DMSO-$d_6$) δ 4.37 (2H, td, J=14.51, 3.77 Hz), 6.16-6.62 (1H, m), 6.81 (1H, td, J=7.54, 1.51 Hz), 7.09 (1H, dd, J=8.29, 1.51 Hz), 7.38 (1H, ddd, J=8.38, 7.06, 1.51 Hz), 7.80 (1H, dd, J=7.54, 1.51 Hz).

B) 1-(2,2-difluoroethoxy)-2-(prop-1-yn-1-yl)benzene

To a mixture of 1-(2,2-difluoroethoxy)-2-iodobenzene (29.5 g), bis(triphenylphosphine)palladium(II) dichloride (4 g), copper(I) iodide (2.97 g), TEA (18 mL) and DMF (50 mL) was added 1M prop-1-yne-THF solution (170 mL), and the mixture was stirred under argon atmosphere at room temperature for 24 hr, and concentrated under reduced pressure. The residue was passed through pad filled with silica gel, and washed with ethyl acetate. The filtrate was washed with water and saturated brine, dried over anhydrous sodium sulfate, and concentrated under reduced pressure. The residue was purified by silica gel column chromatography (ethyl acetate/hexane). To the obtained crude product was added diethyl ether, and the insoluble substance was removed by filtration. The filtrate was concentrated under reduced pressure to give the title compound (23.90 g).

$^1$H NMR (300 MHz, DMSO-$d_6$) δ 2.05 (3H, s), 4.35 (2H, td, J=1 4.49, 3.76 Hz), 6.15-6.61 (1H, m), 6.96 (1H, td, J=7.43, 0.94 Hz), 7.09 (1H, d, J=7.91 Hz), 7.26-7.37 (2H, m).

C) 1-[2-(2,2-difluoroethoxy)phenyl]propane-1,2-dione

To a mixture of 1-(2,2-difluoroethoxy)-2-(prop-1-yn-1-yl)benzene (200 mg), sodium bicarbonate (13.70 mg), magnesium sulfate (30.7 mg), sodium periodate (1090 mg), carbon tetrachloride (1.5 mL), acetonitrile (1.5 mL) and water (3 mL) was added ruthenium(III) chloride (4.23 mg), and the mixture was stirred for 2 hr. To the reaction mixture was added brine, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane) to give the title compound (190 mg).

MS: $[M+H]^+$ 229.1.

D) (3E)-1-[2-(2,2-difluoroethoxy)phenyl]-4-(dimethylamino)but-3-ene-1,2-dione A mixture of 1-[2-(2,2-difluoroethoxy)phenyl]propane-1,2-dione (14.99 g), N,N-dimethylformamide dimethyl acetal (100 mL) and toluene (70 mL) was stirred at 120° C. for 4 hr, and concentrated under reduced pressure. The residue was purified by silica gel column chromatography (ethyl acetate/hexane) to give the title compound (13.50 g).

MS: $[M+H]^+$ 284.1.

E) 3-[2-(2,2-difluoroethoxy)phenyl]pyridazin-4(1H)-one

To a solution of (3E)-1-[2-(2,2-difluoroethoxy)phenyl]-4-(dimethylamino)but-3-ene-1,2-dione (13.5 g) in EtOH (150 mL) was added hydrazine monohydrate (2.6 mL), and the mixture was stirred at 70° C. for 1 hr, and concentrated under reduced pressure. The resulting solid was suspended in ethyl acetate/hexane, and collected by filtration to give the title compound (9.38 g).

MS: $[M+H]^+$ 253.1.

F) 5-bromo-3-[2-(2,2-difluoroethoxy)phenyl]pyridazin-4(1H)-one

To a solution of 3-[2-(2,2-difluoroethoxy)phenyl]pyridazin-4(1H)-one (9.38 g) in DMF (120 mL) was added N-bromosuccinimide (9.27 g) at 0° C., and the mixture was stirred at 0° C. for 1.5 hr. To the reaction mixture was added water at 0° C., and the suspension was stirred at room temperature for 10 min. The precipitate was collected by filtration, and washed with water to give the title compound (10.71 g).

MS: $[M+H]^+$ 331.0.

G) 5-bromo-3-[2-(2,2-difluoroethoxy)phenyl]-1-methylpyridazin-4(1H)-one

To a mixture of 5-bromo-3-[2-(2,2-difluoroethoxy)phenyl]pyridazin-4(1H)-one (600 mg) and THF (6 mL) was added sodium hydride (60% oil, 94 mg) at 0° C., and the mixture was stirred at 0° C. for 30 min. Iodomethane (0.170 mL) was added dropwise thereto at 0° C., and the mixture was stirred at room temperature for 1.5 hr. To the reaction mixture were added saturated aqueous ammonium chloride solution and water under ice-cooling, and the mixture was extracted with ethyl acetate. The organic layer was separated, washed with 5% aqueous sodium thiosulfate solution and saturated brine, dried over anhydrous sodium sulfate, and concentrated under reduced pressure. The residue was purified by silica gel column chromatography (NH, ethyl acetate/hexane) to give the title compound (469 mg).

MS: $[M+H]^+$ 345.0.

H) methyl 6-[2-(2,2-difluoroethoxy)phenyl]-2-methyl-5-oxo-2,5-dihydropyridazine-4-carboxylate A mixture of 5-bromo-3-[2-(2,2-difluoroethoxy)phenyl]-1-methylpyridazin-4(1H)-one (464 mg), dichloro[1,1'-bis(diphenylphosphino)ferrocene]palladium(II) (98 mg), TEA (375 μL) and MeOH (10 mL) was stirred under carbon monoxide (0.5 MPa) atmosphere at 85° C. for 5 hr. The mixture was concentrated under reduced pressure, and the residue was suspended in ethyl acetate. The suspension was filtered through pad filled with NH silica and Celite, and the filtrate was concentrated under reduced pressure. The residue was purified by silica gel column chromatography (NH, ethyl acetate/hexane) to give the title compound (377 mg).

MS: $[M+H]^+$ 325.1.

I) 6-[2-(2,2-difluoroethoxy)phenyl]-2-methyl-5-oxo-2,5-dihydropyridazine-4-carboxylic acid To a mixture of methyl 6-[2-(2,2-difluoroethoxy)phenyl]-2-methyl-5-oxo-2,5-dihydropyridazine-4-carboxylate (169 mg), THF (1.5 mL) and MeOH (0.5 mL) was added 2M aqueous sodium hydroxide solution (0.274 mL) under ice-cooling, and the mixture was stirred at room temperature for 45 min. The reaction mixture was acidified with 1M hydrochloric acid under ice-cooling, and concentrated under reduced pressure. To the residue was added water, and the mixture was extracted with ethyl acetate. The separated organic layer was washed with saturated brine, dried over anhydrous sodium sulfate, and concentrated under reduced pressure. The residue was crystallized from diisopropyl ether/ethyl acetate to give the title compound (151 mg).

MS: $[M+H]^+$ 311.51.

J) 6-[2-(2,2-difluoroethoxy)phenyl]-N-[4-(2-hydroxypropan-2-yl)phenyl]-2-methyl-5-oxo-2,5-dihydropyridazine-4-carboxamide To a solution of 6-[2-(2,2-difluoroethoxy)phenyl]-2-methyl-5-oxo-2,5-dihydropyridazine-4-carboxylic acid (60 mg), 2-(4-aminophenyl)propan-2-ol (38.0 mg) and TEA (54 μL) in DMF (0.8 mL) was added HATU (110 mg) at room temperature, and the mixture was stirred at room temperature for 2.5 hr. To the mixture was added water, and the mixture was extracted with ethyl acetate. The separated organic layer was washed with saturated brine, dried over anhydrous sodium sulfate, and concentrated under reduced pressure. The residue was purified by silica gel column chromatography (ethyl acetate/hexane), and recrystallized from ethyl acetate/diisopropyl ether/heptane to give the title compound (60.6 mg).

$^1H$ NMR (300 MHz, DMSO-$d_6$) δ 1.41 (6H, s), 4.08 (3H, s), 4.34 (2H, td, J=14.60, 3.58 Hz), 4.96 (1H, s), 5.98-6.43 (1H, m), 7.13 (1H, td, J=7.44, 0.94 Hz), 7.25 (1H, d, J=7.91 Hz), 7.35 (1H, dd, J=7.54, 1.51 Hz), 7.41-7.54 (3H, m), 7.55-7.61 (2H, m), 9.12 (1H, s), 12.06 (1H, s).

Example 161

6-[2-(2,2-difluoroethoxy)phenyl]-2-(difluoromethyl)-N-[4-(2-hydroxypropan-2-yl)phenyl]-5-oxo-2,5-dihydropyridazine-4-carboxamide A) 5-bromo-3-[2-(2,2-difluoroethoxy)phenyl]-1-(difluoromethyl)pyridazin-4(1H)-one To a mixture of 5-bromo-3-[2-(2,2-difluoroethoxy)phenyl]pyridazin-4(1H)-one (350 mg) and DMF (5 mL) were added sodium chloro(difluoro)acetate (322 mg) and cesium carbonate (517 mg), and the mixture was stirred at 100° C. for 45 min. To the reaction mixture was added water, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane) to give the title compound (380 mg).

MS: $[M+H]^+$ 381.0.

B) methyl 6-[2-(2,2-difluoroethoxy)phenyl]-2-(difluoromethyl)-5-oxo-2,5-dihydropyridazine-4-carboxylate A mixture of 5-bromo-3-[2-(2,2-difluoroethoxy)phenyl]-1-(difluoromethyl)pyridazin-4(1H)-one (423 mg), [1,1-bis(diphenylphosphino)ferrocene]dichloropalladium(II) (85 mg), TEA (0.32 mL) and MeOH (10 mL) was stirred under 0.5 MPa of carbon monoxide atmosphere at 85° C. for 5 hr. The reaction mixture was concentrated under reduced pressure, and ethyl acetate was added thereto. The insoluble substance was removed by filtration, and the filtrate was concentrated under reduced pressure. The residue was purified by silica gel column chromatography (NH, ethyl acetate/hexane) to give the title compound (308 mg).

MS: $[M+H]^+$ 361.0.

C) 6-[2-(2,2-difluoroethoxy)phenyl]-2-(difluoromethyl)-5-oxo-2,5-dihydropyridazine-4-carboxylic acid To a mixture of methyl 6-[2-(2,2-difluoroethoxy)phenyl]-2-(difluoromethyl)-5-oxo-2,5-dihydropyridazine-4-carboxylate (304 mg), THF (2 mL) and MeOH (1.5 mL) was added 2M aqueous sodium hydroxide solution (0.47 mL) at 0° C., and the mixture was stirred at room temperature for 10 min. To the reaction mixture was added water (3 mL), and the mixture was stirred at room temperature for 10 min. The reaction mixture was acidified with 1M hydrochloric acid (5 mL) at 0° C., and extracted with ethyl acetate. The organic layer was separated, washed with saturated brine, dried over anhydrous sodium sulfate, and concentrated under reduced pressure to give the title compound (285 mg).

MS: $[M+H]^+$ 347.1.

D) 6-[2-(2,2-difluoroethoxy)phenyl]-2-(difluoromethyl)-N-[4-(2-hydroxypropan-2-yl)phenyl]-5-oxo-2,5-dihydropyridazine-4-carboxamide To a mixture of 6-[2-(2,2-difluoroethoxy)phenyl]-2-(difluoromethyl)-5-oxo-2,5-dihydropyridazine-4-carboxylic acid (60 mg), 2-(4-aminophenyl)propan-2-ol (34.1 mg), TEA (48 μL) and DMF (0.8 mL) was added HATU (99 mg), and the mixture was stirred at room temperature for 2 hr. To the reaction mixture was added water, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane), and crystallized from ethyl acetate/hexane to give the title compound (48 mg).

$^1H$ NMR (300 MHz, DMSO-$d_6$) δ 1.41 (6H, s), 4.36 (2H, td, J=14.6, 3.6 Hz), 4.97 (1H, s), 5.93-6.45 (1H, m), 7.16 (1H, td, J=7.4, 0.9 Hz), 7.27 (1H, d, J=7.9 Hz), 7.40 (1H, dd,

J=7.5, 1.9 Hz), 7.43-7.49 (2H, m), 7.50-7.62 (3H, m), 7.69-8.13 (1H, m), 9.42 (1H, s), 11.46 (1H, s).

Example 162

3-oxo-N-[6-(1,1,3,3-tetrafluoro-2-hydroxypropan-2-yl)pyridin-3-yl]-2-[2-(2,2,2-trifluoroethoxy)phenyl]-2,3-dihydropyridazine-4-carboxamide To a solution of 2-(5-aminopyridin-2-yl)-1,1,3,3-tetrafluoropropan-2-ol (51.4 mg) and 3-oxo-2-[2-(2,2,2-trifluoroethoxy)phenyl]-2,3-dihydropyridazine-4-carboxylic acid (60 mg) in DMF (1 mL) and TEA (0.040 mL) was added HATU (87 mg) at room temperature. The mixture was stirred at room temperature for 1 hr. The mixture was poured into water at room temperature, and extracted with ethyl acetate. The organic layer was separated, washed with saturated brine, dried over anhydrous magnesium sulfate, and concentrated under reduced pressure. The residue was purified by silica gel column chromatography (ethyl acetate/hexane), and crystallized from ethyl acetate/diisopropyl ether/hexane to give the title compound (61 mg).

$^1$H NMR (300 MHz, DMSO-$d_6$) δ 4.82 (2H, brs), 6.28-6.89 (2H, m), 7.13 (1H, s), 7.21-7.83 (5H, m), 8.19-8.50 (3H, m), 8.88 (1H, d, J=2.3 Hz), 11.70 (1H, s).

Example 163

6-[2-(2,2-difluoroethoxy)phenyl]-2-(difluoromethyl)-5-oxo-N-[4-(1,1,3,3-tetrafluoro-2-hydroxypropan-2-yl)phenyl]-2,5-dihydropyridazine-4-carboxamide To a mixture of 6-[2-(2,2-difluoroethoxy)phenyl]-2-(difluoromethyl)-5-oxo-2,5-dihydropyridazine-4-carboxylic acid (60 mg), 2-(4-aminophenyl)-1,1,3,3-tetrafluoropropan-2-ol (50.3 mg), TEA (48 μL) and DMF (0.8 mL) was added HATU (99 mg), and the mixture was stirred at room temperature for 2.5 hr. To the reaction mixture was added water, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane), and crystallized from ethyl acetate/diisopropyl ether/heptane to give the title compound (78 mg).

$^1$H NMR (300 MHz, DMSO-$d_6$) δ 4.36 (2H, td, J=14.6, 3.6 Hz), 5.99-6.63 (3H, m), 6.97 (1H, s), 7.12-7.21 (1H, m), 7.27 (1H, d, J=7.9 Hz), 7.40 (1H, dd, J=7.5, 1.5 Hz), 7.51-7.62 (3H, m), 7.68-8.12 (3H, m), 9.43 (1H, s), 11.59 (1H, s).

Example 167

6-[2-(2,2-difluoroethoxy)phenyl]-N-(2,4-difluorophenyl)-2-(2-hydroxy-2-methylpropyl)-5-oxo-2,5-dihydropyridazine-4-carboxamide A) methyl 6-[2-(2,2-difluoroethoxy)phenyl]-5-oxo-2,5-dihydropyridazine-4-carboxylate A mixture of 5-bromo-3-[2-(2,2-difluoroethoxy)phenyl]pyridazin-4(1H)-one (9 g), [1,1-bis(diphenylphosphino)ferrocene]dichloropalladium(II) (1.989 g), TEA (8 mL) and MeOH (160 mL) was stirred under 0.5 MPa of carbon monoxide atmosphere at 85° C. for 5 hr. To the reaction mixture was added MeOH, the insoluble substance was removed by filtration, and the filtrate was concentrated under reduced pressure. To the residue was added ethyl acetate, and the solid was collected by filtration, and washed with water and acetonitrile to give the title compound (7.54 g).

MS: $[M+H]^+$ 311.1.

B) methyl 6-[2-(2,2-difluoroethoxy)phenyl]-2-(2-hydroxy-2-methylpropyl)-5-oxo-2,5-dihydropyridazine-4-carboxylate To a mixture of methyl 6-[2-(2,2-difluoroethoxy)phenyl]-5-oxo-2,5-dihydropyridazine-4-carboxylate (500 mg) and DMF (4 mL) was added 1-chloro-2-methylpropan-2-ol (1 mL) and potassium carbonate (500 mg), and the mixture was stirred under argon atmosphere at 80° C. for 13 hr. To the reaction mixture was added water, and the mixture was extracted with ethyl acetate. The organic layer was separated, washed with saturated brine, dried over anhydrous sodium sulfate, and concentrated under reduced pressure. The residue was purified by silica gel column chromatography (SI and NH, ethyl acetate/hexane) to give the title compound (360 mg).

MS: $[M+H]^+$ 383.1.

C) 6-[2-(2,2-difluoroethoxy)phenyl]-2-(2-hydroxy-2-methylpropyl)-5-oxo-2,5-dihydropyridazine-4-carboxylic acid To a mixture of methyl 6-[2-(2,2-difluoroethoxy)phenyl]-2-(2-hydroxy-2-methylpropyl)-5-oxo-2,5-dihydropyridazine-4-carboxylate (490 mg), THF (1.5 mL) and MeOH (2 mL) was added 2M aqueous sodium hydroxide solution (0.77 mL) under ice-cooling, and the mixture was stirred at room temperature for 30 min. To the reaction mixture was added 1M hydrochloric acid (0.75 mL) at 10° C., and the mixture was concentrated under reduced pressure. To the residue was added water (1 mL), and the mixture was acidified with 1M hydrochloric acid (2 mL). The solid was collected by filtration to give the title compound (456 mg).

MS: $[M+H]^+$ 369.1.

D) 6-[2-(2,2-difluoroethoxy)phenyl]-N-(2,4-difluorophenyl)-2-(2-hydroxy-2-methylpropyl)-5-oxo-2,5-dihydropyridazine-4-carboxamide To a mixture of 6-[2-(2,2-difluoroethoxy)phenyl]-2-(2-hydroxy-2-methylpropyl)-5-oxo-2,5-dihydropyridazine-4-carboxylic acid (50.2 mg), 2,4-difluoroaniline (18 μL), TEA (38 μL) and DMF (0.7 mL) was added HATU (77.4 mg), and the mixture was stirred at room temperature for 2 hr. To the reaction mixture was added water, and the mixture was extracted with a mixed solvent of ethyl acetate/THF=4/1. The organic layer was separated, dried over anhydrous magnesium sulfate, and concentrated under reduced pressure. The precipitate was collected by filtration, and washed with a mixed solvent of ethyl acetate/hexane, and diisopropyl ether to give the title compound (65.6 mg).

$^1$H NMR (300 MHz, DMSO-$d_6$) δ 1.16 (6H, s), 4.23 (2H, s), 4.34 (2H, td, J=14.5, 3.8 Hz), 4.97 (1H, s), 5.94-6.39 (1H, m), 7.07-7.19 (2H, m), 7.25 (1H, d, J=7.9 Hz), 7.31 (1H, dd, J=7.5, 1.5 Hz), 7.40 (1H, ddd, J=11.3, 8.8, 2.8 Hz), 7.46-7.56 (1H, m), 8.43 (1H, td, J=9.1, 6.2 Hz), 9.02 (1H, s), 12.32 (1H, s).

Example 168

6-[2-(2,2-difluoroethoxy)phenyl]-2-(2-hydroxy-2-methylpropyl)-5-oxo-N-[4-(2,2,2-trifluoroethoxy)phenyl]-2,5-dihydropyridazine-4-carboxamide To a mixture of 6-[2-(2,2-difluoroethoxy)phenyl]-2-(2-hydroxy-2-methylpropyl)-5-oxo-2,5-dihydropyridazine-4-carboxylic acid (57 mg), 4-(2,2,2-trifluoroethoxy)aniline (55 mg), TEA (0.043 mL) and DMF (0.7 mL) was added HATU (103 mg), and the mixture was stirred at room temperature for 2 hr. To the reaction mixture was added brine, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane), and recrystallized from ethyl acetate/diisopropyl ether to give the title compound (45 mg).

$^1$H NMR (300 MHz, DMSO-$d_6$) δ 1.16 (6H, s), 4.22 (2H, s), 4.34 (2H, td, J=14.6, 3.6 Hz), 4.73 (2H, q, J=9.0 Hz), 4.96 (1H, s), 5.95-6.41 (1H, m), 7.03-7.16 (3H, m), 7.24 (1H, d, J=8.3 Hz), 7.30 (1H, dd, J=7.5, 1.9 Hz), 7.49 (1H, ddd, J=8.6, 7.2, 1.9 Hz), 7.59-7.68 (2H, m), 9.00 (1H, s), 12.04 (1H, s).

Example 169

2-cyclopropyl-6-[2-(2,2-difluoroethoxy)phenyl]-N-[4-(2-hydroxypropan-2-yl)phenyl]-5-oxo-2,5-dihydropyridazine-4-carboxamide A) 5-bromo-3-[2-(2,2-difluoroethoxy)phenyl]-1-cyclopropylpyridazin-4(1H)-one To a mixture of 5-bromo-3-[2-(2,2-difluoroethoxy)phenyl]pyridazin-4(1H)-one (300 mg), cyclopropylboronic acid (207 mg), pyridine (0.730 mL), TEA (0.379 mL), DMF (1.5 mL) and acetonitrile (4.5 mL) was added copper(II) acetate (247 mg), and the mixture was stirred at 60° C. for 24 hr. The reaction mixture was filtered, and the filtrate was concentrated under reduced pressure. To the residue was added ethyl acetate, and the mixture was washed with saturated aqueous sodium hydrogencarbonate solution and saturated brine, dried over anhydrous sodium sulfate, and concentrated under reduced pressure. The residue was purified by silica gel column chromatography (NH, ethyl acetate/hexane) to give the title compound (267 mg).

MS: $[M+H]^+$ 371.0.

B) methyl 2-cyclopropyl-6-[2-(2,2-difluoroethoxy)phenyl]-5-oxo-2,5-dihydropyridazine-4-carboxylate A mixture of 5-bromo-3-[2-(2,2-difluoroethoxy)phenyl]-1-cyclopropylpyridazin-4(1H)-one (500 mg), [1,1-bis(diphenylphosphino)ferrocene]dichloropalladium(II) (99 mg), TEA (0.376 mL) and MeOH (5 mL) was stirred under 0.5 MPa of carbon monoxide atmosphere at 85° C. for 5 hr. The reaction mixture was concentrated under reduced pressure, to the residue was added ethyl acetate, and the insoluble substance was removed by filtration. The filtrate was concentrated under reduced pressure, and the residue was purified by silica gel column chromatography (NH, ethyl acetate/hexane) to give the title compound (381 mg).

MS: $[M+H]^+$ 351.1.

C) 2-cyclopropyl-6-[2-(2,2-difluoroethoxy)phenyl]-5-oxo-2,5-dihydropyridazine-4-carboxylic acid To a mixture of methyl 2-cyclopropyl-6-[2-(2,2-difluoroethoxy)phenyl]-5-oxo-2,5-dihydropyridazine-4-carboxylate (33 mg), THF (0.4 mL) and MeOH (0.4 mL) was added 2M aqueous sodium hydroxide solution (52 μL) under ice-cooling, and the mixture was stirred at room temperature for 10 min. To the reaction mixture was added water (0.5 mL), and the mixture was stirred at room temperature for 40 min. The reaction mixture was acidified with 1M hydrochloric acid, and extracted with ethyl acetate. The organic layer was separated, washed with saturated brine, dried over anhydrous sodium sulfate, and concentrated under reduced pressure to give the title compound (30.0 mg).

MS: $[M+H]^+$ 337.1.

D) 2-cyclopropyl-6-[2-(2,2-difluoroethoxy)phenyl]-N-[4-(2-hydroxypropan-2-yl)phenyl]-5-oxo-2,5-dihydropyridazine-4-carboxamide To a mixture of 2-cyclopropyl-6-[2-(2,2-difluoroethoxy)phenyl]-5-oxo-2,5-dihydropyridazine-4-carboxylic acid (30 mg), 2-(4-aminophenyl)propan-2-ol (17.54 mg), TEA (0.025 mL) and DMF (0.4 mL) was added HATU (50.9 mg), and the mixture was stirred at room temperature for 1 hr. To the reaction mixture was added brine, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane), and crystallized from ethyl acetate/hexane to give the title compound (27 mg).

$^1$H NMR (300 MHz, DMSO-$d_6$) δ 1.00-1.10 (2H, m), 1.18-1.27 (2H, m), 1.41 (6H, s), 4.18 (1H, tt, J=7.4, 3.7 Hz), 4.34 (2H, td, J=14.6, 3.6 Hz), 4.95 (1H, s), 5.96-6.42 (1H, m), 7.13 (1H, td, J=7.4, 0.9 Hz), 7.24 (1H, d, J=8.3 Hz), 7.36 (1H, dd, J=7.5, 1.9 Hz), 7.41-7.53 (3H, m), 7.55-7.62 (2H, m), 9.15 (1H, s), 12.00 (1H, s).

Example 175

6-[2-(2,2-difluoroethoxy)phenyl]-2-[(oxetan-3-yl)methyl]-5-oxo-N-[4-(1,1,3,3-tetrafluoro-2-hydroxypropan-2-yl)phenyl]-2,5-dihydropyridazine-4-carboxamide A) methyl 6-[2-(2,2-difluoroethoxy)phenyl]-5-oxo-2,5-dihydropyridazine-4-carboxylate A mixture of 5-bromo-3-[2-(2,2-difluoroethoxy)phenyl]pyridazin-4(1H)-one (9 g), [1,1-bis(diphenylphosphino)ferrocene]dichloropalladium(II) (1.989 g), TEA (8 mL) and MeOH (160 mL) was stirred under carbon monoxide (0.5 MPa) atmosphere at 85° C. for 5 hr. The reaction mixture was dissolved in hot methanol, and the catalyst was removed by filtration through Celite, and the filtrate was concentrated under reduced pressure. The residue was suspended in ethyl acetate, and the solid was collected by filtration, and washed with water and acetonitrile to give the title compound (7.54 g).

MS: $[M+H]^+$ 311.1.

B) methyl 6-[2-(2,2-difluoroethoxy)phenyl]-2-[(oxetan-3-yl)methyl]-5-oxo-2,5-dihydropyridazine-4-carboxylate To a mixture of methyl 6-[2-(2,2-difluoroethoxy)phenyl]-5-oxo-2,5-dihydropyridazine-4-carboxylate (483 mg), 3-(bromomethyl)oxetane (260 mg) and DMF (3 mL) was added potassium carbonate (346 mg), and the mixture was stirred under argon atmosphere at 75° C. for 4 hr. To the reaction mixture was added water, and the mixture was extracted with ethyl acetate. The organic layers were combined, washed with saturated brine, dried over anhydrous sodium sulfate, and concentrated under reduced pressure. The residue was purified by silica gel column chromatography (NH, ethyl acetate/hexane) to give the title compound (396 mg).

MS: $[M+H]^+$ 381.1.

C) 6-[2-(2,2-difluoroethoxy)phenyl]-2-[(oxetan-3-yl)methyl]-5-oxo-2,5-dihydropyridazine-4-carboxylic acid To a solution of methyl 6-[2-(2,2-difluoroethoxy)phenyl]-2-[(oxetan-3-yl)methyl]-5-oxo-2,5-dihydropyridazine-4-carboxylate (393 mg) in methanol (2 mL) was added 2M aqueous sodium hydroxide solution (0.78 mL), and the mixture was stirred at room temperature for 30 min. The reaction mixture was acidified with 6M hydrochloric acid, and concentrated under reduced pressure, and the residue was extracted with ethyl acetate. The organic layers were combined, washed with saturated brine, dried over anhydrous sodium sulfate, and concentrated under reduced pressure to give the title compound (379 mg).

MS: $[M+H]^+$ 367.1.

D) 6-[2-(2,2-difluoroethoxy)phenyl]-2-[(oxetan-3-yl)methyl]-5-oxo-N-[4-(1,1,3,3-tetrafluoro-2-hydroxypropan-2-yl)phenyl]-2,5-dihydropyridazine-4-carboxamide To a mixture of 6-[2-(2,2-difluoroethoxy)phenyl]-2-[(oxetan-3-yl)methyl]-5-oxo-2,5-dihydropyridazine-4-carboxylic acid (53 mg), 2-(4-aminophenyl)-1,1,3,3-tetrafluoropropan-2-ol (42.0 mg), TEA (0.040 mL) and DMF (0.6 mL) was added HATU (83 mg), and the mixture was stirred at room temperature for 1 hr. To the reaction mixture was added water, and the mixture was extracted with ethyl acetate. The organic layers were combined, dried over anhydrous sodium sulfate, and concentrated under reduced pressure. The residue was purified by silica gel column chromatography (ethyl acetate/hexane), and the obtained solid was washed with diisopropyl ether/hexane to give the title compound (58 mg).

$^1H$ NMR (300 MHz, DMSO-$d_6$) δ 3.49-3.62 (1H, m), 4.34 (2H, td, J=14.7, 3.4 Hz), 4.47 (2H, t, J=6.4 Hz), 4.61-4.71 (4H, m), 5.98-6.62 (3H, m), 6.95 (1H, s), 7.09-7.18 (1H, m), 7.24 (1H, d, J=7.9 Hz), 7.35 (1H, dd, J=7.5, 1.5 Hz), 7.46-7.53 (1H, m), 7.57 (2H, d, J=9.0 Hz), 7.72 (2H, d, J=8.7 Hz), 9.21 (1H, s), 12.14 (1H, s).

Example 177

6-[2-(2,2-difluoroethoxy)phenyl]-2-(difluoromethyl)-5-oxo-N-[6-(1,1,3,3-tetrafluoro-2-hydroxypropan-2-yl)pyridin-3-yl]-2,5-dihydropyridazine-4-carboxamide To a mixture of 6-[2-(2,2-difluoroethoxy)phenyl]-2-(difluoromethyl)-5-oxo-2,5-dihydropyridazine-4-carboxylic acid (637 mg), 2-(5-aminopyridin-2-yl)-1,1,3,3-tetrafluoropropan-2-ol (495 mg), TEA (0.513 mL) and DMF (6 mL) was added HATU (1049 mg), and the mixture was stirred at room temperature for 1 hr. To the reaction mixture was added water, and the mixture was extracted with ethyl acetate. The organic layers were combined, washed with water and saturated brine, dried over anhydrous sodium sulfate, and concentrated under reduced pressure. The residue was purified by silica gel column chromatography (ethyl acetate/hexane), the objective fraction was concentrated, and the solid was washed with ethyl acetate/heptane to give the title compound (515 mg).

$^1H$ NMR (300 MHz, DMSO-$d_6$) δ 4.36 (2H, td, J=14.6, 3.6 Hz), 6.00-6.75 (3H, m), 7.12 (1H, s), 7.17 (1H, td, J=7.4, 0.9 Hz), 7.28 (1H, d, J=7.9 Hz), 7.41 (1H, dd, J=7.5, 1.9 Hz), 7.50-7.60 (1H, m), 7.68-8.12 (2H, m), 8.28 (1H, dd, J=8.7, 2.3 Hz), 8.88 (1H, d, J=1.9 Hz), 9.47 (1H, s), 11.67 (1H, s).

Example 179

6-[2-(2,2-difluoroethoxy)phenyl]-2-(2,2-difluoroethyl)-N-[4-(2-hydroxypropan-2-yl)phenyl]-5-oxo-2,5-dihydropyridazine-4-carboxamide A) methyl 6-[2-(2,2-difluoroethoxy)phenyl]-2-(2,2-difluoroethyl)-5-oxo-2,5-dihydropyridazine-4-carboxylate To a solution of methyl 6-[2-(2,2-difluoroethoxy)phenyl]-5-oxo-2,5-dihydropyridazine-4-carboxylate (500 mg) in DMF (6 mL) were added successively 2,2-difluoroethyl trifluoromethanesulfonate (0.330 mL) and potassium carbonate (334 mg), and the mixture was stirred at room temperature for 2 hr. To the reaction mixture was added water, and the mixture was extracted with ethyl acetate. The organic layers were combined, washed with saturated brine, dried over anhydrous sodium sulfate, and concentrated under reduced pressure. The residue was purified by silica gel column chromatography (NH, ethyl acetate/hexane) to give the title compound (587 mg).

MS: $[M+H]^+$ 375.1.

B) 6-[2-(2,2-difluoroethoxy)phenyl]-2-(2,2-difluoroethyl)-5-oxo-2,5-dihydropyridazine-4-carboxylic acid A mixture of methyl 6-[2-(2,2-difluoroethoxy)phenyl]-2-(2,2-difluoroethyl)-5-oxo-2,5-dihydropyridazine-4-carboxylate (573 mg), THF (2 mL) and MeOH (2 mL) was cooled to 10° C., 2M aqueous sodium hydroxide solution (0.919 mL) was added thereto, and the mixture was stirred at room temperature for 30 min. The reaction mixture was neutralized with 6M hydrochloric acid, and concentrated under reduced pressure. To the residue was added water, and the mixture was acidified with 1M hydrochloric acid, and extracted with ethyl acetate. The organic layers were combined, washed with saturated brine, dried over anhydrous sodium sulfate, and concentrated under reduced pressure. The residue was suspended in diisopropyl ether, and the solid was collected by filtration to give the title compound (534 mg).

MS: $[M+H]^+$ 361.1.

C) 6-[2-(2,2-difluoroethoxy)phenyl]-2-(2,2-difluoroethyl)-N-[4-(2-hydroxypropan-2-yl)phenyl]-5-oxo-2,5-dihydropyridazine-4-carboxamide To a mixture of 6-[2-(2,2-difluoroethoxy)phenyl]-2-(2,2-difluoroethyl)-5-oxo-2,5-dihydropyridazine-4-carboxylic acid (60 mg), 2-(4-aminophenyl)propan-2-ol (36 mg), TEA (46 μL) and DMF (0.6 mL) was added HATU (95 mg), and the mixture was stirred at room temperature for 2 hr. To the reaction mixture was added water, and the mixture was extracted with ethyl acetate. The organic layers were combined, washed with saturated brine, dried over anhydrous sodium sulfate, and concentrated under reduced pressure. The residue was purified by silica gel column chromatography (ethyl acetate/hexane), and the solid was washed with ethyl acetate/hexane to give the title compound (63 mg).

$^1$H NMR (300 MHz, DMSO-$d_6$) δ 1.41 (6H, s), 4.35 (2H, td, J=14.5, 3.8 Hz), 4.80-4.99 (3H, m), 5.97-6.74 (2H, m), 7.10-7.18 (1H, m), 7.25 (1H, d, J=7.9 Hz), 7.37 (1H, dd, J=7.5, 1.5 Hz), 7.42-7.47 (2H, m), 7.48-7.55 (1H, m), 7.55-7.61 (2H, m), 9.22 (1H, s), 11.86 (1H, s).

Example 182

6-[2-(2,2-difluoroethoxy)phenyl]-N-(2,4-difluorophenyl)-2-(oxetan-3-yl)-5-oxo-2,5-dihydropyridazine-4-carboxamide

A) methyl 6-[2-(2,2-difluoroethoxy)phenyl]-2-(oxetan-3-yl)-5-oxo-2,5-dihydropyridazine-4-carboxylate To a solution of methyl 6-[2-(2,2-difluoroethoxy)phenyl]-5-oxo-2,5-dihydropyridazine-4-carboxylate (400 mg) in DMF (2.5 mL) were added successively 3-iodooxetane (284 μL) and potassium carbonate (356 mg), and the mixture was stirred under argon atmosphere at 90° C. for 5.5 hr. To the reaction mixture was added water, and the mixture was extracted with ethyl acetate. The organic layers were combined, washed with saturated brine, dried over anhydrous sodium sulfate, and concentrated under reduced pressure. The residue was purified by silica gel column chromatography (NH, ethyl acetate/hexane) to give the title compound (398 mg).

MS: $[M+H]^+$ 367.1.

B) 6-[2-(2,2-difluorethoxy)phenyl]-2-(oxetan-3-yl)-5-oxo-2,5-dihydropyridazine-4-carboxylic acid To a solution of methyl 6-[2-(2,2-difluoroethoxy)phenyl]-2-(oxetan-3-yl)-5-oxo-2,5-dihydropyridazine-4-carboxylate (399 mg) in MeOH (3 mL) was added 2M aqueous sodium hydroxide solution (2 mL), and the mixture was stirred at room temperature for 2 hr. To the reaction mixture were added MeOH (2 mL) and THF (2 mL), and the mixture was stirred at room temperature for 12 hr, and concentrated under reduced pressure. To the residue was added water, and the mixture was acidified with 1M hydrochloric acid, and extracted with ethyl acetate. The organic layers were combined, washed with saturated brine, dried over anhydrous sodium sulfate, and concentrated under reduced pressure. The residue was washed with diisopropyl ether/diethyl ether to give the title compound (260 mg).

MS: $[M+H]^+$ 353.1.

C) 6-[2-(2,2-difluoroethoxy)phenyl]-N-(2,4-difluorophenyl)-2-(oxetan-3-yl)-5-oxo-2,5-dihydropyridazine-4-carboxamide To a mixture of 6-[2-(2,2-difluoroethoxy)phenyl]-2-(oxetan-3-yl)-5-oxo-2,5-dihydropyridazine-4-carboxylic acid (50 mg), 2,4-difluoroaniline (0.019 mL), TEA (0.040 mL) and DMF (0.6 mL) was added HATU (81 mg), and the mixture was stirred at room temperature for 1 hr. To the reaction mixture was added water, and the mixture was extracted with ethyl acetate. The organic layers were combined, dried over anhydrous sodium sulfate, and concentrated under reduced pressure. The solid was washed with ethyl acetate to give the title compound (52 mg).

$^1$H NMR (300 MHz, DMSO-$d_6$) δ 4.37 (2H, td, J=14.6, 3.6 Hz), 4.81-4.98 (4H, m), 5.81-5.94 (1H, m), 5.98-6.41 (1H, m), 7.07-7.22 (2H, m), 7.29 (1H, d, J=7.9 Hz), 7.40 (1H, ddd, J=11.5, 8.8, 3.0 Hz), 7.45-7.58 (2H, m), 8.43 (1H, td, J=9.1, 6.2 Hz), 9.10 (1H, s), 12.23 (1H, d, J=1.9 Hz).

Example 190

N-[4-(2-cyanopropan-2-yl)phenyl]-2-methyl-5-oxo-6-[2-(2,2,2-trifluoroethoxy)phenyl]-2,5-dihydropyridazine-4-carboxamide

A) 1-iodo-2-(2,2,2-trifluoroethoxy)benzene

To a solution of 2-iodophenol (15 g) in DMF (110 mL) were added successively cesium carbonate (28.9 g) and 2,2,2-trifluoroethyl trifluoromethanesulfonate (11.79 mL), and the mixture was stirred at room temperature for 48 hr. The reaction mixture was cooled to 0° C., water was added thereto, and the mixture was extracted with ethyl acetate. The organic layers were combined, washed with saturated brine, dried over anhydrous sodium sulfate, and concentrated under reduced pressure. The residue was diluted with diethyl ether, and the mixture was washed with water and saturated brine, dried over anhydrous sodium sulfate, and concentrated under reduced pressure to give the title compound (22.5 g).

$^1$H NMR (300 MHz, DMSO-$d_6$) δ 4.82 (2H, q, J=8.7 Hz), 6.84 (1H, td, J=7.6, 1.3 Hz), 7.14 (1H, dd, J=8.3, 1.1 Hz), 7.40 (1H, ddd, J=8.4, 7.1, 1.5 Hz), 7.82 (1H, dd, J=7.5, 1.5 Hz).

B) 1-(prop-1-yn-1-yl)-2-(2,2,2-trifluoroethoxy)benzene

To a solution of 1-iodo-2-(2,2,2-trifluoroethoxy)benzene (20.59 g) in DMF (50 mL) were added dichlorobis(triphenylphosphine)palladium(II) (2.5 g) and copper iodide (2.1 g) under argon atmosphere, prop-1-yne (100 mL) and TEA (11 mL) were added thereto, and the mixture was stirred at room temperature for 6 hr. Prop-1-yne (15 mL) was added thereto, and the mixture was stirred at room temperature for 16 hr. The reaction mixture was concentrated under reduced pressure, to the residue was added water, and the mixture was extracted with ethyl acetate. The organic layers were combined, washed with water, aqueous sodium hydrogencarbonate solution and saturated brine, dried over anhydrous sodium sulfate, and concentrated under reduced pressure. The residue was filtered through pad filled with silica gel, and the filtrate was concentrated under reduced pressure to give the title compound (12.65 g).

$^1$H NMR (300 MHz, DMSO-$d_6$) δ 2.05 (3H, s), 4.79 (2H, q, J=9.0 Hz), 7.00 (1H, td, J=7.4, 0.9 Hz), 7.14 (1H, d, J=7.9 Hz), 7.28-7.40 (2H, m).

C) 1-[2-(2,2,2-trifluoroethoxy)phenyl]propane-1,2-dione

To a mixture of sodium hydrogencarbonate (0.824 g), anhydrous magnesium sulfate (1.475 g), sodium periodate (31.5 g), ethyl acetate (100 mL), acetonitrile (100 mL) and water (150 mL) was added ruthenium(III) chloride (0.203 g), and the mixture was cooled to 0° C. A solution of 1-(prop-1-yn-1-yl)-2-(2,2,2-trifluoroethoxy)benzene (10.5 g) in ethyl acetate (15 mL) was added thereto at 0° C., and the mixture was stirred at 0° C. for 5 min. To the reaction mixture was added water, the supernatant was separated, and the insoluble substance was removed by filtration through Celite. The organic layer of the filtrate was separated, and the aqueous layer was extracted with ethyl acetate. The organic layers were combined, washed with saturated brine, and the aqueous layer was extracted with ethyl acetate. The organic layers were combined, dried over anhydrous sodium sulfate, and concentrated under reduced pressure. The residue was purified by silica gel column chromatography (ethyl acetate/hexane) to give the title compound (8.21 g).

$^1$H NMR (300 MHz, DMSO-$d_6$) δ 2.37 (3H, s), 4.89 (2H, q, J=8.7 Hz), 7.21-7.28 (1H, m), 7.32 (1H, d, J=8.3 Hz), 7.70-7.80 (2H, m).

D) (3E)-4-(dimethylamino)-1-[2-(2,2,2-trifluoroethoxy)phenyl]but-3-ene-1,2-dione A mixture of 1-[2-(2,2,2-trifluoroethoxy)phenyl]propane-1,2-dione (8.21 g), 1,1-dimethoxy-N,N-dimethylmethanamine (25 mL) and toluene (80 mL) was stirred at 130° C. for 5 hr. N,N-Dimethylformamide dimethyl acetal (15 mL) was added thereto, and the mixture was stirred at 130° C. for 2 hr. The reaction mixture was concentrated under reduced pressure, and the residue was purified by silica gel column chromatography (ethyl acetate/hexane) to give the title compound (6.7 g).

MS: $[M+H]^+$ 302.1.

E) 3-[2-(2,2,2-trifluoroethoxy)phenyl]pyridazin-4(1H)-one

To a solution of (3E)-4-(dimethylamino)-1-[2-(2,2,2-trifluoroethoxy)phenyl]but-3-ene-1,2-dione (6.7 g) in ethanol (60 mL) was added hydrazine monohydrate (1.1 mL), and the mixture was stirred at 60° C. for 2 hr. The reaction mixture was concentrated under reduced pressure, and the residue was suspended in a hot mixed solution of ethyl acetate/hexane, and cooled. The solid was collected by filtration to give the title compound (4.8 g).

MS: $[M+H]^+$ 271.0.

F) 5-bromo-3-[2-(2,2,2-trifluoroethoxy)phenyl]pyridazin-4(1H)-one

To a solution of 3-[2-(2,2,2-trifluoroethoxy)phenyl]pyridazin-4(1H)-one (4.8 g) in DMF (75 mL) was added N-bromosuccinimide (4.1 g) over 30 min at 0° C., and the mixture was stirred at 0° C. for 1.5 hr. N-Bromosuccinimide (0.85 g) was added thereto at 0° C., and the mixture was stirred at 0° C. for 1.5 hr. To the reaction mixture was added water, and the mixture was stirred at 0° C. for 5 min. The solid was collected by filtration, and washed with water to give the title compound (5.55 g).

MS: $[M+H]^+$ 349.0.

G) methyl 5-oxo-6-[2-(2,2,2-trifluoroethoxy)phenyl]-2,5-dihydropyridazine-4-carboxylate A mixture of 5-bromo-3-[2-(2,2,2-trifluoroethoxy)phenyl]pyridazin-4(1H)-one (750 mg), dichloro[1,1'-bis(diphenylphosphino)ferrocene]palladium(II) (157 mg), TEA (0.599 mL) and MeOH (10 mL) was stirred under carbon monoxide (0.5 MPa) atmosphere at 85° C. for 5 hr. To the reaction mixture was added hot MeOH, the insoluble substance was removed by filtration, and the filtrate was concentrated under reduced pressure. The residue was suspended in ethyl acetate, and the solid was collected by filtration, and washed with water and acetonitrile to give the title compound (626 mg).

MS: $[M+H]^+$ 329.1.

H) methyl 2-methyl-5-oxo-6-[2-(2,2,2-trifluoroethoxy)phenyl]-2,5-dihydropyridazine-4-carboxylate To a solution of methyl 5-oxo-6-[2-(2,2,2-trifluoroethoxy)phenyl]-2,5-dihydropyridazine-4-carboxylate (160 mg) in DMF (1.4 mL) were added iodomethane (0.076 mL) and potassium carbonate (101 mg), and the mixture was stirred under argon atmosphere at 75° C. for 1.5 hr. To the reaction mixture was added water, and the mixture was extracted with ethyl acetate. The organic layers were combined, washed with saturated brine, dried over anhydrous sodium sulfate, and concentrated under reduced pressure. The residue was purified by silica gel column chromatography (NH, ethyl acetate/hexane) to give the title compound (181 mg).

MS: $[M+H]^+$ 343.1.

I) 2-methyl-5-oxo-6-[2-(2,2,2-trifluoroethoxy)phenyl]-2,5-dihydropyridazine-4-carboxylic acid To a mixture of methyl 2-methyl-5-oxo-6-[2-(2,2,2-trifluoroethoxy)phenyl]-2,5-dihydropyridazine-4-carboxylate (197 mg), THF (1.5 mL) and MeOH (1.5 mL) was added 2M aqueous sodium hydroxide solution (0.345 mL) at 0° C., and the mixture was stirred at room temperature for 30 min. The reaction mixture was neutralized with 1M hydrochloric acid, and the solvent was evaporated under reduced pressure. The residue was suspended in water and 1M hydrochloric acid, and the resulting solid was collected by filtration to give the title compound (180 mg).

MS: $[M+H]^+$ 329.0.

J) N-[4-(2-cyanopropan-2-yl)phenyl]-2-methyl-5-oxo-6-[2-(2,2,2-trifluoroethoxy)phenyl]-2,5-dihydropyridazine-4-carboxamide To a mixture of 2-methyl-5-oxo-6-[2-(2,2,2-trifluoroethoxy)phenyl]-2,5-dihydropyridazine-4-carboxylic acid (35 mg), 2-(4-aminophenyl)-2-methylpropanenitrile (25.6 mg), DIPEA (0.037 mL) and DMF (1 mL) was added HATU (60.8 mg), and the mixture was stirred at room temperature for 4 hr. To the reaction mixture was added water, and the mixture was extracted with ethyl acetate. The organic layers were combined, washed with saturated brine, dried over anhydrous magnesium sulfate, and concentrated under reduced pressure. The residue was purified by silica gel column chromatography (NH, ethyl acetate/hexane) to give the title compound (41.5 mg).

$^1$H NMR (300 MHz, DMSO-$d_6$) δ 1.68 (6H, s), 4.08 (3H, s), 4.76 (2H, q, J=8.8 Hz), 7.18 (1H, td, J=7.4, 0.9 Hz), 7.29 (1H, d, J=7.9 Hz), 7.39 (1H, dd, J=7.5, 1.9 Hz), 7.48-7.56 (3H, m), 7.68-7.74 (2H, m), 9.14 (1H, s), 12.19 (1H, s).

Example 193 rac-6-[2-(2,2-difluoroethoxy)phenyl]-N-[4-(2-hydroxypropan-2-yl)phenyl]-5-oxo-2-(oxolan-3-yl)-2,5-dihydropyridazine-4-carboxamide A) rac-methyl 6-[2-(2,2-difluoroethoxy)phenyl]-5-oxo-2-(oxolan-3-yl)-2,5-dihydropyridazine-4-carboxylate To a mixture of methyl 6-[2-(2,2-difluoroethoxy)phenyl]-5-oxo-2,5-dihydropyridazine-4-carboxylate (200 mg), ractetrahydrofuran-3-ol (95 mg), triphenylphosphine (270 mg) and THF (2.5 mL) was added bis(2-methoxyethyl) azodicarboxylate (226 mg), and the mixture was stirred at room temperature for 3 hr. To the reaction mixture were added water and saturated brine, and the mixture was extracted with ethyl acetate. The organic layers were combined, washed with saturated brine, dried over anhydrous sodium sulfate, and concentrated under reduced pressure. The residue was purified by silica gel column chromatography (NH, ethyl acetate/hexane) and silica gel column chromatography (methanol/ethyl acetate) to give the title compound (342 mg) as a crude product.

MS: $[M+H]^+$ 381.1.

B) rac-6-[2-(2,2-difluoroethoxy)phenyl]-5-oxo-2-(oxolan-3-yl)-2,5-dihydropyridazine-4-carboxylic acid To a mixture of rac-methyl 6-[2-(2,2-difluoroethoxy)phenyl]-5-oxo-2-(oxolan-3-yl)-2,5-dihydropyridazine-4-carboxylate (342 mg), MeOH (3 mL) and THF (3 mL) was added 2M aqueous sodium hydroxide solution (0.4 mL), and the mixture was stirred at room temperature for 2 hr. The reaction mixture was concentrated under reduced pressure, to the residue was added water, and the mixture was extracted with ethyl acetate. The organic layers were combined, washed with saturated brine, dried over anhydrous sodium sulfate, and concentrated under reduced pressure. To the residue were added ethyl acetate/diisopropyl ether/hexane, and the resulting solid was collected by filtration to give the title compound (155 mg).

MS: $[M+H]^+$ 367.1.

C) rac-6-[2-(2,2-difluoroethoxy)phenyl]-N-[4-(2-hydroxypropan-2-yl)phenyl]-5-oxo-2-(oxolan-3-yl)-2,5-dihydropyridazine-4-carboxamide To a mixture of rac-6-[2-(2,2-difluoroethoxy)phenyl]-5-oxo-2-(oxolan-3-yl)-2,5-dihydropyridazine-4-carboxylic acid (45 mg), 2-(4-aminophenyl)propan-2-ol (24.15 mg), TEA (0.034 mL) and DMF (0.5 mL) was added HATU (70.1 mg), and the mixture was stirred at room temperature for 1 hr. To the reaction mixture were added water and saturated brine, and the mixture was extracted with ethyl acetate. The organic layers were combined, dried over anhydrous sodium sulfate, and concentrated under reduced pressure. The residue was purified by silica gel column chromatography (ethyl acetate/hexane) to give the title compound (2 mg).

$^1$H NMR (300 MHz, DMSO-$d_6$) δ 1.41 (6H, s), 2.22-2.46 (2H, m), 3.78 (1H, td, J=8.1, 6.0 Hz), 3.91-4.00 (2H, m), 4.02-4.10 (1H, m), 4.35 (2H, td, J=14.6, 3.6 Hz), 4.96 (1H, s), 5.24-5.40 (1H, m), 5.96-6.43 (1H, m), 7.09-7.19 (1H, m), 7.25 (1H, d, J=7.9 Hz), 7.36-7.53 (4H, m), 7.54-7.61 (2H, m), 9.13 (1H, s), 12.02 (1H, s).

Example 197

6-acetyl-N-[4-(difluoromethoxy)phenyl]-3-oxo-2-[2-(2,2,2-trifluoroethoxy)phenyl]-2,3-dihydropyridazine-4-carboxamide A) 3-oxo-2-{2-[2-(2,2,2-trifluoroethoxy)phenyl]hydrazinylidene}butanal To a mixture of 2-(2,2,2-trifluoroethoxy)aniline (1.00 g) and 6M hydrochloric acid (5.3 mL) was added dropwise an aqueous solution (2 mL) of sodium nitrite (435.9 mg) at 0° C., and the mixture was stirred at 0° C. for 15 min to prepare an aqueous diazonium salt solution. To a mixture of (3E)-4-(dimethylamino)but-3-en-2-one (600.5 mg), sodium acetate (3.01 g) and MeOH (12 mL) was added dropwise the above aqueous diazonium salt solution at 0° C., and the mixture was stirred at room temperature for 1 hr. The MeOH was evaporated under reduced pressure, to the reaction mixture was added water, and the mixture was extracted with ethyl acetate. The organic layer was separated, washed with saturated brine, dried over anhydrous magnesium sulfate, and concentrated under reduced pressure. The resulting solid was collected by filtration, and washed with diisopropyl ether/hexane to give the title compound (884.7 mg). The filtrate was concentrated under reduced pressure, and the residue was purified by silica gel column chromatography (ethyl acetate/hexane) to give the title compound (271.8 mg).

MS: $[M+H]^+$ 289.0.

B) ethyl 6-acetyl-3-oxo-2-[2-(2,2,2-trifluoroethoxy)phenyl]-2,3-dihydropyridazine-4-carboxylate A mixture of 3-oxo-2-{2-[2-(2,2,2-trifluoroethoxy)phenyl]hydrazinylidene}butanal (1.16 g), diethyl malonate (740 μL), piperidine (0.2 mL) and pyridine (12 mL) was stirred at 120° C. for 3.5 hr. The reaction mixture was concentrated under reduced pressure, and the pyridine was evaporated by azeotrope with toluene. The residue was purified by silica gel column chromatography (ethyl acetate/hexane) to give the title compound (622.5 mg).

MS: $[M+H]^+$ 385.1.

C) 6-acetyl-3-oxo-2-[2-(2,2,2-trifluoroethoxy)phenyl]-2,3-dihydropyridazine-4-carboxylic acid To a solution of ethyl 6-acetyl-3-oxo-2-[2-(2,2,2-trifluoroethoxy)phenyl]-2,3-dihydropyridazine-4-carboxylate (620 mg) in EtOH (10 mL) was added 4M aqueous lithium hydroxide solution (0.6 mL) at room temperature, and the mixture was stirred at room temperature for 1 hr. The reaction mixture was acidified with 6M hydrochloric acid, and the precipitate was collected by filtration to give the title compound (281.6 mg). The filtrate was concentrated under reduced pressure, and the residue was extracted with ethyl acetate. The organic layers were combined, dried over anhydrous magnesium sulfate, and concentrated under reduced pressure to give the title compound (284.6 mg).

MS: $[M+H]^+$ 357.0.

D) 6-acetyl-N-[4-(difluoromethoxy)phenyl]-3-oxo-2-[2-(2,2,2-trifluoroethoxy)phenyl]-2,3-dihydropyridazine-4-carboxamide To a mixture of 6-acetyl-3-oxo-2-[2-(2,2,2-trifluoroethoxy)phenyl]-2,3-dihydropyridazine-4-carboxylic acid (120.7 mg), 4-(difluoromethoxy)aniline (71.1 mg), TEA (193 μL) and DMF (1.5 mL) was added HATU (195.1 mg), and the mixture was stirred at room temperature for 1 hr. To the reaction mixture was added water, and the mixture was extracted with ethyl acetate. The organic layer was separated, dried over anhydrous magnesium sulfate, and concentrated under reduced pressure. The residue was purified by silica gel column chromatography (ethyl acetate/hexane), and the obtained solid was collected by filtration to give the title compound (56.9 mg). The filtrate was concentrated under reduced pressure, and the residue was purified by silica gel column chromatography (ethyl acetate/hexane) to give the title compound (34.1 mg).

$^1$H NMR (300 MHz, DMSO-$d_6$) δ 2.46-2.54 (3H, m), 4.73-5.03 (2H, m), 6.93-7.48 (1H, m), 7.18-7.25 (2H, m), 7.29 (1H, td, J=7.5, 1.1 Hz), 7.41-7.48 (1H, m), 7.58-7.66 (2H, m), 7.72-7.80 (2H, m), 8.58 (1H, s), 11.26 (1H, s).

Example 198 ethyl 5-{[4-(difluoromethoxy)phenyl]carbamoyl}-6-oxo-1-[2-(2,2,2-trifluoroethoxy)phenyl]-1,6-dihydropyridazine-3-carboxylate A) ethyl 3-oxo-2-{2-[2-(2,2,2-trifluoroethoxy)phenyl]hydrazinylidene}propanoate To a mixture of 2-(2,2,2-trifluoroethoxy)aniline (1.01 g) and 6M hydrochloric acid (5.3 mL) was added slowly an aqueous solution (2 mL) of sodium nitrite (443.3 mg) at 0° C., and the mixture was stirred at 0° C. for 15 min to prepare an aqueous diazonium salt solution. To a mixture of ethyl 3-(dimethylamino)prop-2-enoate (765.6 mg), sodium acetate (3.03 g) and EtOH (12 mL) was added the above aqueous diazonium salt solution at 0° C., and the mixture was stirred at room temperature for 1 hr. The reaction mixture was concentrated under reduced pressure, water was added thereto, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (1.30 g).

MS: $[M+H]^+$ 319.0.

B) 5-benzyl 3-ethyl 6-oxo-1-[2-(2,2,2-trifluoroethoxy)phenyl]-1,6-dihydropyridazine-3,5-dicarboxylate To a mixture of ethyl 3-oxo-2-{2-[2-(2,2,2-trifluoroethoxy)phenyl]hydrazinylidene}propanoate (1.30 g), dibenzyl malonate (1.25 mL) and pyridine (13 mL) was added piperidine (0.2 mL), and the mixture was stirred at 120° C. for 2 hr. Piperidine (0.04 mL) was added thereto, and the mixture was stirred at 120° C. for 1 hr. The reaction mixture was concentrated under reduced pressure, and the remaining pyridine was evaporated by azeotrope with toluene. The residue was purified by silica gel column chromatography (ethyl acetate/hexane) to give the title compound (838.7 mg).

MS: $[M+H]^+$ 477.1.

C) 6-(ethoxycarbonyl)-3-oxo-2-[2-(2,2,2-trifluoroethoxy)phenyl]-2,3-dihydropyridazine-4-carboxylic acid A mixture of 5-benzyl 3-ethyl 6-oxo-1-[2-(2,2,2-trifluoroethoxy)phenyl]-1,6-dihydropyridazine-3,5-dicarboxylate (438.4 mg), 10% palladium-carbon (55% wet, 50.5 mg) and EtOH (7 mL) was stirred under normal pressure of hydrogen atmosphere at room temperature for 1 hr. The catalyst was removed by filtration, and the filtrate was concentrated under reduced pressure. The residue was crystallized from ethyl acetate/hexane to give the title compound (267.8 mg). The filtrate was concentrated under reduced pressure to give the title compound (82.8 mg).

MS: $[M+H]^+$ 387.0.

D) ethyl 5-{[4-(difluoromethoxy)phenyl]carbamoyl}-6-oxo-1-[2-(2,2,2-trifluoroethoxy)phenyl]-1,6-dihydropyridazine-3-carboxylate To a mixture of 6-(ethoxycarbonyl)-3-oxo-2-[2-(2,2,2-trifluoroethoxy)phenyl]-2,3-dihydropyridazine-4-carboxylic acid (66 mg), 4-(difluoromethoxy)aniline (32.2 mg), TEA (48 μL) and DMF (1 mL) was added HATU (97.9 mg), and the mixture was stirred at room temperature for 1 hr. To the reaction mixture was added water, and the mixture was dried over anhydrous magnesium sulfate, and concentrated under reduced pressure. The residue was purified by silica gel column chromatography (ethyl acetate/hexane) to give the title compound (74.4 mg).

$^1$H NMR (300 MHz, DMSO-$d_6$) δ 1.32 (3H, t, J=7.2 Hz), 4.38 (2H, q, J=7.2 Hz), 4.68-5.02 (2H, m), 6.93-7.47 (1H, m), 7.17-7.24 (2H, m), 7.28 (1H, td, J=7.5, 1.1 Hz), 7.39-7.47 (1H, m), 7.53-7.66 (2H, m), 7.72-7.80 (2H, m), 8.61 (1H, s), 11.28 (1H, s).

Example 199 rac-N-[4-(difluoromethoxy)phenyl]-6-(1-hydroxyethyl)-3-oxo-2-[2-(2,2,2-trifluoroethoxy)phenyl]-2,3-dihydropyridazine-4-carboxamide To a solution of 6-acetyl-N-[4-(difluoromethoxy)phenyl]-3-oxo-2-[2-(2,2,2-trifluoroethoxy)phenyl]-2,3-dihydropyridazine-4-carboxamide (39.8 mg) in THF (0.8 mL) was added dropwise 1.5M toluene solution (133.4 μL) of isobutylaluminium hydride at −78° C., and the mixture was stirred at −78° C. for 2.5 hr. To the reaction mixture was added aqueous ammonium chloride solution, and the mixture was extracted with ethyl acetate. The organic layer was separated, dried over anhydrous magnesium sulfate, and concentrated under reduced pressure. The residue was purified by high-performance liquid chromatography (acetonitrile/10 mM aqueous ammonium hydrogencarbonate solution) to give the title compound (9.4 mg).

$^1$H NMR (300 MHz, DMSO-$d_6$) δ 1.37 (3H, d, J=6.8 Hz), 4.63-4.93 (3H, m), 5.82 (1H, d, J=5.3 Hz), 6.94-7.45 (1H, m), 7.10-7.28 (3H, m), 7.38 (1H, d, J=8.7 Hz), 7.50-7.65 (2H, m), 7.71-7.82 (2H, m), 8.45 (1H, s), 11.53-11.76 (1H, m).

Example 200

N-[4-(difluoromethoxy)phenyl]-6-(2-hydroxypropan-2-yl)-3-oxo-2-[2-(2,2,2-trifluoroethoxy)phenyl]-2,3-dihydropyridazine-4-carboxamide A) rac-ethyl 5-{[4-(difluoromethoxy)phenyl]carbamoyl}-6-oxo-1-[2-(2,2,2-trifluoroethoxy)phenyl]-1,4,5,6-tetrahydropyridazine-3-carboxylate To a solution of ethyl 5-{[4-(difluoromethoxy)phenyl]carbamoyl}-6-oxo-1-[2-(2,2,2-trifluoroethoxy)phenyl]-1,6-dihydropyridazine-3-carboxylate (49.8 mg) in THF (1 mL) was added sodium triacetoxyborohydride (55.8 mg) at 0° C., and the mixture was stirred at 0° C. for 30 min. EtOH (0.007 mL) was added thereto, and the mixture was stirred at room temperature for 30 min. EtOH (0.007 mL) was added thereto, and the mixture was stirred at room temperature for 1 hr. EtOH (0.007 mL) was added thereto, and the mixture was stirred at room temperature for 2 hr. To the reaction mixture was added aqueous sodium hydrogencarbonate solution, and the mixture was extracted with ethyl acetate. The organic layer was separated, dried over anhydrous magnesium sulfate, and concentrated under reduced pressure to give the title compound (52.4 mg). MS: $[M+H]^+$ 530.2.

B) rac-N-[4-(difluoromethoxy)phenyl]-6-(2-hydroxypropan-2-yl)-3-oxo-2-[2-(2,2,2-trifluoroethoxy)phenyl]-2,3,4,5-tetrahydropyridazine-4-carboxamide To a solution of rac-ethyl 5-{[4-(difluoromethoxy)phenyl]carbamoyl}-6-oxo-1-[2-(2,2,2-trifluoroethoxy)phenyl]-1,4,5,6-tetrahydropyridazine-3-carboxylate (51.5 mg) in THF (1 mL) was added 3M 2-methyltetrahydrofuran solution (0.161 mL) of methylmagnesium bromide at 0° C., and the mixture was stirred at room temperature for 1 hr. 3M 2-methyltetrahydrofuran solution (0.161 mL) of methylmagnesium bromide was added thereto at 0° C., and the mixture was stirred at room temperature for 30 min. To the reaction mixture was added aqueous ammonium chloride solution, and the mixture was extracted with ethyl acetate. The organic layer was separated, dried over anhydrous magnesium sulfate, and concentrated under reduced pressure. The residue was purified by silica gel column chromatography (ethyl acetate/hexane) to give the title compound (30.3 mg).

MS: $[M-H]^-$ 514.1.

C) N-[4-(difluoromethoxy)phenyl]-6-(2-hydroxypropan-2-yl)-3-oxo-2-[2-(2,2,2-trifluoroethoxy)phenyl]-2,3-dihydropyridazine-4-carboxamide To a solution of rac-N-[4-(difluoromethoxy)phenyl]-6-(2-hydroxypropan-2-yl)-3-oxo-2-[2-(2,2,2-trifluoroethoxy)phenyl]-2,3,4,5-tetrahydropyridazine-4-carboxamide (25.9 mg) in toluene (0.6 mL) was added 4,5-dichloro-3,6-dioxocyclohexa-1,4-diene-1,2-dicarbonitrile (16.5 mg), and the mixture was stirred at 100° C. for 1 hr. To the reaction mixture was added water, and the mixture was extracted with ethyl acetate. The organic layer was separated, dried over anhydrous magnesium sulfate, and concentrated under reduced pressure. The residue was purified by silica gel column chromatography (ethyl acetate/hexane) to give the title compound (19.7 mg).

$^1$H NMR (300 MHz, DMSO-$d_6$) δ 1.42 (6H, br s), 4.68-4.94 (2H, m), 5.71 (1H, s), 6.92-7.46 (1H, m), 7.16-7.28 (3H, m), 7.39 (1H, d, J=7.5 Hz), 7.48-7.61 (2H, m), 7.70-7.80 (2H, m), 8.60 (1H, s), 11.68 (1H, s).

The compounds of Examples are shown in the following tables. MS in the tables means actual measured value. The compounds of Examples 2 to 53, 55 to 59, 61, 63 to 68, 70, 71, 74, 76 to 79, 81 to 93, 95 to 97, 99 to 107, 110 to 113, 115 to 118, 120, 122 to 126, 128 to 132, 134, 137 to 139, 141 to 143, 145, 147, 149 to 151, 153, 155 to 157, 159, 160, 164, 165 to 166, 170 to 174, 176, 178, 180, 181, 183 to 189, 191, 192, 194 to 196 and 201 to 203 in the following tables were produced according to the methods described in the above-mentioned Examples, or methods analogous thereto.

TABLE 1-1

| Ex. No. | IUPAC Name | Structure | Additive | MS |
|---|---|---|---|---|
| 1 | 1-(2-methoxyphenyl)-6-methyl-2-oxo-N-(4-phenoxyphenyl)-1,2-dihydropyridine-3-carboxamide | 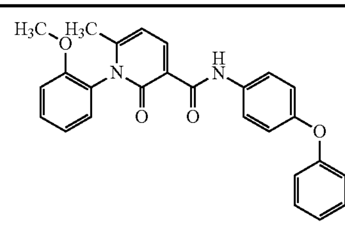 | | 427.2 |
| 2 | 1-(2-methoxyphenyl)-2-oxo-N-(4-phenoxyphenyl)-1,2-dihydropyridine-3-carboxamide | 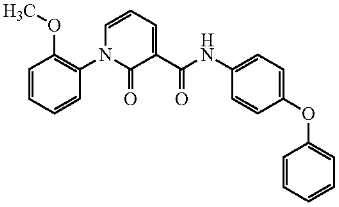 [SMILES: COc1ccccc1-n1cccc(C(=O)Nc2ccc(Oc3ccccc3)cc2)c1=O] | | 413.3 |
| 3 | 1-(4-fluoro-2-methoxyphenyl)-2-oxo-N-(4-phenoxyphenyl)-1,2-dihydropyridine-3-carboxamide | 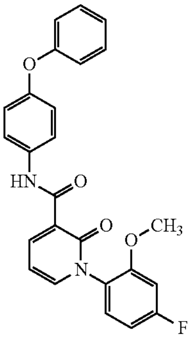 [SMILES: COc1cc(F)ccc1-n1cccc(C(=O)Nc2ccc(Oc3ccccc3)cc2)c1=O] | | 431.2 |

TABLE 1-1-continued

| Ex. No. | IUPAC Name | Structure | Additive | MS |
|---|---|---|---|---|
| 4 | 1-[2-(morpholin-4-yl)phenyl]-2-oxo-N-(4-phenoxyphenyl)-1,2-dihydropyridine-3-carboxamide | 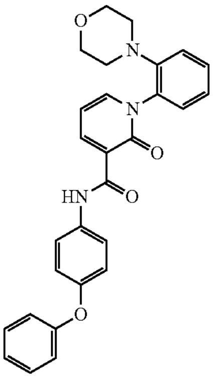 [SMILES: O=C(Nc1ccc(Oc2ccccc2)cc1)c1cccn(-c2ccccc2N2CCOCC2)c1=O] | | 468.3 |
| 5 | 1-(4-fluoro-2-methoxyphenyl)-2-oxo-N-[6-(2,2,2-trifluoroethoxy)pyridin-3-yl]-1,2-dihydropyridine-3-carboxamide | 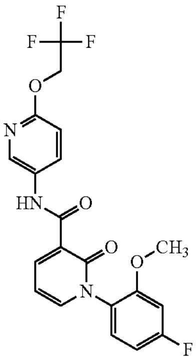 [SMILES: COc1cc(F)ccc1-n1cccc(C(=O)Nc2ccc(OCC(F)(F)F)nc2)c1=O] | | 438.1 |
| 6 | 1-(4-fluoro-2-methoxyphenyl)-2-oxo-N-[4-(trifluoromethoxy)phenyl]-1,2-dihydropyridine-3-carboxamide | 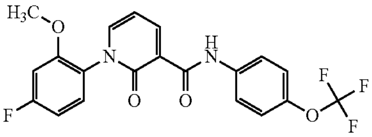 [SMILES: COc1cc(F)ccc1-n1cccc(C(=O)Nc2ccc(OC(F)(F)F)cc2)c1=O] | | 423.1 |
| 7 | N-(6-cyclopropylpyridin-3-yl)-1-(4-fluoro-2-methoxyphenyl)-2-oxo-1,2-dihydropyridine-3-carboxamide | 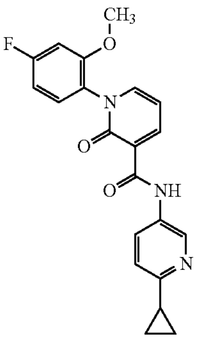 [SMILES: COc1cc(F)ccc1-n1cccc(C(=O)Nc2ccc(C3CC3)nc2)c1=O] | | 380.3 |

TABLE 1-1-continued

| Ex. No. | IUPAC Name | Structure | Additive | MS |
|---|---|---|---|---|
| 8 | 1-(4-fluoro-2-methoxyphenyl)-N-[1-(4-fluorophenyl)-1H-pyrazol-3-yl]-2-oxo-1,2-dihydropyridine-3-carboxamide | 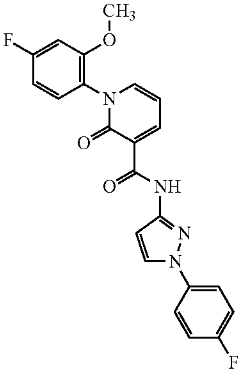 [SMILES: COc1cc(F)ccc1-n1cccc(C(=O)Nc2ccn(-c3ccc(F)cc3)n2)c1=O] | | 423.3 |

TABLE 1-2

| Ex. No. | IUPAC Name | Structure | Additive | MS |
|---|---|---|---|---|
| 9 | 1-(4-fluoro-2-methoxyphenyl)-N-(6-methoxypyridin-3-yl)-2-oxo-1,2-dihydropyridine-3-carboxamide | 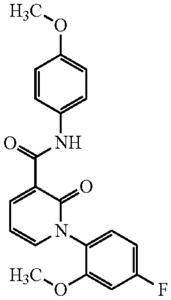 [SMILES: COc1ccc(NC(=O)c2cccn(-c3ccc(F)cc3OC)c2=O)cc1] | | 370.3 |
| 10 | N-[4-(difluoromethoxy)phenyl]-1-(4-fluoro-2-methoxyphenyl)-2-oxo-1,2-dihydropyridine-3-carboxamide | 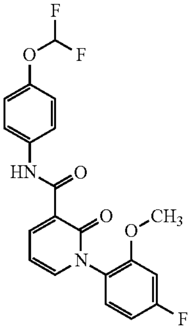 [SMILES: COc1cc(F)ccc1-n1cccc(C(=O)Nc2ccc(OC(F)F)cc2)c1=O] | | 405.2 |
| 11 | 1-(4-fluoro-2-methoxyphenyl)-2-oxo-N-[4-(trifluoromethyl)phenyl]-1,2-dihydropyridine-3-carboxamide | 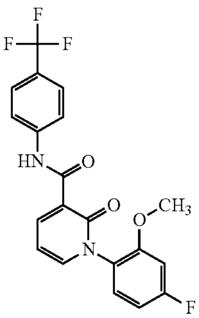 [SMILES: COc1cc(F)ccc1-n1cccc(C(=O)Nc2ccc(C(F)(F)F)cc2)c1=O] | | 407.2 |

TABLE 1-2-continued

| Ex. No. | IUPAC Name | Structure | Additive | MS |
|---|---|---|---|---|
| 12 | N-[1-(4-fluorophenyl)-1H-pyrazol-3-yl]-2-oxo-1-[2-(2,2,2-trifluoroethoxy)phenyl]-1,2-dihydropyridine-3-carboxamide | 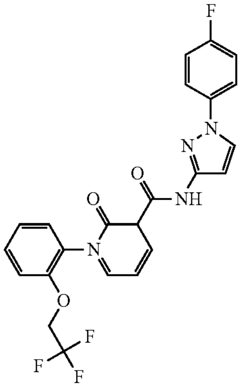 | | 473.2 |
| 13 | N-(6-methoxypyridin-3-yl)-2-oxo-1-[2-(2,2,2-trifluoroethoxy)phenyl]-1,2-dihydropyridine-3-carboxamide | 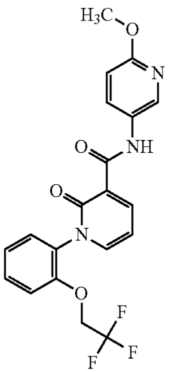 [SMILES: COc1ccc(NC(=O)c2cccn(-c3ccccc3OCC(F)(F)F)c2=O)cn1] | | 420.3 |
| 14 | N-(4-chlorophenyl)-2-oxo-1-[2-(2,2,2-trifluoroethoxy)phenyl]-1,2-dihydropyridine-3-carboxamide | 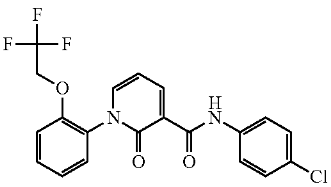 [SMILES: O=C(Nc1ccc(Cl)cc1)c1cccn(-c2ccccc2OCC(F)(F)F)c1=O] | | 423.2 |
| 15 | 2-oxo-1-[2-(2,2,2-trifluoroethoxy)phenyl]-N-[6-(2,2,2-trifluoroethoxy)pyridin-3-yl]-1,2-dihydropyridine-3-carboxamide | 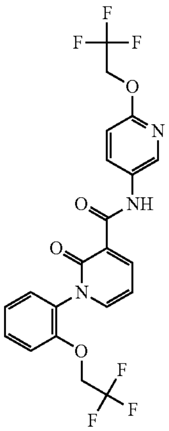 [SMILES: O=C(Nc1ccc(OCC(F)(F)F)nc1)c1cccn(-c2ccccc2OCC(F)(F)F)c1=O] | | 488.1 |

TABLE 1-2-continued

| Ex. No. | IUPAC Name | Structure | Additive | MS |
|---|---|---|---|---|
| 16 | N-[6-(difluoromethoxy)pyridin-3-yl]-1-(4-fluoro-2-methoxyphenyl)-2-oxo-1,2-dihydropyridine-3-carboxamide | 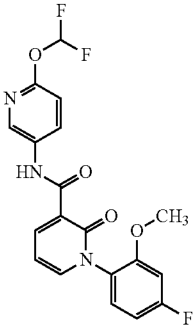 [SMILES: COc1cc(F)ccc1-n1cccc(C(=O)Nc2ccc(OC(F)F)nc2)c1=O] | | 406.2 |

TABLE 1-3

| Ex. No. | IUPAC Name | Structure | Additive | MS |
|---|---|---|---|---|
| 17 | 1-[4-fluoro-2-(morpholin-4-yl)phenyl]-2-oxo-N-(4-phenoxyphenyl)-1,2-dihydropyridine-3-carboxamide | 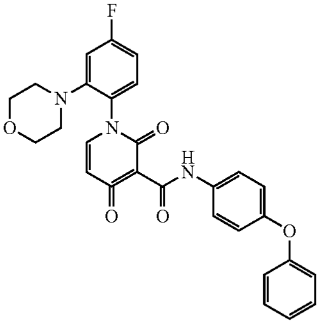 | | 486.2 |
| 18 | 2-(4-fluoro-2-methoxyphenyl)-3-oxo-N-(4-phenoxyphenyl)-2,3-dihydropyridazine-4-carboxamide | 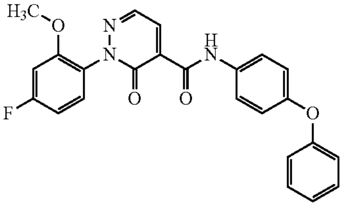 [SMILES: COc1cc(F)ccc1-n1nccc(C(=O)Nc2ccc(Oc3ccccc3)cc2)c1=O] | | 432.1 |
| 19 | 1-(4-fluoro-2-methoxyphenyl)-N-[4-(morpholin-4-yl)phenyl]-2-oxo-1,2-dihydropyridine-3-carboxamide | 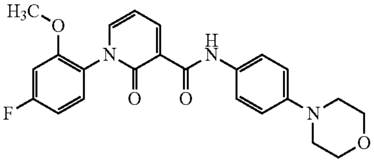 [SMILES: COc1cc(F)ccc1-n1cccc(C(=O)Nc2ccc(N3CCOCC3)cc2)c1=O] | | 424.2 |
| 20 | 2-oxo-1-[2-(2,2,2-trifluoroethoxy)phenyl]-N-[6-(trifluoromethyl)pyridin-3-yl]-1,2-dihydropyridine-3-carboxamide | 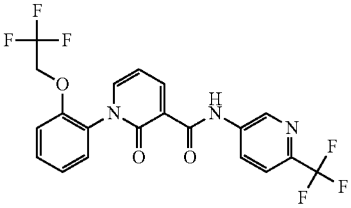 [SMILES: O=C(Nc1ccc(C(F)(F)F)nc1)c1cccn(-c2ccccc2OCC(F)(F)F)c1=O] | | 456.0 |

TABLE 1-3-continued

| Ex. No. | IUPAC Name | Structure | Additive | MS |
|---|---|---|---|---|
| 21 | N-(5-cyclopropylpyridin-2-yl)-2-oxo-1-[2-(2,2,2-trifluoroethoxy)phenyl]-1,2-dihydropyridine-3-carboxamide | 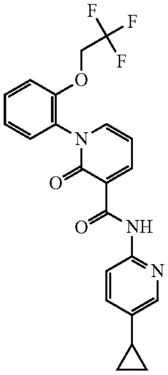 [SMILES: O=C(Nc1ccc(C2CC2)cn1)c1cccn(-c2ccccc2OCC(F)(F)F)c1=O] | | 430.2 |
| 22 | 2-oxo-1-[2-(2,2,2-trifluoroethoxy)phenyl]-N-[1-(2,2,2-trifluoroethyl)-1H-pyrazol-3-yl]-1,2-dihydropyridine-3-carboxamide | 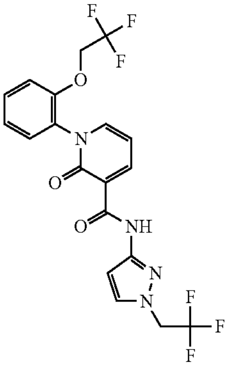 [SMILES: O=C(Nc1ccn(CC(F)(F)F)n1)c1cccn(-c2ccccc2OCC(F)(F)F)c1=O] | | 461.1 |
| 23 | 2-(4-fluoro-2-methoxyphenyl)-3-oxo-N-[6-(2,2,2-trifluoroethoxy)pyridin-3-yl]-2,3-dihydropyridazine-4-carboxamide | 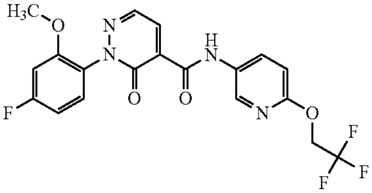 [SMILES: COc1cc(F)ccc1-n1nccc(C(=O)Nc2ccc(OCC(F)(F)F)nc2)c1=O] | | 439.1 |
| 24 | N-(6-cyanopyridin-3-yl)-2-oxo-1-[2-(2,2,2-trifluoroethoxy)phenyl]-1,2-dihydropyridine-3-carboxamide | 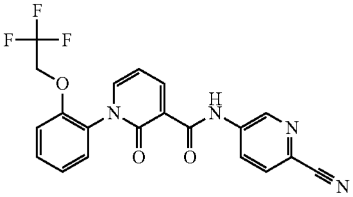 [SMILES: N#Cc1ccc(NC(=O)c2cccn(-c3ccccc3OCC(F)(F)F)c2=O)cn1] | | 415.1 |

TABLE 1-4

| Ex. No. | IUPAC Name | Structure | Additive | MS |
|---|---|---|---|---|
| 25 | 1-[4-fluoro-2-(morpholin-4-yl)phenyl]-2-oxo-N-[6-(2,2,2-trifluoroethoxy)pyridin-3-yl]-1,2-dihydropyridine-3-carboxamide | 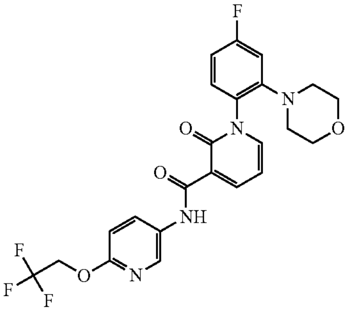 [SMILES: O=C(Nc1ccc(OCC(F)(F)F)nc1)c1cccn(-c2ccc(F)cc2N2CCOCC2)c1=O] | | 493.1 |

TABLE 1-4-continued

| Ex. No. | IUPAC Name | Structure | Additive | MS |
|---|---|---|---|---|
| 26 | 1-[4-fluoro-2-(2,2,2-trifluoroethoxy)phenyl]-2-oxo-N-[6-(2,2,2-trifluoroethoxy)pyridin-3-yl]-1,2-dihydropyridine-3-carboxamide | 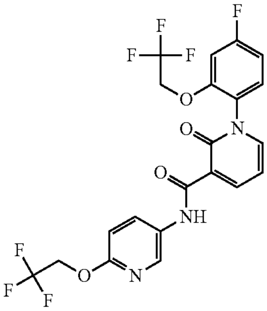 [SMILES: O=C(Nc1ccc(OCC(F)(F)F)nc1)c1cccn(-c2ccc(F)cc2OCC(F)(F)F)c1=O] | | 504.0 |
| 27 | 1-[4-fluoro-2-(2-methoxyethoxy)phenyl]-2-oxo-N-[6-(2,2,2-trifluoroethoxy)pyridin-3-yl]-1,2-dihydropyridine-3-carboxamide | 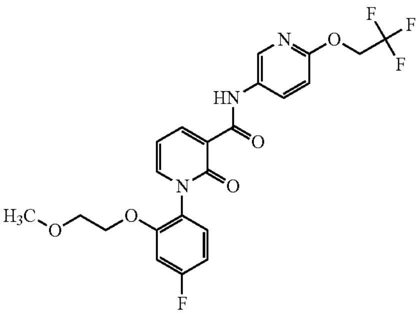 [SMILES: COCCOc1cc(F)ccc1-n1cccc(C(=O)Nc2ccc(OCC(F)(F)F)nc2)c1=O] | | 482.2 |
| 28 | 1-[4-fluoro-2-(2-methoxyethoxy)phenyl]-N-[1-(4-fluorophenyl)-1H-pyrazol-3-yl]-2-oxo-1,2-dihydropyridine-3-carboxamide | 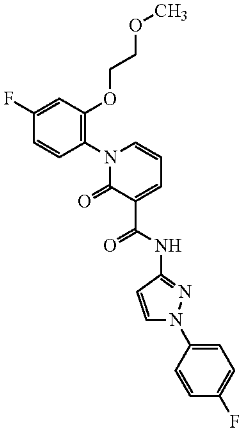 [SMILES: COCCOc1cc(F)ccc1-n1cccc(C(=O)Nc2ccn(-c3ccc(F)cc3)n2)c1=O] | | 467.2 |
| 29 | 2-[4-fluoro-2-(2,2,2-trifluoroethoxy)phenyl]-3-oxo-N-[6-(2,2,2-trifluoroethoxy)pyridin-3-yl]-2,3-dihydropyridazine-4-carboxamide | 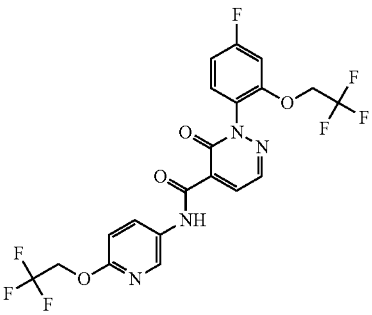 [SMILES: O=C(Nc1ccc(OCC(F)(F)F)nc1)c1ccnn(-c2ccc(F)cc2OCC(F)(F)F)c1=O] | | 505.1 |

TABLE 1-4-continued

| Ex. No. | IUPAC Name | Structure | Additive | MS |
|---|---|---|---|---|
| 30 | 1-(2-cyano-4-fluorophenyl)-2-oxo-N-(4-phenoxyphenyl)-1,2-dihydropyridine-3-carboxamide | 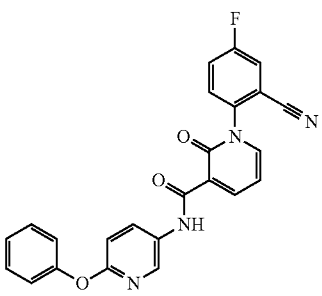 [SMILES: N#Cc1cc(F)ccc1-n1cccc(C(=O)Nc2ccc(Oc3ccccc3)nc2)c1=O] | | 425.9 |
| 31 | N-(5-cyanopyridin-2-yl)-2-oxo-1-[2-(2,2,2-trifluoroethoxy)phenyl]-1,2-dihydropyridine-3-carboxamide | 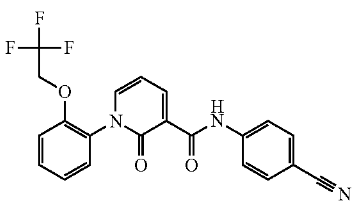 [SMILES: N#Cc1ccc(NC(=O)c2cccn(-c3ccccc3OCC(F)(F)F)c2=O)cc1] | | 415.2 |
| 32 | 1-[4-fluoro-2-(2,2,2-trifluoroethoxy)phenyb-N-[1-methyl-5-(trifluoromethyl)-1H-pyrazol-3-yl]-2-oxo-1,2-dihydropyridine-3-carboxamide | 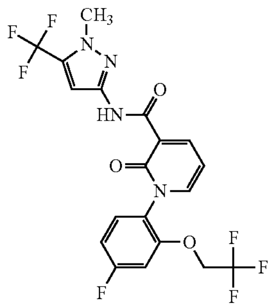 [SMILES: Cn1nc(NC(=O)c2cccn(-c3ccc(F)cc3OCC(F)(F)F)c2=O)cc1C(F)(F)F] | | 476.8 |

TABLE 1-5

| Ex. No. | IUPAC Name | Structure | Additive | MS |
|---|---|---|---|---|
| 33 | 1-[4-fluoro-2-(2,2,2-trifluoroethoxy)phenyl]-N-[1-(2-methylpropyl)-1H-pyrazol-4-yl]-2-oxo-1,2-dihydropyridine-3-carboxamide | 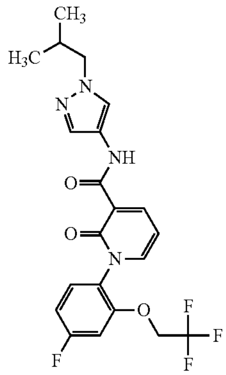 [SMILES: CC(C)Cn1cc(NC(=O)c2cccn(-c3ccc(F)cc3OCC(F)(F)F)c2=O)cn1] | | 453.0 |

TABLE 1-5-continued

| Ex. No. | IUPAC Name | Structure | Additive | MS |
|---|---|---|---|---|
| 34 | N-(1-cyclopropyl-1H-pyrazol-4-yl)-1-[4-fluoro-2-(2,2,2-trifluoroethoxy)phenyl]-2-oxo-1,2-dihydropyridine-3-carboxamide | 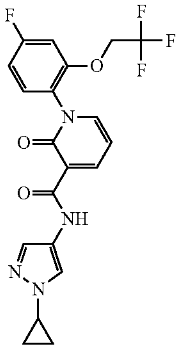 [SMILES: O=C(Nc1cnn(C2CC2)c1)c1cccn(-c2ccc(F)cc2OCC(F)(F)F)c1=O] | | 437.0 |
| 35 | 1-[4-fluoro-2-(2,2,2-trifluoroethoxy)phenyl]-N-{4-[(morpholin-4-yl)methyl]phenyl}-2-oxo-1,2-dihydropyridine-3-carboxamide | 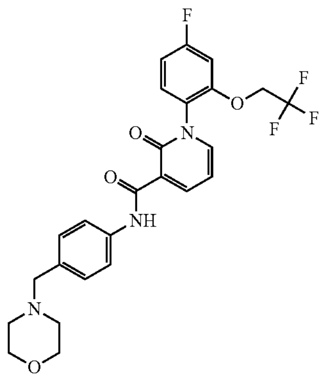 [SMILES: O=C(Nc1ccc(CN2CCOCC2)cc1)c1cccn(-c2ccc(F)cc2OCC(F)(F)F)c1=O] | | 505.9 |
| 36 | 1-[4-fluoro-2-(2,2,2-trifluoroethoxy)phenyl]-2-oxo-N-[2-(trifluoromethyl)pyrimidin-5-yl]-1,2-dihydropyridine-3-carboxamide | 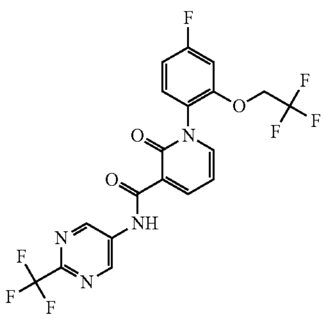 [SMILES: O=C(Nc1cnc(C(F)(F)F)nc1)c1cccn(-c2ccc(F)cc2OCC(F)(F)F)c1=O] | | 474.9 |
| 37 | 1-[4-fluoro-2-(2,2,2-trifluoroethoxy)phenyl]-2-oxo-N-[5-(trifluoromethyl)pyrazin-2-yl]-1,2-dihydropyridine-3-carboxamide | 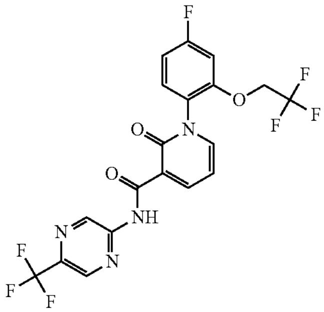 [SMILES: O=C(Nc1cnc(C(F)(F)F)cn1)c1cccn(-c2ccc(F)cc2OCC(F)(F)F)c1=O] | | 474.8 |

TABLE 1-5-continued

| Ex. No. | IUPAC Name | Structure | Additive | MS |
|---|---|---|---|---|
| 38 | 1-[4-fluoro-2-(2,2,2-trifluoroethoxy)phenyl]-2-oxo-N-[6-(trifluoromethyl)pyridazin-3-yl]-1,2-dihydropyridine-3-carboxamide | 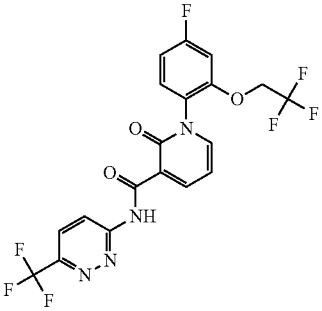 [SMILES: O=C(Nc1ccc(C(F)(F)F)nn1)c1cccn(-c2ccc(F)cc2OCC(F)(F)F)c1=O] | | 474.8 |
| 39 | N-(1-tert-butyl-1H-pyrazol-3-yl)-1-[4-fluoro-2-(2,2,2-trifluoroethoxy)phenyl]-2-oxo-1,2-dihydropyridine-3-carboxamide | 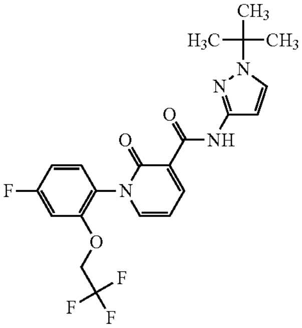 [SMILES: CC(C)(C)n1ccc(NC(=O)c2cccn(-c3ccc(F)cc3OCC(F)(F)F)c2=O)n1] | | 450.9 |
| 40 | N-[1-(cyclopropylmethyl)-1H-pyrazol-4-yl]-1-[4-fluoro-2-(2,2,2-trifluoroethoxy)phenyl]-2-oxo-1,2-dihydropyridine-3-carboxamide | 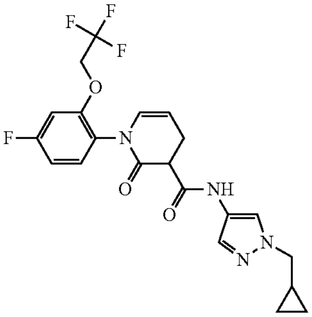 [SMILES: O=C(Nc1cnn(CC2CC2)c1)C1CC=CN(c2ccc(F)cc2OCC(F)(F)F)C1=O] | | 450.9 |

TABLE 1-6

| Ex. No. | IUPAC Name | Structure | Additive | MS |
|---|---|---|---|---|
| 41 | N-(4-cyanophenyl)-1-[4-fluoro-2-(2,2,2-trifluoroethoxy)phenyl]-2-oxo-1,2-dihydropyridine-3-carboxamide | 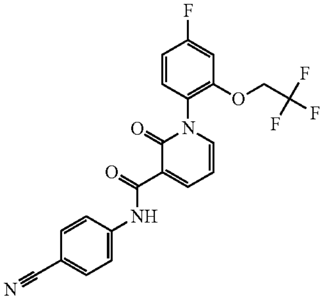 [SMILES: N#Cc1ccc(NC(=O)c2cccn(-c3ccc(F)cc3OCC(F)(F)F)c2=O)cc1] | | 431.8 |

TABLE 1-6-continued

| Ex. No. | IUPAC Name | Structure | Additive | MS |
| --- | --- | --- | --- | --- |
| 42 | 1-[4-fluoro-2-(2,2,2-trifluoroethoxy)phenyl]-N-[4-(2-hydroxypropan-2-yl)phenyl]-2-oxo-1,2-dihydropyridine-3-carboxamide | 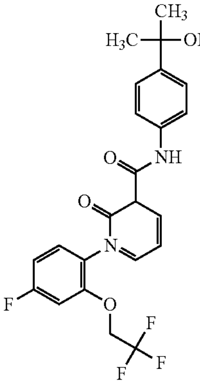 | | 464.9 |
| 43 | 1-[4-fluoro-2-(2,2,2-trifluoroethoxy)phenyl]-2-oxo-N-[4-(piperidine-1-carbonyl)phenyl]-1,2-dihydropyridine-3-carboxamide | 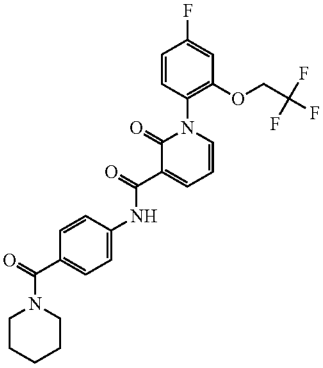 [SMILES: O=C(Nc1ccc(C(=O)N2CCCCC2)cc1)c1cccn(-c2ccc(F)cc2OCC(F)(F)F)c1=O] | | 517.9 |
| 44 | 1-[4-fluoro-2-(2,2,2-trifluoroethoxy)phenyl]-N-(imidazo[1,2-a]pyridin-6-yl)-2-oxo-1,2-dihydropyridine-3-carboxamide | 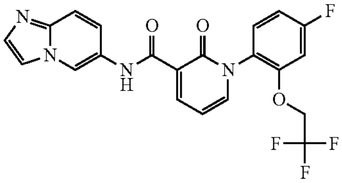 [SMILES: O=C(Nc1ccc2nccn2c1)c1cccn(-c2ccc(F)cc2OCC(F)(F)F)c1=O] | | 444.9 |
| 45 | N-[1-(2,2-difluoroethyl)-1H-pyrazol-4-yl]-1-[4-fluoro-2-(2,2,2-trifluoroethoxy)phenyl]-2-oxo-1,2-dihydropyridine-3-carboxamide | 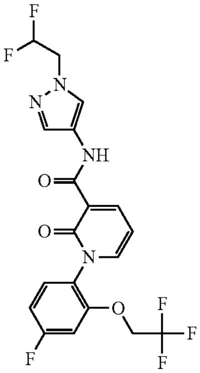 [SMILES: O=C(Nc1cnn(CC(F)F)c1)c1cccn(-c2ccc(F)cc2OCC(F)(F)F)c1=O] | | 458.9 |

TABLE 1-6-continued

| Ex. No. | IUPAC Name | Structure | Additive | MS |
|---|---|---|---|---|
| 46 | N-[1-(difluoromethyl)-1H-pyrazol-4-yl]-1-[4-fluoro-2-(2,2,2-trifluoroethoxy)phenyl]-2-oxo-1,2-dihydropyridine-3-carboxamide | 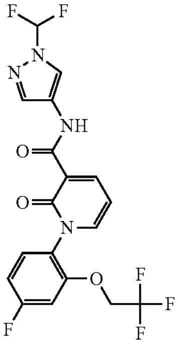 [SMILES: O=C(Nc1cnn(C(F)F)c1)c1cccn(-c2ccc(F)cc2OCC(F)(F)F)c1=O] | | 444.8 |
| 47 | N-[4-fluoro-2-(2,2,2-trifluoroethoxy)phenyl]-2-oxo-N-[5-(trifluoromethyl)-1,2-oxazol-3-yl]-1,2-dihydropyridine-3-carboxamide | 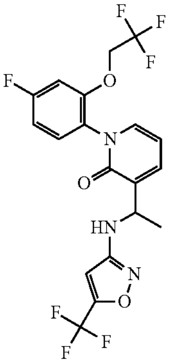 [SMILES: CC(Nc1cc(C(F)(F)F)on1)c1cccn(-c2ccc(F)cc2OCC(F)(F)F)c1=O] | | 465.8 |
| 48 | 1-[4-fluoro-2-(2,2,2-trifluoroethoxy)phenyl]-2-oxo-N-[1-(2,2,2-trifluoroethyl)-1H-pyrazol-4-yl]-1,2-dihydropyridine-3-carboxamide | 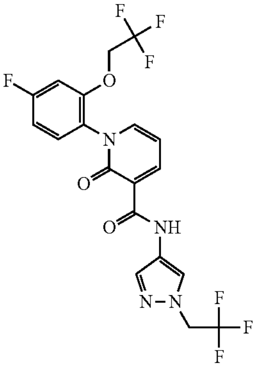 [SMILES: O=C(Nc1cnn(CC(F)(F)F)c1)c1cccn(-c2ccc(F)cc2OCC(F)(F)F)c1=O] | | 478.9 |

TABLE 1-7

| Ex. No. | IUPAC Name | Structure | Additive | MS |
|---|---|---|---|---|
| 49 | N-[6-(difluoromethyl)pyridin-3-yl]-1-[4-fluoro-2-(2,2,2-trifluoroethoxy)phenyl]-2-oxo-1,2-dihydropyridine-3-carboxamide | 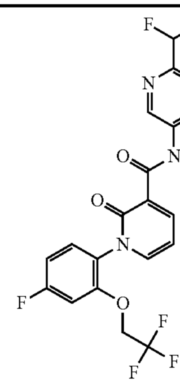 | | 455.8 |

TABLE 1-7-continued

| Ex. No. | IUPAC Name | Structure | Additive | MS |
|---|---|---|---|---|
| 50 | N-[4-(cyclopropylmethoxy)phenyl]-1-[4-fluoro-2-(2,2,2-trifluoroethoxy)phenyl]-2-oxo-1,2-dihydropyridine-3-carboxamide | 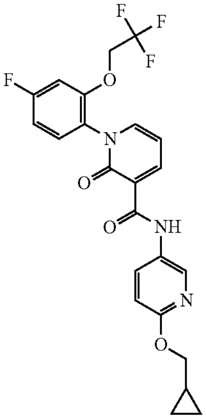 [SMILES: O=C(Nc1ccc(OCC2CC2)nc1)c1cccn(-c2ccc(F)cc2OCC(F)(F)F)c1=O] | | 476.9 |
| 51 | N-[2-(difluoromethoxy)pyrimidin-5-yl]-1-[4-fluoro-2-(2,2,2-trifluoroethoxy)phenyl]-2-oxo-1,2-dihydropyridine-3-carboxamide | 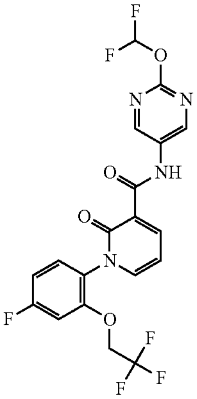 [SMILES: O=C(Nc1cnc(OC(F)F)nc1)c1cccn(-c2ccc(F)cc2OCC(F)(F)F)c1=O] | | 472.8 |
| 52 | 1-(2-cyano-4-fluorophenyl)-2-oxo-N-[6-(2,2,2-trifluoroethoxy)pyridin-3-yl]-1,2-dihydropyridine-3-carboxamide | 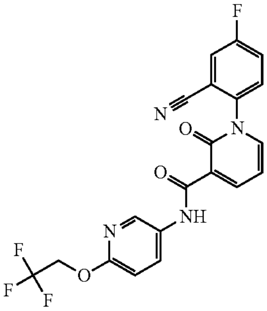 [SMILES: N#Cc1cc(F)ccc1-n1cccc(C(=O)Nc2ccc(OCC(F)(F)F)nc2)c1=O] | | 433.2 |
| 53 | 1-[1-(oxan-4-yl)-1H-pyrazol-5-yl]-2-oxo-N-(4-phenoxyphenyl)-1,2-dihydropyridine-3-carboxamide | 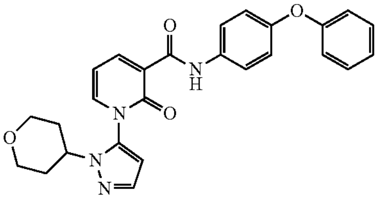 [SMILES: O=C(Nc1ccc(Oc2ccccc2)cc1)c1cccn(-c2ccnn2C2CCOCC2)c1=O] | | 457.2 |

TABLE 1-7-continued

| Ex. No. | IUPAC Name | Structure | Additive | MS |
|---|---|---|---|---|
| 54 | 1-[4-fluoro-2-(2,2,2-trifluoroethoxy)phenyl]-N-[1-(oxan-4-yl)-1H-pyrazol-3-yl]-2-oxo-1,2-dihydropyridine-3-carboxamide | 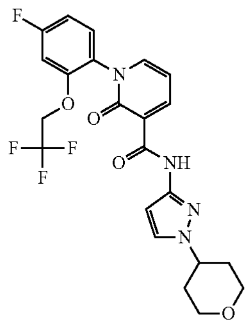 [SMILES: O=C(Nc1ccn(C2CCOCC2)n1)c1cccn(-c2ccc(F)cc2OCC(F)(F)F)c1=O] | | 481.1 |
| 55 | rac-N-{1-[(2,2-difluorocyclopropyl)methyl]-1H-pyrazol-3-yl}-1-[4-fluoro-2-(2,2,2-trifluoroethoxy)phenyl]-2-oxo-1,2-dihydropyridine-3-carboxamide | 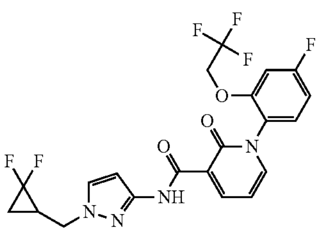 [SMILES: O=C(Nc1ccn(CC2CC2(F)F)n1)c1cccn(-c2ccc(F)cc2OCC(F)(F)F)c1=O] | | 487.1 |
| 56 | 1-[4-fluoro-2-(2,2,3,3,3-pentafluoropropoxy)phenyl]-2-oxo-N-[6-(2,2,2-trifluoroethoxy)pyridin-3-yl]-1,2-dihydropyridine-3-carboxamide | 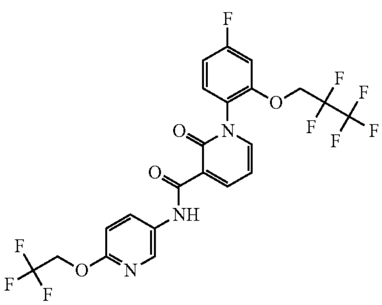 [SMILES: O=C(Nc1ccc(OCC(F)(F)F)nc1)c1cccn(-c2ccc(F)cc2OCC(F)(F)C(F)(F)F)c1=O] | | 556.0 |

45

TABLE 1-8

| Ex. No. | IUPAC Name | Structure | Additive | MS |
|---|---|---|---|---|
| 57 | N-[4-(cyanomethyl)phenyl]-1-[4-fluoro-2-(2,2,2-trifluoroethoxy)phenyl]-2-oxo-1,2-dihydropyridine-3-carboxamide | 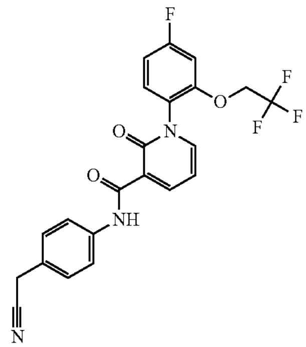 [SMILES: N#CCc1ccc(NC(=O)c2cccn(-c3ccc(F)cc3OCC(F)(F)F)c2=O)cc1] | | 446.1 |

TABLE 1-8-continued

| | | | |
|---|---|---|---|
| 58 | 1-[4-fluoro-2-(2,2,3,3,3-pentafluoropropoxy)phenyl]-N-[4-(2-hydroxypropan-2-yl)phenyl]-2-oxo-1,2-dihydropyridine-3-carboxamide | 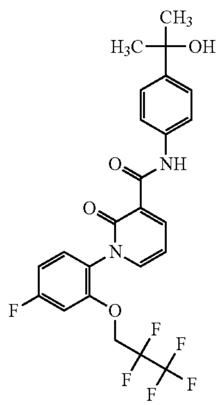 [SMILES: CC(C)(O)c1ccc(NC(=O)c2cccn(-c3ccc(F)cc3OCC(F)(F)C(F)(F)F)c2=O)cc1] | 515.1 |
| 59 | 1-[1-(oxan-4-yl)-1H-pyrazol-5-yl]-2-oxo-N-[6-(2,2,2-trifluoroethoxy)pyridin-3-yl]-1,2-dihydropyridine-3-carboxamide | 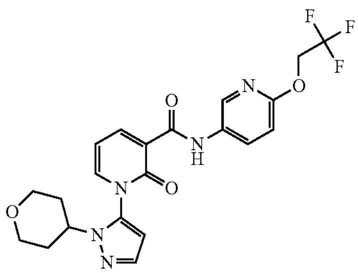 [SMILES: O=C(Nc1ccc(OCC(F)(F)F)nc1)c1cccn(-c2ccnn2C2CCOCC2)c1=O] | 464.1 |
| 60 | 1-[4-fluoro-2-(2,2,2-trifluoroethoxy)phenyl]-N-[4-(2-hydroxy-2-methylpropoxy)phenyl]-2-oxo-1,2-dihydropyridine-3-carboxamide | 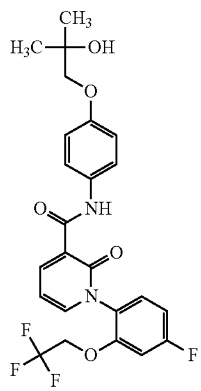 [SMILES: CC(C)(O)COc1ccc(NC(=O)c2cccn(-c3ccc(F)cc3OCC(F)(F)F)c2=O)cc1] | 494.9 |
| 61 | 1-[4-fluoro-2-(2,2,2-trifluoroethoxy)phenyl]-N-[4-(2-hydroxy-2-methylpropyl)phenyl]-2-oxo-1,2-dihydropyridine-3-carboxamide | 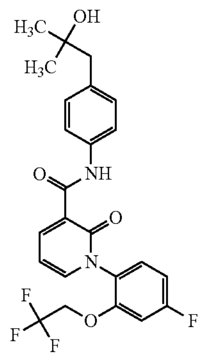 [SMILES: CC(C)(O)Cc1ccc(NC(=O)c2cccn(-c3ccc(F)cc3OCC(F)(F)F)c2=O)cc1] | 478.9 |

TABLE 1-8-continued

| | | | |
|---|---|---|---|
| 62 | 1-[4-fluoro-2-(2,2,2-trifluoroethoxy)phenyl]-2-oxo-N-[1-(2,2,3,3,3-pentafluoropropyl)-1H-pyrazol-4-yl]-1,2-dihydropyridine-3-carboxamide | 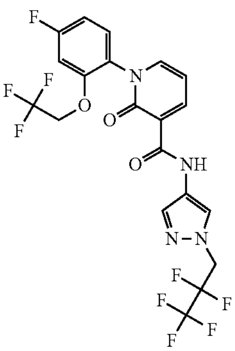 [SMILES: O=C(Nc1cnn(CC(F)(F)C(F)(F)F)c1)c1cccn(-c2ccc(F)cc2OCC(F)(F)F)c1=O] | 528.8 |
| 63 | N-[4-(2-hydroxypropan-2-yl)phenyl]-2-oxo-142-(2,2,2-trifluoroethoxy)phenyl]-1,2-dihydropyridine-3-carboxamide | 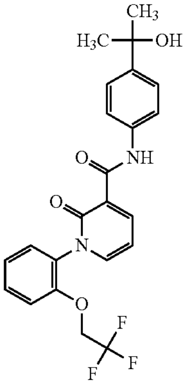 [SMILES: CC(C)(O)c1ccc(NC(=O)c2cccn(-c3ccccc3OCC(F)(F)F)c2=O)cc1] | 447.0 |
| 64 | 1-[4-fluoro-2-(2,2,2-trifluoroethoxy)phenyl]-2-oxo-N-[6-(3,3,3-trifluoropropoxy)pyridin-3-yl]-1,2-dihydropyridine-3-carboxamide | 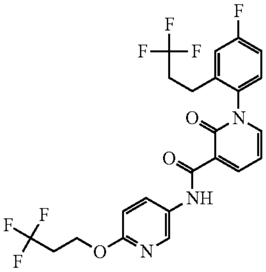 [SMILES: O=C(Nc1ccc(OCCC(F)(F)F)nc1)c1cccn(-c2ccc(F)cc2CCC(F)(F)F)c1=O] | 519.9 |

TABLE 1-9

| Ex. No. | IUPAC Name | Structure | Additive | MS |
|---|---|---|---|---|
| 65 | N-{1-[(3-fluorooxetan-3-yl)methyl]-1H-pyrazol-4-yl}-1-[4-fluoro-2-(2,2,2-trifluoroethoxy)phenyl]-2-oxo-1,2-dihydropyridine-3-carboxamide | 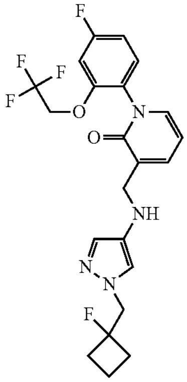 [SMILES: O=c1c(CNc2cnn(CC3(F)CCC3)c2)cccn1-c1ccc(F)cc1OCC(F)(F)F] | | 484.9 |

TABLE 1-9-continued

| Ex. No. | IUPAC Name | Structure | Additive | MS |
|---|---|---|---|---|
| 66 | N-{1-[(1-fluorocyclopropyl)methyl]-1H-pyrazol-4-yl}-1-[4-fluoro-2-(2,2,2-trifluoroethoxy)phenyl]-2-oxo-1,2-dihydropyridine-3-carboxamide | 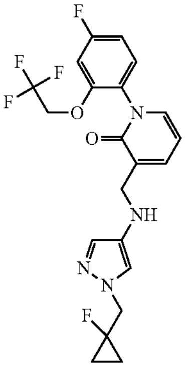 [SMILES: O=c1c(CNc2cnn(CC3(F)CC3)c2)cccn1-c1ccc(F)cc1OCC(F)(F)F] | | 468.9 |
| 67 | 1-[4-fluoro-2-(2-hydroxy-2-methylpropoxy)phenyl]-2-oxo-N-[6-(2,2,2-trifluoroethoxy)pyridin-3-yl]-1,2-dihydropyridine-3-carboxamide | 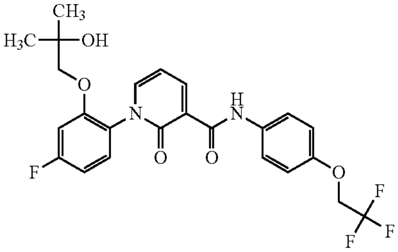 [SMILES: CC(C)(O)COc1cc(F)ccc1-n1cccc(C(=O)Nc2ccc(OCC(F)(F)F)cc2)c1=O] | | 495.9 |
| 68 | N-[4-(2-hydroxypropan-2-yl)phenyl]-1-[2-methyl-6-(2,2,2-trifluoroethoxy)phenyl]-2-oxo-1,2-dihydropyridine-3-carboxamide | 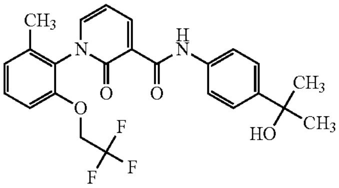 [SMILES: Cc1cccc(OCC(F)(F)F)c1-n1cccc(C(=O)Nc2ccc(C(C)(C)O)cc2)c1=O] | | 461.2 |
| 69 | 1-[4-fluoro-2-(2,2,2-trifluoroethoxy)phenyl]-N-[4-(1-hydroxycyclopropyl)phenyl]-2-oxo-1,2-dihydropyridine-3-carboxamide | 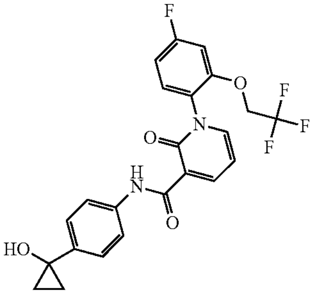 [SMILES: O=C(Nc1ccc(C2(O)CC2)cc1)c1cccn(-c2ccc(F)cc2OCC(F)(F)F)c1=O] | | 463.1 |
| 70 | N-[4-(2-hydroxy-2-methylpropoxy)phenyl]-2-oxo-1-[2-(2,2,2-trifluoroethoxy)phenyl]-1,2-dihydropyridine-3-carboxamide | 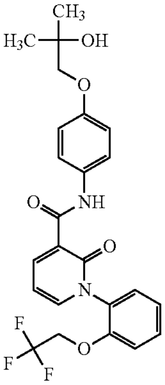 [SMILES: CC(C)(O)COc1ccc(NC(=O)c2cccn(-c3ccccc3OCC(F)(F)F)c2=O)cc1] | | 477.2 |

TABLE 1-9-continued

| Ex. No. | IUPAC Name | Structure | Additive | MS |
|---|---|---|---|---|
| 71 | 1-(2-cyano-4-fluorophenyl)-N-[4-(2-hydroxypropan-2-yl)phenyl]-2-oxo-1,2-dihydropyridine-3-carboxamide | 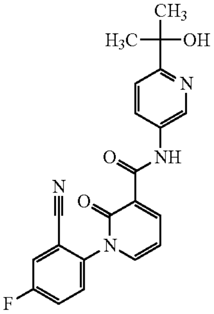 [SMILES: CC(C)(O)c1ccc(NC(=O)c2cccn(-c3ccc(F)cc3C#N)c2=O)cn1] | | 392.2 |
| 72 | 2-oxo-N-[6-(2,2,2-trifluoroethoxy)pyridin-3-yl]-1-[1-(3,3,3-trifluoropropyl)-1H-pyrazol-5-yl]-1,2-dihydropyridine-3-carboxamide | 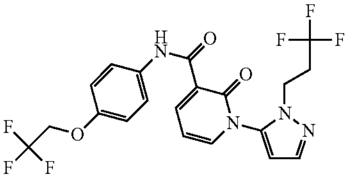 [SMILES: O=C(Nc1ccc(OCC(F)(F)F)cc1)c1cccn(-c2ccnn2CCC(F)(F)F)c1=O] | | 476.1 |

Table 1-10

| Ex. No. | IUPAC Name | Structure | Additive | MS |
|---|---|---|---|---|
| 73 | 1-[4-fluoro-2-(2,2,2-trifluoroethoxy)phenyl]-2-oxo-N-{6-[(2,2,2-trifluoroethoxy)methyl]pyridin-3-yl}-1,2-dihydropyridine-3-carboxamide | 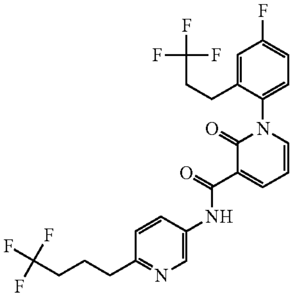 [SMILES: O=C(Nc1ccc(CCCC(F)(F)F)nc1)c1cccn(-c2ccc(F)cc2CCC(F)(F)F)c1=O] | | 520.1 |
| 74 | 2-oxo-N-{6-[(2,2,2-trifluoroethoxy)methyl]pyridin-3-yl}-1-[2-(2,2,2-trifluoroethoxy)phenyl]-1,2-dihydropyridine-3-carboxamide | 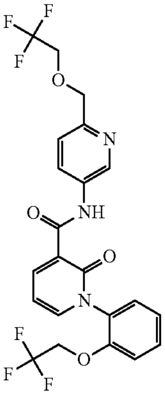 [SMILES: O=C(Nc1ccc(COCC(F)(F)F)nc1)c1cccn(-c2ccccc2OCC(F)(F)F)c1=O] | | 502.1 |

Table 1-10-continued

| Ex. No. | IUPAC Name | Structure | Additive | MS |
|---|---|---|---|---|
| 75 | rac-N-{6-[cyclopropyl(hydroxy)methyl]pyridin-3-yl}-1-[4-fluoro-2-(2,2,2-trifluoroethoxy)phenyl]-2-oxo-1,2-dihydropyridine-3-carboxamide | 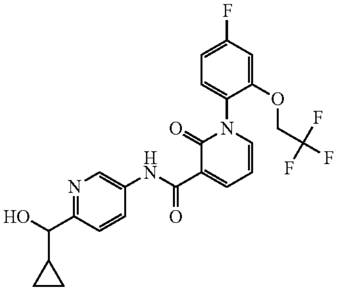 [SMILES: O=C(Nc1ccc(C(O)C2CC2)nc1)c1cccn(-c2ccc(F)cc2OCC(F)(F)F)c1=O] | | 478.2 |
| 76 | rac-N-{6-[cyclopropyl(hydroxy)methyl]pyridin-3-yl}-2-oxo-1-[2-(2,2,2-trifluproethoxy)phenyl]-1,2-dihydropyridine-3-carboxamide | 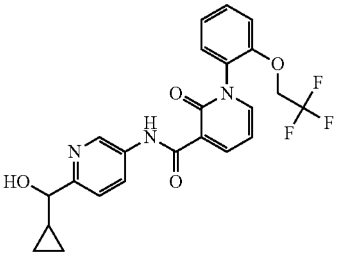 [SMILES: O=C(Nc1ccc(C(O)C2CC2)nc1)c1cccn(-c2ccccc2OCC(F)(F)F)c1=O] | | 460.1 |
| 77 | 2-oxo-N-[4-(1,1,3,3-tetrafluoro-2-hydroxypropan-2-yl)phenyl]-1-[2-(2,2,2-trifluoroethoxy)phenyl]-1,2-dihydropyridine-3-carboxamide | 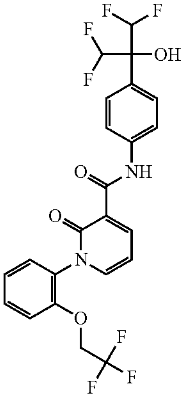 [SMILES: O=C(Nc1ccc(C(O)(C(F)F)C(F)F)cc1)c1cccn(-c2ccccc2OCC(F)(F)F)c1=O] | | 519.1 |
| 78 | 1-[4-fluoro-2-(2,2,2-trifluoroethoxy)phenyl]-2-oxo-N-[4-(1,1,3,3-tetrafluoro-2-hydroxypropan-2-yl)phenyl]-1,2-dihydropyridine-3-carboxamide | 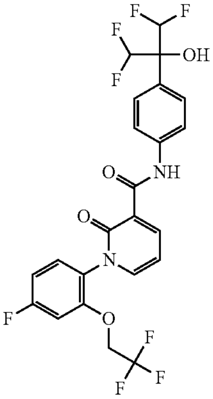 [SMILES: O=C(Nc1ccc(C(O)(C(F)F)C(F)F)cc1)c1cccn(-c2ccc(F)cc2OCC(F)(F)F)c1=O] | | 537.0 |

Table 1-10-continued

| Ex. No. | IUPAC Name | Structure | Additive | MS |
|---|---|---|---|---|
| 79 | 2-oxo-1-[3-(2,2,2-trifluoroethoxy)pyridazin-4-yl]-N-[6-(2,2,2-trifluoroethoxy)pyridin-3-yl]-1,2-dihydropyridine-3-carboxamide | 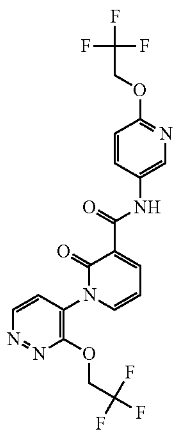 [SMILES: O=C(Nc1ccc(OCC(F)(F)F)nc1)c1cccn(-c2ccnnc2OCC(F)(F)F)c1=O] | | 490.1 |
| 80 | N-[6-(cyanomethyl)pyridin-3-yl]-1-[4-fluoro-2-(2,2,2-trifluoroethoxy)phenyl]-2-oxo-1,2-dihydropyridine-3-carboxamide | 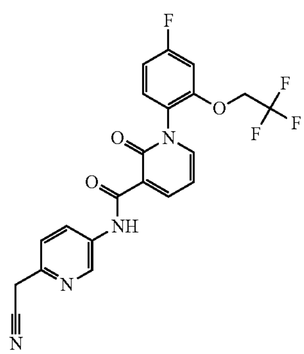 [SMILES: N#CCc1ccc(NC(=O)c2cccn(-c3ccc(F)cc3OCC(F)(F)F)c2=O)cn1] | | 447.1 |

35

TABLE 1-11

| Ex. No. | IUPAC Name | Structure | Additive | MS |
|---|---|---|---|---|
| 81 | N-[1-(4-fluorophenyl)-1H-pyrazol-3-yl]-2-oxo-1-[1-(3,3,3-trifluoropropyl)-1H-pyrazol-5-yl]-1,2-dihydropyridine-3-carboxamide | 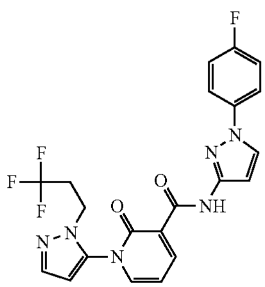 [SMILES: O=C(Nc1ccn(-c2ccc(F)cc2)n1)c1cccn(-c2ccnn2CCC(F)(F)F)c1=O] | | 461.1 |
| 82 | N-[3-fluoro-4-(2-hydroxypropan-2-yl)phenyl]-2-oxo-1-[2-(2,2,2-trifluoroethoxy)phenyl]-1,2-dihydropyridine-3-carboxamide | 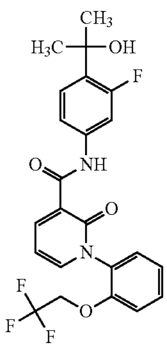 [SMILES: CC(C)(O)c1ccc(NC(=O)c2cccn(-c3ccccc3OCC(F)(F)F)c2=O)cc1F] | | 465.1 |

TABLE 1-11-continued

| Ex. No. | IUPAC Name | Structure | Additive | MS |
|---|---|---|---|---|
| 83 | N-[3-fluoro-4-(2-hydroxypropan-2-yl)phenyl]-1-[4-fluoro-2-(2,2,2-trifluoroethoxy)phenyl]-2-oxo-1,2-dihydropyridine-3-carboxamide | 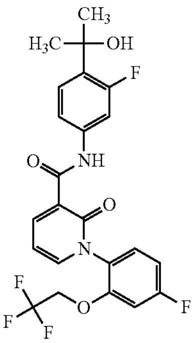 [SMILES: CC(C)(O)c1ccc(NC(=O)c2cccn(-c3ccc(F)cc3OCC(F)(F)F)c2=O)cc1F] | | 483.1 |
| 84 | N-[6-(2-hydroxypropan-2-yl)pyridin-3-yl]-2-oxo-1-[2-(2,2,2-trifluoroethoxy)phenyl]-1,2-dihydropyridine-3-carboxamide | 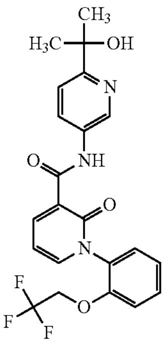 [SMILES: CC(C)(O)c1ccc(NC(=O)c2cccn(-c3ccccc3OCC(F)(F)F)c2=O)cn1] | | 448.1 |
| 85 | 1-[4-fluoro-2-(2,2,2-trifluoroethoxy)phenyl]-N-[6-(2-hydroxypropan-2-yl)pyridin-3-yl]-2-oxo-1,2-dihydropyridine-3-carboxamide | 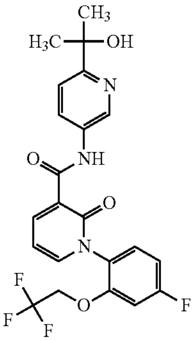 [SMILES: CC(C)(O)c1ccc(NC(=O)c2cccn(-c3ccc(F)cc3OCC(F)(F)F)c2=O)cn1] | | 466.1 |
| 86 | N-[6-(cyanomethyl)pyridin-3-yl]-2-oxo-1-[2-(2,2,2-trifluoroethoxy)phenyl]-1,2-dihydropyridine-3-carboxamide | 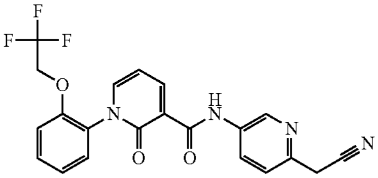 [SMILES: N#CCc1ccc(NC(=O)c2cccn(-c3ccccc3OCC(F)(F)F)c2=O)cn1] | | 429.1 |

TABLE 1-11-continued

| Ex. No. | IUPAC Name | Structure | Additive | MS |
|---|---|---|---|---|
| 87 | N-[6-(2-cyanopropan-2-yl)pyridin-3-yl]-1-[4-fluoro-2-(2,2,2-trifluoroethoxy)phenyl]-2-oxo-1,2-dihydropyridine-3-carboxamide | 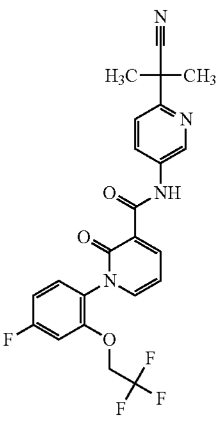 [SMILES: CC(C)(C#N)c1ccc(NC(=O)c2cccn(-c3ccc(F)cc3OCC(F)(F)F)c2=O)cn1] | | 475.1 |
| 88 | N-[6-(2-cyanopropan-2-yl)pyridin-3-yl]-2-oxo-1-[2-(2,2,2-trifluoroethoxy)phenyl]-1,2-dihydropyridine-3-carboxamide | 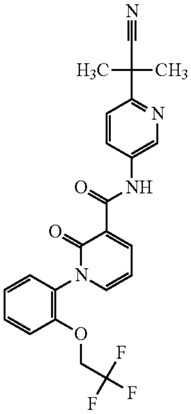 [SMILES: CC(C)(C#N)c1ccc(NC(=O)c2cccn(-c3ccccc3OCC(F)(F)F)c2=O)cn1] | | 457.2 |

TABLE 1-12

| Ex. No. | IUPAC Name | Structure | Additive | MS |
|---|---|---|---|---|
| 89 | N-[4-(1,1,1,3,3,3-hexafluoro-2-hydroxypropan-2-yl)phenyl]-2-oxo-1-[2-(2,2,2-trifluoroethoxy)phenyl]-1,2-dihydropyridine-3-carboxamide | 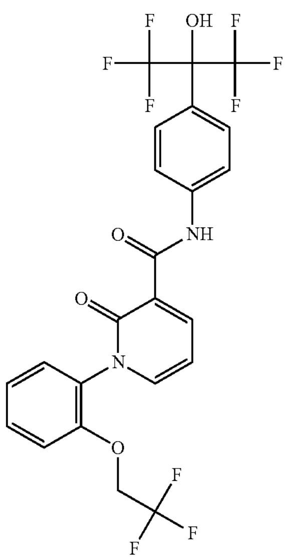 [SMILES: O=C(Nc1ccc(C(O)(C(F)(F)F)C(F)(F)F)cc1)c1cccn(-c2ccccc2OCC(F)(F)F)c1=O] | | 555.0 |

TABLE 1-12-continued
| Ex. No. | IUPAC Name | Structure | Additive | MS |
|---|---|---|---|---|
| 90 | N-[4-(2-hydroxypropan-2-yl)phenyl]-2-oxo-1-[3-(2,2,2-trifluoroethoxy)pyridazin-4-yl]-1,2-dihydropyridine-3-carboxamide | 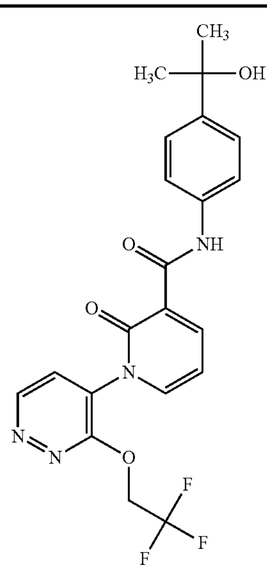 | | 449.2 |
| 91 | 1-[4-fluoro-2-(2,2,2-trifluoroethoxy)phenyl]-N-[6-(2-methoxypropan-2-yl)pyridin-3-yl]-2-oxo-1,2-dihydropyridine-3-carboxamide | 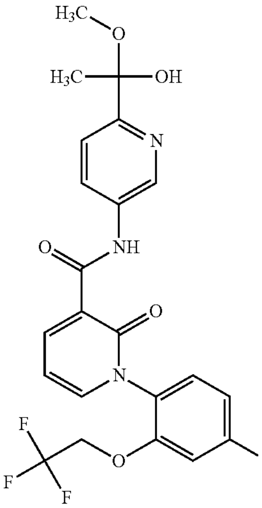 | | 480.1 |
| 92 | N-[6-(2-methoxypropan-2-yl)pyridin-3-yl]-2-oxo-1-[2-(2,2,2-trifluoroethoxy)phenyl]-1,2-dihydropyridine-3-carboxamide | 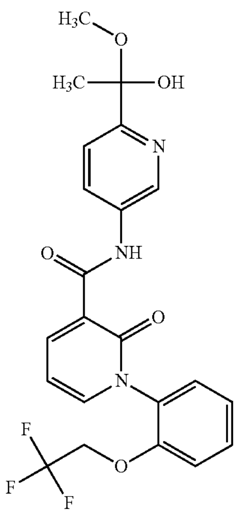 [SMILES: COC(C)(O)c1ccc(NC(=O)c2cccn(-c3ccccc3OCC(F)(F)F)c2=O)cn1] | | 462.1 |

TABLE 1-12-continued
| Ex. No. | IUPAC Name | Structure | Additive | MS |
|---|---|---|---|---|
| 93 | 1-[4-fluoro-2-(2,2,2-trifluoroethoxy)phenyl]-6-oxo-N-[6-(2,2,2-trifluoroethoxy)pyridin-3-yl]-1,6-dihydropyrimidine-5-carboxamide | 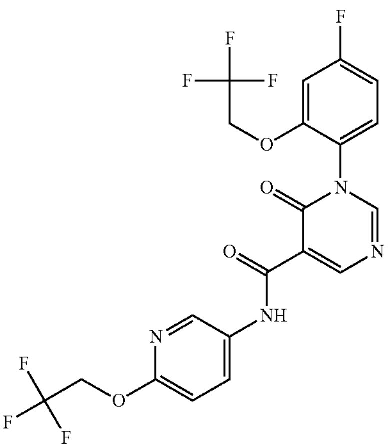 [SMILES: O=C(Nc1ccc(OCC(F)(F)F)nc1)c1cncn(-c2ccc(F)cc2OCC(F)(F)F)c1=O] | | 507.0 |
| 94 | 1-(4-methoxy-1-methyl-1H-pyrazol-5-yl)-2-oxo-N-[6-(2,2,2-trifluoroethoxy)pyridin-3-yl]-1,2-dihydropyridine-3-carboxamide | 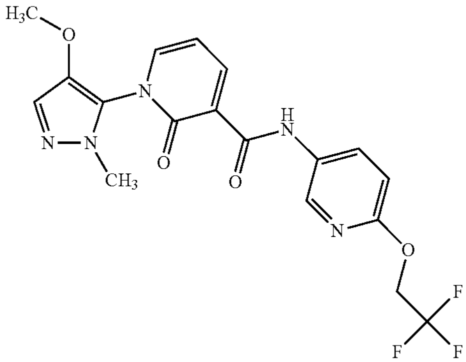 [SMILES: COc1cnn(C)c1-n1cccc(C(=O)Nc2ccc(OCC(F)(F)F)nc2)c1=O] | | 424.2 |
| 95 | 2-[4-fluoro-2-(2,2,2-trifluoroethoxy)phenyl]-N-(2-hydroxypropan-2-yl)phenyl]-3-oxo-2,3-dihydropyridazine-4-carboxamide | 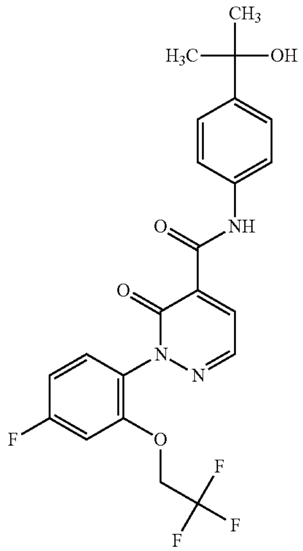 [SMILES: CC(C)(O)c1ccc(NC(=O)c2ccnn(-c3ccc(F)cc3OCC(F)(F)F)c2=O)cc1] | | 466.1 |

TABLE 1-12-continued

| Ex. No. | IUPAC Name | Structure | Additive | MS |
|---|---|---|---|---|
| 96 | N-[4-(1-hydroxycyclobutyl)phenyl]-2-oxo-1-[2-(2,2,2-trifluoroethoxy)phenyl]-1,2-dihydropyridine-3-carboxamide | 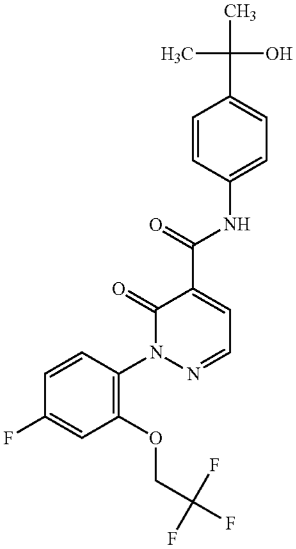 [SMILES: CC(C)(O)c1ccc(NC(=O)c2ccnn(-c3ccc(F)cc3OCC(F)(F)F)c2=O)cc1] | | 459.1 |

TABLE 1-13

| Ex. No. | IUPAC Name | Structure | Additive | MS |
|---|---|---|---|---|
| 97 | 1-[4-fluoro-2-(2,2,2-trifluoroethoxy)phenyl]-N-[4-(1-hydroxycyclobutyl)phenyl]-2-oxo-1,2-dihydropyridine-3-carboxamide | 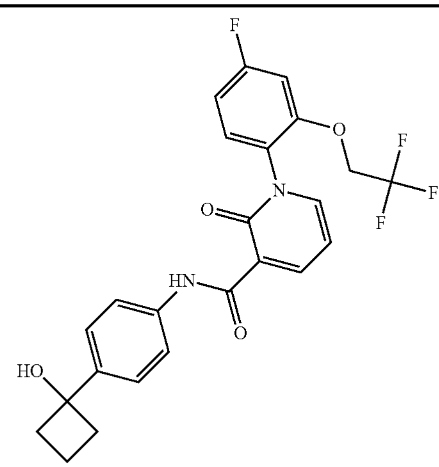 | | 477.1 |
| 98 | 1-[4-fluoro-2-(2,2,2-trifluoroethoxy)phenyl]-N-4-(2-hydroxypropan-2-yl)phenyl]-6-oxo-1,6-dihydropyrimidine-5-carboxamide | 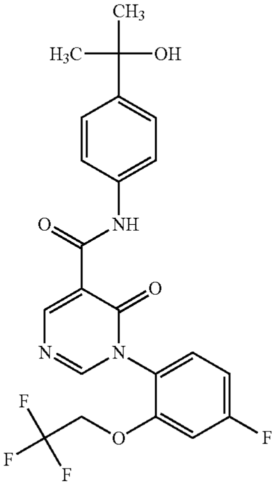 [SMILES: CC(C)(O)c1ccc(NC(=O)c2cncn(-c3ccc(F)cc3OCC(F)(F)F)c2=O)cc1] | | 466.1 |

TABLE 1-13-continued

| Ex. No. | IUPAC Name | Structure | Additive | MS |
|---|---|---|---|---|
| 99 | 1-[2-(2,2-difluoropropoxy)phenyl]-N-[4-(2-hydroxypropan-2-yl)phenyl]-2-oxo-1,2-dihydropyridine-3-carboxamide | 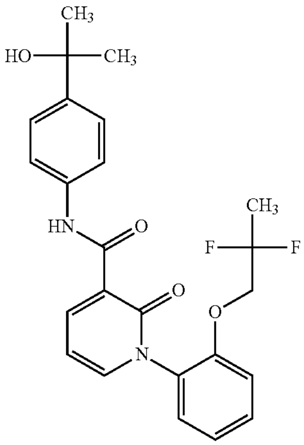 [SMILES: CC(F)(F)COc1ccccc1-n1cccc(C(=O)Nc2ccc(C(C)(C)O)cc2)c1=O] | | 443.1 |
| 100 | 1-[4-fluoro-2-(2,2,2-trifluoroethoxy)phenyl]-N-[4-(2-hydroxypropan-2-yl)phenyl]-6-methyl-2-oxo-1,2-dihydropyridine-3-carboxamide | 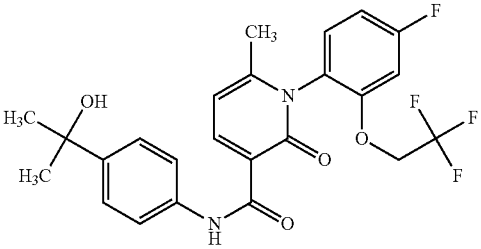 [SMILES: Cc1ccc(C(=O)Nc2ccc(C(C)(C)O)cc2)c(=O)n1-c1ccc(F)cc1OCC(F)(F)F] | | 479.1 |
| 101 | 1-[2-(2,2-difluoroethoxy)-4-fluorophenyl]-2-oxo-N-[6-(2,2,2-trifluoroethoxy)pyridin-3-yl]-1,2-dihydropyridine-3-carboxamide | 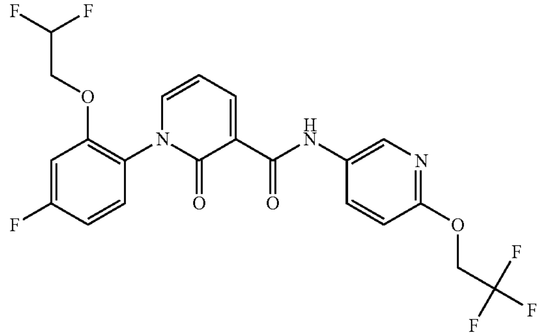 [SMILES: O=C(Nc1ccc(OCC(F)(F)F)nc1)c1cccn(-c2ccc(F)cc2OCC(F)F)c1=O] | | 488.1 |
| 102 | 1-[2-(2,2-difluoroethoxy)-4-fluorophenyl]-N-[4-(2-hydroxypropan-2-yl)phenyl]-2-oxo-1,2-dihydropyridine-3-carboxamide | 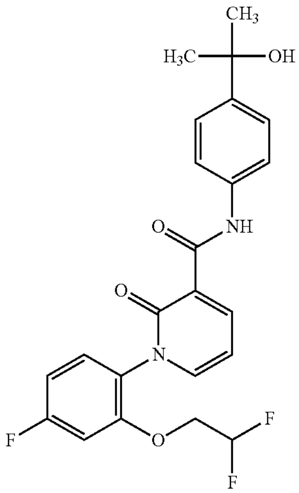 [SMILES: CC(C)(O)c1ccc(NC(=O)c2cccn(-c3ccc(F)cc3OCC(F)F)c2=O)cc1] | | 447.2 |

TABLE 1-13-continued

| Ex. No. | IUPAC Name | Structure | Additive | MS |
|---|---|---|---|---|
| 103 | 1-[4-fluoro-2-(2,2,2-trifluoroethoxy)phenyl]-N-[4-(1,1,1,3,3,3-hexafluoro-2-hydroxypropan-2-yl)phenyl]-2-oxo-1,2-dihydropyridine-3-carboxamide | 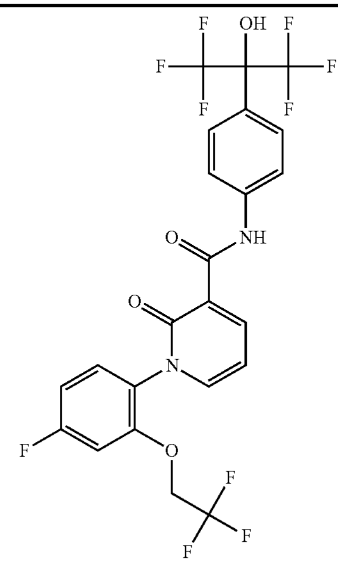 | | 573.1 |
| 104 | 1-(2-cyano-4-fluorophenyl)-N-[4-(1,1,1,3,3,3-hexafluoro-2-hydroxypropan-2-yl)phenyl]-2-oxo-1,2-dihydropyridine-3-carboxamide | 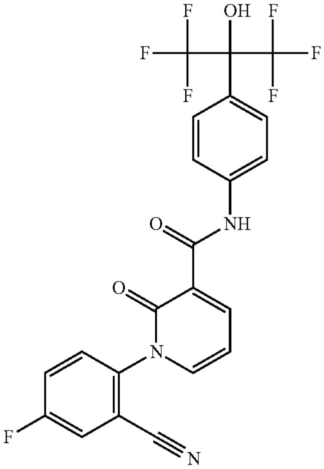 [SMILES: N#Cc1cc(F)ccc1-n1cccc(C(=O)Nc2ccc(C(O)(C(F)(F)F)C(F)(F)F)cc2)c1=O] | | 500.0 |

TABLE 1-14

| Ex. No. | IUPAC Name | Structure | Additive | MS |
|---|---|---|---|---|
| 105 | 1-[4-fluoro-2-(2-hydroxy-2-methylpropoxy)phenyl]-N-[4-(1,1,1,3,3,3-hexafluoro-2-hydroxypropan-2-yl)phenyl]-2-oxo-1,2-dihydropyridine-3-carboxamide | 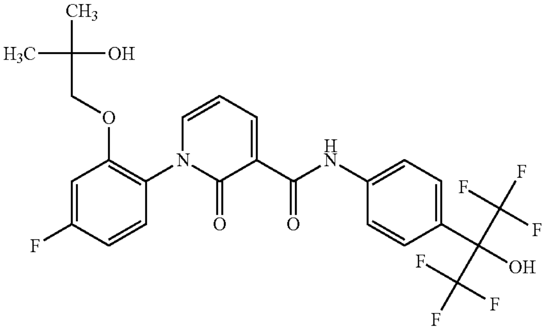 [SMILES: CC(C)(O)COc1cc(F)ccc1-n1cccc(C(=O)Nc2ccc(C(O)(C(F)(F)F)C(F)(F)F)cc2)c1=O] | | 563.0 |

TABLE 1-14-continued
| Ex. No. | IUPAC Name | Structure | Additive | MS |
|---|---|---|---|---|
| 106 | 2-[4-fluoro-2-(2,2,3,3,3-pentafluoropropoxy)phenyl]-N-[4-(2-hydroxypropan-2-yl)phenyl]-3-oxo-2,3-dihydropyridazine-4-carboxamide | 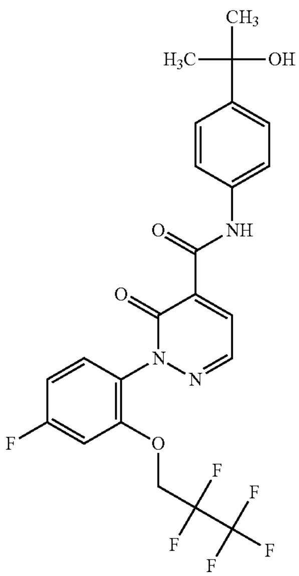 [SMILES: CC(C)(O)c1ccc(NC(=O)c2ccnn(-c3ccc(F)cc3OCC(F)(F)C(F)(F)F)c2=O)cc1] | | 516.0 |
| 107 | 1-[4-fluoro-2-(2,2,2-trifluoroethoxy)phenyl]-N-[4-(2-hydroxypropan-2-yl)phenyl]-5-methyl-2-oxo-1,2-dihydropyridine-3-carboxamide | 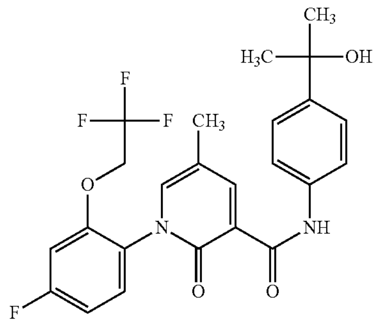 [SMILES: Cc1cc(C(=O)Nc2ccc(C(C)(C)O)cc2)c(=O)n(-c2ccc(F)cc2OCC(F)(F)F)c1] | | 479.1 |
| 108 | 1-[4,5-difluoro-2-(2,2,2-trifluoroethoxy)phenyl]-N-[4-(2-hydroxypropan-2-yl)phenyl]-2-oxo-1,2-dihydropyridine-3-carboxamide | 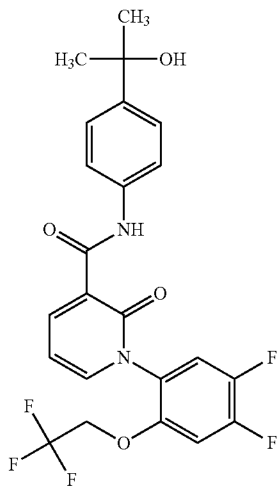 [SMILES: CC(C)(O)c1ccc(NC(=O)c2cccn(-c3cc(F)c(F)cc3OCC(F)(F)F)c2=O)cc1] | | 483.1 |

TABLE 1-14-continued
| Ex. No. | IUPAC Name | Structure | Additive | MS |
|---|---|---|---|---|
| 109 | 2-[2-(2,2-difluoroethoxy)phenyl]-6-methyl-3-oxo-N-[6-(1,1,3,3-tetrafluoro-2-hydroxypropan-2-yl)pyridin-3-yl]-2,3-dihydropyridazine-4-carboxamide | 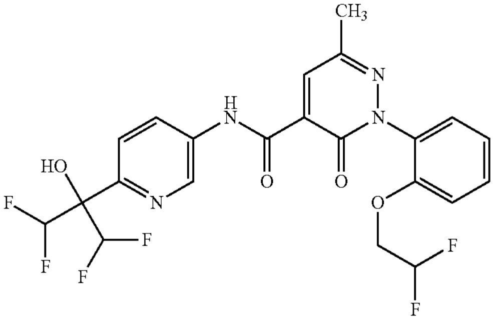 [SMILES: Cc1cc(C(=O)Nc2ccc(C(O)(C(F)F)C(F)F)nc2)c(=O)n(-c2ccccc2OCC(F)F)n1] | | 516.9 |
| 110 | 2-oxo-N-[6-(2,2,2-trifluoroethoxy)pyridin-3-yl]-1-[5-(2,2,2-trifluoroethoxy)pyrimidin-4-yl]-1,2-dihydropyridine-3-carboxamide | 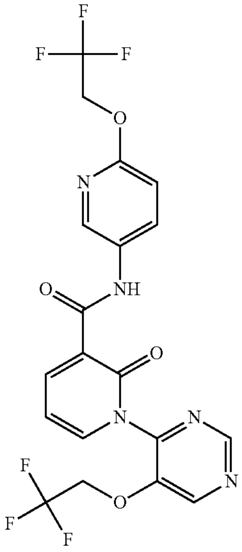 [SMILES: O=C(Nc1ccc(OCC(F)(F)F)nc1)c1cccn(-c2ncncc2OCC(F)(F)F)c1=O] | | 490.1 |
| 111 | 1-[3,4-difluoro-2-(2,2,2-trifluoroethoxy)phenyl]-N-[4-(2-hydroxypropan-2-yl)phenyl]-2-oxo-1,2-dihydropyridine-3-carboxamide | 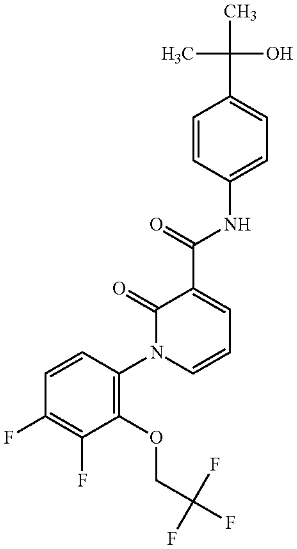 [SMILES: CC(C)(O)c1ccc(NC(=O)c2cccn(-c3ccc(F)c(F)c3OCC(F)(F)F)c2=O)cc1] | | 483.1 |

TABLE 1-14-continued
| Ex. No. | IUPAC Name | Structure | Additive | MS |
| --- | --- | --- | --- | --- |
| 112 | 2-[4-fluoro-2-(2,2,2-trifluoroethoxy)phenyl]-N-[6-(2-hydroxypropan-2-yl)pyridin-3-yl]-3-oxo-2,3-dihydropyridazine-4-carboxamide | 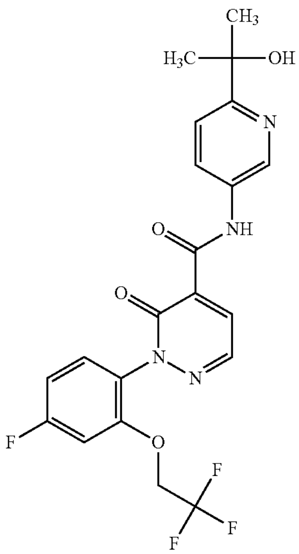 | | 467.1 |
TABLE 1-15
| Ex. No. | IUPAC Name | Structure | Additive | MS |
| --- | --- | --- | --- | --- |
| 113 | 1-[5-fluoro-2-(2,2,2-trifluoroethoxy)phenyl]-N-[4-(2-hydroxypropan-2-yl)phenyl]-2-oxo-1,2-dihydropyridine-3-carboxamide | 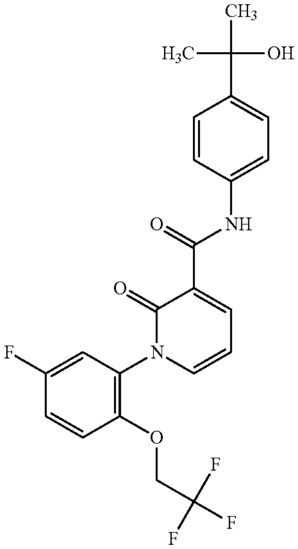 [SMILES: CC(C)(O)c1ccc(NC(=O)c2cccn(-c3cc(F)ccc3OCC(F)(F)F)c2=O)cc1] | | 465.1 |

TABLE 1-15-continued
| Ex. No. | IUPAC Name | Structure | Additive | MS |
|---|---|---|---|---|
| 114 | N-[4-(2-hydroxypropan-2-yl)phenyl]-2-oxo-2'-(2,2,2-trifluoroethoxy)-2H-[1,3'-bipyridine]-3-carboxamide | 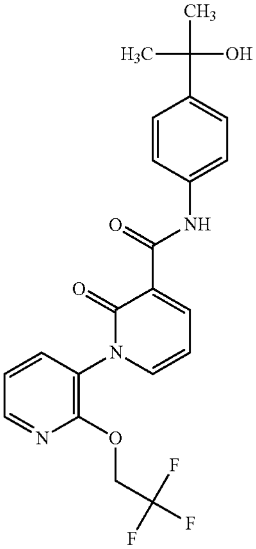 [SMILES: CC(C)(O)c1ccc(NC(=O)c2cccn(-c3cccnc3OCC(F)(F)F)c2=O)cc1] | | 448.1 |
| 115 | (R or S)-N-{6-[cyclopropyl(hydroxy)methyl]pyridin-3-yl}-1-[4-fluoro-2-(2,2,2-trifluoroethoxy)phenyl]-2-oxo-1,2-dihydropyridine-3-carboxamide | 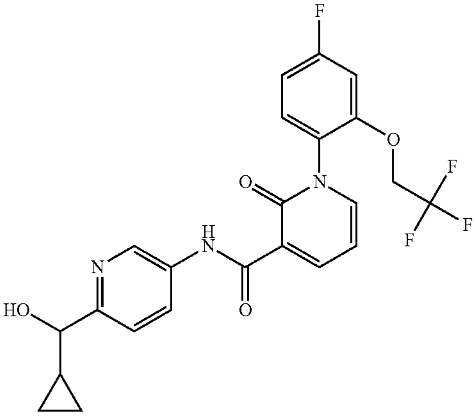 [SMILES: O=C(Nc1ccc(C(O)C2CC2)nc1)c1cccn(-c2ccc(F)cc2OCC(F)(F)F)c1=O] | | 478.1 |
| 116 | (R or S)-N-{6-[cyclopropyl(hydroxy)methyl]pyridin-3-yl}-1-[4-fluoro-2-(2,2,2-trifluoroethoxy)phenyl]-2-oxo-1,2-dihydropyridine-3-carboxamide | 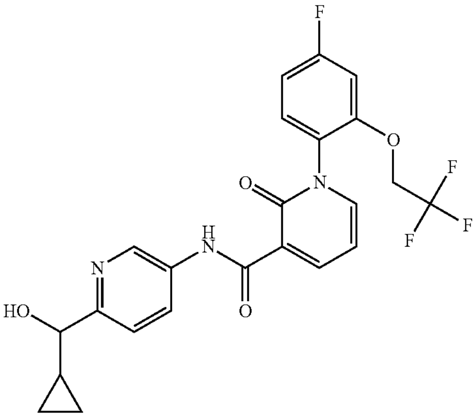 [SMILES: O=C(Nc1ccc(C(O)C2CC2)nc1)c1cccn(-c2ccc(F)cc2OCC(F)(F)F)c1=O] | | 478.2 |

TABLE 1-15-continued
| Ex. No. | IUPAC Name | Structure | Additive | MS |
|---|---|---|---|---|
| 117 | 2-[4-fluoro-2-(2,2,2-trifluoroethoxy)phenyl]-3-oxo-N-[6-(1,1,3,3-tetrafluoro-2-hydroxypropan-2-yl)pyridin-3-yl]-2,3-dihydropyridazine-4-carboxamide | 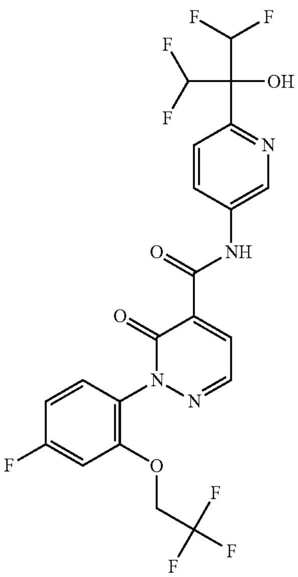 [SMILES: O=C(Nc1ccc(C(O)(C(F)F)C(F)F)nc1)c1ccnn(-c2ccc(F)cc2OCC(F)(F)F)c1=O] | | 539.0 |
| 118 | 1-[4,5-difluoro-2-(2,2,2-trifluoroethoxy)phenyl]-2-oxo-N-[6-(1,1,3,3-tetrafluoro-2-hydroxypropan-2-yl)pyridin-3-yl]-1,2-dihydropyridine-3-carboxamide | 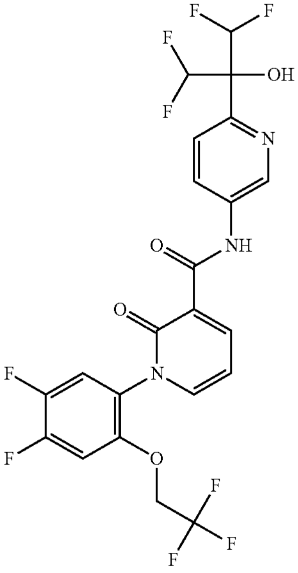 [SMILES: O=C(Nc1ccc(C(O)(C(F)F)C(F)F)nc1)c1cccn(-c2cc(F)c(F)cc2OCC(F)(F)F)c1=O] | | 556.0 |

TABLE 1-15-continued
| Ex. No. | IUPAC Name | Structure | Additive | MS |
| --- | --- | --- | --- | --- |
| 119 | N-[6-(2-hydroxypropan-2-yl)pyridin-3-yl]-2-oxo-1-[5-(2,2,2-trifluoroethoxy)pyrimidin-4-yl]-1,2-dihydropyridine-3-carboxamide | 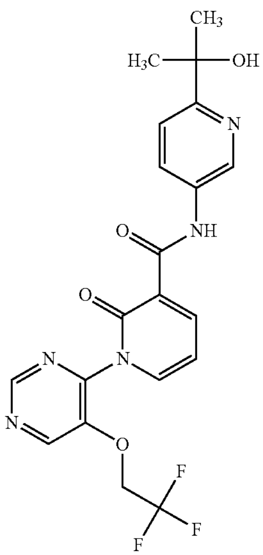 [SMILES: CC(C)(O)c1ccc(NC(=O)c2cccn(-c3ncncc3OCC(F)(F)F)c2=O)cn1] | | 450.1 |
| 120 | N-[6-(2-hydroxypropan-2-yl)pyridin-3-yl]-2-oxo-2'-(2,2,2-trifluoroethoxy)-2H-[1,3'-bipyridine]-3-carboxamide | 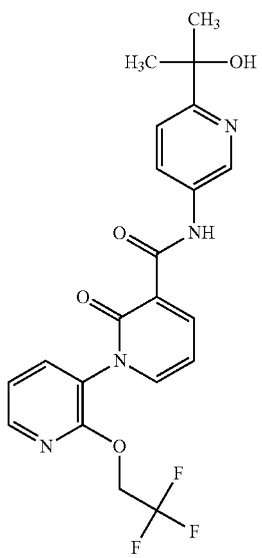 [SMILES: CC(C)(O)c1ccc(NC(=O)c2cccn(-c3cccnc3OCC(F)(F)F)c2=O)cn1] | | 449.1 |

TABLE 1-16
| Ex. No. | IUPAC Name | Structure | Additive | MS |
|---|---|---|---|---|
| 121 | rac-2-oxo-1-[3-(2,2,2-trifluoroethoxy)pyridazin-4-yl]-N-[6-(1,1,1-trifluoro-2-hydroxypropan-2-yl)pyridin-3-yl]-1,2-dihydropyridine-3-carboxamide | 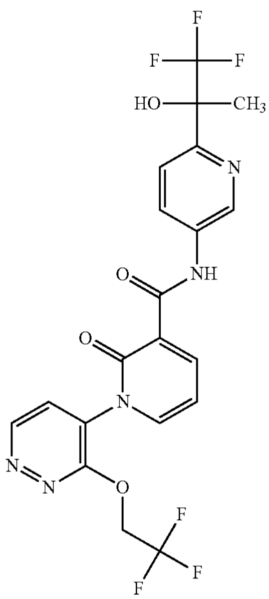 [SMILES: CC(O)(c1ccc(NC(=O)c2cccn(-c3ccnnc3OCC(F)(F)F)c2=O)cn1)C(F)(F)F] | | 504.1 |
| 122 | 2-oxo-N-[6-(1,1,3,3-tetrafluoro-2-hydroxypropan-2-yl)pyridin-3-yl]-1-[3-(2,2,2-trifluoroethoxy)pyridazin-4-yl]-1,2-dihydropyridine-3-carboxamide | 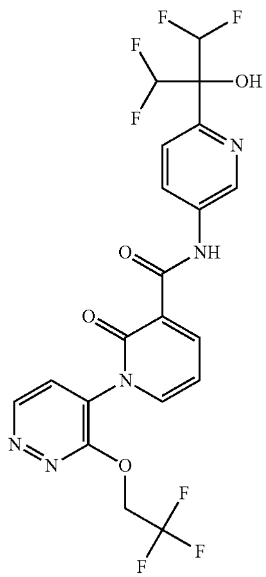 [SMILES: O=C(Nc1ccc(C(O)(C(F)F)C(F)F)nc1)c1cccn(-c2ccnnc2OCC(F)(F)F)c1=O] | | 522.0 |

TABLE 1-16-continued
| Ex. No. | IUPAC Name | Structure | Additive | MS |
|---|---|---|---|---|
| 123 | 2-oxo-N-[6-(1,1,3,3-tetrafluoro-2-hydroxypropan-2-yl)pyridin-3-yl]-2'-(2,2,2-trifluoroethoxy)-2H-[1,3'-bipyridine]-3-carboxamide | 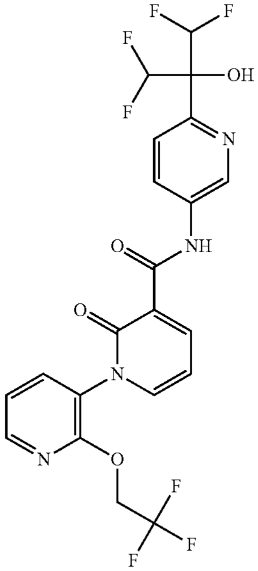 [SMILES: O=C(Nc1ccc(C(O)(C(F)F)C(F)F)nc1)c1cccn(-c2cccnc2OCC(F)(F)F)c1=O] | | 521.0 |
| 124 | 1-[5-fluoro-2-(2,2,2-trifluoroethoxy)phenyl]-2-oxo-N-[6-(1,1,3,3-tetrafluoro-2-hydroxypropan-2-yl)pyridin-3-yl]-1,2-dihydropyridine-3-carboxamide | 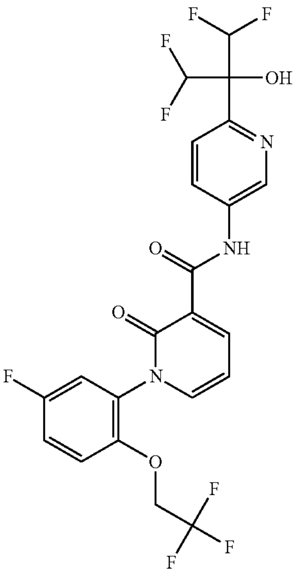 [SMILES: O=C(Nc1ccc(C(O)(C(F)F)C(F)F)nc1)c1cccn(-c2cc(F)ccc2OCC(F)(F)F)c1=O] | | 538.0 |

TABLE 1-16-continued
| Ex. No. | IUPAC Name | Structure | Additive | MS |
| --- | --- | --- | --- | --- |
| 125 | 1-[5-fluoro-2-(2,2,2-trifluoroethoxy)phenyl]-N-[6-(2-hydroxypropan-2-yl)pyridin-3-yl]-2-oxo-1,2-dihydropyridine-3-carboxamide | 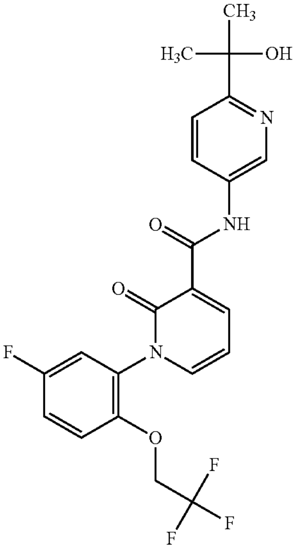 [SMILES: CC(C)(O)c1ccc(NC(=O)c2cccn(-c3cc(F)ccc3OCC(F)(F)F)c2=O)cn1] | | 466.1 |
| 126 | N-[6-(2-hydroxypropan-2-yl)pyridin-3-yl]-3-oxo-2-[2-(2,2,2-trifluoroethoxy)phenyl]-2,3-dihydropyridazine-4-carboxamide | 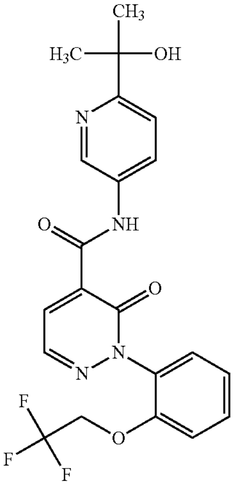 [SMILES: CC(C)(O)c1ccc(NC(=O)c2ccnn(-c3ccccc3OCC(F)(F)F)c2=O)cn1] | | 449.1 |
| 127 | N-[4-(2-hydroxypropan-2-yl)phenyl]-3-oxo-2-[2-(2,2,2-trifluoroethoxy)phenyl]-2,3-dihydropyridazine-4-carboxamide | 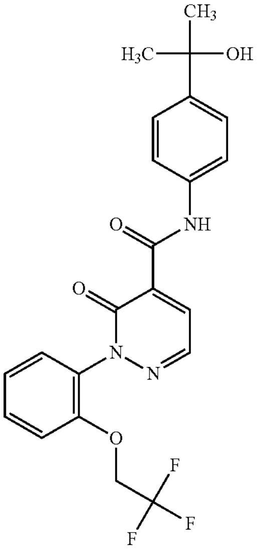 [SMILES: CC(C)(O)c1ccc(NC(=O)c2ccnn(-c3ccccc3OCC(F)(F)F)c2=O)cc1] | | 448.2 |

TABLE 1-16-continued

| Ex. No. | IUPAC Name | Structure | Additive | MS |
|---|---|---|---|---|
| 128 | N-[5-(2-hydroxypropan-2-yl)pyridin-2-yl]-3-oxo-2-[2-(2,2,2-trifluoroethoxy)phenyl]-2,3-dihydropyridazine-4-carboxamide | 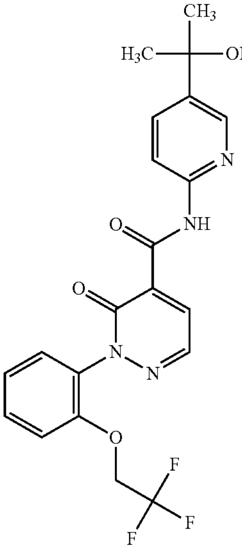 | | 449.2 |

TABLE 1-17

| Ex. No. | IUPAC Name | Structure | Additive | MS |
|---|---|---|---|---|
| 129 | N-[6-(2-hydroxypropan-2-yl)pyridin-3-yl]-6-methyl-3-oxo-2-[2-(2,2,2-trifluoroethoxy)phenyl]-2,3-dihydropyridazine-4-carboxamide | 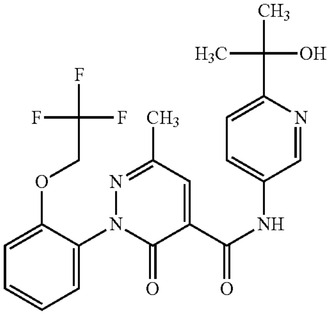 [SMILES: Cc1cc(C(=O)Nc2ccc(C(C)(C)O)nc2)c(=O)n(-c2ccccc2OCC(F)(F)F)n1] | | 463.1 |
| 130 | N-[5-(2-hydroxypropan-2-yl)pyridin-2-yl]-6-methyl-3-oxo-2-[2-(2,2,2-trifluoroethoxy)phenyl]-2,3-dihydropyridazine-4-carboxamide | 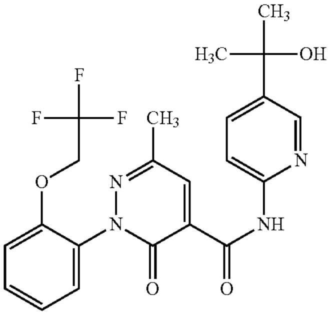 [SMILES: Cc1cc(C(=O)Nc2ccc(C(C)(C)O)cn2)c(=O)n(-c2ccccc2OCC(F)(F)F)n1] | | 463.2 |

TABLE 1-17-continued
| Ex. No. | IUPAC Name | Structure | Additive | MS |
|---|---|---|---|---|
| 131 | N-[4-(2-hydroxypropan-2-yl)phenyl]-6-methyl-3-oxo-2-[2-(2,2,2-trifluoroethoxy)phenyl]-2,3-dihydropyridazine-4-carboxamide | 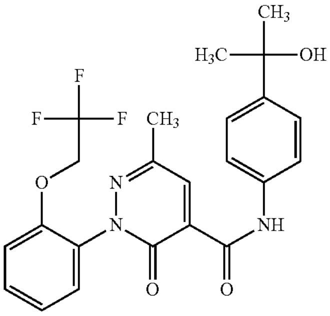 [SMILES: Cc1cc(C(=O)Nc2ccc(C(C)(C)O)cc2)c(=O)n(-c2ccccc2OCC(F)(F)F)n1] | | 462.2 |
| 132 | 2-[2-(2,2-difluoroethoxy)phenyl]-N-[5-(2-hydroxypropan-2-yl)pyridin-2-yl]-3-oxo-2,3-dihydropyridazine-4-carboxamide | 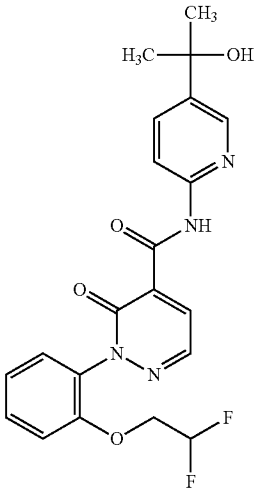 [SMILES: CC(C)(O)c1ccc(NC(=O)c2ccnn(-c3ccccc3OCC(F)F)c2=O)nc1] | | 431.2 |
| 133 | 2-[2-(2,2-difluoroethoxy)phenyl]-N-[4-(2-hydroxypropan-2-yl)phenyl]-3-oxo-2,3-dihydropyridazine-4-carboxamide | 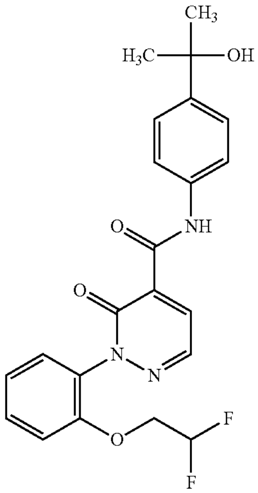 [SMILES: CC(C)(O)c1ccc(NC(=O)c2ccnn(-c3ccccc3OCC(F)F)c2=O)cc1] | | 430.2 |

TABLE 1-17-continued

| Ex. No. | IUPAC Name | Structure | Additive | MS |
|---|---|---|---|---|
| 134 | 2-[2-(2,2-difluoroethoxy)phenyl]-N-[6-(2-hydroxypropan-2-yl)pyridin-3-yl]-3-oxo-2,3-dihydropyridazine-4-carboxamide | 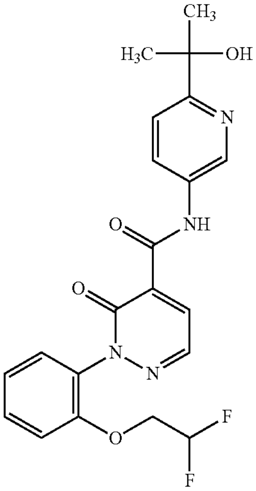 [SMILES: CC(C)(O)c1ccc(NC(=O)c2ccnn(-c3ccccc3OCC(F)F)c2=O)cn1] | | 431.2 |
| 135 | 2-[2-(2,2-difluoroethoxy)phenyl]-N-[6-(2-hydroxypropan-2-yl)pyridin-3-yl]-6-methyl-3-oxo-2,3-dihydropyridazine-4-carboxamide | 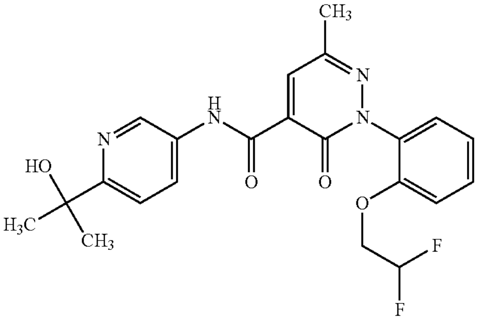 [SMILES: Cc1cc(C(=O)Nc2ccc(C(C)(C)O)nc2)c(=O)n(-c2ccccc2OCC(F)F)n1] | | 445.2 |
| 136 | 2-[2-(2,2-difluoroethoxy)phenyl]-N-[4-(2-hydroxypropan-2-yl)phenyl]-6-methyl-3-oxo-2,3-dihydropyridazine-4-carboxamide | 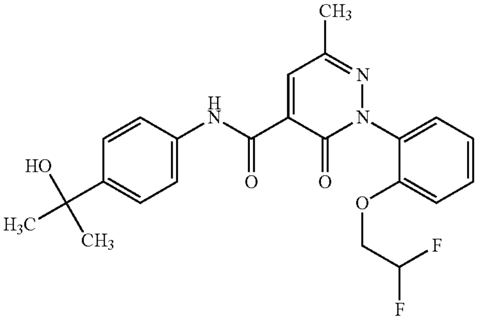 [SMILES: Cc1cc(C(=O)Nc2ccc(C(C)(C)O)cc2)c(=O)n(-c2ccccc2OCC(F)F)n1] | | 444.2 |

TABLE 1-18

| Ex. No. | IUPAC Name | Structure | Additive | MS |
|---|---|---|---|---|
| 137 | 2-[2-(2,2-difluoroethoxy)phenyl]-N-[5-(2-hydroxypropan-2-yl)pyridin-2-yl]-6-methyl-3-oxo-2,3-dihydropyridazine-4-carboxamide | 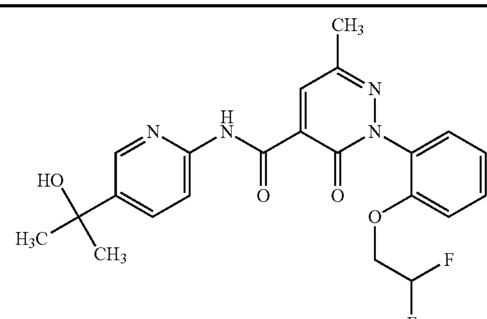 | | 445.2 |

TABLE 1-18-continued
| Ex. No. | IUPAC Name | Structure | Additive | MS |
|---|---|---|---|---|
| 138 | rac-N-[4-(1-hydroxyethyl)phenyl]-3-oxo-2-[2-(2,2,2-trifluoroethoxy)phenyl]-2,3-dihydropyridazine-4-carboxamide | 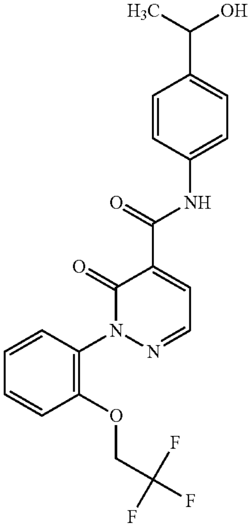 [SMILES: CC(O)c1ccc(NC(=O)c2ccnn(-c3ccccc3OCC(F)(F)F)c2=O)cc1] | | 434.2 |
| 139 | rac-2-[2-(2,2-difluoroethoxy)phenyl]-N-[4-(1-hydroxyethyl)phenyl]-6-methyl-3-oxo-2,3-dihydropyridazine-4-carboxamide | 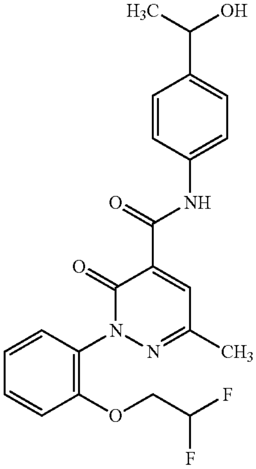 [SMILES: Cc1cc(C(=O)Nc2ccc(C(C)O)cc2)c(=O)n(-c2ccccc2OCC(F)F)n1] | | 430.2 |
| 140 | rac-N-[5-(1-hydroxyethyl)pyridin-2-yl]-3-oxo-2-[2-(2,2,2-trifluoroethoxy)phenyl]-2,3-dihydropyridazine-4-carboxamide | 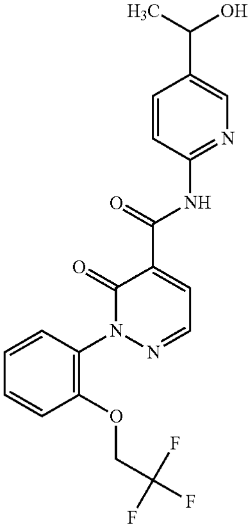 [SMILES: CC(O)c1ccc(NC(=O)c2ccnn(-c3ccccc3OCC(F)(F)F)c2=O)nc1] | | 435.2 |

TABLE 1-18-continued
| Ex. No. | IUPAC Name | Structure | Additive | MS |
| --- | --- | --- | --- | --- |
| 141 | 2-[2-(2,2-difluoroethoxy)phenyl]-6-methyl-N-[4-(oxetan-3-yl)phenyl]-3-oxo-2,3-dihydropyridazine-4-carboxamide | 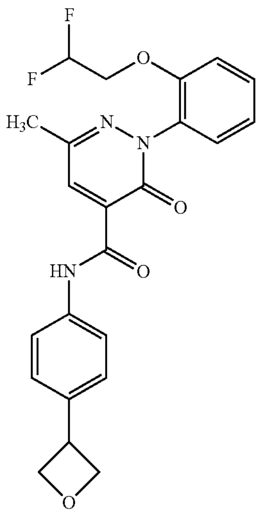 [SMILES: Cc1cc(C(=O)Nc2ccc(C3COC3)cc2)c(=O)n(-c2ccccc2OCC(F)F)n1] | | 442.2 |
| 142 | 2-[2-(2,2-difluoroethoxy)phenyl]-N-[4-(2-hydroxypropan-2-yl)-3-methylphenyl]-3-oxo-2,3-dihydropyridazine-4-carboxamide | 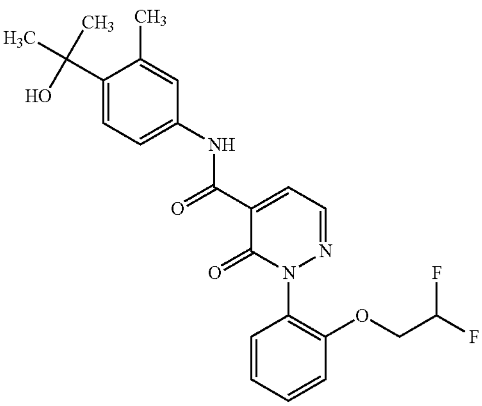 [SMILES: Cc1cc(NC(=O)c2ccnn(-c3ccccc3OCC(F)F)c2=O)ccc1C(C)(C)O] | | 444.2 |
| 143 | 2-[2-(2,2-difluoroethoxy)phenyl]-N-[4-(2-hydroxypropan-2-yl)-2-methylphenyl]-3-oxo-2,3-dihydropyridazine-4-carboxamide | 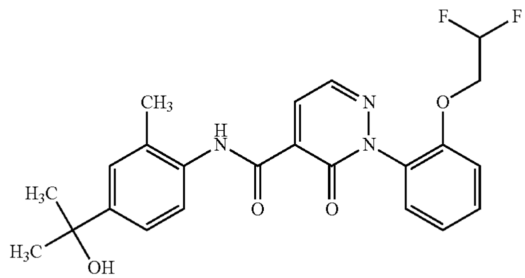 [SMILES: Cc1cc(C(C)(C)O)ccc1NC(=O)c1ccnn(-c2ccccc2OCC(F)F)c1=O] | | 444.2 |

TABLE 1-18-continued

| Ex. No. | IUPAC Name | Structure | Additive | MS |
|---|---|---|---|---|
| 144 | rac-2-[2-(2,2-difluoroethoxy)phenyl]-3-oxo-N-[4-(oxolan-2-yl)phenyl]-2,3-dihydropyridazine-4-carboxamide | 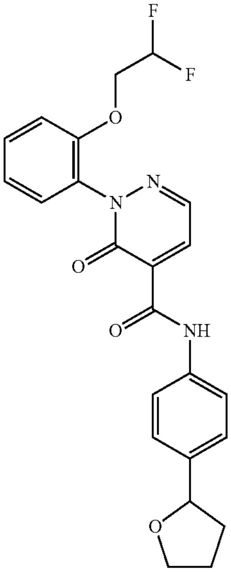 [SMILES: O=C(Nc1ccc(C2CCCO2)cc1)c1ccnn(-c2ccccc2OCC(F)F)c1=O] | | 442.2 |

TABLE 1-19

| Ex. No. | IUPAC Name | Structure | Additive | MS |
|---|---|---|---|---|
| 145 | rac-2-[2-(2,2-difluoroethoxy)phenyl]-3-oxo-N-[4-(oxolan-3-yl)phenyl]-2,3-dihydropyridazine-4-carboxamide | 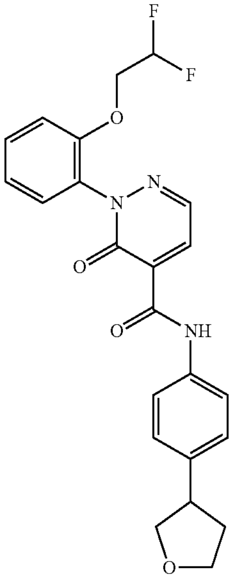 [SMILES: O=C(Nc1ccc(C2CCOC2)cc1)c1ccnn(-c2ccccc2OCC(F)F)c1=O] | | 442.2 |
| 146 | 2-[2-(2,2-difluoroethoxy)phenyl]-N-[2-fluoro-4-(2-hydroxypropan-2-yl)phenyl]-6-methyl-3-oxo-2,3-dihydropyridazine-4-carboxamide | 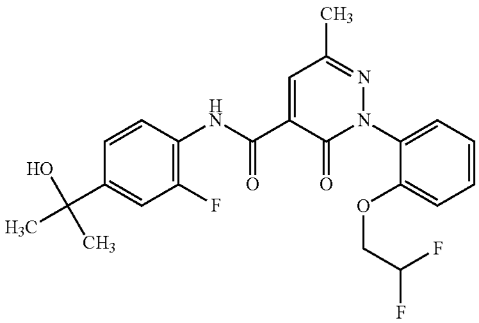 [SMILES: Cc1cc(C(=O)Nc2ccc(C(C)(C)O)cc2F)c(=O)n(-c2ccccc2OCC(F)F)n1] | | 462.2 |

TABLE 1-19-continued

| Ex. No. | IUPAC Name | Structure | Additive | MS |
|---|---|---|---|---|
| 147 | 2-[2-(2,2-difluoroethoxy)phenyl]-N-[2-fluoro-4-(2-hydroxypropan-2-yl)phenyl]-3-oxo-2,3-dihydropyridazine-4-carboxamide | 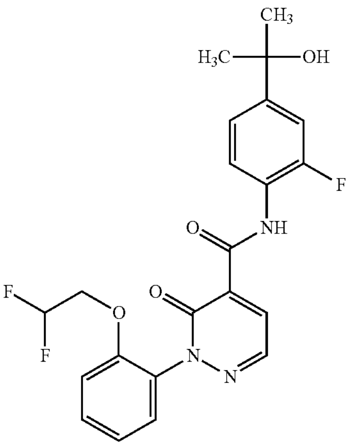 [SMILES: CC(C)(O)c1ccc(NC(=O)c2ccnn(-c3ccccc3OCC(F)F)c2=O)c(F)c1] | | 448.2 |
| 148 | N-[2-fluoro-4-(2-hydroxypropan-2-yl)phenyl]-3-oxo-2-[2-(2,2,2-trifluoroethoxy)phenyl]-2,3-dihydropyridazine-4-carboxamide | 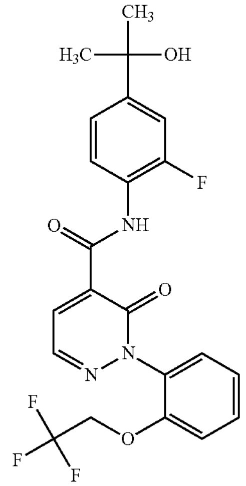 [SMILES: CC(C)(O)c1ccc(NC(=O)c2ccnn(-c3ccccc3OCC(F)(F)F)c2=O)c(F)c1] | | 466.1 |
| 149 | N-[2-chloro-4-(2-hydroxypropan-2-yl)phenyl]-2-[2-(2,2-difluoroethoxy)phenyl]-6-methyl-3-oxo-2,3-dihydropyridazine-4-carboxamide | 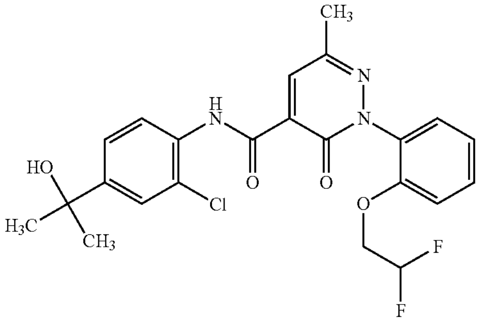 [SMILES: Cc1cc(C(=O)Nc2ccc(C(C)(C)O)cc2Cl)c(=O)n(-c2ccccc2OCC(F)F)n1] | | 478.1 |
| 150 | 2-[2-(2,2-difluoroethoxy)phenyl]-N-[2,6-difluoro-4-(2-hydroxypropan-2-yl)phenyl]-6-methyl-3-oxo-2,3-dihydropyridazine-4-carboxamide | 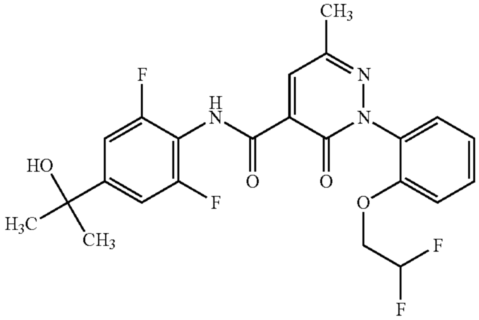 [SMILES: Cc1cc(C(=O)Nc2c(F)cc(C(C)(C)O)cc2F)c(=O)n(-c2ccccc2OCC(F)F)n1] | | 480.2 |

TABLE 1-19-continued

| Ex. No. | IUPAC Name | Structure | Additive | MS |
|---|---|---|---|---|
| 151 | 2-[2-(2,2-difluoroethoxy)phenyl]-N-[4-(2-hydroxypropan-2-yl)-2-methoxyphenyl]-6-methyl-3-oxo-2,3-dihydropyridazine-4-carboxamide | 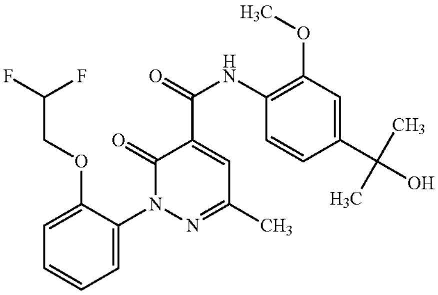 [SMILES: COc1cc(C(C)(C)O)ccc1NC(=O)c1cc(C)nn(-c2ccccc2OCC(F)F)c1=O] | | 474.2 |
| 152 | 2-[2-(2,2-difluoroethoxy)phenyl]-6-methyl-3-oxo-N-[4-(1,1,3,3-tetrafluoro-2-hydroxypropan-2-yl)phenyl]-2,3-dihydropyridazine-4-carboxamide | 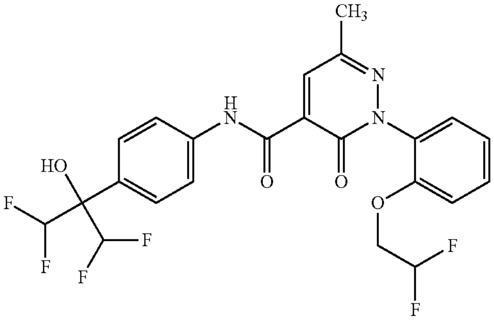 [SMILES: Cc1cc(C(=O)Nc2ccc(C(O)(C(F)F)C(F)F)cc2)c(=O)n(-c2ccccc2OCC(F)F)n1] | | 516.1 |

TABLE 1-20

| Ex. No. | IUPAC Name | Structure | Additive | MS |
|---|---|---|---|---|
| 153 | 2-[2-(2,2-difluoroethoxy)phenyl]-3-oxo-N-[4-(1,1,3,3-tetrafluoro-2-hydroxypropan-2-yl)phenyl]-2,3-dihydropyridazine-4-carboxamide | 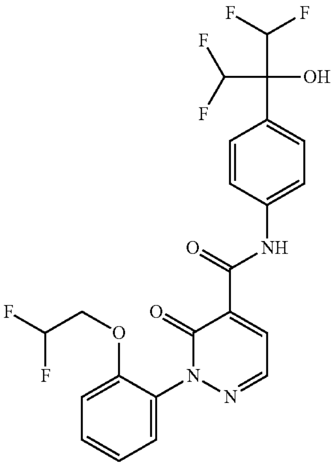 [SMILES: O=C(Nc1ccc(C(O)(C(F)F)C(F)F)cc1)c1ccnn(-c2ccccc2OCC(F)F)c1=O] | | 502.1 |
| 154 | N-[2-cyano-4-(2-hydroxypropan-2-yl)phenyl]-2-[2-(2,2-difluoroethoxy)phenyl]-6-methyl-3-oxo-2,3-dihydropyridazine-4-carboxamide | 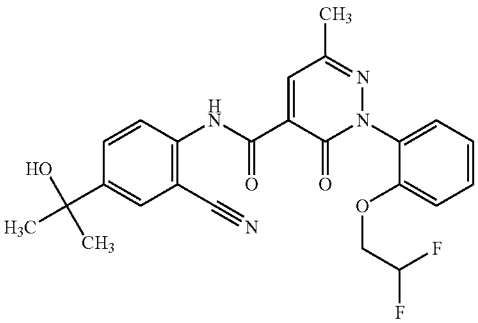 [SMILES: Cc1cc(C(=O)Nc2ccc(C(C)(C)O)cc2C#N)c(=O)n(-c2ccccc2OCC(F)F)n1] | | 469.2 |

TABLE 1-20-continued

| Ex. No. | IUPAC Name | Structure | Additive | MS |
|---|---|---|---|---|
| 155 | 3-oxo-N-[4-(1,1,3,3-tetrafluoro-2-hydroxypropan-2-yl)phenyl]-2-[2-(2,2,2-trifluoroethoxy)phenyl]-2,3-dihydropyridazine-4-carboxamide | 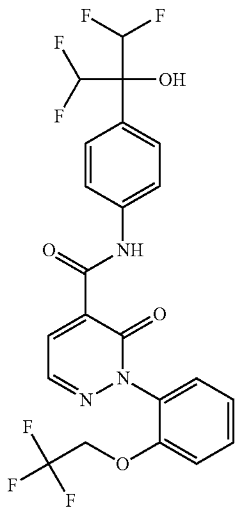 [SMILES: O=C(Nc1ccc(C(O)(C(F)F)C(F)F)cc1)c1ccnn(-c2ccccc2OCC(F)(F)F)c1=O] | | 520.1 |
| 156 | 2-[2-(2,2-difluoroethoxy)phenyl)-N-[2-fluoro-4-(1,1,3,3-tetrafluoro-2-hydroxypropan-2-yl)phenyl]-6-methyl-3-oxo-2,3-dihydropyridazine-4-carboxamide | 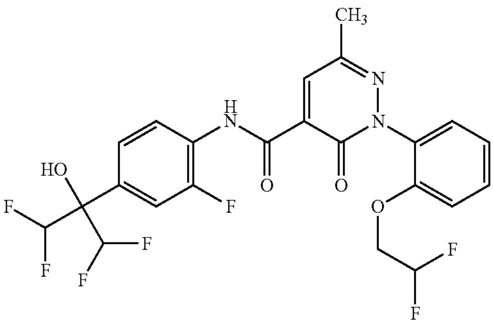 [SMILES: Cc1cc(C(=O)Nc2ccc(C(O)(C(F)F)C(F)F)cc2F)c(=O)n(-c2ccccc2OCC(F)F)n1] | | 532.1 |
| 157 | 2-[2-(2,2-difluoroethoxy)phenyl]-N-[2-fluoro-4-(1,1,3,3-tetrafluoro-2-hydroxypropan-2-yl)phenyl]-3-oxo-2,3-dihydropyridazine-4-carboxamide | 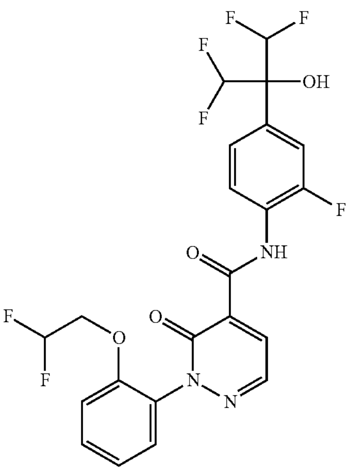 [SMILES: O=C(Nc1ccc(C(O)(C(F)F)C(F)F)cc1F)c1ccnn(-c2ccccc2OCC(F)F)c1=O] | | 518.1 |

TABLE 1-20-continued

| Ex. No. | IUPAC Name | Structure | Additive | MS |
| --- | --- | --- | --- | --- |
| 158 | 6-[2-(2,2-difluoroethoxy)phenyl]-N-[4-(2-hydroxypropan-2-yl)phenyl]-2-methyl-5-oxo-2,5-dihydropyridazine-4-carboxamide | 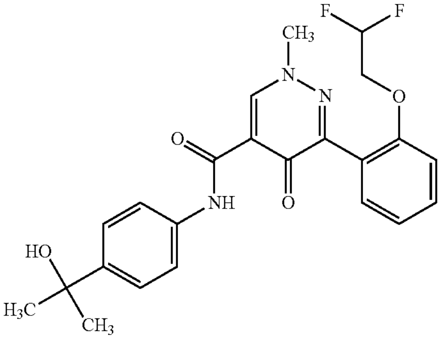 [SMILES: Cn1cc(C(=O)Nc2ccc(C(C)(C)O)cc2)c(=O)c(-c2ccccc2OCC(F)F)n1] | | 444.2 |
| 159 | 6-[2-(2,2-difluoroethoxy)phenyl]-2-methyl-5-oxo-N-[4-(1,1,3,3-tetrafluoro-2-hydroxypropan-2-yl)phenyl]-2,5-dihydropyridazine-4-carboxamide | 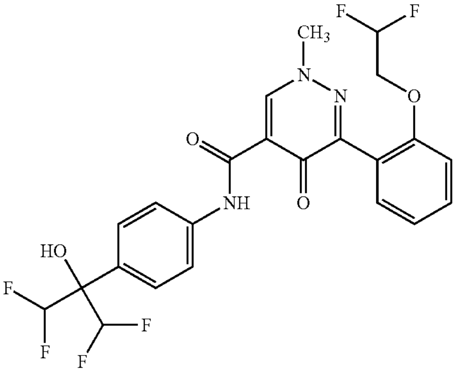 [SMILES: Cn1cc(C(=O)Nc2ccc(C(O)(C(F)F)C(F)F)cc2)c(=O)c(-c2ccccc2OCC(F)F)n1] | | 516.1 |
| 160 | N-[2-chloro-4-(1,1,3,3-tetrafluoro-2-hydroxypropan-2-yl)phenyl]-2-[2-(2,2-difluoroethoxy)phenyl]-3-oxo-2,3-dihydropyridazine-4-carboxamide | 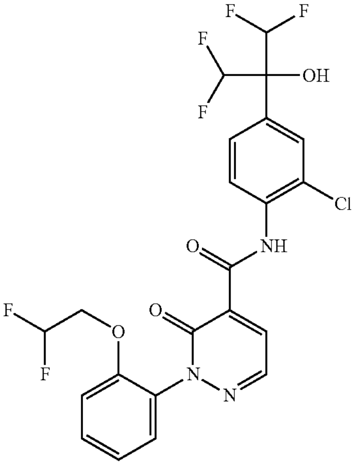 [SMILES: O=C(Nc1ccc(C(O)(C(F)F)C(F)F)cc1Cl)c1ccnn(-c2ccccc2OCC(F)F)c1=O] | | 534.0 |

TABLE 1-21

| Ex. No. | IUPAC Name | Structure | Additive | MS |
|---|---|---|---|---|
| 161 | 6-[2-(2,2-difluoroethoxy)phenyl]-2-(difluoromethyl)-N-[4-(2-hydroxypropan-2-yl)phenyl]-5-oxo-2,5-dihydropyridazine-4-carboxamide | 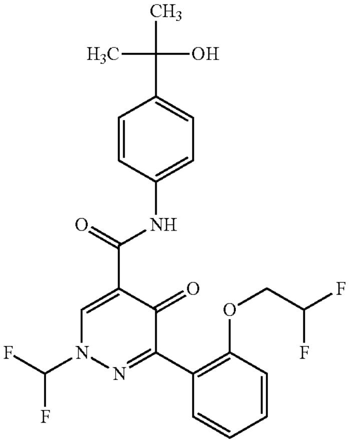 [SMILES: CC(C)(O)c1ccc(NC(=O)c2cn(C(F)F)nc(-c3ccccc3OCC(F)F)c2=O)cc1] | | 480.1 |
| 162 | 3-oxo-N-[6-(1,1,3,3-tetrafluoro-2-hydroxypropan-2-yl)pyridin-3-yl]-2-[2-(2,2,2-trifluoroethoxy)phenyl]-2,3-dihydropyridazine-4-carboxamide | 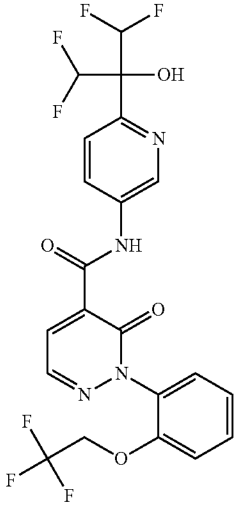 [SMILES: O=C(Nc1ccc(C(O)(C(F)F)C(F)F)nc1)c1ccnn(-c2ccccc2OCC(F)(F)F)c1=O] | | 520.9 |
| 163 | 6-[2-(2,2-difluoroethoxy)phenyl]-2-(difluoromethyl)-5-oxo-N-[4-(1,1,3,3-tetrafluoro-2-hydroxypropan-2-yl)phenyl]-2,5-dihydropyridazine-4-carboxamide | 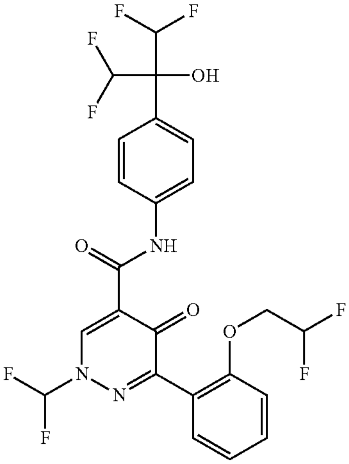 | | 551.8 |

TABLE 1-21-continued

| Ex. No. | IUPAC Name | Structure | Additive | MS |
|---|---|---|---|---|
| 164 | 6-[2-(2,2-difluoroethoxy)phenyl]-N-[4-(2-hydroxy-2-methylpropoxy)phenyl]-2-methyl-5-oxo-2,5-dihydropyridazine-4-carboxamide | 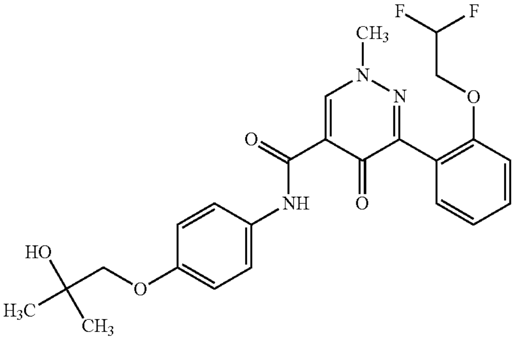 [SMILES: Cn1cc(C(=O)Nc2ccc(OCC(C)(C)O)cc2)c(=O)c(-c2ccccc2OCC(F)F)n1] | | 474.2 |
| 165 | 6-[2-(2,2-difluoroethoxy)phenyl]-2-(difluoromethyl)-N-[4-(2-hydroxy-2-methylpropoxy)phenyl]-5-oxo-2,5-dihydropyridazine-4-carboxamide | 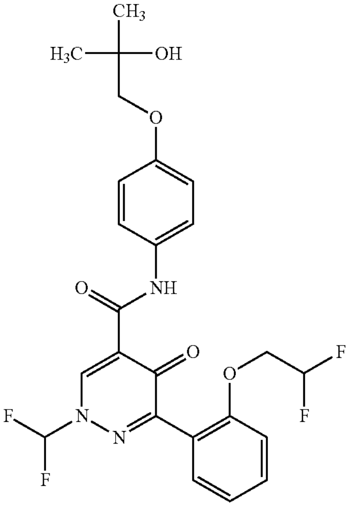 [SMILES: CC(C)(O)COc1ccc(NC(=O)c2cn(C(F)F)nc(-c3ccccc3OCC(F)F)c2=O)cc1] | | 510.1 |
| 166 | N-[4-(2-hydroxypropan-2-yl)phenyl]-2-methyl-5-oxo-6-[2-(2,2,2-trifluoroethoxy)pheny]-2,5-dihydropyridazine-4-carboxamide | 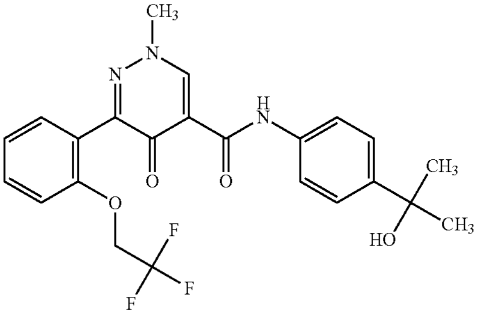 [SMILES: Cn1cc(C(=O)Nc2ccc(C(C)(C)O)cc2)c(=O)c(-c2ccccc2OCC(F)(F)F)n1] | | 462.1 |
| 167 | 6-[2-(2,2-difluoroethoxy)phenyl]-N-(2,4-difluorophenyl)-2-(2-hydroxy-2-methylpropyl)-5-oxo-2,5-dihydropyridazine-4-carboxamide | 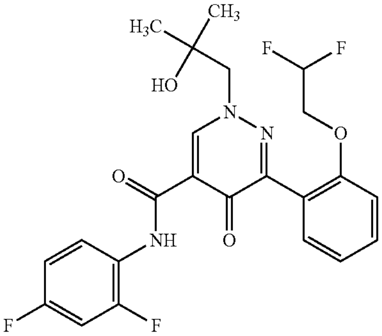 [SMILES: CC(C)(O)Cn1cc(C(=O)Nc2ccc(F)cc2F)c(=O)c(-c2ccccc2OCC(F)F)n1] | | 480.2 |

TABLE 1-21-continued

| Ex. No. | IUPAC Name | Structure | Additive | MS |
|---|---|---|---|---|
| 168 | 6-[2-(2,2-difluoroethoxy)phenyl]-2-(2-hydroxy-2-methylpropyl)-5-oxo-N-[4-(2,2,2-trifluoroethoxy)phenyl]-2,5-dihydropyridazine-4-carboxamide | 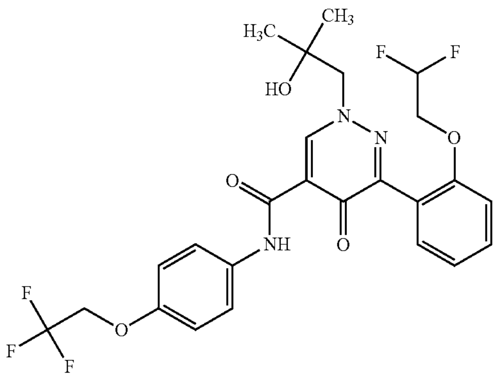 [SMILES: CC(C)(O)Cn1cc(C(=O)Nc2ccc(OCC(F)(F)F)cc2)c(=O)c(-c2ccccc2OCC(F)F)n1] | | 542.1 |

TABLE 1-22

| Ex. No. | IUPAC Name | Structure | Additive | MS |
|---|---|---|---|---|
| 169 | 2-cyclopropyl-6-[2-(2,2-difluoroethoxy)phenyl]-N-[4-(2-hydroxypropan-2-yl)phenyl]-5-oxo-2,5-dihydropyridazine-4-carboxamide | 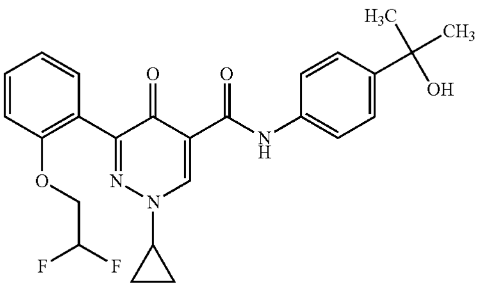 [SMILES: CC(C)(O)c1ccc(NC(=O)c2cn(C3CC3)nc(-c3ccccc3OCC(F)F)c2=O)cc1] | | 470.2 |
| 170 | ethyl 5-({2-[2-(2,2-difluoroethoxy)phenyl]-6-methyl-3-oxo-2,3-dihydropyridazine-4-carbonyl}amino)thiophene-2-carboxylate | 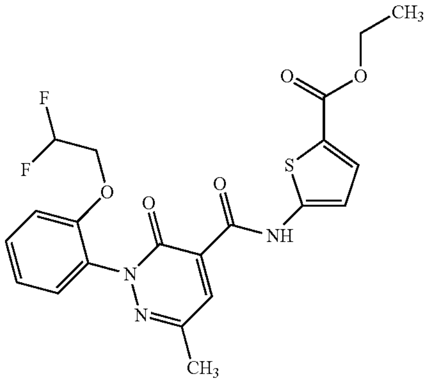 [SMILES: CCOC(=O)c1ccc(NC(=O)c2cc(C)nn(-c3ccccc3OCC(F)F)c2=O)s1] | | 464.1 |
| 171 | 6-[2-(2,2-difluoroethoxy)phenyl]-N-(4-fluorophenyl)-2-(2-hydroxy-2-methylpropyl)-5-oxo-2,5-dihydropyridazine-4-carboxamide | 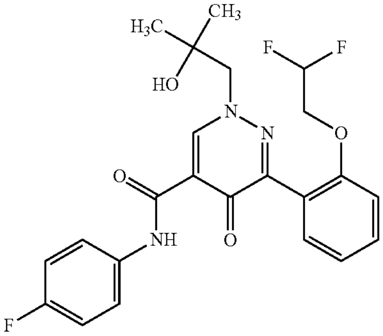 [SMILES: CC(C)(O)Cn1cc(C(=O)Nc2ccc(F)cc2)c(=O)c(-c2ccccc2OCC(F)F)n1] | | 462.2 |

TABLE 1-22-continued

| Ex. No. | IUPAC Name | Structure | Additive | MS |
|---|---|---|---|---|
| 172 | N-[4-(2-cyanopropan-2-yl)phenyl]-6-[2-(2,2-difluoroethoxy)phenyl]-2-methyl-5-oxo-2,5-dihydropyridazine-4-carboxamide | 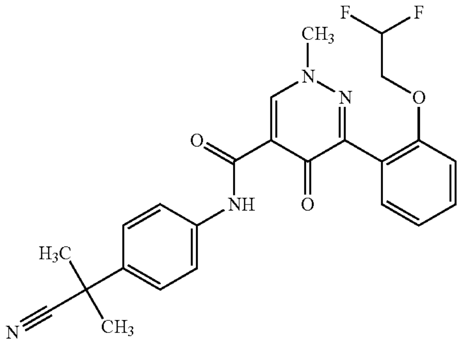 [SMILES: Cn1cc(C(=O)Nc2ccc(C(C)(C)C#N)cc2)c(=O)c(-c2ccccc2OCC(F)F)n1] | | 453.2 |
| 173 | 6-[2-(2,2-difluoroethoxy)phenyl]-N-[4-(difluoromethoxy)phenyl]-2-(2-hydroxy-2-methylpropyl)-5-oxo-2,5-dihydropyridazine-4-carboxamide | 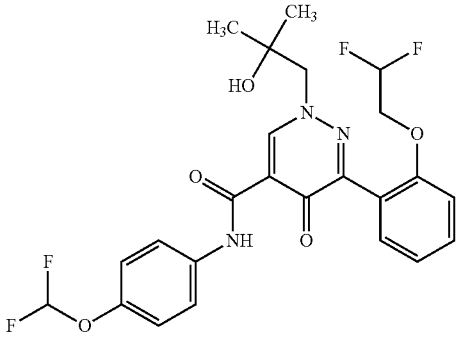 [SMILES: CC(C)(O)Cn1cc(C(=O)Nc2ccc(OC(F)F)cc2)c(=O)c(-c2ccccc2OCC(F)F)n1] | | 510.2 |
| 174 | 6-[2-(2,2-difluoroethoxy)phenyl]-2-(2-hydroxy-2-methylpropyl)-N-[4-(2-hydroxypropan-2-yl)phenyl]-5-oxo-2,5-dihydropyridazine-4-carboxamide | 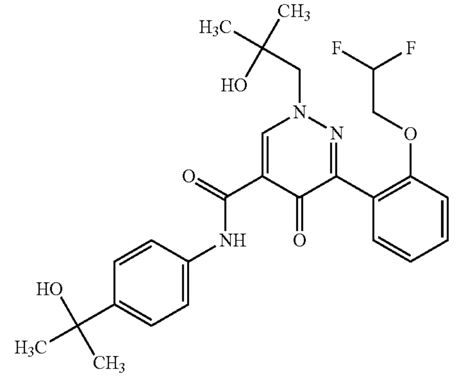 [SMILES: CC(C)(O)Cn1cc(C(=O)Nc2ccc(C(C)(C)O)cc2)c(=O)c(-c2ccccc2OCC(F)F)n1] | | 502.2 |
| 175 | 6-[2-(2,2-difluoroethoxy)phenyl]-2-[(oxetan-3-yl)methyl]-5-oxo-N-[4-(1,1,3,3-tetrafluoro-2-hydroxypropan-2-yl)phenyl]-2,5-dihydropyridazine-4-carboxamide | 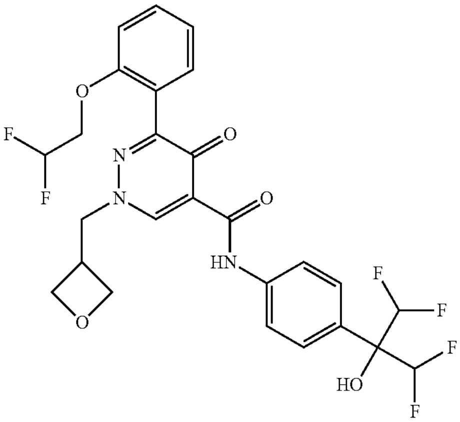 [SMILES: O=C(Nc1ccc(C(O)(C(F)F)C(F)F)cc1)c1cn(CC2COC2)nc(-c2ccccc2OCC(F)F)c1=O] | | 572.1 |

TABLE 1-22-continued

| Ex. No. | IUPAC Name | Structure | Additive | MS |
|---|---|---|---|---|
| 176 | 6-[2-(2,2-difluoroethoxy)phenyl]-2-methyl-5-oxo-N-[6-(1,1,3,3-tetrafluoro-2-hydroxypropan-2-yl)pyridin-3-yl]-2,5-dihydropyridazine-4-carboxamide | 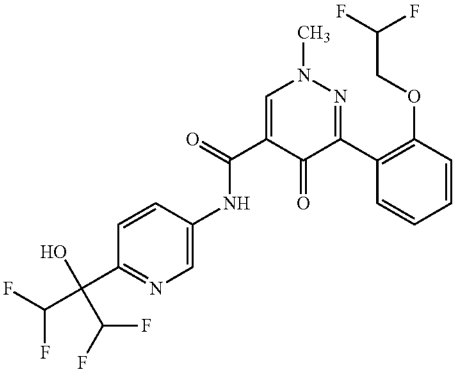 [SMILES: Cn1cc(C(=O)Nc2ccc(C(O)(C(F)F)C(F)F)nc2)c(=O)c(-c2ccccc2OCC(F)F)n1] | | 517.1 |

TABLE 1-23

| Ex. No. | IUPAC Name | Structure | Additive | MS |
|---|---|---|---|---|
| 177 | 6-[2-(2,2-difluoroethoxy)phenyl]-2-(difluoromethyl)-5-oxo-N-[6-(1,1,3,3-tetrafluoro-2-hydroxypropan-2-yl)pyridin-3-yl]-2,5-dihydropyridazine-4-carboxamide | 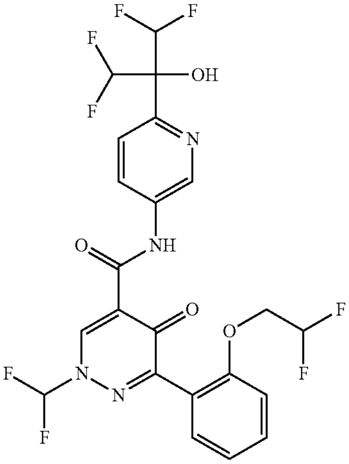 [SMILES: O=C(Nc1ccc(C(O)(C(F)F)C(F)F)nc1)c1cn(C(F)F)nc(-c2ccccc2OCC(F)F)c1=O] | | 553.1 |
| 178 | 6-[2-(2,2-difluoroethoxy)phenyl]-2-(2-hydroxy-2-methylpropyl)-5-oxo-N-[6-(1,1,3,3-tetrafluoro-2-hydroxypropan-2-yl)pyridin-3-yl]-2,5-dihydropyridazine-4-carboxamide | 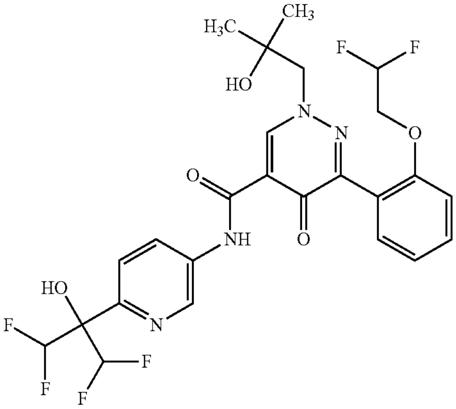 [SMILES: CC(C)(O)Cn1cc(C(=O)Nc2ccc(C(O)(C(F)F)C(F)F)nc2)c(=O)c(-c2ccccc2OCC(F)F)n1] | | 575.2 |

TABLE 1-23-continued

| Ex. No. | IUPAC Name | Structure | Additive | MS |
| --- | --- | --- | --- | --- |
| 179 | 6-[2-(2,2-difluoroethoxy)phenyl]-2-(2,2-difluoroethyl)-N-[4-(2-hydroxypropan-2-yl)phenyl]-5-oxo-2,5-dihydropyridazine-4-carboxamide | 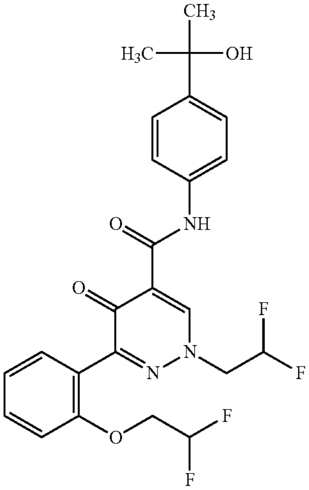 [SMILES: CC(C)(O)c1ccc(NC(=O)c2cn(CC(F)F)nc(-c3ccccc3OCC(F)F)c2=O)cc1] | | 494.2 |
| 180 | 6-[2-(2,2-difluoroethoxy)phenyl]-N-[4-(2-hydroxypropan-2-yl)phenyl]-2-[(oxetan-3-yl)methyl]-5-oxo-2,5-dihydropyridazine-4-carboxamide | 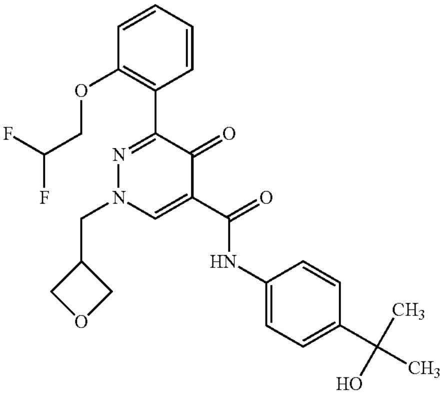 [SMILES: CC(C)(O)c1ccc(NC(=O)c2cn(CC3COC3)nc(-c3ccccc3OCC(F)F)c2=O)cc1] | | 500.2 |
| 181 | 6-[2-(2,2-difluoroethoxy)phenyl]-N-(2,4-difluorophenyl)-2-[(oxetan-3-yl)methyl]-5-oxo-2,5-dihydropyridazine-4-carboxamide | 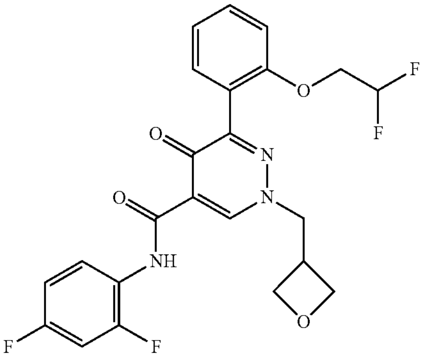 [SMILES: O=C(Nc1ccc(F)cc1F)c1cn(CC2COC2)nc(-c2ccccc2OCC(F)F)c1=O] | | 478.1 |
| 182 | 6-[2-(2,2-difluoroethoxy)phenyl]-N-(2,4-difluorophenyl)-2-(oxetan-3-yl)-5-oxo-2,5-dihydropyridazine-4-carboxamide | 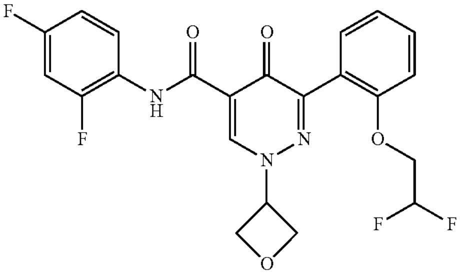 [SMILES: O=C(Nc1ccc(F)cc1F)c1cn(C2COC2)nc(-c2ccccc2OCC(F)F)c1=O] | | 464.1 |

TABLE 1-23-continued

| Ex. No. | IUPAC Name | Structure | Additive | MS |
|---|---|---|---|---|
| 183 | 6-[2-(2,2-difluoroethoxy)phenyn-N-[4-(2-hydroxypropan-2-yl)phenyl]-2-(oxetan-3-yl)-5-oxo-2,5-dihydropyridazine-4-carboxamide | 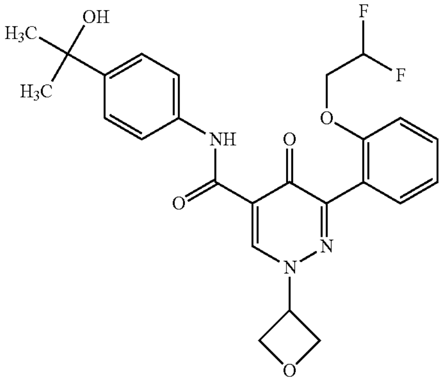 [SMILES: CC(C)(O)c1ccc(NC(=O)c2cn(C3COC3)nc(-c3ccccc3OCC(F)F)c2=O)cc1] | | 486.2 |
| 184 | 6-[2-(2,2-difluoroethoxy)phenyl]-2-(oxetan-3-yl)-5-oxo-N-[4-(1,1,3,3-tetrafluoro-2-hydroxypropan-2-yl)phenyl]-2,5-dihydropyridazine-4-carboxamide | 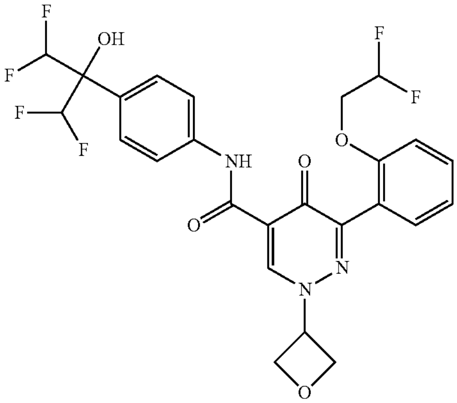 [SMILES: O=C(Nc1ccc(C(O)(C(F)F)C(F)F)cc1)c1cn(C2COC2)nc(-c2ccccc2OCC(F)F)c1=O] | | 558.2 |

TABLE 1-24

| Ex. No. | IUPAC Name | Structure | Additive | MS |
|---|---|---|---|---|
| 185 | 6-[2-(2,2-difluoroethoxy)phenyl]-N-[4-(difluoromethyl)phenyl]-2-methyl-5-oxo-2,5-dihydropyridazine-4-carboxamide | 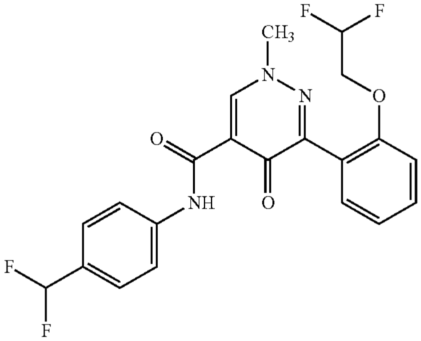 [SMILES: Cn1cc(C(=O)Nc2ccc(C(F)F)cc2)c(=O)c(-c2ccccc2OCC(F)F)n1] | | 436.0 |

TABLE 1-24-continued

| Ex. No. | IUPAC Name | Structure | Additive | MS |
|---|---|---|---|---|
| 186 | 6-[2-(2,2-difluoroethoxy)phenyl]-2-(2,2-difluoroethyl)-5-oxo-N-[6-(1,1,3,3-tetrafluoro-2-hydroxypropan-2-yl)pyridin-3-yl]-2,5-dihydropyridazine-4-carboxamide | 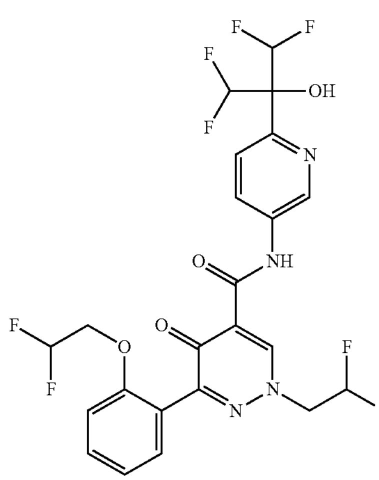 | | 566.8 |
| 187 | 6-[2-(2,2-difluoroethoxy)phenyl]-2-(oxetan-3-yl)-5-oxo-N-[6-(1,1,3,3-tetrafluoro-2-hydroxypropan-2-yl)pyridin-3-yl]-2,5-dihydropyridazine-4-carboxamide | 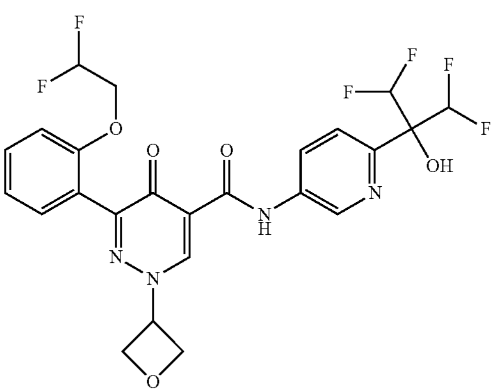 [SMILES: O=C(Nc1ccc(C(O)(C(F)F)C(F)F)nc1)c1cn(C2COC2)nc(-c2ccccc2OCC(F)F)c1=O] | | 558.9 |
| 188 | 6-[2-(2,2-difluoroethoxy)phenyl]-2-[(oxetan-3-yl)methyl]-5-oxo-N-[6-(1,1,3,3-tetrafluoro-2-hydroxypropan-2-yl)pyridin-3-yl]-2,5-dihydropyridazine-4-carboxamide | 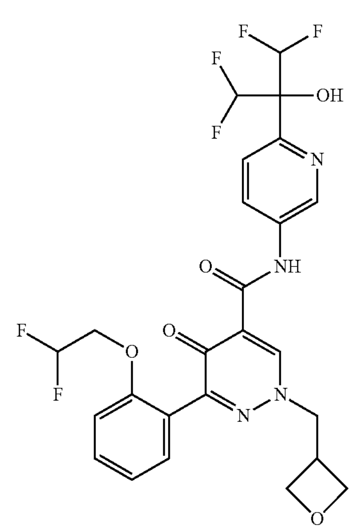 [SMILES: O=C(Nc1ccc(C(O)(C(F)F)C(F)F)nc1)c1cn(CC2COC2)nc(-c2ccccc2OCC(F)F)c1=O] | | 572.9 |

TABLE 1-24-continued

| Ex. No. | IUPAC Name | Structure | Additive | MS |
|---|---|---|---|---|
| 189 | 2-cyclopropyl-6-[2-(2,2-difluoroethoxy)phenyl]-5-oxo-N-[6-(1,1,3,3-tetrafluoro-2-hydroxypropan-2-yl)pyridin-3-yl]-2,5-dihydropyridazine-4-carboxamide | 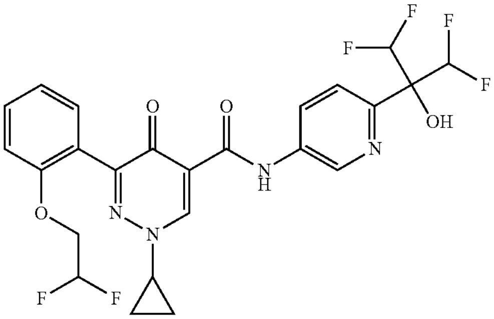 [SMILES: O=C(Nc1ccc(C(O)(C(F)F)C(F)F)nc1)c1cn(C2CC2)nc(-c2ccccc2OCC(F)F)c1=O] | | 542.9 |
| 190 | N-[4-(2-cyanopropan-2-yl)phenyl]-2-methyl-5-oxo-6-[2-(2,2,2-trifluoroethoxy)phenyl]-2,5-dihydropyridazine-4-carboxamide | 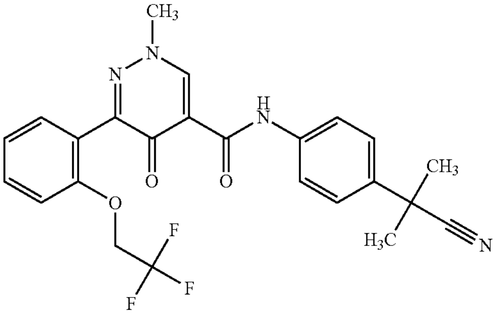 [SMILES: Cn1cc(C(=O)Nc2ccc(C(C)(C)C#N)cc2)c(=O)c(-c2ccccc2OCC(F)(F)F)n1] | | 470.9 |
| 191 | N-[4-(2-cyanopropan-2-yl)phenyl]-6-[2-(2,2-difluoroethoxy)phenyl]-2-(oxetan-3-yl)-5-oxo-2,5-dihydropyridazine-4-carboxamide | 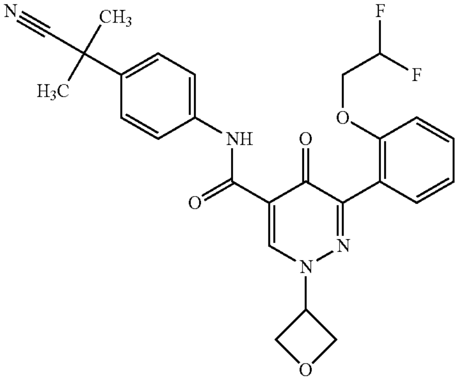 [SMILES: CC(C)(C#N)c1ccc(NC(=O)c2cn(C3COC3)nc(-c3ccccc3OCC(F)F)c2=O)cc1] | | 495.0 |
| 192 | N-[4-(2-cyanopropan-2-yl)phenyl]-2-cyclopropyl-6-[2-(2,2-difluoroethoxy)phenyl]-5-oxo-2,5-dihydropyridazine-4-carboxamide | 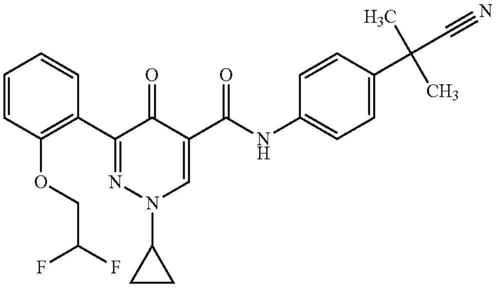 [SMILES: CC(C)(C#N)c1ccc(NC(=O)c2cn(C3CC3)nc(-c3ccccc3OCC(F)F)c2=O)cc1] | | 479.0 |

TABLE 1-25
| Ex. No. | IUPAC Name | Structure | Additive | MS |
|---|---|---|---|---|
| 193 | rac-6-[2-(2,2-difluoroethoxy)phenyl]-N-[4-(2-hydroxypropan-2-yl)phenyl]-5-oxo-2-(oxolan-3-yl)-2,5-dihydropyridazine-4-carboxamide | 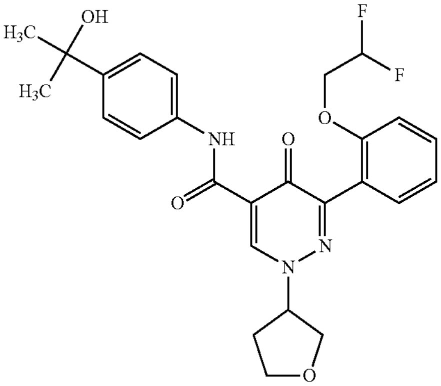 [SMILES: CC(C)(O)c1ccc(NC(=O)c2cn(C3CCOC3)nc(-c3ccccc3OCC(F)F)c2=O)cc1] | | 500.0 |
| 194 | ethyl 4-({2-[2-(2,2-difluoroethoxy)phenyl]-6-methyl-3-oxo-2,3-dihydropyridazine-4-carbonyl}amino)benzoate | 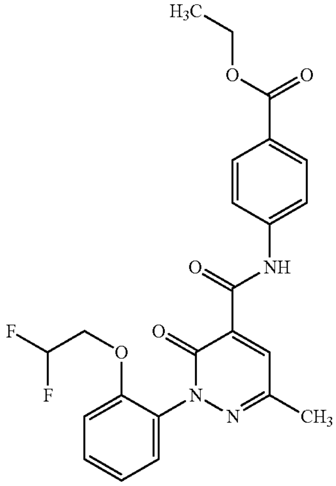 [SMILES: CCOC(=O)c1ccc(NC(=O)c2cc(C)nn(-c3ccccc3OCC(F)F)c2=O)cc1] | | 458.0 |
| 195 | rac-6-[2-(2,2-difluoroethoxy)phenyl]-5-oxo-2-(oxolan-3-yl)-N-[6-(1,1,3,3-tetrafluoro-2-hydroxypropan-2-yl)pyridin-3-yl]-2,5-dihydropyridazine-4-carboxamide | 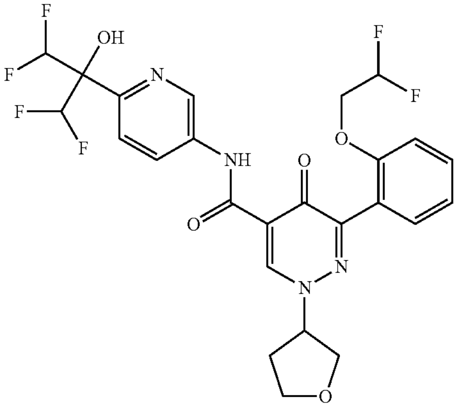 [SMILES: O=C(Nc1ccc(C(O)(C(F)F)C(F)F)nc1)c1cn(C2CCOC2)nc(-c2ccccc2OCC(F)F)c1=O] | | 572.9 |

TABLE 1-25-continued

| Ex. No. | IUPAC Name | Structure | Additive | MS |
| --- | --- | --- | --- | --- |
| 196 | rac-6-[2-(2,2-difluoroethoxy)phenyl]-5-oxo-2-(oxolan-3-yl)-N-[4-(1,1,3,3-tetrafluoro-2-hydroxypropan-2-yl)phenyl]-2,5-dihydropyridazine-4-carboxamide | 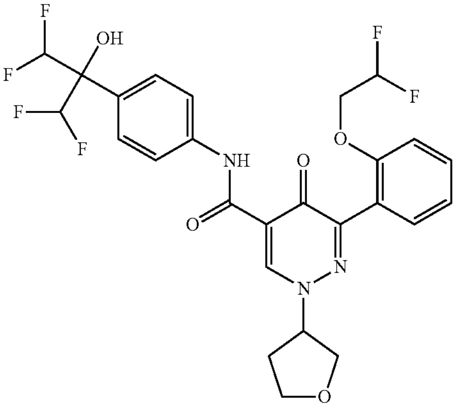 [SMILES: O=C(Nc1ccc(C(O)(C(F)F)C(F)F)cc1)c1cn(C2CCOC2)nc(-c2ccccc2OCC(F)F)c1=O] | | 571.9 |
| 197 | 6-acetyl-N-[4-(difluoromethoxy)phenyl]-3-oxo-2-[2-(2,2,2-trifluoroethoxy)phenyl]-2,3-dihydropyridazine-4-carboxamide | 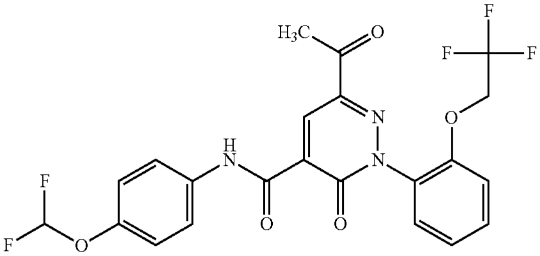 [SMILES: CC(=O)c1cc(C(=O)Nc2ccc(OC(F)F)cc2)c(=O)n(-c2ccccc2OCC(F)(F)F)n1] | | 495.9 |
| 198 | ethyl 5-{[4-(difluoromethoxy)phenyl]carbamoyl}-6-oxo-1-[2-(2,2,2-trifluoroethoxy)phenyl]-1,6-dihydropyridazine-3-carboxylate | 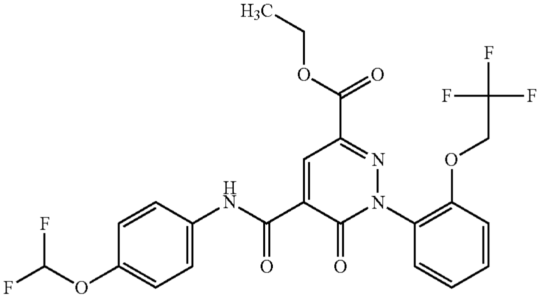 [SMILES: CCOC(=O)c1cc(C(=O)Nc2ccc(OC(F)F)cc2)c(=O)n(-c2ccccc2OCC(F)(F)F)n1] | | 525.9 |
| 199 | rac-N-[4-(difluoromethoxy)phenyl]-6-(1-hydroxyethyl)-3-oxo-2-[2-(2,2,2-trifluoroethoxy)phenyl]-2,3-dihydropyridazine-4-carboxamide | 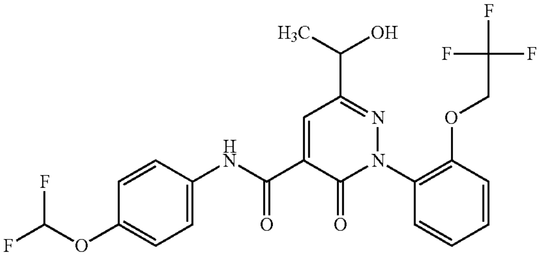 [SMILES: CC(O)c1cc(C(=O)Nc2ccc(OC(F)F)cc2)c(=O)n(-c2ccccc2OCC(F)(F)F)n1] | | 500.1 |
| 200 | N-[4-(difluoromethoxy)phenyl]-6-(2-hydroxypropan-2-yl)-3-oxo-2-[2-(2,2,2-trifluoroethoxy)phenyl]-2,3-dihydropyridazine-4-carboxamide | 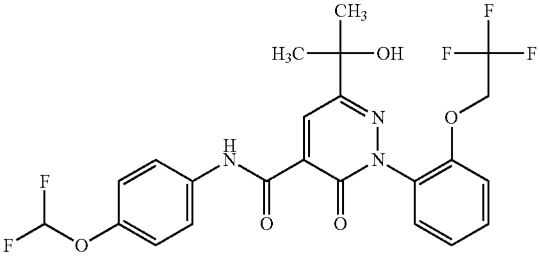 [SMILES: CC(C)(O)c1cc(C(=O)Nc2ccc(OC(F)F)cc2)c(=O)n(-c2ccccc2OCC(F)(F)F)n1] | | 514.1 |

TABLE 1-26

| Ex. No. | IUPAC Name | Structure | Additive | MS |
|---|---|---|---|---|
| 201 | N-[4-(2-cyanopropan-2-yl)phenyl]-6-(2-hydroxypropan-2-yl)-3-oxo-2-[2-(2,2,2-trifluoroethoxy)phenyl]-2,3-dihydropyridazine-4-carboxamide | 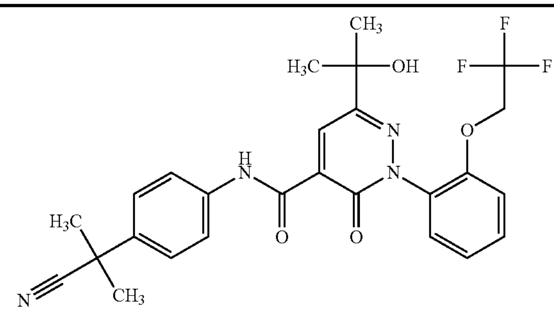 | | 514.9 |
| 202 | 6-(2-hydroxypropan-2-yl)-N-[4-(2-hydroxypropan-2-yl)phenyl]-3-oxo-2-[2-(2,2,2-trifluoroethoxy)phenyl]-2,3-dihydropyridazine-4-carboxamide | 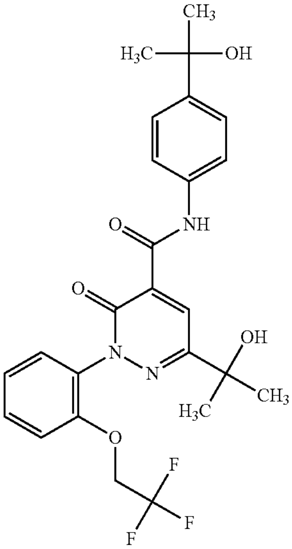 [SMILES: CC(C)(O)c1ccc(NC(=O)c2cc(C(C)(C)O)nn(-c3ccccc3OCC(F)(F)F)c2=O)cc1] | | 505.9 |
| 203 | 6-(2-hydroxypropan-2-yl)-3-oxo-N-[4-(prop-1-en-2-yl)phenyl]-2-[2-(2,2,2-trifluoroethoxy)phenyl]-2,3-dihydropyridazine-4-carboxamide | 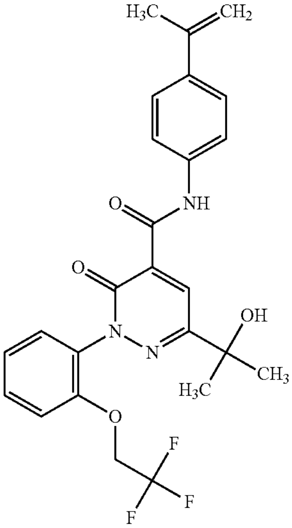 [SMILES: C=C(C)c1ccc(NC(=O)c2cc(C(C)(C)O)nn(-c3ccccc3OCC(F)(F)F)c2=O)cc1] | | 487.9 |

Experimental Example 1

Glucosylceramide Synthase (GCS) Assay

In enzyme assay, a microsome fraction obtained by transient expression by Expi293F™ cells (catalog number: A14527, Thermo Fisher Scientific) was used as a glucosylceramide synthase source. Liposomal C8 ceramide and UDP-glucose were used as substrates. For each substrate concentration, 1.7 μM UDP-glucose, which is equal to the Km value, and 3 μM C8 ceramide were used. After the enzymatic reaction, the analysis was performed with Rapidfire MS/MS (API-4000™, SCIEX), and C8 glucosylceramide was quantified to evaluate the inhibitory activity of the test compound against glucosylceramide synthase activity.

PcDNA3.3TOPO vector (catalog number: K830001, Thermo Fisher Scientific) into which the human GCS gene was inserted was introduced into Expi293F™ Cells (catalog number: A14527, Thermo Fisher Scientific) by using Expi-Fectamine™ 293 Transfection Kit (catalog number: A14525, Thermo Fisher Scientific). The cultured cells were dissolved in D-PBS (catalog number: 048-29805, Fuji Film Wako Pure Chemical Industries, Ltd.) containing 1 mM PMSF, and the solution was allowed to stand on ice for 30 minutes, and then subjected to cell disruption (homogenized). The disruption solution was centrifuged at 10,000×g for 20 minutes at 4° C., and the obtained supernatant was centrifuged at 142,400×g for 60 minutes at 4° C. The obtained precipitate was resuspended in a D-PBS solution containing 1 mM PMSF, and homogenized again to prepare as a microsome fraction. Protein quantification was performed by the CBB method.

A 1 mM compound solution prepared by dissolving the test compound in DMSO was added to a 384-well plate by 100 nL so that the final concentration of the test compound was 10 μM. Next, a substrate solution consisting of 3.4 μM UDP-glucose and 6 μM C8 ceramide was added by 5 μL, followed by an enzyme solution consisting of a 25 μg/mL microsome fraction by 5 μL. C8 ceramide was prepared from liposomes composed of 15 mol % C8 ceramide and 85 mol % dioleoyl phosphatidylcholine (1,2-dioleoyl-sn-glycero-3-phosphocholine: DOPC). The enzymatic reaction was carried out in a solution consisting of 20 mM tris-hydrochloric acid buffer (pH 7.5), 0.01% Tween 20, 0.01% bovine serum albumin and 1 mM dithiothreitol at room temperature for 60 min. Then, a solution consisting of 75% isopropanol and 1% formic acid containing 0.25 μM N-Octadecanoyl-D35-psichosine (catalog number: 1914, Matreya) as an internal standard substance was added by 60 μL to stop the enzymatic reaction. 5 μL of the centrifugal supernatant of the obtained reaction product was analyzed by Rapidfire MS/MS (Agilent Technologies) using API-4000™ (SCIEX), and the C8 glucosylceramide was quantified to evaluate the inhibitory activity of the test compound against the glucosylceramide synthase activity. The inhibitory activity of the test compound was evaluated when the C8 glucosylceramide level in the enzyme-free solution was considered as 100% inhibitory and the enzyme activity of the DMSO group in the absence of the compound was considered as 0% inhibitory.

The results are shown in Table 2 below.

TABLE 2

| Example | GCS enzyme inhibitory rate at 10 μM (%) |
|---|---|
| 1 | 71 |
| 2 | 95 |
| 3 | 92 |
| 4 | 93 |
| 5 | 68 |
| 6 | 52 |
| 7 | 57 |
| 8 | 66 |
| 11 | 88 |
| 12 | 97 |
| 13 | 96 |
| 14 | 99 |
| 15 | 100 |
| 16 | 69 |
| 17 | 81 |
| 18 | 76 |
| 19 | 55 |
| 20 | 100 |

TABLE 2-continued

| Example | GCS enzyme inhibitory rate at 10 μM (%) |
|---|---|
| 21 | 99 |
| 22 | 77 |
| 23 | 87 |
| 24 | 98 |
| 25 | 81 |
| 26 | 100 |
| 27 | 75 |
| 29 | 97 |
| 30 | 55 |
| 31 | 92 |
| 33 | 76 |
| 35 | 85 |
| 36 | 86 |
| 37 | 83 |
| 38 | 97 |
| 40 | 69 |
| 41 | 88 |
| 42 | 99 |
| 43 | 95 |
| 47 | 89 |
| 48 | 70 |
| 49 | 97 |
| 50 | 100 |
| 51 | 84 |
| 52 | 85 |
| 55 | 88 |
| 56 | 100 |
| 57 | 95 |
| 58 | 99 |
| 60 | 92 |
| 61 | 95 |
| 62 | 77 |
| 63 | 100 |
| 64 | 99 |
| 66 | 60 |
| 67 | 89 |
| 68 | 97 |
| 69 | 99 |
| 70 | 97 |
| 73 | 99 |
| 74 | 99 |
| 75 | 96 |
| 76 | 98 |
| 77 | 100 |
| 78 | 100 |
| 79 | 87 |
| 80 | 71 |
| 82 | 99 |
| 83 | 98 |
| 84 | 98 |
| 85 | 94 |
| 86 | 88 |
| 87 | 99 |
| 88 | 100 |
| 89 | 100 |
| 90 | 90 |
| 91 | 89 |
| 92 | 95 |
| 93 | 99 |
| 95 | 99 |
| 96 | 100 |
| 97 | 99 |
| 98 | 98 |
| 99 | 99 |
| 100 | 70 |
| 101 | 99 |
| 102 | 98 |
| 103 | 100 |
| 104 | 95 |
| 105 | 99 |
| 106 | 99 |
| 107 | 100 |
| 108 | 95 |
| 109 | 100 |
| 110 | 99 |
| 111 | 98 |

TABLE 2-continued

| Example | GCS enzyme inhibitory rate at 10 μM (%) |
|---|---|
| 112 | 94 |
| 113 | 98 |
| 114 | 96 |
| 115 | 86 |
| 116 | 97 |
| 117 | 100 |
| 118 | 97 |
| 119 | 74 |
| 120 | 74 |
| 121 | 90 |
| 122 | 95 |
| 123 | 99 |
| 124 | 99 |
| 125 | 82 |
| 126 | 97 |
| 127 | 100 |
| 128 | 98 |
| 129 | 99 |
| 130 | 99 |
| 131 | 100 |
| 132 | 96 |
| 133 | 100 |
| 134 | 94 |
| 135 | 98 |
| 136 | 100 |
| 137 | 99 |
| 138 | 99 |
| 139 | 99 |
| 140 | 87 |
| 141 | 99 |
| 142 | 98 |
| 143 | 97 |
| 144 | 100 |
| 145 | 99 |
| 146 | 100 |
| 147 | 100 |
| 148 | 100 |
| 149 | 100 |
| 150 | 94 |
| 151 | 53 |
| 152 | 100 |
| 153 | 100 |
| 154 | 83 |
| 155 | 100 |
| 156 | 100 |
| 157 | 100 |
| 158 | 100 |
| 159 | 100 |
| 160 | 100 |
| 161 | 100 |
| 162 | 100 |
| 163 | 100 |
| 164 | 94 |
| 165 | 98 |
| 166 | 100 |
| 168 | 96 |
| 169 | 100 |
| 170 | 65 |
| 172 | 100 |
| 173 | 95 |
| 174 | 91 |
| 175 | 100 |
| 176 | 100 |
| 177 | 100 |
| 178 | 97 |
| 179 | 99 |
| 180 | 96 |
| 181 | 97 |
| 182 | 90 |
| 183 | 100 |
| 184 | 100 |
| 185 | 79 |
| 186 | 100 |
| 187 | 100 |
| 188 | 99 |
| 189 | 100 |

TABLE 2-continued

| Example | GCS enzyme inhibitory rate at 10 μM (%) |
|---|---|
| 190 | 100 |
| 191 | 100 |
| 192 | 100 |
| 193 | 99 |
| 194 | 97 |
| 195 | 100 |
| 196 | 100 |
| 197 | 99 |
| 198 | 98 |
| 199 | 100 |
| 200 | 99 |
| 201 | 100 |
| 202 | 99 |
| 203 | 99 |

As is clear from Table 2, it was confirmed that the compound of the present invention had a glucosylceramide synthase inhibitory action.

Experimental Example 2

The inhibitory effect of the compound of the present invention on glucosylceramide synthase in mice can be evaluated by glucosylceramide lowering effect after oral administration as follows.

For the experiment, using C57BL/6J mice, the test compound is prepared in a 0.5% methylcellulose suspension, and orally administered. After the administration, the blood and cerebral cortex are collected, the plasma is prepared from the blood, and methanol is added to the cerebral cortex to prepare a homogenate. A mixed solution of isopropanol and ethanol is added to the obtained plasma and the methanol homogenate of the cerebral cortex, and the lipids are extracted. The glucosylceramide concentrations of the extracted samples are measured by LC/MS/MS. The glucosylceramide lowering effect (% control) is calculated from the following formula: (glucosylceramide concentration in the test compound administration group)/(glucosylceramide concentration in the 0.5% methylcellulose suspension administration group)×100.

Experimental Example 3

The glucosylsphingosine lowering effect of the compound of the present invention due to the inhibitory effect on glucosylceramide synthase in mice can be evaluated by measuring glucosylceramide and glucosylsphingosine concentrations after oral administration as follows.

For the experiment, using Gba D409V KI mice, which are model mice for Gaucher's disease in which glucosylsphingosine is accumulated in tissues, the test compound is prepared in a 0.5% methylcellulose suspension, and orally administered. After the administration, the blood and cerebral cortex are collected, the plasma is prepared from the blood, and methanol is added to the cerebral cortex to prepare a homogenate. A mixed solution of isopropanol and ethanol is added to the obtained plasma and the methanol homogenate of the cerebral cortex, and the lipids are extracted. The glucosylceramide and glucosylsphingosine concentrations of the extracted samples are measured by LC/MS/MS. The glucosylceramide lowering effect (% control) is calculated from the following formula: (glucosylceramide concentration in the test compound administration group)/(glucosylceramide concentration in the 0.5% methylcellulose suspension administration group)×100. The glucosylsphingosine lowering effect (% control) is calculated from the following formula: (glucosylsphingosine concentration in the test compound administration group)/(glucosylsphingosine concentration in the 0.5% methylcellulose suspension administration group)×100.

Formulation Examples

Medicaments containing the compound of the present invention as an active ingredient can be produced, for example, by the following formulations.

1. Capsule

| | |
|---|---|
| (1) compound obtained in Example 1 | 10 mg |
| (2) lactose | 90 mg |
| (3) microcrystalline cellulose | 70 mg |
| (4) magnesium stearate | 10 mg |
| 1 capsule | 180 mg |

The total amount of the above-mentioned (1), (2) and (3) and 5 mg of (4) are blended and granulated, and 5 mg of the remaining (4) is added. The whole mixture is sealed in a gelatin capsule.

2. Tablet

| | |
|---|---|
| (1) compound obtained in Example 1 | 10 mg |
| (2) lactose | 35 mg |
| (3) cornstarch | 150 mg |
| (4) microcrystalline cellulose | 30 mg |
| (5) magnesium stearate | 5 mg |
| 1 tablet | 230 mg |

The total amount of the above-mentioned (1), (2) and (3), 20 mg of (4) and 2.5 mg of (5) are blended and granulated, and 10 mg of the remaining (4) and 2.5 mg of the remaining (5) are added, and the mixture is compression formed to give a tablet.

INDUSTRIAL APPLICABILITY

According to the present invention, a compound having an excellent glucosylceramide synthase inhibitory action, which is expected to be useful as an agent for the prophylaxis or treatment of lysosomal storage diseases (e.g., Gaucher's disease), neurodegenerative diseases (e.g., Parkinson's disease, Lowy body dementia, multiple-system atrophy) and the like, can be provided.

This application is based on patent application No. 2019-139174 filed on Jul. 29, 2019 in Japan, the contents of which are encompassed in full herein.

The invention claimed is:

1. A compound represented by the formula (I):

(I)

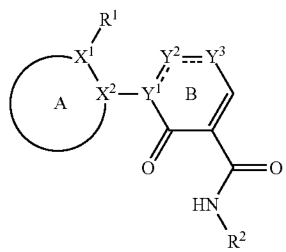

wherein $X^1$ is C or N, $X^2$ is C or N,

------ is a single bond or a double bond,

Ring A is an optionally further substituted 5- or 6-membered aromatic ring, $R^1$ is a cyano group, a $C_{1-6}$ alkyl group substituted by 1 to 5 fluorine atoms, an optionally substituted hydroxy group, an optionally substituted amino group, or an optionally substituted cyclic group, $Y^1$ is $CR^a$ wherein $R^a$ is absent, a hydrogen atom or a substituent, or N, $Y^2$ is $CR^bR^c$ wherein $R^b$ is a hydrogen atom or a substituent, and $R^c$ is absent, a hydrogen atom or a substituent, or $NR^d$ wherein $R^d$ is absent, a hydrogen atom or a substituent, $Y^3$ is $CR^eR^f$ wherein $R^e$ is a hydrogen atom or a substituent, and $R^f$ is absent, a hydrogen atom or a substituent, or $NR^g$ wherein $R^g$ is absent, a hydrogen atom or a substituent, Ring B is a 6-membered ring, and $R^2$ is

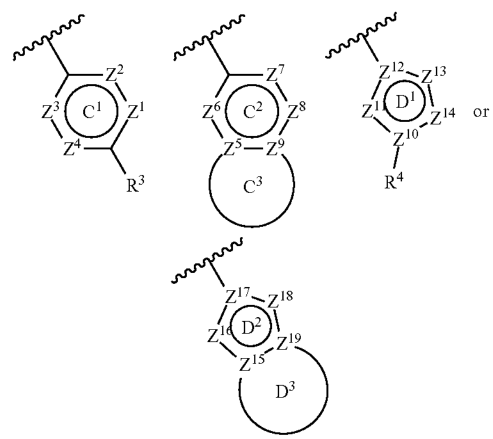

wherein $Z^1$ is $CR^h$ wherein $R^h$ is a hydrogen atom or a substituent, or N, $Z^2$ is $CR^i$ wherein $R^i$ is a hydrogen atom or a substituent, or N, $Z^3$ is $CR^j$ wherein $R^j$ is a hydrogen atom or a substituent, or N, $Z^4$ is $CR^k$ wherein $R^k$ is a hydrogen atom or a substituent, or N, $Z^5$ is C or N, $Z^6$ is $CR^l$ wherein $R^l$ is a hydrogen atom or a substituent, or N, $Z^7$ is $CR^m$ wherein $R^m$ is a hydrogen atom or a substituent, or N, $Z^8$ is $CR^n$ wherein $R^n$ is a hydrogen atom or a substituent, or N, $Z^9$ is C or N, $Z^{10}$ is C or N, $Z^{11}$ is $CR^o$ wherein $R^o$ is a hydrogen atom or a substituent, $NR^p$ wherein $R^p$ is absent, a hydrogen atom or a substituent, O or S, $Z^{12}$ is C or N, $Z^{13}$ is $CR^q$ wherein $R^q$ is a hydrogen atom or a substituent, $NR^r$ wherein $R^r$ is absent, a hydrogen atom or a substituent, O or S, $Z^{14}$ is $CR^s$ wherein $R^s$ is a hydrogen atom or a substituent, $NR^t$ wherein $R^t$ is absent, a hydrogen atom or a substituent, O or S, $Z^{15}$ is C or N, $Z^{16}$ is $CR^u$ wherein $R^u$ is a hydrogen atom or a substituent, $NR^v$ wherein $R^v$ is absent, a hydrogen atom or a substituent, O or S, $Z^{17}$ is C or N, $Z^{18}$ is $CR^w$ wherein $R^w$ is a hydrogen atom or a substituent, $NR^x$ wherein $R^x$ is absent, a hydrogen atom or a substituent, O or S, $Z^{19}$ is C or N, Ring $C^1$ and Ring $C^2$ are each independently a 6-membered aromatic ring, Ring $C^3$ is an optionally substituted ring, $R^3$ is a halogen atom, a cyano group, an optionally substituted $C_{1-6}$ alkyl group, an optionally substituted cyclic group, an optionally substituted amino group, $SO_2R^7$ or $OR^8$, $R^7$ is a substituent, $R^8$ is a hydrogen atom, an optionally substituted $C_{1-6}$ alkyl group, an optionally substituted saturated cyclic group, or an optionally substituted monocyclic unsaturated cyclic group, Ring $D^1$ and Ring $D^2$ are each independently a 5-membered aromatic ring, Ring $D^3$ is an optionally substituted ring, and $R^4$ is a substituent, or a salt thereof.

2. The compound or salt according to claim 1, wherein $X^1$ is C or N;

$X^2$ is C;

Ring A is a 5- or 6-membered aromatic ring optionally further substituted by 1 to 3 substituents selected from (1) a halogen atom, and (2) a $C_{1-6}$ alkyl group, in addition to $R^1$ and the group represented by the formula:

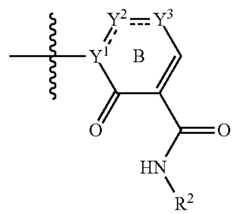

wherein each symbol is defined as in claim 1;

$R^1$ is (1) a cyano group, (2) a $C_{1-6}$ alkyl group substituted by 1 to 5 fluorine atoms, (3) a $C_{1-6}$ alkoxy group optionally substituted by 1 to 5 substituents selected from (i) a halogen atom, (ii) a hydroxy group, and (iii) a $C_{1-6}$ alkoxy group, or (4) a 3- to 8-membered monocyclic non-aromatic heterocyclic group;

$Y^1$ is C or N;

$Y^2$ is $CR^{b'}$ wherein $R^{b'}$ is (1) a hydrogen atom, or (2) a $C_{1-6}$ alkyl group, or N;

$Y^3$ is $CR^{e'}$ wherein $R^{e'}$ is (1) a hydrogen atom, (2) a $C_{1-6}$ alkyl group optionally substituted by 1 to 5 hydroxy groups, (3) a $C_{1-6}$ alkyl-carbonyl group, or (4) a $C_{1-6}$ alkoxy-carbonyl group, or $NR^{g'}$ wherein $R^{g'}$ is (1) absent, (2) a $C_{1-6}$ alkyl group optionally substituted by 1 to 5 substituents selected from (i) a halogen atom, (ii) a hydroxy group, and (iii) a 3- to 8-membered monocyclic non-aromatic heterocyclic group, (3) a $C_{3-6}$ cycloalkyl group, or (4) a 3- to 8-membered monocyclic non-aromatic heterocyclic group; and $R^2$ is a group represented by the formula:

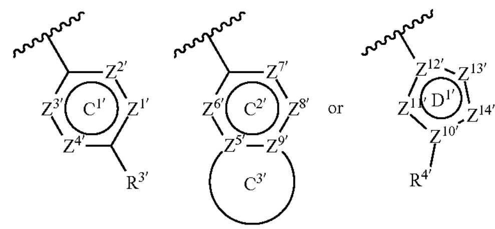

wherein $Z^{1'}$ is $CR^{h'}$ wherein $R^{h'}$ is a hydrogen atom, a halogen atom or a $C_{1-6}$ alkyl group, or N, $Z^{2'}$ is $CR^{i'}$ wherein $R^{i'}$ is a hydrogen atom, a halogen atom, a cyano group, a $C_{1-6}$ alkyl group or a $C_{1-6}$ alkoxy group, or N, $Z^{3'}$ is $CR^{j'}$ wherein $R^{j'}$ is a hydrogen atom or a halogen atom, or N, $Z^{4'}$ is CH or N, $Z^{5'}$ is N, $Z^{6'}$ is CH, $Z^{7'}$ is CH, $Z^{8'}$ is CH, $Z^{9'}$ is C, $Z^{10'}$ is C or N, $Z^{11'}$ is CH, N or S, $Z^{12'}$ is C, $Z^{13'}$ is CH or N, $Z^{14'}$ is $CR^{s'}$ wherein $R^{s'}$ is a hydrogen atom or an optionally halogenated $C_{1-6}$ alkyl group, N or O, Ring $C^{1'}$ is a 6-membered aromatic ring, Ring $C^{2'}$ is a 6-membered aromatic ring, Ring $C^{3'}$ is a 5-membered ring, $R^{3'}$ is (1) a halogen atom, (2) a cyano group, (3) a $C^{1-6}$ alkyl group optionally substituted by 1 to 8 substituents selected from (i) a halogen atom, (ii) a cyano group, (iii) a hydroxy group, (iv) a $C_{3-6}$ cycloalkyl group, (v) an optionally halogenated $C_{1-6}$ alkoxy group, (vi) a 3- to 8-membered monocyclic non-aromatic heterocyclic group, and (vii) an oxo group, (4) a $C_{2-6}$ alkenyl group, (5) a cyclic group optionally substituted by 1 to 3 hydroxy groups, or (6) $OR^{g'}$ wherein $R^{g'}$ is (a) a $C_{1-6}$ alkyl group optionally substituted by 1 to 3 substituents selected from (i) a halogen atom, (ii) a hydroxy group, and (iii) a $C_{3-6}$ cycloalkyl group, or (b) a $C_{6-10}$ aryl group, Ring $D^{1'}$ is a 5-membered aromatic ring, and $R^{4'}$ is (1) a $C_{1-6}$ alkyl group optionally substituted by 1 to 5 substituents selected from (i) a halogen atom, (ii) a $C_{3-6}$ cycloalkyl group optionally substituted by 1 to 3 halogen atoms, and (iii) a 3- to 8-membered monocyclic non-aromatic heterocyclic group optionally substituted by 1 to 3 halogen atoms, (2) a $C_{3-6}$ cycloalkyl group, (3) a $C_{6-10}$ aryl group optionally substituted by 1 to 3 halogen atoms, (4) a $C_{1-6}$ alkoxy-carbonyl group, or (5) a 3- to 8-membered monocyclic non-aromatic heterocyclic group.

3. The compound or salt according to claim 1, wherein $X^1$ is C;

$X^2$ is C;

Ring A is a benzene ring optionally further substituted by 1 to 3 halogen atoms, in addition to $R^1$ and the group represented by the formula:

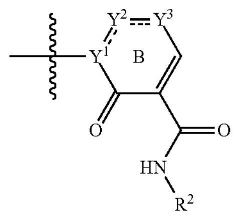

wherein each symbol is defined as in claim 1;

$R^1$ is a $C_{1-6}$ alkoxy group substituted by 1 to 5 halogen atoms;

$Y^1$ is C or N;

$Y^2$ is N;

$Y^3$ is $CR^{e'}$ wherein $R^{e'}$ is (1) a hydrogen atom, or (2) a $C_{1-6}$ alkyl group, or $NR^{g''}$ wherein $R^{g''}$ is (1) a $C_{1-6}$ alkyl group optionally substituted by 1 to 5 substituents selected from (i) a halogen atom, and (ii) a hydroxy group, or (2) a $C_{3-6}$ cycloalkyl group; and $R^2$ is a group represented by the formula

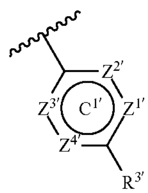

wherein $Z^{1'}$ is CH or N, $Z^{2'}$ is CH or CF, $Z^{3'}$ is CH, $Z^{4'}$ is CH, and $R^{3'}$ is a $C_{1-6}$ alkyl group optionally substituted by 1 to 5 substituents selected from a halogen atom and a hydroxy group.

4. N-[4-(2-Hydroxypropan-2-yl)phenyl]-3-oxo-2-[2-(2,2,2-trifluoroethoxy)phenyl]-2,3-dihydropyridazine-4-carboxamide or a salt thereof.

5. 2-[2-(2,2-Difluoroethoxy)phenyl]-N-[4-(2-hydroxypropan-2-yl)phenyl]-3-oxo-2,3-dihydropyridazine-4-carboxamide or a salt thereof.

6. 2-[2-(2,2-Difluoroethoxy)phenyl]-N-[4-(2-hydroxypropan-2-yl)phenyl]-6-methyl-3-oxo-2,3-dihydropyridazine-4-carboxamide or a salt thereof.

7. A medicament comprising the compound or salt according to claim 1.

8. A method for inhibiting glucosylceramide synthase in a mammal, which comprises administering an effective amount of the compound or salt according to claim 1 to the mammal.

9. A method for preventing or treating a lysosomal storage disease or a neurodegenerative disease in a mammal, which comprises administering an effective amount of the compound or salt according to claim 1 to the mammal, wherein the lysosomal storage disease is Gaucher's disease, Fabry's disease, GMI-gangliosidosis, GM2 activator deficiency, Tay-Sachs disease or Sandhoffs disease, and wherein the neurodegenerative disease is Parkinson's disease, Lewy body dementia or multiple-system atrophy.

10. The method according to claim 9 for treating a lysosomal storage disease, wherein the lysosomal storage disease is Gaucher's disease, Fabry's disease, GMI-gangliosidosis, GM2 activator deficiency, Tay-Sachs disease or Sandhoffs disease.

11. The method according to claim 9 for treating a neurodegenerative disease, wherein the neurodegenerative disease is Parkinson's disease, Lewy body dementia or multiple-system atrophy.

12. A compound or a salt thereof, wherein the compound is selected from the group consisting of:

1-(2-methoxyphenyl)-6-methyl-2-oxo-N-(4-phenoxyphenyl)-1,2-dihydropyridine-3-carboxamide, 1-(2-methoxyphenyl)-2-oxo-N-(4-phenoxyphenyl)-1,2-dihydropyridine-3-carboxamide, 1-(4-fluoro-2-methoxyphenyl)-2-oxo-N-(4-phenoxyphenyl)-1,2-dihydropyridine-3-carboxamide, 1-[2-(morpholin-4-yl)phenyl]-2-oxo-N-(4-phenoxyphenyl)-1,2-dihydropyridine-3-carboxamide, 1-(4-fluoro-2-methoxyphenyl)-2-oxo-N-[6-(2,2,2-trifluoroethoxy)pyridin-3-yl]-1,2-dihydropyridine-3-carboxamide, 1-(4-fluoro-2-methoxyphenyl)-2-oxo-N-[4-(trifluoromethoxy)phenyl]-1,2-dihydropyridine-3-carboxamide, N-(6-cyclopropylpyridin-3-yl)-1-(4-fluoro-2-methoxyphenyl)-2-oxo-1,2-dihydropyridine-3-carboxamide, 1-(4-fluoro-2-methoxyphenyl)-N-[1-(4-fluorophenyl)-1H-pyrazol-3-yl]-2-oxo-1,2-dihydropyridine-3-carboxamide, 1-(4-fluoro-2-methoxyphenyl)-N-(6-methoxypyridin-3-yl)-2-oxo-1,2-dihydropyridine-3-carboxamide, N-[4-(difluoromethoxy)phenyl]-1-(4-fluoro-2-methoxyphenyl)-2-oxo-1,2-dihydropyridine-3-carboxamide, 1-(4-fluoro-2-methoxyphenyl)-2-oxo-N-[4-(trifluoromethyl)phenyl]-1,2-dihydropyridine-3-carboxamide, N-[1-(4-fluorophenyl)-1H-pyrazol-3-yl]-2-oxo-1-[2-(2,2,2-trifluoroethoxy)phenyl]-1,2-dihydropyridine-3-carboxamide, N-(6-methoxypyridin-3-yl)-2-oxo-1-[2-(2,2,2-trifluoroethoxy)phenyl]-1,2-dihydropyridine-3-carboxamide, N-(4-chlorophenyl)-2-oxo-1-[2-(2,2,2-trifluoroethoxy)phenyl]-1,2-dihydropyridine-3-carboxamide, 2-oxo-1-[2-(2,2,2-trifluoroethoxy)phenyl]-N-[6-(2,2,2-trifluoroethoxy)pyridin-3-yl]-1,2-dihydropyridine-3-carboxamide, N-[6-(difluoromethoxy)pyridin-3-yl]-1-(4-fluoro-2-methoxyphenyl)-2-oxo-1,2-dihydropyridine-3-carboxamide, 1-[4-fluoro-2-(morpholin-4-yl)phenyl]-2-oxo-N-(4-phenoxyphenyl)-1,2-dihydropyridine-3-carboxamide, 2-(4-fluoro-2-methoxyphenyl)-3-oxo-N-(4-phenoxyphenyl)-2,3-dihydropyridazine-4-carboxamide, 1-(4-fluoro-2-methoxyphenyl)-N-[4-(morpholin-4-yl)phenyl]-2-oxo-1,2-dihydropyridine-3-carboxamide, 2-oxo-1-[2-(2,2,2-trifluoroethoxy)phenyl]-N-[6-(trifluoromethyl)pyridin-3-yl]-1,2-dihydropyridine-3-carboxamide, N-(5-cyclopropylpyridin-2-yl)-2-oxo-1-[2-(2,2,2-trifluoroethoxy)phenyl]-1,2-dihydropyridine-3-carboxamide, 2-oxo-1-[2-(2,2,2-trifluoroethoxy)phenyl]-N-[1-(2,2,2-trifluoroethyl)-1H-pyrazol-3-yl]-1,2-dihydropyridine-3-carboxamide, 2-(4-fluoro-2-methoxyphenyl)-3-oxo-N-[6-(2,2,2-trifluoroethoxy)pyridin-3-yl]-2,3-dihydropyridazine-4-carboxamide, N-(6-cyanopyridin-3-yl)-2-oxo-1-[2-(2,2,2-trifluoroethoxy)phenyl]-1,2-dihydropyridine-3-carboxamide, 1-[4-fluoro-2-(morpholin-4-yl)phenyl]-2-oxo-N-[6-(2,2,2-trifluoroethoxy)pyridin-3-yl]-1,2-dihydropyridine-3-carboxamide, 1-[4-fluoro-2-(2,2,2-trifluoroethoxy)phenyl]-2-oxo-N-[6-(2,2,2-trifluoroethoxy)pyridin-3-yl]-1,2-dihydropyridine-3-carboxamide, 1-[4-fluoro-2-(2-methoxyethoxy)phenyl]-2-oxo-N-[6-(2,2,2-trifluoroethoxy)pyridin-3-yl]-1,2-dihydropyridine-3-carboxamide, 1-[4-fluoro-2-(2-methoxyethoxy)phenyl]-N-[1-(4-fluorophenyl)-1H-pyrazol-3-yl]-2-oxo-1,2-dihydropyridine-3-carboxamide, 2-[4-fluoro-2-(2,2,2-trifluoroethoxy)phenyl]-3-oxo-N-[6-(2,2,2-trifluoroethoxy)pyridin-3-yl]-2,3-dihydropyridazine-4-carboxamide, 1-(2-cyano-4-fluorophenyl)-2-oxo-N-(4-phenoxyphenyl)-1,2-dihydropyridine-3-carboxamide, N-(5-cyanopyridin-2-yl)-2-oxo-1-[2-(2,2,2-trifluoroethoxy)phenyl]-1,2-dihydropyridine-3-carboxamide, 1-[4-fluoro-2-(2,2,2-trifluoroethoxy)phenyl]-N-[1-methyl-5-(trifluoromethyl)-1H-pyrazol-3-yl]-2-oxo-1,2-dihydropyridine-3-carboxamide, 1-[4-fluoro-2-(2,2,2-trifluoroethoxy)phenyl]-N-[1-(2-methylpropyl)-1H-pyrazol-4-yl]-2-oxo-1,2-dihydropyridine-3-carboxamide, N-(1-cyclopropyl-1H-pyrazol-4-yl)-1-[4-fluoro-2-(2,2,2-trifluoroethoxy)phenyl]-2-oxo-1,2-dihydropyridine-3-carboxamide, 1-[4-fluoro-2-(2,2,2-trifluoroethoxy)phenyl]-N-{4-[(morpholin-4-yl)methyl]phenyl}-2-oxo-1,2-dihydropyridine-3-carboxamide, 1-[4-fluoro-2-(2,2,2-trifluoroethoxy)phenyl]-2-oxo-N-[2-(trifluoromethyl)pyrimidin-5-yl]-1,2-dihydropyridine-3-carboxamide, 1-[4-fluoro-2-(2,2,2-trifluoroethoxy)phenyl]-2-oxo-N-[5-(trifluoromethyl) pyrazin-2-yl]-1,2-dihydropyridine-3-carboxamide, 1-[4-fluoro-2-(2,2,2-trifluoroethoxy)phenyl]-2-oxo-N-[6-(trifluoromethyl)pyridazin-3-yl]-1,2-dihydropyridine-3-carboxamide, N-(1-tert-butyl-1H-pyrazol-3-yl)-1-[4-fluoro-2-(2,2,2-trifluoroethoxy)phenyl]-2-oxo-1,2-dihydropyridine-3-carboxamide, N-[1-(cyclopropylmethyl)-1H-pyrazol-4-yl]-1-[4-fluoro-2-(2,2,2-trifluoroethoxy)phenyl]-2-oxo-1,2-dihydropyridine-3-carboxamide, N-(4-cyanophenyl)-1-[4-fluoro-2-(2,2,2-trifluoroethoxy)phenyl]-2-oxo-1,2-dihydropyridine-3-carboxamide, 1-[4-fluoro-2-(2,2,2-trifluoroethoxy)phenyl]-N-[4-(2-hydroxypropan-2-yl)phenyl]-2-oxo-1,2-dihydropyridine-3-carboxamide, 1-[4-fluoro-2-(2,2,2-trifluoroethoxy)phenyl]-2-oxo-N-[4-(piperidine-1-carbonyl)phenyl]-1,2-dihydropyridine-3-carboxamide, 1-[4-fluoro-2-(2,2,2-trifluoroethoxy)phenyl]-N-(imidazo[1,2-a]pyridin-6-yl)-2-oxo-1,2-dihydropyridine-3-carboxamide, N-[1-(2,2-difluoroethyl)-1H-pyrazol-4-yl]-1-[4-fluoro-2-(2,2,2-trifluoroethoxy)phenyl]-2-oxo-1,2-dihydropyridine-3-carboxamide, N-[1-(difluoromethyl)-1H-pyrazol-4-yl]-1-[4-fluoro-2-(2,2,2-trifluoroethoxy)phenyl]-2-oxo-1,2-dihydropyridine-3-carboxamide, 1-[4-fluoro-2-(2,2,2-trifluoroethoxy)phenyl]-2-oxo-N-[5-(trifluoromethyl)-1,2-oxazol-3-yl]-1,2-dihydropyridine-3-carboxamide, 1-[4-fluoro-2-(2,2,2-trifluoroethoxy)phenyl]-2-oxo-N-[1-(2,2,2-trifluoroethyl)-1H-pyrazol-4-yl]-1,2-dihydropyridine-3-carboxamide, N-[6-(difluoromethyl)pyridin-3-yl]-1-[4-fluoro-2-(2,2,2-trifluoroethoxy)phenyl]-2-oxo-1,2-dihydropyridine-3-carboxamide, N-[4-(cyclopropylmethoxy)phenyl]-1-[4-fluoro-2-(2,2,2-trifluoroethoxy)phenyl]-2-oxo-1,2-dihydropyridine-3-carboxamide, N-[2-(difluoromethoxy)pyrimidin-5-yl]-1-[4-fluoro-2-(2,2,2-trifluoroethoxy)phenyl]-2-oxo-1,2-dihydropyridine-3-carboxamide, 1-(2-cyano-4-fluorophenyl)-2-oxo-N-[6-(2,2,2-trifluoroethoxy)pyridin-3-yl]-1,2-dihydropyridine-3-carboxamide, 1-[1-(oxan-4-yl)-1H-pyrazol-5-yl]-2-oxo-N-(4-phenoxyphenyl)-1,2-dihydropyridine-3-carboxamide, 1-[4-fluoro-2-(2,2,2-trifluoroethoxy)phenyl]-N-[1-(oxan-4-yl)-1H-pyrazol-3-yl]-2-oxo-1,2-dihydropyridine-3-carboxamide, rac-N-{1-[(2,2-difluorocyclopropyl)methyl]-1H-pyrazol-3-yl}-1-[4-fluoro-2-(2,2,2-trifluoroethoxy)phenyl]-2-oxo-1,2-dihydropyridine-3-carboxamide, 1-[4-fluoro-2-(2,2,3,3,3-pentafluoropropoxy)phenyl]-2-oxo-N-[6-(2,2,2-trifluoroethoxy)pyridin-3-yl]-1,2-dihydropyridine-3-carboxamide, N-[4-(cyanomethyl)phenyl]-1-[4-fluoro-2-(2,2,2-trifluoroethoxy)phenyl]-2-oxo-1,2-dihydropyridine-3-carboxamide, 1-[4-fluoro-2-(2,2,3,3,3-pentafluoropropoxy)phenyl]-N-[4-(2-hydroxypropan-2-yl)phenyl]-2-oxo-1,2-dihydropyridine-3-carboxamide, 1-[1-(oxan-4-yl)-1H-pyrazol-5-yl]-2-oxo-N-[6-(2,2,2-trifluoroethoxy)pyridin-3-yl]-1,2-dihydropyridine-3-carboxamide, 1-[4-fluoro-2-(2,2,2-trifluoroethoxy)phenyl]-N-[4-(2-hydroxy-2-methylpropoxy)phenyl]-2-oxo-1,2-dihydropyridine-3-carboxamide, 1-[4-fluoro-2-(2,2,2-trifluoroethoxy)phenyl]-N-[4-(2-hydroxy-2-methylpropyl)phenyl]-2-oxo-1,2-dihydropyridine-3-carboxamide, 1-[4-fluoro-2-(2,2,2-trifluoroethoxy)phenyl]-2-oxo-N-[1-(2,2,3,3,3-pentafluoropropyl)-1H-pyrazol-4-yl]-1,2-dihydropyridine-3-carboxamide, N-[4-(2-hydroxypropan-2-yl)phenyl]-2-oxo-1-[2-(2,2,2-trifluoroethoxy)phenyl]-1,2-dihydropyridine-3-carboxamide, 1-[4-fluoro-2-(2,2,2-trifluoroethoxy)phenyl]-2-oxo-N-[6-(3,3,3-trifluoropropoxy)pyridin-3-yl]-1,2-dihydropyridine-3-carboxamide, N-{1-[(3-fluorooxetan-3-yl)methyl]-1H-pyrazol-4-yl}-1-[4-fluoro-2-(2,2,2-trifluoroethoxy)phenyl]-2-oxo-1,2-dihydropyridine-3-carboxamide, N-{1-[(1-fluorocyclopropyl)methyl]-1H-pyrazol-4-yl}-1-[4-fluoro-2-(2,2,2-trifluoroethoxy)phenyl]-2-oxo-1,2-dihydropyridine-3-carboxamide, 1-[4-fluoro-2-(2-hydroxy-2-methylpropoxy)phenyl]-2-oxo-N-[6-(2,2,2-trifluoroethoxy)pyridin-3-yl]-1,2-dihydropyridine-3-carboxamide, N-[4-(2-hydroxypropan-2-yl)phenyl]-1-[2-methyl-6-(2,2,2-trifluoroethoxy)phenyl]-2-oxo-1,2-dihydropyridine-3-carboxamide, 1-[4-fluoro-2-(2,2,2-trifluoroethoxy)phenyl]-N-[4-(1-hydroxycyclopropyl)phenyl]-2-oxo-1,2-dihydropyridine-3-carboxamide, N-[4-(2-hydroxy-2-methylpropoxy)phenyl]-2-oxo-1-[2-(2,2,2-trifluoroethoxy)phenyl]-1,2-dihydropyridine-3-carboxamide, 1-(2-cyano-4-fluorophenyl)-N-[4-(2-hydroxypropan-2-yl)phenyl]-2-oxo-1,2-dihydropyridine-3-carboxamide, 2-oxo-N-[6-(2,2,2-trifluoroethoxy)pyridin-3-yl]-1-[1-(3,3,3-trifluoropropyl)-1H-pyrazol-5-yl]-1,2-dihydropyridine-3-carboxamide, 1-[4-fluoro-2-(2,2,2-trifluoroethoxy)phenyl]-2-oxo-N-{6-[(2,2,2-trifluoroethoxy)methyl]pyridin-3-yl}-1,2-dihydropyridine-3-carboxamide, 2-oxo-N-{6-[(2,2,2-trifluoroethoxy)methyl]pyridin-3-yl}-1-[2-(2,2,2-trifluoroethoxy)phenyl]-1,2-dihydropyridine-3-carboxamide, rac-N-{6-[cyclopropyl(hydroxy)methyl]pyridin-3-yl}-1-[4-fluoro-2-(2,2,2-trifluoroethoxy)phenyl]-2-oxo-1,2-dihydropyridine-3-carboxamide, rac-N-{6-[cyclopropyl(hydroxy)methyl]pyridin-3-yl}-2-oxo-1-[2-(2,2,2-trifluoroethoxy)phenyl]-1,2-dihydropyridine-3-carboxamide, 2-oxo-N-[4-(1,1,3,3-tetrafluoro-2-hydroxypropan-2-yl)phenyl]-1-[2-(2,2,2-trifluoroethoxy)phenyl]-1,2-dihydropyridine-3-carboxamide, 1-[4-fluoro-2-(2,2,2-trifluoroethoxy)phenyl]-2-oxo-N-[4-(1,1,3,3-tetrafluoro-2-hydroxypropan-2-yl)phenyl]-1,2-dihydropyridine-3-carboxamide, 2-oxo-1-[3-(2,2,2-trifluoroethoxy)pyridazin-4-yl]-N-[6-(2,2,2-trifluoroethoxy)pyridin-3-yl]-1,2-dihydropyridine-3-carboxamide, N-[6-(cyanomethyl)pyridin-3-yl]-1-[4-fluoro-2-(2,2,2-trifluoroethoxy)phenyl]-2-oxo-1,2-dihydropyridine-3-carboxamide, N-[1-(4-fluorophenyl)-1H-pyrazol-3-yl]-2-oxo-1-[1-(3,3,3-trifluoropropyl)-1H-pyrazol-5-yl]-1,2-dihydropyridine-3-carboxamide, N-[3-fluoro-4-(2-hydroxypropan-2-yl)phenyl]-2-oxo-1-[2-(2,2,2-trifluoroethoxy)phenyl]-1,2-dihydropyridine-3-carboxamide, N-[3-fluoro-4-(2-hydroxypropan-2-yl)phenyl]-1-[4-fluoro-2-(2,2,2-trifluoroethoxy)phenyl]-2-oxo-1,2-dihydropyridine-3-carboxamide, N-[6-(2-hydroxypropan-2-yl)pyridin-3-yl]-2-oxo-1-[2-(2,2,2-trifluoroethoxy)phenyl]-1,2-dihydropyridine-3-carboxamide, 1-[4-fluoro-2-(2,2,2-trifluoroethoxy)phenyl]-N-[6-(2-hydroxypropan-2-yl)pyridin-3-yl]-2-oxo-1,2-dihydropyridine-3-carboxamide, N-[6-(cyanomethyl)pyridin-3-yl]-2-oxo-1-[2-(2,2,2-trifluoroethoxy)phenyl]-1,2-dihydropyridine-3-carboxamide, N-[6-(2-cyanopropan-2-yl)pyridin-3-yl]-1-[4-fluoro-2-(2,2,2-trifluoroethoxy)phenyl]-2-oxo-1,2-dihydropyridine-3-carboxamide, N-[6-(2-cyanopropan-2-yl)pyridin-3-yl]-2-oxo-1-[2-(2,2,2-trifluoroethoxy)phenyl]-1,2-dihydropyridine-3-carboxamide, N-[4-(1,1,1,3,3,3-hexafluoro-2-hydroxypropan-2-yl)phenyl]-2-oxo-1-[2-(2,2,2-trifluoroethoxy)phenyl]-1,2-dihydropyridine-3-carboxamide, N-[4-(2-hydroxypropan-2-yl)phenyl]-2-oxo-1-[3-(2,2,2-trifluoroethoxy)pyridazin-4-yl]-1,2-dihydropyridine-3-carboxamide, 1-[4-fluoro-2-(2,2,2-trifluoroethoxy)phenyl]-N-[6-(2-methoxypropan-2-yl)pyridin-3-yl]-2-oxo-1,2-dihydropyridine-3-carboxamide, N-[6-(2-methoxypropan-2-yl)pyridin-3-yl]-2-oxo-1-[2-(2,2,2-trifluoroethoxy)phenyl]-1,2-dihydropyridine-3-carboxamide, 1-[4-fluoro-2-(2,2,2-trifluoroethoxy)phenyl]-6-oxo-N-[6-(2,2,2-trifluoroethoxy)pyridin-3-yl]-1,6-dihydropyrimidine-5-carboxamide, 1-(4-methoxy-1-methyl-1H-pyrazol-5-yl)-2-oxo-N-[6-(2,2,2-trifluoroethoxy)pyridin-3-yl]-1,2-dihydropyridine-3-carboxamide, 2-[4-fluoro-2-(2,2,2-trifluoroethoxy)phenyl]-N-[4-(2-hydroxypropan-2-yl)phenyl]-3-oxo-2,3-dihydropyridazine-4-carboxamide, N-[4-(1-hydroxycyclobutyl)phenyl]-2-oxo-1-[2-(2,2,2-trifluoroethoxy)phenyl]-1,2-dihydropyridine-3-carboxamide, 1-[4-fluoro-2-(2,2,2-trifluoroethoxy)phenyl]-N-[4-(1-hydroxycyclobutyl)phenyl]-2-oxo-1,2-dihydropyridine-3-carboxamide, 1-[4-fluoro-2-(2,2,2-trifluoroethoxy)phenyl]-N-[4-(2-hydroxypropan-2-yl)phenyl]-6-oxo-1,6-dihydropyrimidine-5-carboxamide, 1-[2-(2,2-difluoropropoxy)phenyl]-N-[4-(2-hydroxypropan-2-yl)phenyl]-2-oxo-1,2-dihydropyridine-3-carboxamide, 1-[4-fluoro-2-(2,2,2-trifluoroethoxy)phenyl]-N-[4-(2-hydroxypropan-2-yl)phenyl]-6-methyl-2-oxo-1,2-dihydropyridine-3-carboxamide, 1-[2-(2,2-difluoroethoxy)-4-fluorophenyl]-2-oxo-N-[6-(2,2,2-trifluoroethoxy)pyridin-3-yl]-1,2-dihydropyridine-3-carboxamide, 1-[2-(2,2-difluoroethoxy)-4-fluorophenyl]-N-[4-(2-hydroxypropan-2-yl)phenyl]-2-oxo-1,2-dihydropyridine-3-carboxamide, 1-[4-fluoro-2-(2,2,2-trifluoroethoxy)phenyl]-N-[4-(1,1,1,3,3,3-hexafluoro-2-hydroxypropan-2-yl)phenyl]-2-oxo-1,2-dihydropyridine-3-carboxamide, 1-(2-cyano-4-fluorophenyl)-N-[4-(1,1,1,3,3,3-hexafluoro-2-hydroxypropan-2-yl)phenyl]-2-oxo-1,2-dihydropyridine-3-carboxamide, 1-[4-fluoro-2-(2-hydroxy-2-methylpropoxy)phenyl]-N-[4-(1,1,1,3,3,3-hexafluoro-2-hydroxypropan-2-yl)phenyl]-2-oxo-1,2-dihydropyridine-3-carboxamide, 2-[4-fluoro-2-(2,2,3,3,3-pentafluoropropoxy)phenyl]-N-[4-(2-hydroxypropan-2-yl)phenyl]-3-oxo-2,3-dihydropyridazine-4-carboxamide, 1-[4-fluoro-2-(2,2,2-trifluoroethoxy)phenyl]-N-[4-(2-hydroxypropan-2-yl)phenyl]-5-methyl-2-oxo-1,2-dihydropyridine-3-carboxamide, 1-[4,5-difluoro-2-(2,2,2-trifluoroethoxy)phenyl]-N-[4-(2-hydroxypropan-2-yl)phenyl]-2-oxo-1,2-dihydropyridine-3-carboxamide, 2-[2-(2,2-difluoroethoxy)phenyl]-6-methyl-3-oxo-N-[6-(1,1,3,3-tetrafluoro-2-hydroxypropan-2-yl)pyridin-3-yl]-2,3-dihydropyridazine-4-carboxamide, 2-oxo-N-[6-(2,2,2-trifluoroethoxy)pyridin-3-yl]-1-[5-(2,2,2-trifluoroethoxy)pyrimidin-4-yl]-1,2-dihydropyridine-3-carboxamide, 1-[3,4-difluoro-2-(2,2,2-trifluoroethoxy)phenyl]-N-[4-(2-hydroxypropan-2-yl)phenyl]-2-oxo-1,2-dihydropyridine-3-carboxamide, 2-[4-fluoro-2-(2,2,2-trifluoroethoxy)phenyl]-N-[6-(2-hydroxypropan-2-yl)pyridin-3-yl]-3-oxo-2,3-dihydropyridazine-4-carboxamide, 1-[5-fluoro-2-(2,2,2-trifluoroethoxy)phenyl]-N-[4-(2-hydroxypropan-2-yl)phenyl]-2-oxo-1,2-dihydropyridine-3-carboxamide, N-[4-(2-hydroxypropan-2-yl)phenyl]-2-oxo-2'-(2,2,2-trifluoroethoxy)-2H-[1,3'-bipyridine]-3-carboxamide, (R or S)—N-{6-[cyclopropyl(hydroxy)methyl]pyridin-3-yl}-1-[4-fluoro-2-(2,2,2-trifluoroethoxy)phenyl]-2-oxo-1,2-dihydropyridine-3-carboxamide, (R or S)—N-{6-[cyclopropyl(hydroxy)methyl]pyridin-3-yl}-1-[4-fluoro-2-(2,2,2-trifluoroethoxy)phenyl]-2-oxo-1,2-dihydropyridine-3-carboxamide, 2-[4-fluoro-2-(2,2,2-trifluoroethoxy)phenyl]-3-oxo-N-[6-(1,1,3,3-tetrafluoro-2-hydroxypropan-2-yl)pyridin-3-yl]-2,3-dihydropyridazine-4-carboxamide, 1-[4,5-difluoro-2-(2,2,2-trifluoroethoxy)phenyl]-2-oxo-N-[6-(1,1,3,3-tetrafluoro-2-hydroxypropan-2-yl)pyridin-3-yl]-1,2-dihydropyridine-3-carboxamide, N-[6-(2-hydroxypropan-2-yl)pyridin-3-yl]-2-oxo-1-[5-(2,2,2-trifluoroethoxy)pyrimidin-4-yl]-1,2-dihydropyridine-3-carboxamide, N-[6-(2-hydroxypropan-2-yl)pyridin-3-yl]-2-oxo-2'-(2,2,2-trifluoroethoxy)-2H-[1,3'-bipyridine]-3-carboxamide, rac-2-oxo-1-[3-(2,2,2-trifluoroethoxy)pyridazin-4-yl]-N-[6-(1,1,1-trifluoro-2-hydroxypropan-2-yl)pyridin-3-yl]-1,2-dihydropyridine-3-carboxamide, 2-oxo-N-[6-(1,1,3,3-tetrafluoro-2-hydroxypropan-2-yl)pyridin-3-yl]-1-[3-(2,2,2-trifluoroethoxy)pyridazin-4-yl]-1,2-dihydropyridine-3-carboxamide, 2-oxo-N-[6-(1,1,3,3-tetrafluoro-2-hydroxypropan-2-yl)pyridin-3-yl]-2'-(2,2,2-trifluoroethoxy)-2H-[1,3'-bipyridine]-3-carboxamide, 1-[5-fluoro-2-(2,2,2-trifluoroethoxy)phenyl]-2-oxo-N-[6-(1,1,3,3-tetrafluoro-2-hydroxypropan-2-yl)pyridin-3-yl]-1,2-dihydropyridine-3-carboxamide, 1-[5-fluoro-2-(2,2,2-trifluoroethoxy)phenyl]-N-[6-(2-hydroxypropan-2-yl)pyridin-3-yl]-2-oxo-1,2-dihydropyridine-3-carboxamide, N-[6-(2-hydroxypropan-2-yl)pyridin-3-yl]-3-oxo-2-[2-(2,2,2-trifluoroethoxy)phenyl]-2,3-dihydropyridazine-4-carboxamide, N-[4-(2-hydroxypropan-2-yl)phenyl]-3-oxo-2-[2-(2,2,2-trifluoroethoxy)phenyl]-2,3-dihydropyridazine-4-carboxamide, N-[5-(2-hydroxypropan-2-yl)pyridin-2-yl]-3-oxo-2-[2-(2,2,2-trifluoroethoxy)phenyl]-2,3-dihydropyridazine-4-carboxamide, N-[6-(2-hydroxypropan-2-yl)pyridin-3-yl]-6-methyl-3-oxo-2-[2-(2,2,2-trifluoroethoxy)phenyl]-2,3-dihydropyridazine-4-carboxamide, N-[5-(2-hydroxypropan-2-yl)pyridin-2-yl]-6-methyl-3-oxo-2-[2-(2,2,2-trifluoroethoxy)phenyl]-2,3-dihydropyridazine-4-carboxamide, N-[4-(2-hydroxypropan-2-yl)phenyl]-6-methyl-3-oxo-2-[2-(2,2,2-trifluoroethoxy)phenyl]-2,3-dihydropyridazine-4-carboxamide, 2-[2-(2,2-difluoroethoxy)phenyl]-N-[5-(2-hydroxypropan-2-yl)pyridin-2-yl]-3-oxo-2,3-dihydropyridazine-4-carboxamide, 2-[2-(2,2-difluoroethoxy)phenyl]-N-[4-(2-hydroxypropan-2-yl)phenyl]-3-oxo-2,3-dihydropyridazine-4-carboxamide, 2-[2-(2,2-difluoroethoxy)phenyl]-N-[6-(2-hydroxypropan-2-yl)pyridin-3-yl]-3-oxo-2,3-dihydropyridazine-4-carboxamide, 2-[2-(2,2-difluoroethoxy)phenyl]-N-[6-(2-hydroxypropan-2-yl)pyridin-3-yl]-6-methyl-3-oxo-2,3-dihydropyridazine-4-carboxamide, 2-[2-(2,2-difluoroethoxy)phenyl]-N-[4-(2-hydroxypropan-2-yl)phenyl]-6-methyl-3-oxo-2,3-dihydropyridazine-4-carboxamide, 2-[2-(2,2-difluoroethoxy)phenyl]-N-[5-(2-hydroxypropan-2-yl)pyridin-2-yl]-6-methyl-3-oxo-2,3-dihydropyridazine-4-carboxamide, rac-N-[4-(1-hydroxyethyl)phenyl]-3-oxo-2-[2-(2,2,2-trifluoroethoxy)phenyl]-2,3-dihydropyridazine-4-carboxamide, rac-2-[2-(2,2-difluoroethoxy)phenyl]-N-[4-(1-hydroxyethyl)phenyl]-6-methyl-3-oxo-2,3-dihydropyridazine-4-carboxamide, rac-N-[5-(1-hydroxyethyl)pyridin-2-yl]-3-oxo-2-[2-(2,2,2-trifluoroethoxy)phenyl]-2,3-dihydropyridazine-4-carboxamide, 2-[2-(2,2-difluoroethoxy)phenyl]-6-methyl-N-[4-(oxetan-3-yl)phenyl]-3-oxo-2,3-dihydropyridazine-4-carboxamide, 2-[2-(2,2-difluoroethoxy)phenyl]-N-[4-(2-hydroxypropan-2-yl)-3-methylphenyl]-3-oxo-2,3-dihydropyridazine-4-carboxamide, 2-[2-(2,2-difluoroethoxy)phenyl]-N-[4-(2-hydroxypropan-2-yl)-2-methylphenyl]-3-oxo-2,3-dihydropyridazine-4-carboxamide, rac-2-[2-(2,2-difluoroethoxy)phenyl]-3-oxo-N-[4-(oxolan-2-yl)phenyl]-2,3-dihydropyridazine-4-carboxamide, rac-2-[2-(2,2-difluoroethoxy)phenyl]-3-oxo-N-[4-(oxolan-3-yl)phenyl]-2,3-dihydropyridazine-4-carboxamide, 2-[2-(2,2-difluoroethoxy)phenyl]-N-[2-fluoro-4-(2-hydroxypropan-2-yl)phenyl]-6-methyl-3-oxo-2,3-dihydropyridazine-4-carboxamide, 2-[2-(2,2-difluoroethoxy)phenyl]-N-[2-fluoro-4-(2-hydroxypropan-2-yl)phenyl]-3-oxo-2,3-dihydropyridazine-4-carboxamide, N-[2-fluoro-4-(2-hydroxypropan-2-yl)phenyl]-3-oxo-2-[2-(2,2,2-trifluoroethoxy)phenyl]-2,3-dihydropyridazine-4-carboxamide, N-[2-chloro-4-(2-hydroxypropan-2-yl)phenyl]-2-[2-(2,2-difluoroethoxy)phenyl]-6-methyl-3-oxo-2,3-dihydropyridazine-4-carboxamide, 2-[2-(2,2-difluoroethoxy)phenyl]-N-[2,6-difluoro-4-(2-hydroxypropan-2-yl)phenyl]-6-methyl-3-oxo-2,3-dihydropyridazine-4-carboxamide, 2-[2-(2,2-difluoroethoxy)phenyl]-N-[4-(2-hydroxypropan-2-yl)-2-methoxyphenyl]-6-methyl-3-oxo-2,3-dihydropyridazine-4-carboxamide, 2-[2-(2,2-difluoroethoxy)phenyl]-6-methyl-3-oxo-N-[4-(1,1,3,3-tetrafluoro-2-hydroxypropan-2-yl)phenyl]-2,3-dihydropyridazine-4-carboxamide, 2-[2-(2,2-difluoroethoxy)phenyl]-3-oxo-N-[4-(1,1,3,3-tetrafluoro-2-hydroxypropan-2-yl)phenyl]-2,3-dihydropyridazine-4-carboxamide, N-[2-cyano-4-(2-hydroxypropan-2-yl)phenyl]-2-[2-(2,2-difluoroethoxy)phenyl]-6-methyl-3-oxo-2,3-dihydropyridazine-4-carboxamide, 3-oxo-N-[4-(1,1,3,3-tetrafluoro-2-hydroxypropan-2-yl)phenyl]-2-[2-(2,2,2-trifluoroethoxy)phenyl]-2,3-dihydropyridazine-4-carboxamide, 2-[2-(2,2-difluoroethoxy)phenyl]-N-[2-fluoro-4-(1,1,3,3-tetrafluoro-2-hydroxypropan-2-yl)phenyl]-6-methyl-3-oxo-2,3-dihydropyridazine-4-carboxamide, 2-[2-(2,2-difluoroethoxy)phenyl]-N-[2-fluoro-4-(1,1,3,3-tetrafluoro-2-hydroxypropan-2-yl)phenyl]-3-oxo-2,3-dihydropyridazine-4-carboxamide, 6-[2-(2,2-difluoroethoxy)phenyl]-N-[4-(2-hydroxypropan-2-yl)phenyl]-2-methyl-5-oxo-2,5-dihydropyridazine-4-carboxamide, 6-[2-(2,2-difluoroethoxy)phenyl]-2-methyl-5-oxo-N-[4-(1,1,3,3-tetrafluoro-2-hydroxypropan-2-yl)phenyl]-2,5-dihydropyridazine-4-carboxamide, N-[2-chloro-4-(1,1,3,3-tetrafluoro-2-hydroxypropan-2-yl)phenyl]-2-[2-(2,2-difluoroethoxy)phenyl]-3-oxo-2,3-dihydropyridazine-4-carboxamide, 6-[2-(2,2-difluoroethoxy)phenyl]-2-(difluoromethyl)-N-[4-(2-hydroxypropan-2-yl)phenyl]-5-oxo-2,5-dihydropyridazine-4-carboxamide, 3-oxo-N-[6-(1,1,3,3-tetrafluoro-2-hydroxypropan-2-yl)pyridin-3-yl]-2-[2-(2,2,2-trifluoroethoxy)phenyl]-2,3-dihydropyridazine-4-carboxamide, 6-[2-(2,2-difluoroethoxy)phenyl]-2-(difluoromethyl)-5-oxo-N-[4-(1,1,3,3-tetrafluoro-2-hydroxypropan-2-yl)phenyl]-2,5-dihydropyridazine-4-carboxamide, 6-[2-(2,2-difluoroethoxy)phenyl]-N-[4-(2-hydroxy-2-methylpropoxy)phenyl]-2-methyl-5-oxo-2,5-dihydropyridazine-4-carboxamide, 6-[2-(2,2-difluoroethoxy)phenyl]-2-(difluoromethyl)-N-[4-(2-hydroxy-2-methylpropoxy)phenyl]-5-oxo-2,5-dihydropyridazine-4-carboxamide, N-[4-(2-hydroxypropan-2-yl)phenyl]-2-methyl-5-oxo-6-[2-(2,2,2-trifluoroethoxy)phenyl]-2,5-dihydropyridazine-4-carboxamide, 6-[2-(2,2-difluoroethoxy)phenyl]-N-(2,4-difluorophenyl)-2-(2-hydroxy-2-methylpropyl)-5-oxo-2,5-dihydropyridazine-4-carboxamide, 6-[2-(2,2-difluoroethoxy)phenyl]-2-(2-hydroxy-2-methylpropyl)-5-oxo-N-[4-(2,2,2-trifluoroethoxy)phenyl]-2,5-dihydropyridazine-4-carboxamide, 2-cyclopropyl-6-[2-(2,2-difluoroethoxy)phenyl]-N-[4-(2-hydroxypropan-2-yl)phenyl]-5-oxo-2,5-dihydropyridazine-4-carboxamide, ethyl 5-({2-[2-(2,2-difluoroethoxy)phenyl]-6-methyl-3-oxo-2,3-dihydropyridazine-4-carbonyl}amino)thiophene-2-carboxylate, 6-[2-(2,2-difluoroethoxy)phenyl]-N-(4-fluorophenyl)-2-(2-hydroxy-2-methylpropyl)-5-oxo-2,5-dihydropyridazine-4-carboxamide, N-[4-(2-cyanopropan-2-yl)phenyl]-6-[2-(2,2-difluoroethoxy)phenyl]-2-methyl-5-oxo-2,5-dihydropyridazine-4-carboxamide, 6-[2-(2,2-difluoroethoxy)phenyl]-N-[4-(difluoromethoxy)phenyl]-2-(2-hydroxy-2-methylpropyl)-5-oxo-2,5-dihydropyridazine-4-carboxamide, 6-[2-(2,2-difluoroethoxy)phenyl]-2-(2-hydroxy-2-methylpropyl)-N-[4-(2-hydroxypropan-2-yl)phenyl]-5-oxo-2,5-dihydropyridazine-4-carboxamide, 6-[2-(2,2-difluoroethoxy)phenyl]-2-[(oxetan-3-yl)methyl]-5-oxo-N-[4-(1,1,3,3-tetrafluoro-2-hydroxypropan-2-yl)phenyl]-2,5-dihydropyridazine-4-carboxamide, 6-[2-(2,2-difluoroethoxy)phenyl]-2-methyl-5-oxo-N-[6-(1,1,3,3-tetrafluoro-2-hydroxypropan-2-yl)pyridin-3-yl]-2,5-dihydropyridazine-4-carboxamide, 6-[2-(2,2-difluoroethoxy)phenyl]-2-(difluoromethyl)-5-oxo-N-[6-(1,1,3,3-tetrafluoro-2-hydroxypropan-2-yl)pyridin-3-yl]-2,5-dihydropyridazine-4-carboxamide, 6-[2-(2,2-difluoroethoxy)phenyl]-2-(2-hydroxy-2-methylpropyl)-5-oxo-N-[6-(1,1,3,3-tetrafluoro-2-hydroxypropan-2-yl)pyridin-3-yl]-2,5-dihydropyridazine-4-carboxamide, 6-[2-(2,2-difluoroethoxy)phenyl]-2-(2,2-difluoroethyl)-N-[4-(2-hydroxypropan-2-yl)phenyl]-5-oxo-2,5-dihydropyridazine-4-carboxamide, 6-[2-(2,2-difluoroethoxy)phenyl]-N-[4-(2-hydroxypropan-2-yl)phenyl]-2-[(oxetan-3-yl)methyl]-5-oxo-2,5-dihydropyridazine-4-carboxamide, 6-[2-(2,2-difluoroethoxy)phenyl]-N-(2,4-difluorophenyl)-2-[(oxetan-3-yl)methyl]-5-oxo-2,5-dihydropyridazine-4-carboxamide, 6-[2-(2,2-difluoroethoxy)phenyl]-N-(2,4-difluorophenyl)-2-(oxetan-3-yl)-5-oxo-2,5-dihydropyridazine-4-carboxamide, 6-[2-(2,2-difluoroethoxy)phenyl]-N-[4-(2-hydroxypropan-2-yl)phenyl]-2-(oxetan-3-yl)-5-oxo-2,5-dihydropyridazine-4-carboxamide, 6-[2-(2,2-difluoroethoxy)phenyl]-2-(oxetan-3-yl)-5-oxo-N-[4-(1,1,3,3-tetrafluoro-2-hydroxypropan-2-yl)phenyl]-2,5-dihydropyridazine-4-carboxamide, 6-[2-(2,2-difluoroethoxy)phenyl]-N-[4-(difluoromethyl)phenyl]-2-methyl-5-oxo-2,5-dihydropyridazine-4-carboxamide, 6-[2-(2,2-difluoroethoxy)phenyl]-2-(2,2-difluoroethyl)-5-oxo-N-[6-(1,1,3,3-tetrafluoro-2-hydroxypropan-2-yl)pyridin-3-yl]-2,5-dihydropyridazine-4-carboxamide, 6-[2-(2,2-difluoroethoxy)phenyl]-2-(oxetan-3-yl)-5-oxo-N-[6-(1,1,3,3-tetrafluoro-2-hydroxypropan-2-yl)pyridin-3-yl]-2,5-dihydropyridazine-4-carboxamide, 6-[2-(2,2-difluoroethoxy)phenyl]-2-[(oxetan-3-yl)methyl]-5-oxo-N-[6-(1,1,3,3-tetrafluoro-2-hydroxypropan-2-yl)pyridin-3-yl]-2,5-dihydropyridazine-4-carboxamide, 2-cyclopropyl-6-[2-(2,2-difluoroethoxy)phenyl]-5-oxo-N-[6-(1,1,3,3-tetrafluoro-2-hydroxypropan-2-yl)pyridin-3-yl]-2,5-dihydropyridazine-4-carboxamide, N-[4-(2-cyanopropan-2-yl)phenyl]-2-methyl-5-oxo-6-[2-(2,2,2-trifluoroethoxy)phenyl]-2,5-dihydropyridazine-4-carboxamide, N-[4-(2-cyanopropan-2-yl)phenyl]-6-[2-(2,2-difluoroethoxy)phenyl]-2-(oxetan-3-yl)-5-oxo-2,5-dihydropyridazine-4-carboxamide, N-[4-(2-cyanopropan-2-yl)phenyl]-2-cyclopropyl-6-[2-(2,2-difluoroethoxy)phenyl]-5-oxo-2,5-dihydropyridazine-4-carboxamide, rac-6-[2-(2,2-difluoroethoxy)phenyl]-N-[4-(2-hydroxypropan-2-yl)phenyl]-5-oxo-2-(oxolan-3-yl)-2,5-dihydropyridazine-4-carboxamide, ethyl 4-({2-[2-(2,2-difluoroethoxy)phenyl]-6-methyl-3-oxo-2,3-dihydropyridazine-4-carbonyl}amino)benzoate, rac-6-[2-(2,2-difluoroethoxy)phenyl]-5-oxo-2-(oxolan-3-yl)-N-[6-(1,1,3,3-tetrafluoro-2-hydroxypropan-2-yl)pyridin-3-yl]-2,5-dihydropyridazine-4-carboxamide, rac-6-[2-(2,2-difluoroethoxy)phenyl]-5-oxo-2-(oxolan-3-yl)-N-[4-(1,1,3,3-tetrafluoro-2-hydroxypropan-2-yl)phenyl]-2,5-dihydropyridazine-4-carboxamide, 6-acetyl-N-[4-(difluoromethoxy)phenyl]-3-oxo-2-[2-(2,2,2-trifluoroethoxy)phenyl]-2,3-dihydropyridazine-4-carboxamide, ethyl 5-{[4-(difluoromethoxy)phenyl]carbamoyl}-6-oxo-1-[2-(2,2,2-trifluoroethoxy)phenyl]-1,6-dihydropyridazine-3-carboxylate, rac-N-[4-(difluoromethoxy)phenyl]-6-(1-hydroxyethyl)-3-oxo-2-[2-(2,2,2-trifluoroethoxy)phenyl]-2,3-dihydropyridazine-4-carboxamide, N-[4-(difluoromethoxy)phenyl]-6-(2-hydroxypropan-2-yl)-3-oxo-2-[2-(2,2,2-trifluoroethoxy)phenyl]-2,3-dihydropyridazine-4-carboxamide, N-[4-(2-cyanopropan-2-yl)phenyl]-6-(2-hydroxypropan-2-yl)-3-oxo-2-[2-(2,2,2-trifluoroethoxy)phenyl]-2,3-dihydropyridazine-4-carboxamide, 6-(2-hydroxypropan-2-yl)-N-[4-(2-hydroxypropan-2-yl)phenyl]-3-oxo-2-[2-(2,2,2-trifluoroethoxy)phenyl]-2,3-dihydropyridazine-4-carboxamide, and 6-(2-hydroxypropan-2-yl)-3-oxo-N-[4-(prop-1-en-2-yl)phenyl]-2-[2-(2,2,2-trifluoroethoxy)phenyl]-2,3-dihydropyridazine-4-carboxamide.

* * * * *